(12) United States Patent
Chatterjee et al.

(10) Patent No.: US 12,203,115 B2
(45) Date of Patent: Jan. 21, 2025

(54) UNIVERSAL PLATFORM FOR GENETIC CODE EXPANSION

(71) Applicant: Trustees of Boston College, Chestnut Hill, MA (US)

(72) Inventors: Abhishek Chatterjee, Brookline, MA (US); James Italia, Brighton, MA (US)

(73) Assignee: Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 16/934,484

(22) Filed: Jul. 21, 2020

(65) Prior Publication Data

US 2021/0002626 A1    Jan. 7, 2021

Related U.S. Application Data

(63) Continuation of application No. 15/609,900, filed on May 31, 2017, now Pat. No. 10,717,975.

(60) Provisional application No. 62/345,308, filed on Jun. 3, 2016.

(51) Int. Cl.
*C12N 9/00* (2006.01)
*C12P 21/00* (2006.01)

(52) U.S. Cl.
CPC ............ *C12N 9/93* (2013.01); *C12P 21/00* (2013.01); *C12Y 601/01002* (2013.01)

(58) Field of Classification Search
None
See application file for complete search history.

(56) References Cited

PUBLICATIONS

Cervettini et al., Nature Biotechnology, vol. 38, pp. 989-999, Aug. 2020.*
Choi et al., RNA (2003), 9(4), 386-393.*
Anderson, J.C. et al., "An Expanded Genetic Code with a Functional Quadruplet Codon," Proceedings of the National Academy of Sciences, vol. 101, No. 20, pp. 7566-7571 (2004). Six pages.
Antonczak, A.K. et al., "Importance of Single Molecular Determinants in the Fidelity of Expanded Genetic Codes," Proceedings of the National Academy of Sciences, vol. 108, No. 4, pp. 1320-1325 (2011). Six pages.
Chatterjee, A. et al., "A Trytophanyl-tRNA Synthetase/tRNA Pair for Unnatural Amino Acid Mutagenesis in *E. coli*," Angewandte Chemistry International Edition, vol. 52, pp. 5106-5109, 2013. Ten pages.
Chatterjee, A. et al., "A Versatile Platform for Single- and Multiple-Unnatural Amino Acid Mutagenesis in *Escherichia coli*," Biochemistry, vol. 52, No. 10, pp. 1828-1837 (2013). Twenty-three pages.
Chatterjee, A. et al., "Efficient Viral Delivery System for Unnatural Amino Acid Mutagenesis in Mammalian Cells," Proceedings of the National Academy of Sciences, vol. 110, No. 29, pp. 11803-11808 (2013). Six pages.
Chatterjee, A. et al., "Evolution of Multiple, Mutually Orthogonal prolyl-tRNA synthetase/tRNA Pairs for Unnatural Amino Acid Mutagenesis in *Escherichia coli*," Proceedings of the National Academy of Sciences, vol. 109, No. 37, pp. 14841-14846 (2012). Six pages.
Chin, J.W. et al., "An Expanded Eurkaryotic Genetic Code," Science, vol. 301, pp. 964-967 (2003). Five pages.
Chin, J.W., Expanding and Reprogramming the Genetic Code of Cells and Animals. Annual Review of Biochemistry, vol. 83, pp. 379-408 (2014). Thirty-four pages.
Cooley, R.B. et al., "Gleaning Unexpected Fruits from Hard-Won Synthetases: Probing Principles of Permissivity in Non-Canonical Amino Acid-tRNA Synthetases," ChemBioChem, vol. 15, No. 12, pp. 1810-1819 (2014). Twenty-four pages.
Dumas, A. et al., "Designing Logical Codon Reassignment—Expanding the Chemistry in Biology," Chemical Science, vol. 6, pp. 50-69 (2015). Twenty pages.
Ellefson, J.W. et al., "Directed Evolution of Genetic Parts and Circuits by Compartmentalized Partnered Replication," Nature Biotechnology, vol. 32, pp. 97-101 (2014). Eight pages.
Guo, J. et al., "Evolution of Amber Suppressor tRNAs for Efficient Bacterial Production of Unnatural Amino Acid-Containing Proteins," Angewandte Chemistry International Edition, vol. 48, pp. 9148-9151 (2009). Ten pages.
Iraha, F. et al., "Functional Replacement of the Endogenous tyrosyl-tRNA Synthetase-tRNATyr Pair by the Archaeal Tyrosine Pair in *Escherichia coli* for Genetic Code Expansion," Nucleic Acids Research, vol. 38, No. 11, pp. 3682-3691 (2010). Ten pages.
Italia, J.S et al., "An Orthogonalized Platform for Genetic Code Expansion in Both Bacteria and Eukaryotes," Nature Chemical Biology, vol. 13, pp. 446-453, Apr. 2017, and Supplemental Information, pp. S1-S18. Twenty-six pages.
Jahn, M. et al., "Anticodon and Acceptor Stem Nucleotides in tRNA(Gln) Are Major Recognition Elements for *E. coli* glutaminyl-tRNA Synthetase," Nature, vol. 352, pp. 258-260 (1991).
Kopelowitz, J. et al., "Influence of Codon Context on UGA Suppression and Readthrough," Journal of Molecular Biology, vol. 225, pp. 261-269 (1992).
Li, M. et al., "An Efficient Synthesis of 5-azidotryptophan," Tetrahedron Letters, vol. 35, No. 34, pp. 6255-6258 (1994).
Liu, C., et al., "Adding New Chemistries to the Genetic Code," Annual Review of Biochemistry, vol. 79, pp. 413-444 2010. Thirty-five pages.
Melancon, C.E. et al., "One Plasmid Selection System for the Rapid Evolution of Aminoacyl-tRNA Synthetases," Bioorganic Medical Chemistry Letters, vol. 19, No. 14, pp. 3845-3847 (2009). Six pages.
Neumann, H. et al., "Encoding Multiple Unnatural Amino Acids via Evolution of a Quadruplet-Decoding Ribosome," Nature, vol. 464, pp. 441-444 (2010). Five pages.

(Continued)

*Primary Examiner* — Richard G Hutson
(74) *Attorney, Agent, or Firm* — HoustonHogle LLP

(57) ABSTRACT

Methods and compositions are described for selecting and identifying orthogonal aminoacyl synthetase-tRNA pairs and their use to incorporate unnatural amino acids in a site-specific manner in proteins. Specifically described is a novel *E. coli* tyrptophanyl synthetase-tRNA pair that functions as both an opal and amber suppressor and that incorporates tryptophan analogs into proteins.

7 Claims, 47 Drawing Sheets
(38 of 47 Drawing Sheet(s) Filed in Color)
Specification includes a Sequence Listing.

(56) References Cited

PUBLICATIONS

O'Donoghue, P. et al., "Near-Cognate Suppression of Amber, Opal and Quadruplet Codons Competes with aminoacyl-tRNAPyl for Genetic Code Expansion," Federation of European Biochemical Societies Letters, vol. 586, pp. 3931-3937 (2012). Seven pages.
Prather, N.E. et al., "Primary Structure of an Unusual Glycine tRNA UGA Suppressor," Nucleic Acids Research, vol. 9, No. 23, pp. 6421-6428 (1981). Eight pages.
Raftery, L.A. et al., "Defined Set of Cloned Termination Suppressors: In Vivo Activity of Isogenetic UAG, UAA, and UGA Suppressor tRNAs," Journal of Bacteriology, vol. 158, No. 3, pp. 849-859 (1984). Eleven pages.
Rogers, M.J. et al., "Switching tRNA(Gln) Identity from Glutamine to Tryptophan," Proceedings of the National Academy of Sciences, vol. 89, pp. 3463-3467 (1992). Five pages.
Santoro, S.W. et al., "An Efficient System for the Evolution of Aminoacyl-tRNA Synthetase Specificity," Nature Biotechnology, vol. 20, pp. 1044-1048 (2002). Six pages.
Soll, L. et al., "Recessive Lethal Nonsense Suppressor in *Escherichia coli* which Inserts Glutamine," Nature, vol. 223, pp. 1340-1342 (1969). Three pages.
Syn, C.K. et al., "A Scalable Protocol for the Isolation of Large-Sized Genomic DNA within an Hour from Several Bacteria," Analytical Biochemistry, vol. 278, pp. 86-90 (2000). Five pages.
Wan, W. et al., "A Facile System for Genetic Incorporation of Two Different Noncanonical Amino Acids into One Protein in *Escherichia coli*," Angewandte Chemie International Edition, vol. 49, pp. 3211-3214 (2010). Four pages.
Wan, W. et al., "Pyrrolysyl-tRNA Synthetase: An Ordinary Enzyme but an Outstanding Genetic Code Expansion Tool," Biochimica et Biophysica Acta, vol. 1844, No. 6, pp. 1059-1070 (2014). Thirty-two pages.
Wang, H.H. et al., "Programming Cells by Multiplex Genome Engineering and Accelerated Evolution," Nature, vol. 460, No. 7257, pp. 894-898 (2009). Fourteen pages.
Wang, L. et al., "Expanding the Genetic Code of *Escherichia coli*," Science, vol. 292, pp. 498-500 (2001). Four pages.
Warming, S. et al., "Simple and Highly Efficient BAC Recombineering Using galK Selection," Nucleic Acids Research, vol. 33, No. 4, e36 (2005). Twelve pages.
Xiao, H. et al., "Genetic Incorporation of Multiple Unnatural Amino Acids into Proteins in Mammalian Cells," Angewandte Chemistry International Edition, vol. 52, pp. 14080-14083 (2013). Four pages.
Young, D.D. et al., "An Evolved aminoacyl-tRNA Synthetase with Atypical Polysubstrate Specificity," Biochemistry, vol. 50, pp. 1894-1900 (2011). Seven pages.
Young, T.S. et al., "An Enhanced System for Unnatural Amino Acid Mutagenesis in *E. coli*," Journal of Molecular Biology, vol. 395, pp. 361-374 (2010). Fourteen pages.
Zhang, Z. et al., "Selective Incorporation of 5-hydroxytryptophan into Proteins in Mammalian Cells," Proceedings of the National Academy of Sciences, vol. 101, No. 24, pp. 8882-8887 (2004). Six pages.
Ngo, T. et al., "Computational Complexity, Protein Structure Prediction, and the Levinthal Paradox," The Protein Folding Problem and Tertiary Structure Prediction, Merz et al. (ed.), pp. 433 and 492-495 (1994). Five pages.
Hughes, R.A., et al., "Rational Design of an Ortogonal Tryptophanyl Nonsense Suppressor tRNA," Nucleic Acids Research, 38(19): 6813-6830 (2010).
Italia et al., "Mutually Orthogonal Nonsense-Suppression Systems and Conjugation Chemistries for Precise Protein Labeling at up to Three Distinct Sites," J Am Chem Soc., vol. 141(15), pp. 6204-6212, Apr. 2019. 9 pages.

\* cited by examiner

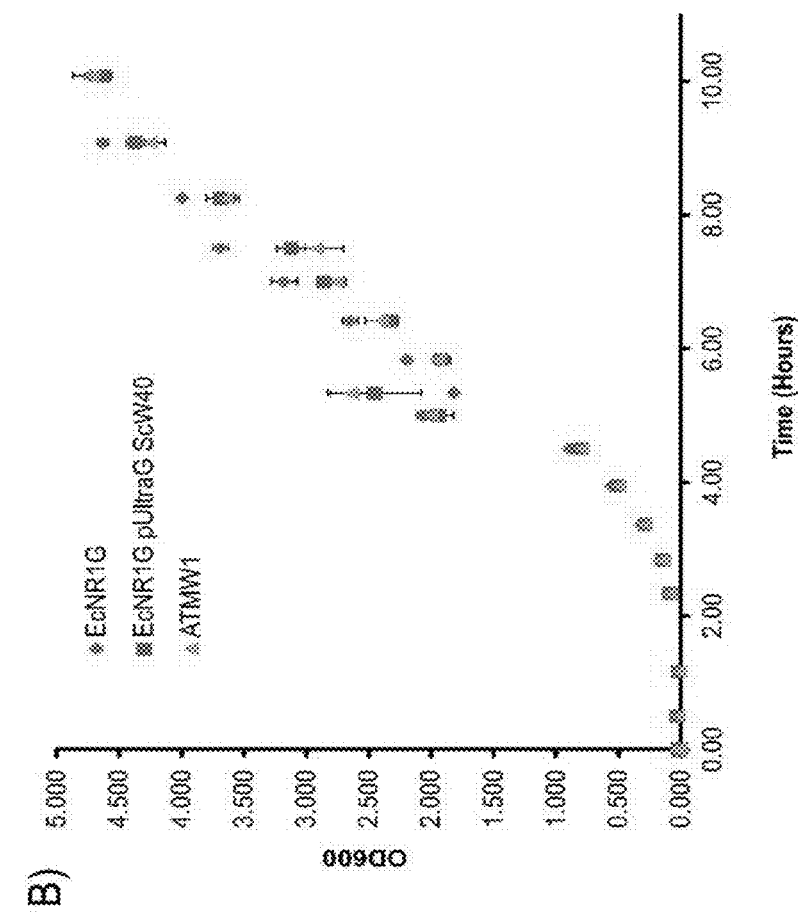
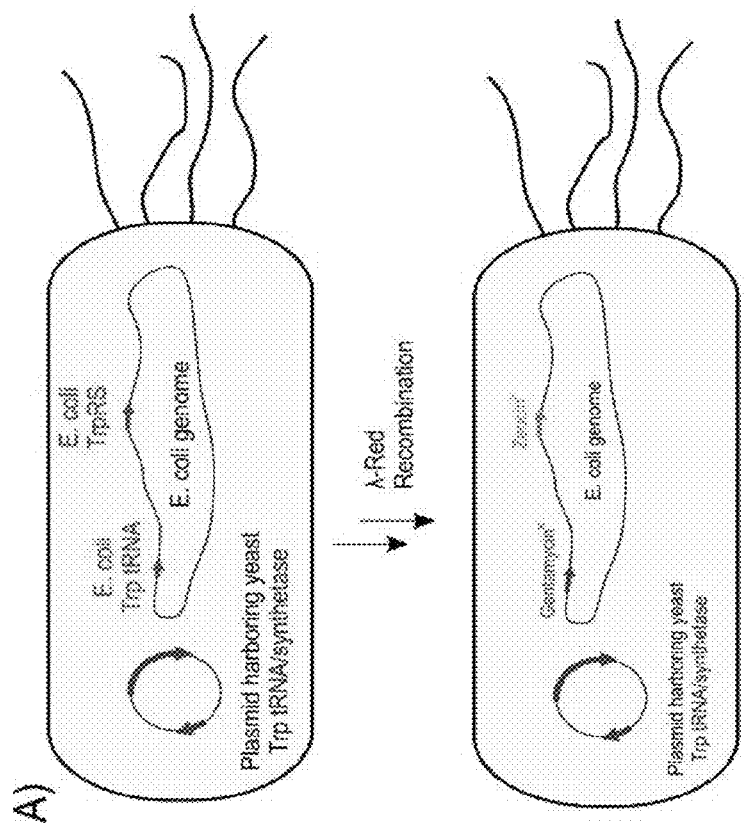
Figure 2A
Figure 2B

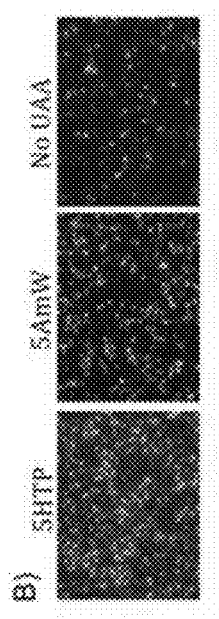
Figure 11B
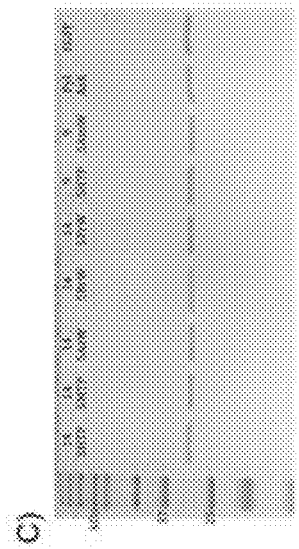
Figure 11D
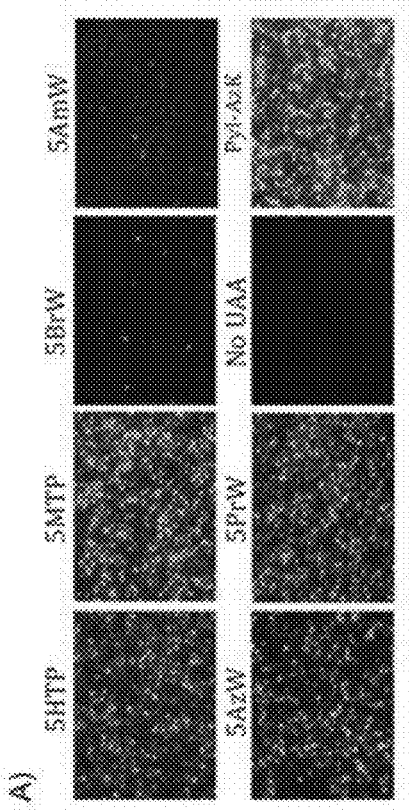
Figure 11A
Figure 11C

*trpS::Zeo<sup>R</sup> PCR cassette*
EM-7 promoter (red); Zeo<sup>R</sup> (green); CYC1 terminator (blue); TrpRS flanking homology (black)
ATCAGTCTATAAATGACCTTCTGCCCGCATTAGGGCTTCCGCATAGCGAAAATCAGGAATCGAAA
AAGGTGTTGACAATTAATCATCGGCATAGTATATTGGCATAGTATAATACGACAAGGTGAGGAA
CTAAACCATGGCCAAGCTGACCAGTGCCGTTCCGGTGCTCACCGCGCGCGACGTCGCCGGAGCGG
TCGAGTTCTGGACCGACCGGCTCGGGTTCTCCCGGGACTTCGTGGAGGACGACTTCGCCGGTGTG
GTCCGGGACGACGTGACCCTGTTCATCAGCGCGGTCCAGGACCAGGTGGTGCCGGACAACACCCT
GGCCTGGGTGTGGGTGCGCGGCCTGGACGAGCTGTACGCCGAGTGGTCGGAGGTCGTGTCCACGA
ACTTCCGGGACGCCTCCGGGCCGGCCATGACCGAGATCGGCGAGCAGCCGTGGGGCGGGAGTTC
GCCCTGCGCGACCCGGCCGGCAACTGCGTGCACTTCGTGGCCGAGGAGCAGGACTGACACGTCCG
ACGGCGGCCCACGGGTCCCAGGCCTCGGAGATCCGTCCCCTTTTCCTTTGTCGATATCATGTAA
TTAGTTATGTCACGCTTACATTCACGCCCTCCCCCACATCCGCTCTAACCGAAAAGGAAGGAGT
TAGACAACCTGAAGTCTAGGTCGCTATTTATTTTTTATAGTTATGTTAGTATTAAGAACGTTA
TTTATATTTCAAATTTTCTTTTTTTCTGTACAGACGCGTGTACGCATGTAACATTATACTGAA
AACCTTGCTTGAGAAGGTTTTGGGACGCTCGAAGGCTTTAATTTGCAAGCTTTCACTATTGCTGG
CAAATTGCGCTTTGTTCATGCCGGATGCGGCGTGAACGCCTTATCCGGCCTACA

Figure 12A

*trpT::Gent<sup>R</sup> PCR cassette*
Gent<sup>R</sup> (green); trpT flanking homology (red)
CAGTCGGTTAGAATACCTGCCTGTCACGCAGGGGTCGCGGGTTCGAGTCCCGTCCGTTCCGCCA
CCCTAATTACGCACACCGTGGAAACGGATGAAGGCACGAACCCAGTTGACATAAGCCTGTTCGGT
TCGTAAACTGTAATGCAAGTAGCGTATGCGCTCACGCAACTGGTCCAGAACCTTGACCGAACGCA
GCGGTGGTAACGGCGCAGTGGCGGTTTTCATGGCTTGTTATGACTGTTTTTTTGTACAGTCTATG
CCTCGGGCATCCAAGCAGCAAGCGCGTTACGCCGTGGGTCGATGTTTGATGTTATGGAGCAGCAA
CGATGTTACGCAGCAGCAACGATGTTACGCAGCAGGGCAGTCGCCCTAAAACAAAGTTAGGTGGC
TCAAGTATGGGCATCATTCGCACATGTAGGCTCGGCCCTGACCAAGTCAAATCCATGCGGGCTGC
TCTTGATCTTTTCGGTCGTGAGTTCGGAGACGTAGCCACCTACTCCCAACATCAGCCGGACTCCG
ATTACCTCGGGAACTTGCTCCGTAGTAAGACATTCATCGCGCTTGCTGCCTTCGACCAAGAAGCG
GTTGTTGGCGCTCTCGCGGCTTACGTTCTGCCCAGGTTTGAGCAGCCGCGTAGTGAGATCTATAT
CTATGATCTCGCAGTCTCCGGCGAGCACCGGAGGCAGGGCATTGCCACCGCGCTCATCAATCTCC
TCAAGCATGAGGCCAACGCGCTTGGTGCTTATGTGATCTACGTGCAAGCAGATTACGGTGACGAT
CCCGCAGTGGCTCTCTATACAAAGTTGGGCATACGGGAAGAAGTGATGCACTTTGATATCGACCC
AAGTACCGCCACCTAACAATTCGTTCAAGCCGAGATCGGCTTCCCGGGAAATCATCCTTAGCGAA
AGCTAAGGATTTTTTTTATCTGAAATAACCCTCTCCGAAGTAAATCCTTCTACCG

Figure 12B

λ-RED::galK PCR cassette
galK (green); galK promoter (blue); lambda deletion homology (red)
GCTATGAAATAGAAAAATGAATCCGTTGAAGCCTGCTTTTTTATACTAACTTGAGCGAAACGGG
AAGCCTGTTGACAATTAATCATCGGCAtagtatatcggcatagtataatacgacaaggtgaggaactaaacccagga
ggcagatcatgagtctgaaagaaaaaacacaatctctgtttgccaacgcatttggctaccctgccactcacaccattcaggcgcctgg
ccgcgtgaatttgattggtgaacacaccgactacaacgacggtttcgttctgccctgcgcgattgattatcaaaccgtgatcagttgtg
caccacgcgatgaccgtaaagttcgcgtgatggcagccgattatgaaaatcagctcgacgagttttccctcgatgcgcccattgtcgc
acatgaaaactatcaatgggctaactacgttcgtggcgtggtgaaacatctgcaactgcgtaacaacagcttcggcggcgtggacat
ggtgatcagcggcaatgtgccgcagggtgccgggttaagttcttccgcttcactggaagtcgcggtcggaaccgtattgcagcagctt
tatcatctgccgctggacggcgcacaaatcgcgcttaacggtcaggaagcagaaaaccagtttgtaggctgtaactgcgggatcatg
gatcagctaattccgcgctcggcaagaaagatcatgccttgctgatcgattgccgctcactggggaccaaagcagtttccatgccca
aaggtgtggctgtcgtcatcatcaacagtaacttcaaacgtaccctggttggcagcgaatacaacacccgtcgtgaacagtgcgaaa
ccggtgcgcgtttcttccagcagccagcctgcgtgatgtcaccattgaagagttcaacgctgttgcgcgatgaactggaccgatcgt
ggcaaaacgcgtgcgtcatatactgactgaaaacgcccgcaccgttgaagctgccagcgcgctggagcaaggcgacctgaaacgt
atgggcgagttgatggcggagtctcatgcctctatgcgcgatgatttcgaaatcaccgtgccgcaaattgacactctggtagaaatcg
tcaaagctgtgattggcgacaaaggtggcgtacgcatgaccggcggcggatttggcggctgtatcgtcgcgctgatcccggaagag
ctggtgcctgccgtacagcaagctgtcgctgaacaatatgaagcaaaaacaggtattaaagagactttttacgtttgtaaaccatcac
AAGGAGCAGGACAGTGCTGAATATTACAACGCGGCAGCATTATGAGCTGGCAGGAGAAAATCAA
CGCGGC

Figure 12C

GGtaattccgcttcgcaacatgtgagcaccggtttattgactacAggaagcagtgtgaccgtgtgcttctcaaatgcctgaggccag
tttgctcaggctctccccgtggaggtaataattgacgatatgatcagtgcacggctaactaagcggcctgctgactttctcgccgatca
aaaggcatttctgctattaagggattgacgagggcgtatctgcgcagtaagatgcgccccgcattGAAgcGGTGGCTCAAgGG
TAGAGCTggcgcCTCcAAAgcgcctGGtTGCAGGTTCAAgTCCTGcCCgtTTCACCAaattcgaaaagcctgct
caacgagcaggctttttttgcatgctcgagcagctcagggtcgaatttgCCATGGcggccACCAGGTacCACCGGCGcctca
ggcatttgagaagcacacggtcacactgcttccggtagtcaataaaccggtaaaccagcaatagacataagcggctatttaacgac
cctgccctgaaccgacgaccgggtcatcgtggccggatcttgcggccccctcggcttgaacgaattgttagacattatttgccgactac
cttggtgatctcgcctttcacgtagtggacaaattcttccaactgatctgcgcgcgaggccaagcgatcttcttcttgtccaagataagc
ctgtctagcttcaagtatgacgggctgatactgggccggcaggcgctccattgcccagtcggcagcgacatccttcggcgcgatttg
ccggttactgcgctgtaccaaatgcgggacaacgtaagcactacatttcgctcatcgccagcccagtcgggcggcgagttccatagc
gttaaggtttcatttagcgcctcaaatagatcctgttcaggaaccggatcaaagagttcctccgccgctggacctaccaaggcaacgc
tatgttctcttgcttttgtcagcaagatagccagatcaatgtcgatcgtggctggctcgaagatacctgcaagaatgtcattgcgctgc
cattctccaaattgcagttcgcgcttagctggataacgccacggaatgatgtcgtcgtgcacaacaatggtgacttctacagcgcgga
gaatctcgctctctccaggggaagccgaagtttccaaaaggtcgttgatcaaagctcgccgcgttgtttcatcaagccttacggtcac
cgtaaccagcaaatcaatatcactgtgtggcttcaggccgccatccactgcggagccgtacaaatgtacggccagcaacgtcggtc
gagatggcgctcgatgacgccaactacctctgatagttgagtcgatacttcggcgatcaccgcttccctcatactcttcctttttcaata
ttattgaagcatttatcagggttattgtctcatgagcggatacatatttgaatgtatttagaaaaataaacaaatagctagctcactcgg
tcgctacgctccgggcgtgagactgcggcgggcgctgcggacacatacaaagttacccacagattccgtggataagcaggggacta
acatgtgaggcaaaacagcagggccgcgccggtggcgttttccataggctccgccctcctgccagagttcacataaacagacgctt
ttccggtgcatctgtgggagccgtgaggctcaaccatgaatctgacagtacgggcgaaacccgacaggacttaaagatccccaccg
ttttccggcgggtcgctccctcttgcgctctcctgttccgaccctgccgtttaccggatacctgttccgcctttctcccttacgggaagtgt
ggcgctttctcatagctcacacactggtatctcggctcggtgtaggtcgttcgctccaagctgggctgtaagcaagaactccccgttca
gcccgactgctgcgccttatccggtaactgttcacttgagtccaacccggaaaagcacggtaaaacgccactggcagcagccattgg
taactgggagttcgcagaggatttgtttagctaaacacgcggttgctcttgaagtgtgcgccaaagtccggctacactggaaggaca
gatttggttgctgtgctctgcgaaagccagttaccacggttaagcagttccccaactgacttaaccttcgatcaaaccacctcccagg
tggttttttcgtttacagggcaaaagattacgcgcagaaaaaaaggatctcaagaagatcctttgatcttttctactgaaccgctctag
agtcatcaatcatccccataatccttgttagattatcaatttaaaaaactaacagttgtcagcctgtcccgctttaatatcatacgccgt
tatacgttgtttacgctttAaggagGCGGCCGCATGAGCAACGACGAAACTGTAGAGAAAGTCACCCAACAA
GTGTCGGAACTAAAAAGCACAGATGTTAAAGAGCAAGTAGTTACACCTTGGGATGTGGAAGGTG
GGGTTGATGAACAAGGTAGAGCCCAAAATATTGATTACGACAAATTGATCAAACAATTCGGTAC
TAAGCCGGTCAACGAAGAAACCCTGAAGAGATTCAAGCAAGTGACGGGTCGTGAACCACATCAT
TTTTTGCGTAAGGGATTGTTTTTCAGTGAGCGTGACTTCACTAAAATATTAGACCTTTACGAAC
AAGGCAAACCATTTTTCCTATACACTGGTAGAGGTCCTTCGAGCGATTCTATGCACTTGGGTCAT
ATGATCCCTTTTGTCTTCACCAAATGGTTACAGGAAGTGTTTGACGTACCATTAGTCATAGAGTT
GACAGATGACGAAAAATTTTTATTCAAACACAAGTTGACCATCAATGACGTTAAGAATTTTGCC
CGTGAAAATGCCAAGGATATCATTGCTGTTGGCTTTGACCCAAAGAACACCTTTATCTTTTCTGA
TTTGCAATACATGGGTGGTGCATTTTACGAAACTGTAGTAAGAGTTTCCAGACAAATTACAGGA
TCCACTGCAAAGGCTGTTTTCGGGTTTAATGACTCCGACTGTATTGGTAAGTTCCATTTTGCCTC
CATTCAAATTGCTACCGCATTCCCAAGCTCATTTCCTAATGTGTTAGGCTTGCCTGATAAGACAC
CATGTTTGATTCCATGTGCAATTGACCAAGATCCATATTTCAGAGTTTGTAGGGATGTCGCGGAT
AAATTGAAGTACTCCAAACCTGCTTTGCTTCATTCCAGATTCTTTCCAGCTTTGCAAGGTTCCAC
GACCAAAATGTCAGCCTCTGATGATACCACTGCCATTTTCATGACCGATACACCAAAGCAAATTC
AAAAGAAAATTAACAAGTACGCATTCAGCGGTGGTCAAGTGTCCGCCGACCTACATAGAGAATT
AGGTGGTAATCCCGATGTCGATGTTGCATACCAATACTTGTCATTTTTCAAGGATGACGATGTTT
TCTTGAAGGAATGCTATGACAAATATAAGTCCGGTGAATTACTATCAGGTGAAATGAAGAAACT
GTGTATCGAGACTCTGCAAGAATTCGTTAAGGCGTTCCAGGAACGCAGAGCTCAGGTGGACGAA
GAGACCTTGGACAAATTCATGGTCCCACATAAGTTGGTTTGGGCGAAAAGGAAAGACTTGTCG
CACCTAAGCCAAAAACTAAGCAAGAAAAGAAGTAAGCGGCCGCtttcaaacgctaaattgcctgatgcgctac
gcttatcaggcctacatgatctctgcaatatattgagtttgcgtgcttttgtaggccggataaggcgttcacgccgcatccgcaagaa
acagcaaacaatccaaaacgccgcgttcagcggcgttttttctgcttttcttcgcgaattaattccgcttcgcaacatgtgagcaccgg
tttattgactacctgca

Figure 13B pRepAC-EcWtR-TAG gccctteeggctggctggtttattgctgataaatctggagccggtgagcgtgggtctcgcggtatcattgcagcactggggccagatg
gtaagccctcccgtatcgtagttatctacacgacggggagtcaggcaactatggatgaacgaaatagacagatcgctgagataggt
gcctcactgattaagcattggtaactgtcagaccaagtttactcatatatactttagattgatttaaaacttcattttaatttaaaagga
tctaggtgaagatccttttgataatctcatgaccaaaatcccttaacgtgagttttcgttccactgagcgtcagaccccttaataagat
gatcttcttgagatcgttttggtctgcgcgtaatctcttgctctgaaaacgaaaaaaccgccttgcagggcggtttttcgaaggttctct
gagctaccaactctttgaaccgaggtaactggcttggaggagcgcagtcaccaaaacttgtcctttcagtttagccttaaccggcgca
tgacttcaagactaactcctctaaatcaattaccagtggctgctgccagtggtgcttttgcatgtctttccgggttggactcaagacgat
agttaccggataaggcgcagcggtcggactgaacgggggtcgtgcatacagtccagcttggagcgaactgcctacccggaactg
agtgtcaggcgtggaatgagacaaacgcggccataacagcggaatgacaccggtaaaccgaaaggcaggaacaggagagcgca
cgagggagccgccaggggaaacgcctggtatctttatagtcctgtcgggtttcgccaccactgatttgagcgtcagatttcgtgatg
cttgtcagggggggcggagcctatggaaaaacggctttgccgcggccctctcacttccctgttaagtatcttcctggcatcttccaggaa
atctccgccccgttcgtaagccatttccgctcgccgcagtcgaacgaccgagcgtagcgagtcagtgagcgaggaagcggaatatat
cctgtatcacatattctgctgacgcaccggtgcagccttttttctcctgccacatgaagcacttcactgacaccctcatcagtgccaaca
tagtaagccagtatacactccgctagcgctgatgtccggcggtgcttttgccgttacgcaccacccgtcagtagctgaacaggagg
gacagctgatagaaacagaagccactggagcacctcaaaaacaccatcatacactaaatcagtaagttggcagcatcacccgacg
cactttgcgccgaataaatacctgtgacggaagatcacttcgcagaataaataaatcctggtgtccctgttgataccgggaagccctg
ggccaacttttggcgaaaatgagacgttgatcggcacgtaagaggttccaactttcaccataatgaaataagatcactaccgggcgt
attttttgagttatcgagattttcaggagctaaggaagctaaaatggagaaaaaaatcactggatataccaccgttgatatatcccaa
tggcatcgtaaagaacattttgaggcatttcagtcagttgctcaatgtacctataaccagaccgttcagctggatattacggcctttta
aagacgtgaaagaaaaataagcacaagttttatccggcctttattcacattcttgcccgcctgatgaatgctcatccggaattcgtat
ggcaatgaaacgcggtgagctggtgatatgggatagtgttcaccctgttacaccgttttccatgagcaaactgaaacgttttcatgc
tctggagtgaataccactaggatttccggcagttctacacatatattcgcaagatgtggcgtgttacggtgaaaacctggcctattc
cctaaagggtttattgagaatatgttttcgtctcagccaatccctgggtgagtttcaccagtttgatttaaacgtggccaatatggac
aacttcttcgccccgttttcaccatgggcaaatattatacgcaaggcgacaaggtgctgatgccgctggcgattcaggttcatcatgc
cgtttgtgatggcttccatgtcggcagaatgcttaatgaattacaacagtactgcgatgagtggcagggcggggcgtaatttttttaag
gcagttattggtgcccttaaacgcctggttgctacgcctgaataagtgataataagcggatgaatggcagaaattcgaaagcaaatt
cgacccggtcgtcggttcagggcagggtcgttaaatagccgcttatgtctattgctggtttaccggtttattgactaccggaagcagtg
tgaccgtgtgcttctcaaatgcctgaggccagtttgctcaggctctccccgtggaggtaataattgacgatatgatcatttattctgcct
cccagagcatgataaaaacggttagcgcttcgttaatacagatgtaggtgttccacagggtagccagcagcatcctgcgatgcagat
ccggaacataatggACTAGTgcgcttgtttcggcgggactgttgtaactcagaataagaaatgaggccgctcatggcgttctgttg
cccgtctcactggtgaaaagaaaaacaaccctggcgccgcttctttgagcgaacgatcaaaaataagtggcgccccatcaaaaaaa
tattctcaacataaaaaactttgtgtaatacttgtaacgctGAATTCAGGGGCGTAGTTCAATTGGTAGAGCACCG
GTCTctaAAACCGGGTGtTGGGAGTTCGAGTCTCTCCGCCCCTGCCACTGCAGATccttagcgaaagcta

Figure 14B aggattttttttaagcttggcactggccgtcgttttacaacgtcgtgactgggaaaaccctggcgttacccaacttaatcgccttgcagc
acatcccctttcgccagttgagcaccgccgccgcaaggaatggtGaattcaggaTCTAAGGAGcccgagatgcgccgcgtgc
ggctgctggagatggcggacgcgatggatatgttctgccaagggttggtttgcgcattcacagttctccgcaagaattgattggctcc
aattcttggagtggtgaatccgttagcgaggtgccgccggcttccattcaggtcgaggtggcccggctccatgcaccgcgacgcaac
gcggggaggcagacaaggtatagggcggcgcctacaatccatgccaacccgttccatgtgctcgccgaggcggcataaatcgccgt
gacgatcagcggtccaatgatcgaagttaggctggtaagagccgcgagcgatccttgaagctgtccctgatggtcgtcatctacctg
cctggacagcatggcctgcaacgcgggcatcccgatgccgccggaagcgagaagaatcataatggggaaggccatccagcctcgc
gtcgcgaacgccagcaagacgtagcccagcgcgtcggccgccatgccggcgataatggcctgcttctcgccgaaacgtttggtggc
gggaccagtgacgaaggcttgagcgagggcgtgcaagattccgaataccgcaagcgacaggccgatcatcgtcgcgctccagcga
aagcggtcctcgccgaaaaatgacccagagcgctgccggcacctgtcctacgagttgcatgataaagaagacagtcataagtgcggc
gacgatagtcatgccccgcgccaccggaaggagctgactgggttgaaggctctcaagggcatcggtcgacgctctcccttatgcga
ctcctgcattaggaagcagcccagtagtaggttgaggccgttgagcaccgccgccgcaaggaatggtgcatgcaaggagatggcg
cccaacagtccccggccacggggcctgccaccataccacgccgaaacaagcgctcatgagcccgaagtggcgagcccgatctt
ccccatcggtgatgtcggcgatataggcgccagcaaccgcacctgtggcgccggtgatgccggccacgatgcgtccggcgtagagg
atccacaggacgggtgtggtcgccatgatcgcgtagtcgatagtggctccaagtagcgaagcgagcaggactgggcggcggccaa
agcggtcggacagtgctccgagaacgggtgcgcatagaaattgcatcaacgcatatagcgctagcagcacgccatagtgactggc
gatgctgtcggaatggacgatatcccgcaagaggcccggcagtaccggcataaccaagctatgcctacagcatccagggtgacg
gtgccgaggatgacgatgagcgcattgttagatttcatacacggtgcctgactgcgttagcaatttaactgtgataaactaccgcatta
aagcttatcgatgataagctgtcaaacatgagaattacaacttatatcgtatggggctgacttcaggtgctacattgctcaaagatgc
agggggtaaaagctaaccgcatctttaccgacaaggcatccggcagttcaacagatcgggaagggctggatttgctgaggatgaagg
tggaggaaggtgatgtcattctggtgaagaagctcgaccgtcttggccgcgacaccgccgacatgatccaactgataaaagagtttg
atgctcagggtgtagcggttcggtttattgacgacgggatcagtaccgacggtgatatggggcaaatggtggtcaccatcctgtcggc
tgtggcacaggctgaacgccggaggatcctccgggccgttgcttcgcaacgttcaaatccgctcccggcggatttgtcctactcagga
gagcgttcaccgacaaacaacagataaaacgaaaggcccagtctttcgactgagcctttcgttttatttgatgcctggcagttccctac
tctcgcatggggagaccccacactaccatcggcgctacggcgtttcacttctgagttcggcatggggtcaggtgggaccaccgcgct
actgccgccaggcaaattctgttttatcagaccgcttctgcgttctgatttaatctgtatcaggctgaaaatcttctctcatccgacgtct
taggcgaaggcgaagtccgactctaagatgtcacggaggttcaagttacctttagccggaagtgctggcattttgtccaattgagact
cgtgcaactggtcagcgaactggtcgtagaaatcagccagtacatcacaagactcatatgtgtcaaccatagtttcgcgcactgcttt
gaacaggttcgcagcgtcagccggaatggtaccgaaggagtcgtgaatcagtgcaaaagattcgattccgtacttctcgtgtgccca
cactacagtcttacgaaggtggctaccgtcttggctgtgtacaaagttaggagcgataccagactcctgtttgtgtgcatcaatctcgc
tatctttgttggtgttaatggtaggctgtaagcggaactgaccgaggaacatcaggttcaagcgcgtctgaataggcttcttgtattcct
gccacacagggaaaccatcaggagttacccaatgcacagcgcaacgcttgcgaagaatctctccagtcttcttatctttgacctcagc
agccagcagcttagcagcagacttaagccagttcattgcttcaaccgcagctaccaccgtcacgctcacagattcccaaatcagctta
gccatgtatccagcagcctgattcggctgagtgaacatcagacccttgccggaatcaatagctggctgaatggtatcttccagcactt
gttgacggaagccgaactctttggaccccgtaagccagcgtcatgactgaacgcttagtcacactgcgagtaacaccgtaagccagcc
attgaccagccagtgccttagtgcccagcttgactttctcagagatttcaccagtgttctcatcggtcacggtaactacttcgttatcgg
tccccattgattgcgtctgcttgtagaatctcgttgacttcttagcaacaatcccgtagatgtcctgaacggttcactaggaagcaagt
taaccgcgcgaccacctacctcatccggagcatcgcggagaagtgctggatgccagagcaagacccgtcaaacgccagcggaag
ggagcagttatagctcaggccgtggtgctgtaccccagcgtactcaaagcagaacgcaaggaagcagaacggagaatcttgctca
gcccaccaagtgttctccagtggagacttagcgcaagccatgatgttctcgtggttttcctcaatgaacttgatgcgctcagggaacg
gaaccttatcgacacccgcacagtttgcaccgtggattttcagccagtagtaaccttcttaccgattggtttacctttcgccagcgtaa
gcagtccttggtcatatcgttaccttgcgggtgaacattgacacagcgtaaacacgaccgcgccagtccatgttgtaagggaacca
gatggcctatggttagcaaacttattggcttgctcaagcatgaactcaaggctgatacggcgagacttgcgagccttgtccttgcggt
acacagcagcggcagcacgtttcacgcggtgagagcctcaggattcatgtcgatgtcttccggtttcatcgggagttcttcacgctc
aatcgcagggatgtcctcgaccggacaatgcttccacttggtgattacgttggcgaccgctaggacttcttgttgattttccatgcggt
gttttgcgcaatgttaatcgctttgtacacctcaggcatgtaaacgtcttcgtagcgcatcagtgctttcttactgtgagtacgcaccag

```
cgccagaggacgacgaccgttagcccaatagccaccaccagtaatgccagtccacggcttaggaggaactacgcaaggttggaac
atcggagagatgccagccagcgcacctgcacgggttgcgatagcctcagcgtattcaggtgcgagttcgatagtctcagagtcttga
cctactacgccagcattttggcggtgtaagctaaccattccggttgactcaatgagcatctcgatgcagcgtactctacatgaataga
gtcttccttatgccacgaagaccacgcctcgccaccgagtagacccttagagagcatgtcagcctcgacaacttgcataaatgctttc
ttgtagacgtgccctacgcgcttgttgagttgttcctcaacgttttctgaagtgcttagcttcaaggtcacggatacgaccgaagcga
gcctcgtcctcaatggcccgaccgattgcgcttgctacagcctgaacggttgtattgtcagcactggttaggcaagccagagtggtctt
aatggtgatgtacgctacggcttccggcttgatttcctacaggaactggaaggctgtcgggcgcttgccgcgcttagctttcacttcct
caaaccagtcgttgatgcgtgcaatcatcttaggagtagggtagtgatgagaggcttggccggcagcgttatccgcaacctcaccag
ctttaagttgacgctcaaacatcttgcggaagcgtgcttcacccatctcgtaagactcatgctcaagggccaactgttcgcgagctaa
acgctcaccgtaatggtcagccagagtgttgaacgggatagcagccagttcgatgtcagagaagtcgtcttagcaatgttaatggt
attctagtgcacggtaatcatggtcatggttaattcctcctgttagcccaaaaaacgggtatggagaaacagtagagagttgcgataa
aaagcgtcaggtaggatccgctaatcttatggataaaaatgctatggcatagcaaagtgtgacgccgtgcaaataatcaatgtggac
ttttctgccgtgattatagacacttttgttacgcgttttttgtcatggctttggtcccgctttgttacagaatgcttttaataagcggggttac
cggtttggttagcgagaagagccagtaaaagacgcagtgacggcaatgtctgatgcaatatggacaattggtttcttctctgaatggc
gggagtatgaaaagtatggctgaagcgcaaaatgatcccctgctgccgggatactcgtttaatgcccatctggtggcgggtttaacg
ccgattgaggccaacggttatctcgattttttatcgaccgaccgctgggaatgaaaggttatattctcaatctcaccattcgcggtcag
ggggtggtgaaaaatcagggacgagaatttgtttgccgaccgggtgatattttgctgttcccgccaggagagattcatcactacggtc
gtcatccggaggctcgcgaatggtatcaccagtgggtttactttcgtccgcgcgcctactggcatgaatggcttaactggccgtcaat
atttgccaatacgggggttctttcgcccggatgaagcgcaccagccgcatttcagcgacctgtttgggcaaatcattaacgccgggcaa
gggaagggcgctattcggagctgctggcgataaatctgcttgagcaattgttactgcggcgcatggaagcgattaacgagtcgctc
catccaccgatggataatcgggtacgcgaggcttgtcagtacatcagcgatcacctggcagacagcaattttgatatcgccagcgtc
gcacagcatgtttgcttgtcgccgtcgcgtctgtcacatcttttccgccagcagttagggattagcgtcttaagctggcgcgaggacca
acgtatcagccaggcgaagctgcttttgagcaccacccggatgcctatcgccaccgtcggtcgcaatgttggttttgacgatcaactc
tatttctcgcgggtatttaaaaaatgcaccggggccagcccgagcgagttccgtgccggttgtgaagaaaaagtgaatgatgtagcc
gtcaagttgtcataattggtaacgaatcagacaattgacggcttgacggagtagcataggggtttgcagaatccctgcttcgtccatttg
acaggcacattatgcatgccgcttcgccttcgcgcgcgaattgatctgctgcctcgcgcgtttcggtgatgacggtgaaaacctctga
cacatgcagctcccggagacggtcacagcctgcagcaaaaaacccctcaagacccgtttagaggccccaaggggttatgctagtta
ttgctcagcggtggcagcagcgcaactcagcttcctttcgggctttgttatttgtagagctcatccatgccatgtgtaatcccagcagcag
ttacaaactcaagaaggaccatgtggtcacgcttttcgttgggatctttcgaaagggcagattgtgtcgacaggtaatggttgtctggt
aaaaggacagggccatcgccaattggagtattttgttgataatggtctgctagttgaacggatccatcttcaatgttgtggcgaattttt
gaagttagctttgattccattcttttgtttgtctgccgtgatgtatacattgtgtgagttatagttgtactcgagtttgtgtccgagaatgtt
tccatcttctttaaaatcaataccttttaactcgatacgattaacaagggtatcaccttcaaacttgacttcagcacgcgtcttgtagttc
ccgtcatcttttgaaagatatagtgcgttcctgtacataaccttcgggcatggcactcttgaaaaagtcatgccgtttcatatgatccgg
ataacgggaaaagcattgaacaccataagagaaagtagtgacaagtgttggccatggaacaggtagttttccagtagtgcaaataa
atttaagggtaagttttccgtatgttgcatcaccttcaccctctccactgacagaaaatttgtgccattaacatcaccatctaattcaac
aagaattgggacaactccagtgaaaagttcttctccttactcatatgtatatctccttcttaaagttaaacaaaattatttctagaggg
aaaccgttgtggtctccctatagtgagtcgtattaatttcgcgggatcg
```

Figure 14B cont.

cgcgtccgccatctccagcagccgcacgcggcgcatcttgggctccttgcatgcaccattccttgcggcggcggtgctcaacggcctc
aacctactactgggctgcttcctaatgcaggagtcgcataagggagagcgtctggcgaaagggggatgtgctgcaaggcgattaag
ttgggtaacgccagggttttccagtcacgacgttgtaaaacgacggccagtgccaagcttaaaaaaaaatccttagctttcgctaagg
atcaTATGCCTAGGTGGCAGGGGCGGAGAGACTCGAACTCCCAaCACCCGGTTTTGAAGACCGGTG
CTCTACCAATTGAACTACGCCCCTGAATTCagcgttacaagtattacacaaagttttttatgttgagaatattttttga
tggggcgccacttatttttgatcgttcgctcaaagaagcggcgccagggttgttttctttttcaccagtgagacgggcaacagaacGG
TACCtctagacaattggtgcacttcaaaaatcgatgagctgttgacaattaatcatcgaactagtgttgataccgggaagccctggg
ccaacttttggcgaaaatgagacgttgatcggcacgtaagaggttccaactttcaccataatgaaataagatcactaccgggcgtatt
ttttgagttatcgagattttcaggagctaaggaagctaaaatggagaaaaaaatcactggatataccaccgttgatatatccaaatgg
catcgtaaagaacatttgaggcatttcagtcagttgctcaatgtacctataaccagaccgttcagctggatattacggccttttaaag
accgtaaagaaaataagcacaagttttatccggcctttattcacattcttgcccgcctgatgaatgctcatccggaattccgtatggc
aatgaaagacggtgagctggtgatatgggatagtgttcaccctgttacaccgttttccatgagTGATctgaaacgttttcatcgctc
tggagtgaataccacgacgatttccggcagtttctacacatatattcgcaagatgtggcgtgttacggtgaaaacctggcctatttccc
taaagggtttattgagaatatgtttttcgtctcagccaatccctgggtgagtttcaccagttttgatttaaacgtggccaatatggacaa
cttcttcgcccccgttttcaccatgggcaaatattatacgcaaggcgacaaggtgctgatgccgctggcgattcaggttcatcatgccg
tTtgtgatggcttccatgtcggcagaatgcttaatgaattacaacagtactgcgatgagtggcagggcggggcgtaattttttttaagg
cagttattggtgcccttaaacgcctggttgctacgcctgaataagtgataataagcggatgaatggcagaaatTCGCTGCAgcag
catcaaagttctggtgctggtagctgcgccagaaggtatcgctgcgctggaaaaagcgcacccggacgtcgaactgtataccgcatc
gattgatcagggactgaacgagcacggatacattattccgggcctcggcgatgccggtgacaaaatctttggtacgaaataaagaat
tcgaagcttgggcccgaacaaaaactcatctcagaagaggatctgaatagcgccgtcgaccatcaccatcatcatcattgagtttaa
acgacgtccagcttggctgttttggcggatgagagaagattttcagcctgatacagattaaatcagaacgcagaagcggtctgataa
aacagaatttgcctggcggcagtagcgcggtggtcccacctgaccccatgccgaactcagaagtgaaacgccgtagcgccgatggt
agtgtgaggcctccatgcgagagtagggaactgccaggcatcaaataaaacgaaaggctcagtcgaaagactgggcctttcgttt
tatctgttgtttgtcggtgaacgatatctgcttttcttcggatccctcgagagatctccatgggctagcggagtgtatactggcttactat
gttggcactgatgagggtgtcagtgaagtgcttcatgtggcaggagaaaaaaggctgcaccggtgcgtcagcagaatatgtgatac
aggatatattccgcttcctcgctcactgactcgctacgctcggtcgttcgactgcggcgagcggaaatggcttacgaacggggcgga
gatttcctggaagatgccaggaagatacttaacagggaagtgagagggccgcggcaaagccgttttccataggctccgccccctg
acaagcatcacgaaatctgacgctcaaatcagtggtggcgaaacccgacaggactataaagataccaggcgtttccccctggcggc
tccctcgtgcgctctcctgttcctgcctttcggtttaccggtgtcattccgctgttatggccgcgtttgtctcattccacgcctgacactca
gttccgggtaggcagttcgctccaagctggactgtatgcacgaaccccccgttcagtccgaccgctgcgccttatccggtaactatcg
tcttgagtccaacccggaaagacatgcaaaagcaccactggcagcagccactggtaattgatttagaggagttagtcttgaagtcat
gcgccggttaaggctaaactgaaaggacaagttttggtgactgcgctcctccaagccagttacctcggttcaaagagttggtagctca
gagaaccttcgaaaaaccgccctgcaaggcggttttttcgttttcagagcaagagattacgcgcagaccaaaacgatctcaagaag

Figure 15B

```
atcatcttattaaggggtctgacgcacatgtaatgtagcacctgaagtcagccccatacgatataagttgtaattctcatgtttgacag
cttatcatcgataagctttaatgcggtagtttatcacagttaaattgctaacgcagtcaggcaccgtgtatgaaatctaacaatgcgct
catcgtcatcctcggcaccgtcaccctggatgctgtaggcataggcttggttatgccggtactgccgggcctcttgcgggatatcgtc
attccgacagcatcgccagtcactatggcgtgctgctagcgctatatgcgttgatgcaatttctatgcgcacccgttctcggagcactg
tccgaccgctttggccgccgcccagtcctgctcgcttcgctacttggagccactatcgactacgcgatcatggcgaccacacccgtcc
gtggattctctacgccggacgcatcgtggccggcatcaccggcgccacaggtgcggttgctggcgcctatatcgccgacatcaccga
tggggaagatcgggctcgccacttcgggctcatgagcgcttgtttcggcgtgggtatggtggcaggccccgtggccggggggactgtt
gggcgccatctccttgcatgcaccattccttgcggcggcggtgctcaacggcctcaacctactactgggctgcttcctaatgcaggag
tcgcataagggagagcgtcgaccgatgcccttgagagccttcaacccagtcagctccttccggtgggcgcggggcatgactatcgtc
gccgcacttatgactgtcttctttatcatgcaactcgtaggacaggtgccggcagcgctctgggtcattttcggcgaggaccgctttcg
ctggagcgcgacgatgatcggcctgtcgcttgcggtattcggaatcttgcacgccctcgctcaagccttcgtcactggtcccgccacc
aaacgtttcggcgagaagcaggccattatcgccggcatggcggccgacgcgctgggctacgtcttgctggcgttcgcgacgcgagg
ctggatggccttccccattatgattcttctcgcttccggcggcatcgggatgcccgcgttgcaggccatgctgtccaggcaggtagat
acgaccatcagggacagcttcaaggatcgctcgcggctcttaccagcctaacttcgatcattggaccgctgatcgtcacggcgattt
tgccgcctcggcgagcacatggaacgggttggcatggattgtaggcgccgccctataccttgtctgcctccccgcgttgcgtcgcgg
gcatggagccgggccacctcgacctgaatggaagccggcggcacctcgctaacggattcaccactccaagaattggagccaatca
attcttgcggagaactgtgaatgcgcaaaccaacccttggcagaacatatccat
```

Figure 15B cont.

pRepJI-EcW cgcgtccgccatctccagcagccgcacgcggcgcatcttgggctccttgcatgcaccattccttgcggcggcggtgctcaacggcctc
aacctactactgggctgcttcctaatgcaggagtcgcataagggagagcgtctggcgaaaggggatgtgctgcaaggcgattaag
ttgggtaacgccagggttttcccagtcacgacgttgtaaaacgacggccagtgccaagcttaaaaaaaatccttagctttcgctaagg
atcaTATGCCTAGGTGGCAGGGGCGGAGAGACTCGAACTCCCAaCACCCGGTTTTGAAGACCGGTG
CTCTACCAATTGAACTACGCCCCTGAATTCagcgttacaagtattacacaaagttttttatgttgagaatatttttttga
tggggcgccacttattttttgatcgttcgctcaaagaagcggcgccagggttgtttttcttttcaccagtgagacgggcaacagaacGG
TACctctagacaattggtgcacttcaaaaaatcgatgagctgttgacaattaatcatcgaactagtgttgataccgggaagccctggg
ccaacttttggcgaaaatgagacgttgatcggcacgtaagaggttccaactttcaccataatgaaataagatcactaccgggcgtatt
ttttgagttatcgagattttcaggagctaaggaagctaaaatggagaaaaaatcactggatataccaccgttgatatatcccaatgg
catcgtaaagaacatttgaggcatttcagtcagttgctcaatgtacctataaccagaccgttcagctggatattacggcctttttaaag
accgtaaagaaaataagcacaagtttatccggcctttattcacattcttgccggctgatgaatgctcatccggaattccgtatggc
aatgaaagacggtgagctggtgatatgggatagtgttcacccttgttacaccgttttccatgagTGATctgaaacgttttcatcgctc
tggagtgaataccacgacgatttccggcagtttctacacatatattcgcaagatggtggcgtgttacggtgaaaacctggcctatttccc
taaagggtttattgagaatatgtttttcgtctcagccaatccctgggtgagtttcaccagttttgatttaaacgtggccaatatggacaa
cttcttcgccccgttttcaccatgggcaaatattatacgcaaggcgacaaggtgctgatgccgctggcgattcaggttcatcatgccg

Figure 16B tTtgtgatggcttccatgtcggcagaatgcttaatgaattacaacagtactgcgatgagtggcagggcgggcgtaattttttttaagg
cagttattggtgcccttaaacgccggttgctacgcctgaataagtgataataagcggatgaatggcagaaatTCGCTGCAggct
actcaggagagcgttcaccgacaaacaacagataaaacgaaaggcccagtctttcgactgagcctttcgttttatttgatgcctggca
gttccctactctcgcatggggagaccccacactaccatcggcgctacggcgtttcacttctgagttcggcatggggtcaggtgggacc
accgcgctactgccgccaggcaaattctgttttatcagaccgcttctgcgttctgatttaatctgtatcaggctgaaaatcttctctcatc
cgacgtcttaggcgaaggcgaagtccgactctaagatgtcacggaggttcaagttacctttagccggaagtgctggcattttgtccaa
ttgagactcgtgcaactggtcagcgaactggtcgtagaaatcagccagtacatcacaagactcatatgtgtcaaccatagtttcgcgc
actgctttgaacaggttcgcagcgtcagccggaatggtaccgaaggagtcgtgaatcagtgcaaaagattcgattccgtacttctcgt
gtgcccacactacagtcttacgaaggtggctaccgtcttggctgtgtacaaagttaggagcgataccagactcctgtttgtgtgcatca
atctcgctatctttgttggtgttaatggtaggctgtaagcggaactgaccgaggaacatcaggttcaagcgcgtctgaataggcttctt
gtattcctgccacacagggaaaccatcaggagttacccaatgcacagcgcaacgcttgcgaagaatctctccagtcttcttatcttg
acctcagcagccagcagcttagcagcagacttaagccagttcattgcttcaaccgcagctaccaccgtcacgctcacagattccaa
atcagcttagccatgtatccagcagcctgattcggctgagtgaacatcagacccttgccggaatcaatagctggctgaatggtatctt
ccagcacttgttgacggaagccgaactctttggacccgtaagccagcgtcatgactgaacgcttagtcacactgcgagtaacaccgt
aagccagccattgaccagccagtgccttagtgcccagcttgactttctcagagatttcaccagtgttctcatcggtcacggtaactact
tcgttatcggtcccattgattgcgtctgcttgtagaatctcgttgactttcttagcaacaatcccgtagatgtcctgaacggttcactag
gaagcaagttaacgcgcgaccacctacctcatctcggagcatcgcggagaagtgctggatgccagagcaagacccgtcaaacgc
cagcggaagggagcagttatagctcaggccgtggtgctgtaccccagcgtactcaaagcagaacgcaaggaagcagaacggaga
atcttgctcagccaccaagtgttctccagtggagactagcgcaagccatgatgttctcgtggttttcctcaatgaacttgatgcgctc
agggaacggaaccttatcgacacccgcacagtttgcaccgtggattttcagccagtagtaaccttcctaccgattggtttacctttcg
ccagcgtaagcagtcctttggtcatatcgttaccttgcgggttgaacattgacacagcgtaaacacgaccgcgccagtccatgttgta
agggaaccagatggccttatggttagcaaacttattggcttgctcaagcatgaactcaaggctgatacgcgcgagacttgcgagcctt
gtccttgcggtacacagcagcggcagcacgtttccacgcggtgagagcctcaggattcatgtcgatgtcttccggtttcatcgggagt
tcttcacgctcaatcgcagggatgtcctcgaccggacaatgcttccacttggtgattacgttggcgaccgcAaggacttctttgttgat
tttccatgcggtgttttgcgcaatgttaatcgctttgtacacctcaggcatgtaaacgtcttcgtagcgcatcagtgctttcttactgtga
gtacgcaccagcgccagaggacgacgaccgttagcccaatagccaccaccagtaatgccagtccacggcttaggaggaactacgc
aaggttggaacatcggagagatgccagccagcgcacctgcacgggttgcgatagcctcagcgtattcaggtgcgagttcgatagtct
cagagtcttgacctactacgccagcattttggcggtgtaagctaaccattccggttgactcaatgagcatctcgatgcagcgtactcct
acatgaatagagtcttccttatgccacgaagaccacgcctcgccaccgagtagacccttagagagcatgtcagcctcgacaacttgc
ataaatgctttcttgtagacgtgccctacgcgcttgttgagttgttcctcaacgtttttcttgaagtgcttagcttcaaggtcacggatac
gaccgaagcgagcctcgtcctcaatggcccgaccgattgcgcttgctacagcctgaacggttgtattgtcagcactggttaggcaag
ccagagtggtcttaatggtgatgtacgctacggcttccggcttgatttctcacaggaactggaaggctgtcgggcgcttgccgcgctta
gctttcacttcctcaaaccagtcgttgatgcgtgcaatcatcttagggagtagggtagtgatgagaggcttggcggcagcgttatccg
caacctcaccagctttaagttgacgctcaaacatctgcggaaagcgtgcttcacccatctcgtaagactcatgctcaagggccaactg
ttcgcgagctaaacgctcaccgtaatggtcagccagagtgttgaacgggatagcagccagtcgatgtcagagaagtcgttcttagc
aatgttaatggtattTCAgtgcacggtaatcatggtcatggttaattcctcctgttagcccaaaaaacgggtatggagaaacagtag
agagttgcgataaaaagcgtcaggtaggatccgctaatcttatggataaaaatgctatggcatagcaaagtgtgacgccgtgcaaat
aatcaatgtggacttttctgccgtgattatagacacttttgttacgcgttttttgtcatggctttggtcccgctttgttacagaatgcttttaa
taagcggggttaccggtttggttagcgagaagagccagtaaaagacgcagtgacggcaatgtctgatgcaatatggacaattggttt
cttctctgaatggcgggagtatgaaaagtatggctgaagcgcaaaatgatcccctgctgccgggatactcgtttaatgcccatctggt
ggcgggtttaacgccgattgaggccaacggttatctcgattttttatcgaccgaccgctgggaatgaaaggttatattctcaatctca
ccattcgcggtcaggggtggtgaaaaatcagggacgagaatttgtttgccgaccgggtgatattttgctgttcccgccaggagaga
ttcatcactacggtcgtcatccggaggctcgcgaatggtatcaccagtgggtttactttcgtccgcgcgcctactggcatgaatggctt
aactggccgtcaatatttgccaatacggggttcttttcgcccggatgaagcgcaccagccgcatttcagcgacctgtttgggcaaatca
ttaacgccgggcaaggggaagggcgctattcggagctgctggcgataaatctgcttgagcaattgttactgcggcgcatggaagcg
attaacgagtcgctccatccaccgatggataatcgggtacgcgaggcttgtcagtacatcagcgatcacctggcagacagcaattt

```
gatatcgccagcgtcgcacagcatgtttgcttgtcgccgtcgcgtctgtcacatctttccgccagcagttagggattagcgtcttaagc
tggcgcgaggaccaacgtatcagccaggcgaagctgcttttgagcaccacccggatgcctatcgccaccgtcggtcgcaatgttggt
tttgacgatcaactctatttctcgcgggtatttaaaaaatgcaccggggccagcccgagcgagttccgtgccggttgtgaagaaaaa
gtgaatgatgtagccgtcaagttgtcataattggtaacgaatcagacaattgacggcttgacggagtagcatagggtttgcagaatc
cctgcttcgtccatttgacaggcacattatgcatgccgcttcgccttcgcgcgcgaattgatctgctgcctcgcgcgtttcggtgatgac
ggtgaaaacctctgacacatgcagctcccggagacggtcacagcctgcagcaaaaaacccctcaagacccgtttagaggccccaa
ggggttatgctagttattgctcagcggtggcagcagccaactcagcttcctttcgggctttgttatttgtagagctcatccatgccatgt
gtaatccagcagcagttacaaactcaagaaggaccatgtggtcacgcttttcgttgggatctttcgaaagggcagattgtgtcgaca
ggtaatggttgtctggtaaaaggacagggccatcgccaattggagtattttgttgataatggtctgctagttgaacggatccatcttca
atgttgtggcgaattttgaagttagctttgattccattcttttgtttgtctgccgtgatgtatacattgtgtgagttatagttgtactcgagt
ttgtgtccgagaatgtttccatcttctttaaaatcaataccttttaactcgatacgattaacaagggtatcaccttcaaacttgacttcag
cacgcgtcttgtagttcccgtcatctttgaaagatatagtgcgttcctgtacataaccttcgggcatggcactcttgaaaaagtcatgcc
gtttcatatgatccggataacgggaaaagcattgaacaccataagagaaagtagtgacaagtgttggccatggaacaggtagttttc
cagtagtgcaaataaatttaagggtaagttttccgtatgttgcatcaccttcaccctctccactgacagaaaatttgtgcccattaacat
caccatctaattcaacaagaattgggacaactccagtgaaaagttcttctccttttactcatatgtatatctccttcttaaagttaaacaa
aattatttctagagggaaaccgttgtggtctccctatagtgagtcgtattaatttcgcgggatcggcccttccggctggctggtttattg
ctgataaatctggagccggtgagcgtgggtctcgcggtatcattgcagcactggggccagatggtaagccctcccgtagcggccgcc
ctgcagcagcatcaaagttctggtgctggtagctgcgccagaaggtatcgctgcgctggaaaaagcgcacccggacgtcgaactgt
ataccgcatcgattgatcagggactgaacgagcacggatacattattccgggcctcggcgatgccggtgacaaaatctttggtacga
aataaagaattcgaagcttgggcccgaacaaaaactcatctcagaagaggatctgaatagcgccgtcgaccatcaccatcatcatc
attgagtttaaacgacgtccagcttggctgttttggcggatgagagaagattttcagcctgatacagattaaatcagaacgcagaagc
ggtctgataaaacagaatttgcctggcggcagtagcgcggtggtcccacctgacccatgccgaactcagaagtgaaacgccgtag
cgccgatggtagtgtgaggcctccatgcgagagtagggaactgccaggcatcaaataaaacgaaaggctcagtcgaaagactgg
gcctttcgttttatctgttgtttgtcggtgaacgatatctgcttttcttcggatccctcgagagatctccatgggctagcggagtgtatact
ggcttactatgttggcactgatgagggtgtcagtgaagtgcttcatgtggcaggagaaaaaaggctgcaccggtgcgtcagcagaat
atgtgatacaggatatattccgcttcctcgctcactgactcgctacgctcggtcgttcgactgcggcgagcggaaatggcttacgaac
ggggcggagatttcctggaagatgccaggaagatacttaacagggaagtgagagggccgcggcaaagccgttttccataggctcc
gccccctgacaagcatcacgaaatctgacgctcaaatcagtggtggcgaaacccgacaggactataaagataccaggcgtttccc
cctggcggctccctcgtgcgctctcctgttcctgccttccggtttaccggtgtcattccgctgttatggccgcgtttgtctcattccacgcc
tgacactcagttccgggtaggcagttcgctccaagctggactgtatgcacgaaccccccgttcagtccgaccgctgcgccttatccgg
taactatcgtcttgagtccaacccggaaagacatgcaaaagcaccactggcagcagccactggtaattgatttagaggagttagtctt
gaagtcatgcgccggttaaggctaaactgaaaggacaagttttggtgactgcgctcctccaagccagttacctcggttcaaagagtt
ggtagctcagagaaccttcgaaaaaccgccctgcaaggcggttttttcgttttcagagcaagagattacgcgcagaccaaaacgatc
tcaagaagatcatcttattaaggggtctgacgcacatgtaatgtagcacctgaagtcagccccatacgatataagttgtaattctcatg
tttgacagcttatcatcgataagctttaatgcggtagtttatcacagttaaattgctaacgcagtcaggcaccgtgtatgaaatctaac
aatgcgctcatcgtcatcctcggcaccgtcaccctggatgctgtaggcataggcttggttatgccggtactgccgggcctcttgcggg
atatcgtccattccgacagcatcgccagtcactatggcgtgctgctagcgctatatgcgttgatgcaatttctatgcgcacccgttctcg
gagcactgtccgaccgctttggccgccgcccagtcctgctcgcttcgctacttggagccactatcgactacgcgatcatggcgaccac
acccgtcctgtggattctctacgccggacgcatcgtggccggcatcaccggcgccacaggtgcggttgctggcgcctatatcgccga
catcaccgatggggaagatcgggctcgccacttcgggctcatgagcgcttgtttcggcgtgggtatggtggcaggccccgtggccgg
gggactgttgggcgccatctccttgcatgcaccattccttgcggcggcggtgctcaacggcctcaacctactactgggctgcttcctaa
tgcaggagtcgcataagggagagcgtcgaccgatgcccttgagagccttcaacccagtcagctccttccggtgggcgcggggcatg
actatcgtcgccgcacttatgactgtcttctttatcatgcaactcgtaggacaggtgccggcagcgctctgggtcattttcggcgagga
ccgctttcgctggagcgcgacgatgatcggcctgtcgcttgcggtattcggaatcttgcacgccctcgctcaagccttcgtcactggtc
ccgccaccaaacgtttcggcgagaagcaggccattatcgccggcatggcggccgacgcgctgggctacgtcttgctggcgttcgcg
acgcgaggctggatggccttccccattatgattcttctcgcttccggcggcatcgggatgcccgcgttgcaggccatgctgtccaggc
```

Figure 16B cont.

aggtagatgacgaccatcagggacagcttcaaggatcgctcgcggctcttaccagcctaacttcgatcattggaccgctgatcgtca
cggcgatttatgccgcctcggcgagcacatggaacgggttggcatggattgtaggcgccgccctataccttgtctgcctccccgcgtt
gcgtcgcggtgcatggagccgggccacctcgacctgaatggaagccggcggcacctcgctaacggattcaccactccaagaattgg
agccaatcaattcttgcggagaactgtgaatgcgcaaaccaacccttggcagaacatatccat
pNegJ2-EcW

Figure 16B cont.

gggtggtgcgtaacggcaaaagcaccgccggacatcagcgctagcggagtgtatactggcttactatgttggcactgatgagggtgt
cagtgaagtgcttcatgtggcaggagaaaaaaggctgcaccggtgcgtcagcagaatatgtgatacaggatatattccgcttcctcg
ctcactgactcgctacgctcggtcgttcgactgcggcgagcggaaatggcttacgaacggggcggagatttcctggaagatgccag
gaagatacttaacagggaagtgagagggccgcggcaaagccgttttttccataggctccgcccccctgacaagcatcacgaaatctg
acgctcaaatcagtggtggcgaaacccgacaggactataaagataccaggcgtttccccctggcggctccctcgtgcgctctcctgtt
cctgcctttcggtttaccggtgtcattccgctgttatggccgcgtttgtctcattccacgcctgacactcagttccgggtaggcagttcgc
tccaagctggactgtatgcacgaaccccccgttcagtccgaccgctgcgccttatccggtaactatcgtcttgagtccaacccggaaa
gacatgcaaaagcaccactggcagcagccactggtaattgatttagaggagttagtcttgaagtcatgcgccggttaaggctaaact
gaaaggacaagtttggtgactgcgctcctccaagccagttacctcggttcaaagagttggtagctcagagaaccttcgaaaaaccg
ccctgcaaggcggttttttcgttttcagagcaagagattacgcgcagaccaaaacgatctcaagaagatcatcttattaatcagataa
aatatttctagatttcagtgcaatttatctcttcaaatgtagcacctgaagtcagccccatacgatataagttgtaattctcatgtttgac
agcttatcatcgataagcttgcaatttatctcttcaaatgtagcacctgaagtcagccccatacgatataagttgtaattctcatgttagt
catgccccgcgcccaccggaaggagctgactgggttgaaggctctcaagggcatcggtcgagatcccggtgcctaatgagtgagct
aacttacattaattgcgttgcgctcactgcccgctttccagtcgggaaacctgtcgtgccagctgcattaatgaatcggccaacgcgc
ggggagaggcggtttgcgtattgggcgccagggtggtttttcttttcaccagtgagacgggcaacagctgattgcccttcaccgcctg
gccctgagagagttgcagcaagcggtccacgctggtttgccccagcaggcgaaaatcctgtttgatggtggttaacggcgggatata
acatgagctgtcttcggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttgccagccagccagacgcagacgcg
ccgagacagaacttaatgggcccgctaacagcgcgatttgctggtgacccaatgcgaccagatgctccacgcccagtcgcgtaccgt
cttcatgggagaaaataatactgttgatgggtgtctggtcagagacatcaagaaataacgccggaacattagtgcaggcagcttcca
cagcaatggcatcctggtcatccagcggatagttaatgatcagcccactgacgcgttgcgcgagaagattgtgcaccgccgctttac
aggcttcgacgccgcttcgttctaccatcgacaccaccacgctggcacccagttgatcggcgcgagatttaatcgccgcgacaatttg
cgacggcgcgtgcagggccagactggaggtggcaacgccaatcagcaacgactgtttgccgccagttgttgtgccacgcggttgg

Figure 17B gaatgtaattcagctccgccatcgccgcttccacttttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcg
ctatcatgccataccgcgaaaggttttgcgccattcgatggtgtccgggatctcgacgctctcccttatgcgactcctgcattaggctca
ctataggggaattgtgagcggataacaattcccctctagagtttgacagcattatcatcgatctcgagaaatcataaaaaatttatttg
ctttgtgagcggataacaattataatagattcaattgtgagcggataacaatttcacacagaattcattaaagaggagaaattacatA
TGAGCAAAGGAGAAGAACTTTTCACTGGAGTTGTCCCAATTCTTGTTGAATTAGATGGTGATGT
TAATGGGCACAAATTTTCTGTCCGTGGAGAGGGTGAAGGTGATGCTACAAACGGAAAACTCACC
CTTAAATTTATTTGCACTACTGGAAAACTACCTGTTCCGTGGCCAACACTTGTCACTACTCTGAC
CTATGGTGTTCAATGCTTTTCCCGTTATCCGGATCACATGAAACGGCATGACTTTTTCAAGAGTG
CCATGCCCGAAGGTTATGTACAGGAACGCACTATATCTTTCAAAGATGACGGGACCTACAAGACG
CGTGCTGAAGTCAAGTTTGAAGGTGATACCCTTGTTAATCGTATCGAGTTAAAGGGTATTGATT
TTAAAGAAGATGGAAACATTCTTGGACACAAACTCGAGTACAACTTTAACTCACACAATGTATA
GATCACGGCAGACAAACAAAAGAATGGAATCAAAGCTAACTTCAAAATTCGCCACAACGTTGAA
GATGGTTCCGTTCAACTAGCAGACCATTATCAACAAAATACTCCAATTGGCGATGGCCCTGTCCT
TTTACCAGACAACCATTACCTGTCGACACAATCTGTCCTTTCGAAAGATCCCAACGAAAAGCGTG
ACCACATGGTCCTTCTTGAGTTTGTAACTGCTGCTGGGATTACACATGGCATGGATGAGCTCTAC
AAAGGATCCCACCACCACCACCACCACTAAaagcttaattagctgagcttggactcctgttgatagatccagtaatga
cctcagaactccatctggatttgttcagaacgctcggttgccgccgggcgttttttattggtgagaatccaagctagcttggcgCTGC
Agtgtgcttctcaaatgcctgaggccagtttgctcaggctctccccgtggaggtaataattgacgatatgatcagtgcacggctaact
aagcggcctgctgacttctcgccgatcaaaaggcattttgctattaagggattgacgagggcgTATCTgcgcagtaagatgcgc
cccgcatttAGGGGCGTAGTTCAATTGGTAGAGCACCGGTCTCtAAAACCGGGTGtTGGGAGTTCGAG
TCTCTCCGCCCCTGCCAAATTCGAAAAGCCTGCTCAACGAGCAGGCTTTTTTGCATGCTCGAGCA
GCTCAGGGTCGAATTTGCTTTCGAatttctgccattcatccgcttattatcacttattcaggcgtagcaaccaggcgttttaa
gggcaccaataactgccttaaaaaaattacgccccgccctgccactcatcgcagtactgttgtaattcattaagcattctgccgacatg
gaagccatcacaAacggcatgatgaacctgaatcgccagcggcatcagcaccttgtcgccttgcgtataatatttgcccatggtgaa
aacgggggcgaagaagttgtccatattggccacgtttaaatcaaaactggtgaaactcacccagggattggctgagacgaaaaaca
tattctcaataaacccttaggaaataggccaggttttcaccgtaacacgccacatcttgcgaatatatgtgtagaaactgccggaa
atcgtcgtggtattcactccagagcgatgaaaacgtttcagtttgctcatggaaaacggtgtaacaagggtgaacactatcccatatc
accagctcaccgtctttcattgccatacggaattccggatgagcattcatcaggcgggcaagaatgtgaataaaggccggataaaac
ttgtgcttattttttctttacggtctttaaaaaggccgtaatatccagctgaacggtctggttataggtacattgagcaactgactgaaat
gcctcaaaatgttctttacgatgccattgggatatatcaacggtggtatatccagtgatttttttctccatttttagcttccttagctcctga
aaatctcgataactcaaaaaatacgcccggtagtgatcttatttcattatggtgaaagttggaacctcttacgtgccgatcaacgtctc
attttcgccaaaagttggcccagggcttcccggtatcaacagggacaccaggatttatttattctgcgaagtgatcttccgtcacaggt
atttattcggcgcaaagtgcgtcgggtgatgctgccaacttactgatttagtgtatgatggtgttttgaggtgctccagtggcttctgtt
tctatcagctgtccctcctgttcagctactgacg

Figure 17B cont.

gggtggtgcgtaacggcaaaagcaccgccggacatcagcgctagcggagtgtatactggcttactatgttggcactgatgagggtgt
cagtgaagtgcttcatgtggcaggagaaaaaaggctgcaccggtgcgtcagcagaatatgtgatacaggatatattccgcttcctcg
ctcactgactcgctacgctcggtcgttcgactgcggcgagcggaaatggcttacgaacggggcggagatttcctggaagatgccag
gaagatacttaacagggaagtgagagggccgcggcaaagccgttttccataggctccgcccccctgacaagcatcacgaaatctg
acgctcaaatcagtggtggcgaaacccgacaggactataaagataccaggcgtttccccctggcggctccctcgtgcgctctcctgtt
cctgcctttcggtttaccggtgtcattccgctgttatggccgcgtttgtctcattccacgcctgacactcagttccggggtaggcagttcgc
tccaagctggactgtatgcacgaacccccgttcagtccgaccgctgcgccttatccggtaactatcgtcttgagtccaacccggaaa
gacatgcaaaagcaccactggcagcagccactggtaattgatttagaggagttagtcttgaagtcatgcgccggttaaggctaaact
gaaaggacaagtttggtgactgcgctcctccaagccagttacctcggttcaaagagttggtagctcagagaacrttcgaaaaaccg
ccctgcaaggcggttttttcgttttcagagcaagagattacgcgcagaccaaaacgatctcaagaagatcatcttattaatcagataa
aatatttctagatttcagtgcaatttatctcttcaaatgtagcacctgaagtcagccccatacgatataagttgtaattctcatgtttgac
agcttatcatcgataagcttgcaatttatctcttcaaatgtagcacctgaagtcagccccatacgatataagttgtaattctcatgttagt
catgccccgcgcccaccggaaggagctgactgggttgaaggctctcaagggcatcggtcgagatcccggtgcctaatgagtgagct
aacttacattaattgcgttgcgctcactgcccgctttccagtcgggaaacctgtcgtgccagctgcattaatgaatcggccaacgcgc
ggggagaggcggtttgcgtattgggcgccagggtggttttcttttcaccagtgagacgggcaacagctgattgcccttcaccgcctg
gccctgagagagttgcagcaagcggtccacgctggtttgccccagcaggcgaaaatcctgtttgatggtggttaacggcgggatata
acatgagctgtcttcggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttatgccagccagccagacgcagacgcg
ccgagacagaacttaatgggcccgctaacagcgcgatttgctggtgacccaatgcgaccagatgctccacgcccagtcgcgtaccgt
cttcatgggagaaaataatactgttgatgggtgtctggtcagagacatcaagaaataacgccggaacattagtgcaggcagcttcca
cagcaatggcatcctggtcatccagcggatagttaatgatcagcccactgacgcgttgcgcgagaagattgtgcaccgccgctttac
aggcttcgacgccgcttcgttctaccatcgacaccaccacgctggcacccagttgatcggcgcgagatttaatcgccgcgacaatttg
cgacggcgcgtgcagggccagactggaggtggcaacgccaatcagcaacgactgtttgcccgccagttgttgtgccacgcggttgg
gaatgtaattcagctccgccatcgccgcttccacttttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcg
ctatcatgccataccgcgaaaggttttgcgccattcgatggtgtccgggatctcgacgctctcccttatgcgactcctgcattaggctca
ctataggggaattgtgagcggataacaattcccctctagagtttgacagcattGtcatcgatctcgagaaatcataaaaaatttatttg
ctttgtgagcggataacaattataatagattcaattgtgagcggataacaatttcacacagaattcattaaagaggagaaattacatA
TGAGCAAAGGAGAAGAACTTTTCACTGGAGTTGTCCCAATTCTTGTTGAATTAGATGGTGATGT
TAATGGGCACAAATTTTCTGTCCGTGGAGAGGGTGAAGGTGATGCTACAAACGGAAAACTCACC
CTTAAATTTATTTGCACTACTGGAAAACTACCTGTTCCGTGGCCAACACTTGTCACTACTCTGAC
CTatGGTGTTCAATGCTTTTCCCGTTATCCGGATCACATGAAACGGCATGACTTTTTCAAGAGTGC
CATGCCCGAAGGTTATGTACAGGAACGCACTATATCTTTCAAAGATGACGGGACCTACAAGACGC

Figure 18B

```
GTGCTGAAGTCAAGTTTGAAGGTGATACCCTTGTTAATCGTATCGAGTTAAAGGGTATTGATTT
TAAAGAAGATGGAAACATTCTTGGACACAAACTCGAGTACAACTTTAACTCACACAATGTATgaA
TCACGGCAGACAAACAAAAGAATGGAATCAAAGCTAACTTCAAAATTCGCCACAACGTTGAAGA
TGGTTCCGTTCAACTAGCAGACCATTATCAACAAAATACTCCAATTGGCGATGGCCCTGTCCTTT
TACCAGACAACCATTACCTGTCGACACAATCTGTCCTTTCGAAAGATCCCAACGAAAAGCGTGAC
CACATGGTCCTTCTTGAGTTTGTAACTGCTGCTGGGATTACACATGGCATGGATGAGCTCTACAA
AGGATCCACCACCACCACCACCACTAAaagcttaattagctgagcttggactcctgttgatagatccagtaatgacct
cagaactccatctggatttgttcagaacgctcggttgccgccgggcgttttttattggtgagaatccaagctagcttggcgCTGCAgt
gtgcttctcaaatgcctgaggccagtttgctcaggctctccccgtggaggtaataattgacgatatgatcagtgcacggctaactaag
cggcctgctgactttctcgccgatcaaaaggcattttgctattaagggattgacgagggcgTATCTgcgcagtaagatgcgccccg
catttAGGGGCGTAGTTCAATTGGTAGAGCACCGGTCTTCAAAACCGGGTGtTGGGAGTTCGAGTCT
CTCCGCCCCTGCCAAATTCGAAAAGCCTGCTCAACGAGCAGGCTTTTTTGCATGCTCGAGCAGCT
CAGGGTCGAATTTGCTTTCGAatttctgccattcatccgcttattatcacttattcaggcgtagcaaccaggcgtttaaggg
caccaataactgccttaaaaaaattacgccccgccctgccactcatcgcagtactgttgtaattcattaagcattctgccgacatggaa
gccatcacaAacggcatgatgaacctgaatcgccagcggcatcagcaccttgtcgccttgcgtataatatttgcccatggtgaaaac
gggggcgaagaagttgtccatattggccacgtttaaatcaaaactggtgaaactcacccagggattggctgagacgaaaaacatat
tctcaataaaccctttagggaaataggccaggttttcaccgtaacacgccacatcttgcgaatatatgtgtagaaactgccggaaatc
gtcgtggtattcactccagagcgatgaaaacgtttcagtttgctcatggaaaacggtgtaacaaggtgaacactatccatatcacc
agctcaccgtctttcattgccatacggaattccggatgagcattcatcaggcgggcaagaatgtgaataaaggccggataaaacttg
tgcttatttttctttacggtctttaaaaaggccgtaatatccagctgaacggtctggttataggtacattgagcaactgactgaaatgcc
tcaaaatgttcttacgatgccattgggatatatcaacggtggtatatccagtgatttttttctccattttagcttccttagctcctgaaaa
tctcgataactcaaaaaatacgcccggtagtgatcttatttcattatggtgaaagttggaacctcttacgtgccgatcaacgtctcatt
tcgccaaaagttggcccagggcttcccggtatcaacagggacaccaggatttatttattctgcgaagtgatcttccgtcacaggtattt
attcggcgcaaagtgcgtcgggtgatgctgccaacttactgatttagtgtatgatggtgttttgaggtgctccagtggcttctgtttcta
tcagctgtccctcctgttcagctactgacg
```

Figure 18B cont.

```
gggtggtgcgtaacggcaaaagcaccgccggacatcagcgctagcggagtgtatactggcttactatgttggcactgatgagggtgt
cagtgaagtgcttcatgtggcaggagaaaaaaggctgcaccggtgcgtcagcagaatatgtgatacaggatatattccgcttcctcg
ctcactgactcgctacgctcggtcgttcgactgcggcgagcggaaatggcttacgaacggggcggagatttcctggaagatgccag
gaagatacttaacagggaagtgagagggccgcggcaaagccgttttttccataggctccgccccccctgacaagcatcacgaaatctg
acgctcaaatcagtggtggcgaaacccgacaggactataaagataccaggcgtttccccctggcggctccctcgtgcgctctcctgtt
cctgcctttcggtttaccggtgtcattccgctgttatggccgcgtttgtctcattccacgcctgacactcagttccgggtaggcagttcgc
tccaagctggactgtatgcacgaacccccgttcagtccgaccgctgcgccttatccggtaactatcgtcttgagtccaacccggaaa
gacatgcaaaagcaccactggcagcagccactggtaattgatttagaggagttagtcttgaagtcatgcgccggttaaggctaaact
gaaaggacaagttttggtgactgcgctcctccaagccagttacctcggttcaaagagttggtagctcagagaaccttcgaaaaacg
ccctgcaaggcggttttttcgttttcagagcaagagattacgcgcagaccaaaacgatctcaagaagatcatcttattaatcagataa
aatatttctagatttcagtgcaatttatctcttcaaatgtagcacctgaagtcagccccatacgatataagttgtaattctcatgtttgac
agcttatcatcgataagcttgcaatttatctcttcaaatgtagcacctgaagtcagccccatacgatataagttgtaattctcatgttagt
catgccccgcgcccaccggaaggagctgactgggttgaaggctctcaagggcatcggtcgagatcccggtgcctaatgagtgagct
aacttacattaattgcgttgcgctcactgcccgctttccagtcgggaaacctgtcgtgccagctgcattaatgaatcggccaacgcgc
ggggagaggcggtttgcgtattgggcgccagggtggttttttctttcaccagtgagacgggcaacagctgattgcccttcaccgcctg
gccctgagagagttgcagcaagcggtccacgctggtttgccccagcaggcgaaaatcctgtttgatggtggttaacggcgggatata
acatgagctgtcttcggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttatgccagccagccagacgcagacgcg
```

Figure 19 ccgagacagaacttaatgggcccgctaacagcgcgatttgctggtgacccaatgcgaccagatgctccacgcccagtcgcgtaccgt
cttcatgggagaaaataatactgttgatggggtgtctggtcagagacatcaagaaataacgccggaacattagtgcaggcagcttcca
cagcaatggcatcctggtcatccagcggatagttaatgatcagcccactgacgcgttgcgcgagaagattgtgcaccgccgctttac
aggcttcgacgccgcttcgttctaccatcgacaccaccacgctggcacccagttgatcggcgcgagatttaatcgccgcgacaatttg
cgacggcgcgtgcagggccagactggaggtggcaacgccaatcagcaacgactgtttgcccgccagttgttgtgccacgcggttgg
gaatgtaattcagctccgccatcgccgcttccacttttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcg
ctatcatgccataccgcgaaaggttttgcgccattcgatggtgtccgggatctcgacgctctcccttatgcgactcctgcattaggGA
GCTGTTGACAATTAATCATCGGCTCGTATAATGTGTGGAATTGTGAGCGGATAACAATTTCACAa
AGGAggtGCggccgcatgactaagcccatcgttttttGCTggcgcacagccctcaggtgaattgaccattggtaactacatgggtg
cgctgcgtcagtgggtaaacatgcaggatgactaccattgcatttactgtatcgttgaccaacacgcgatcaccgtgcgccaggatgc
acagaagctgcgtaaagcgacgctggatacgctggccttgtatctggcttgtggtatcgatcctgagaaaagcaccattttttgttcagt
cccacgtgccggaacatgcacagttaggctgggcactgaactgctatacctacttcggcgaactgagtcgcatgacgcagtttaaag
ataaatctgcgcgttatgccgagaacatcaacgctggtctgtttgactatccggtgctgatggcagcggacatcctgctgtatcaaact
aatctgGGTCCTTGTggtgaagaccagaaacagcacctcgaactgagccgcgatattgcccagcgtttcaacgcgctgtatggc
gagatctttaaggtgccggagccgtttattccgaaatctggcgcgcgcgtaatgtcgctgctggagccgaccaagaagatgtccaag
tctgacgataatcgcaataacgttatcggcctgctggaagatccgaaatcggtagtgaagaaaatcaaacgtgcggtcactgactcc
gacgagccgcggtagttcgctacgatgtgcagaacaaagcgggcgtttccaacctgttggatatcctttcagcggtaacgggccag
agcatcccagaactggaaaaacagttcgaaggcaagatgtatggtcatctgaaaggtgaagtggctgatgccgtttccggtatgctg
actgaattgcaggaacgctatcaccgtttccgcaacgatgaagccttcctgcaacaggtgatgaaagatggcgcggaaaaagccag
cgcgcacgcttcccgtacgctaaaagcggtgtacgaagcgattggttttgtggcgaagccgtaagcGGCCGCgtttaaacggtctc
cagcttggctgttttggcggatgagagaagattttcagcctgatacagattaaatcagaacgcagaagcggtctgataaaacagaat
ttgcctggcggcagtagcgcggtggtcccacctgaccccatgccgaactcagaagtgaaacgccgtagcgccgatggtagtgtggg
gtctccccatgcgagagtagggaactgccaggcatcaaataaaacgaaaggctcagtcgaaagactgggccttgtttgtgagctcc
cggtcatcaatcatccccataatccttgttagCCTGCAgtgtgcttctcaaatgcctgaggccagtttgctcaggctctccccgtgga
ggtaataattgacgatatgatcagtgcacggctaactaagcggcctgctgactttctcgccgatcaaaaggcattttgctattaaggg
attgacgagggcgTATCTgcgcagtaagatgcgccccgcatttAGGGGCGTAGTTCAATTGGTAGAGCACCGGT
CTTCAAAACCGGGTGtTGGGAGTTCGAGTCTCTCCGCCCCTGCCAAATTCGAAAAGCCTGCTCAAC
GAGCAGGCTTTTTTGCATGctcgagcagctcagggtcgaatttgCtttcgaatttctgccattcatccgcttattatcacttat
tcaggcgtagcaaccaggcgtttaagggcaccaataactgccttaaaaaaattacgccccgccctgccactcatcgcagtactgttgt
aattcattaagcattctgccgacatggaagccatcacaAacggcatgatgaacctgaatcgccagcggcatcagcaccttgtcgcct
tgcgtataatatttgcccatggtgaaaacgggggcgaagaagttgtccatattggccacgtttaaatcaaaactggtgaaactcaccc
agggattggctgagacgaaaaacatattctcaataaacccttagggaaataggccaggttttcaccgtaacacgccacatcttgcg
aatatatgtgtagaaactgccggaaatcgtcgtggtattcactccagagcgatgaaaacgtttcagtttgctcatggaaaacggtgta
acaagggtgaacactatcccatatcaccagctcaccgtctttcattgccatacggaattccggatgagcattcatcaggcgggcaag
aatgtgaataaaggccggataaaacttgtgcttattttctttacggtctttaaaaaggccgtaatatccagctgaacggtctggttata
ggtacattgagcaactgactgaaatgcctcaaaatgttctttacgatgccattgggatatatcaacggtggtatatccagtgatttttttt
ctccatttagcttccttagctcctgaaaatctcgataactcaaaaaatacgcccggtagtgatcttatttcattatggtgaaagttgga
acctcttacgtgccgatcaacgtctcattttcgccaaaagttggcccagggcttcccggtatcaacagggacaccaggatttatttatt
ctgcgaagtgatcttccgtcacaggtatttattcggcgcaaagtgcgtcgggtgatgctgccaacttactgatttagtgtatgatggtgt
ttttgaggtgctccagtggcttctgtttctatcagctgtccctcctgttcagctactgacg

Figure 19 cont.

ATGACTAAGCCCATCGTTTTTgctGGCGCACAGCCCTCAGGTGAATTGACCATTGGTAAGTACATG
GGTGCGCTGCGTCAGTGGGTAAACATGCAGGATGACTACCATTGCATTTACTGTATCGTTGACCA
ACACGCGATCACCGTGCGCCAGGATGCACAGAAGCTGCGTAAAGCGACGCTGGATACGCTGGCCT
TGTATCTGGCTTGTGGTATCGATCCTGAGAAAAGCACCATTTTTGTTCAGTCCCACGTGCCGGAA
CATGCACAGTTAGGCTGGGCACTGAACTGCTATACCTACTTCGGCGAACTGAGTCGCATGACGCA
GTTTAAAGATAAATCTGCGCGTTATGCCGAGAACATCAACGCTGGTCTGTTTGACTATCCGGTGC
TGATGGCAGCGGACATCCTGCTGTATCAAACTAATCTGagtcctgctGGTGAAGACCAGAAACAGCA
CCTCGAACTGAGCCGCGATATTGCCCAGCGTTTCAACGCGCTGTATGGCGAGATCTTTAAGGTGC
CGGAGCCGTTTATTCCGAAATCTGGCGCGCGTAATGTCGCTGCTGGAGCCGACCAAGAAGATG
TCCAAGTCTGACGATAATCGCAATAACGTTATCGGCCTGCTGGAAGATCCGAAATCGGTAGTGA
AGAAAATCAAACGTGCGGTCACTGACTCCGACGAGCCGCCGGTAGTTCGCTACGATGTGCAGAAC
AAAGCGGGCGTTTCCAACCTGTTGGATATCCTTTCAGCGGTAACGGGCCAGAGCATCCCAGAACT
GGAAAAACAGTTCGAAGGCAAGATGTATGGTCATCTGAAAGGTGAAGTGGCTGATGCCGTTTCC
GGTATGCTGACTGAATTGCAGGAACGCTATCACCGTTTCCGCAACGATGAAGCCTTCCTGCAACA
GGTGATGAAAGATGGCGCGGAAAAAGCCAGCGCGCACGCTTCCCGTACGCTAAAAGCGGTGTACG
AAGCGATTGGTTTTGTGGCGAAGCCGTAA

Figure 20 cttttgctgagttgaaggatccGCGGCCGCtcgggttgtcagcctgtcccgcttataagatcatacgccgttatacgttgtttacgct
ttgaggaatcccaTATGatgactaagcccatcgttttagtggcgcacagccctcaggtgaattgaccattggtaactacatgggtg
cgctgcgtcagtgggtaaacatgcaggatgactaccattgcatttactgtatcgttgaccaacacgcgatcaccgtgcgccaggatgc
acagaagctgcgtaaagcgacgctggatacgctggccttgtatctggcttgtggtatcgatcctgagaaaagcaccatttttgttcagt
cccacgtgccggaacatgcacagttaggctgggcactgaactgctatacctacttcggcgaactgagtcgcatgacgcagtttaaag
ataaatctgcgcgttatgccgagaacatcaacgctggtctgtttgactatccggtgctgatggcagcggacatcctgctgtatcaaact
aatctggtaccggtgggtgaagaccagaaacagcacctcgaactgagccgcgatattgcccagcgtttcaacgcgctgtatggcga
gatctttaaggtgccggagccgtttattccgaaatctggcgcgcgcgtaatgtcgctgctggagccgaccaagaagatgtccaagtct
gacgataatcgcaataacgttatcggcctgctggaagatccgaaatcggtagtgaagaaaatcaaacgtgcggtcactgactccga
cgagccgccggtagttcgctacgatgtgcagaacaaagcgggcgtttccaacctgttggatatcctttcagcggtaacgggccagag
catcccagaactggaaaaacagttcgaaggcaagatgtatggtcatctgaaaggtgaagtggctgatgccgtttccggtatgctgac
tgaattgcaggaacgctatcaccgtttccgcaacgatgaagccttcctgcaacaggtgatgaaagatggcgcggaaaaagccagcg
cgcacgcttcccgtacgctaaaagcggtgtacgaagcgattggttttgtggcgaagccgtaaCTGCAgtttcaaacgctaaattgc
ctgatgcgctacgcttatcaggcctacatgatctctgcaatatattgagtttgcgtgcttttgtaggccggataaggcgttcacgccgca
tccggcaagaaacagcaaacaatccaaaacgccgcgttcagcggcgttttttctgcttttcttcgcgaattaattccgcttcgcacatg
tgagcaaaaggccagcaaaaggccaggaaccgtaaaaaggccgcgttgctggcgtttttccataggctccgcccccctgacgagca
tcacaaaaatcgacgctcaagtcagaggtggcgaaacccgacaggactataaagataccaggcgtttccccctggaagctccctcg
tgcgctctcctgttccgaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgaccgctgcgccttatcc
ggtaactatcgtcttgagtccaacccggtaagacacgacttatcgccactggcagcagccactggtaacaggattagcagagcgag
gtatgtaggcggtgctacagagttcttgaagtggtggcctaactacggctacactagaaggacagtatttggtatctgcgctctgctg
aagccagttaccttcggaaaaagagttggtagctcttgatccggcaaacaaaccaccgctggtagcggtggtttttttgtttgcaagc
agcagattacgcgcagaaaaaaaggatctcaagaagatcctttgatcttttctacggggtctgacgctcagtggaacgaaaactcac
gttaagggattttggtcatgaacaataaaactgtctgcttacataaacagtaatacaagggggtgttatgagccatattcaacgggaaa
cgtcttgctcgaggccgcgattaaattccaacatggatgctgatttatatgggtataaatgggctcgcgataatgtcgggcaatcagg
tgcgacaatctatcgattgtatgggaagcccgatgcgccagagttgtttctgaaacatggcaaaggtagcgttgccaatgatgttaca
gatgagatggtcagactaaactggctgacggaatttatgcctcttccgaccatcaagcatttatccgtactcctgatgatgcatggtt
actcaccactgcgatccccgggaaaacagcattccaggtattagaagaatatcctgattcaggtgaaaatattgttgatgcgctggca
gtgttcctgcgccggttgcattcgattcctgtttgtaattgtccttttaacagcgatcgcgtatttcgtctcgctcaggcgcaatcacgaa
tgaataacggtttggttgatgcgagtgattttgatgacgagcgtaatggctggcctgttgaacaagtctggaaagaaatgcataagct
tttgccattctcaccggattcagtcgtcactcatggtgatttctcacttgataaccttatttttgacgaggggaaattaataggttgtattg
atgttggacgagtcggaatcgcagaccgataccaggatcttgccatcctatggaactgcctcggtgagttttctccttcattacagaaa
cggctttttcaaaaatatggtattgataatcctgatatgaataaattgcagtttcatttgatgctcgatgagttttttctaatcagaattggt
taattggttgtaacactggcagagcattacgctgacttgacgggacggcggctttgttgaataaatcgaa

Figure 21B

Atgactaagcccatcgttttgctggcgcacagccctcaggtgaattgaccattggtaactacatgggtgcgctgcgtcagtgggtaa
acatgcaggatgactaccattgcatttactgtatcgttgaccaacacgcgatcaccgtgcgccaggatgcacagaagctgcgtaaag
cgacgctggatacgctggccttgtatctggcttgtggtatcgatcctgagaaaagcaccattttttgttcagtcccacgtgccggaacat
gcacagttaggctgggcactgaactgctatacctacttcggcgaactgagtcgcatgacgcagtttaaagataaatctgcgcgttatg
ccgagaacatcaacgctggtctgtttgactatccggtgctgatggcagcggacatcctgctgtatcaaactaatctgggtccttgtggt
gaagaccagaaacagcacctcgaactgagccgcgatattgcccagcgtttcaacgcgctgtatggcgagatctttaaggtgccgga
gccgtttattccgaaatctggcgcgcgcgtaatgtcgctgctggagccgaccaagaagatgtccaagtctgacgataatcgcaataa
cgttatcggcctgctggaagatccgaaatcggtagtgaagaaaatcaaacgtgcggtcactgactccgacgagccgccggtagttc
gctacgatgtgcagaacaaagcgggcgtttccaacctgttggatatcctttcagcggtaacgggccagagcatcccagaactggaa
aaacagttcgaaggcaagatgtatggtcatctgaaaggtgaagtggctgatgccgtttccggtatgctgactgaattgcaggaacgc
tatcaccgtttccgcaacgatgaagccttcctgcaacaggtgatgaaagatggcgcggaaaaagccagcgcgcacgcttcccgtac
gctaaaagcggtgtacgaagcgattggttttgtggcgaagccgtaa

Figure 22

ATGACTAAGCCCATCGTTTTTgctGGCGCACAGCCCTCAGGTGAATTGACCATTGGTAACTACATG
GGTGCGCTGCGTCAGTGGGTAAACATGCAGGATGACTACCATTGCATTTACTGTATCGTTGACCA
ACACGCGATCACCGTGCGCCAGGATGCACAGAAGCTGCGTAAAGCGACGCTGGATACGCTGGCCT
TGTATCTGGCTTGTGGTATCGATCCTGAGAAAAGCACCATTTTTGTTCAGTCCCACGTGCCGGAA
CATGCACAGTTAGGCTGGGCACTGAACTGCTATACCTACTTCGGCGAACTGAGTCGCATGACGCA
GTTTAAAGATAAATCTGCGCGTTATGCCGAGAACATCAACGCTGGTCTGTTTGACTATCCGGTGC
TGATGGCAGCGGACATCCTGCTGTATCAAACTAATCTGagtcctgctGGTGAAGACCAGAAACAGCA
CCTCGAACTGAGCCGCGATATTGCCCAGCGTTTCAACGCGCTGTATGGCGAGATCTTTAAGGTGC
CGGAGCCGTTTATTCCGAAATCTGGCGCGCGCGTAATGTCGCTGCTGGAGCCGACCAAGAAGATG
TCCAAGTCTGACGATAATCGCAATAACGTTATCGGCCTGCTGGAAGATCCGAAATCGGTAGTGA
AGAAAATCAAACGTGCGGTCACTGACTCCGACGAGCCGCCGGTAGTTCGCTACGATGTGCAGAAC
AAAGCGGGCGTTTCCAACCTGTTGGATATCCTTTCAGCGGTAACGGGCCAGAGCATCCCAGAACT
GGAAAAACAGTTCGAAGGCAAGATGTATGGTCATCTGAAAGGTGAAGTGGCTGATGCCGTTTCC
GGTATGCTGACTGAATTGCAGGAACGCTATCACCGTTTCCGCAACGATGAAGCCTTCCTGCAACA
GGTGATGAAAGATGGCGCGGAAAAAGCCAGCGCGCACGCTTCCCGTACGCTAAAAGCGGTGTACG
AAGCGATTGGTTTTGTGGCGAAGCCGTAA

Figure 23 ttctctgtcacagaatgaaaattttctgtcatctcttcgttattaatgtttgtaattgactgaatatcaacgcttatttgcagcctgaatg
gcgaatgggacgcgccctgtagcggcgcattaagcgcggcgggtgtggtggttacgcgcagcgtgaccgctacacttgccagcgcc
ctagcgccgctcctttcgctttcttcccttcctttctcgccacgttcgccggctttccccgtcaagctctaaatcgggggctcccttagg
gttccgatttagtgctttacggcacctcgaccccaaaaaacttgattagggtgatggttcacgtagtgggccatcgccctgatagacg
gtttttcgccctttgacgttggagtccacgttctttaatagtggactcttgttccaaactggaacaacactcaaccctatctcggtctatt
cttttgatttataagggattttgccgatttcggcctattggttaaaaaatgagctgatttaacaaaaatttaacgcgaattttaacaaaa
tattaacgtttacaatttcaggtggcacttttcggggaaatgtgcgcggaacccctatttgtttatttttctaaatacattcaaatatgtat
ccgctcatgagacaataaccctgataaatgcttcaataatattgaaaaaggaagagtatggcgtagagtattcaacatttccgtgtcg
cccttattcccttttttgcggcattttgccttcctgttttttgctcacccagaaacgctggtgaaagtaaaagatgctgaagatcagttggg
tgcacgagtgggttacatcgaactggatctcaacagcggtaagatccttgagagttttcgccccgaagaacgttttccaatgatgagc
acttttaaagttctgctatgtggcgcggtattatcccgtattgacgccgggcaagagcaactcggtcgccgcatacactattctcagaa
tgacttggttgagtactcaccagtcacagaaaagcatcttacggatggcatgacagtaagagaattatgcagtgctgccataaccat
gagtgataacactgcggccaacttacttctgacaacgatcggaggaccgaaggagctaaccgcttttttgcacaacatgggggatca
tgtaactcgccttgatcgttgggaaccggagctgaatgaagccataccaaacgacgagcgtgacaccacgatgcctgtagcaatgg
caacaacgttgcgcaaactattaactggcgaactacttactctagcttcccggcaacaattaatagactggatggaggcggataaag
ttgcaggaccacttctgcgctcggcccttccggctggctggtttattgctgataaatctggagccggtgagcgtgggtctcgcggtatc

Figure 24B attgcagcactggggccagatggtaagccctcccgtatcgtagttatctacacgacggggagtcaggcaactatggatgaacgaaat
agacagatcgctgagataggtgcctcactgattaagcattggtaactgtcagaccaagtttactcatatatactttagattgatttaaa
acttcattttaatttaaaaggatctaggtgaagatccttttttgataatctcatgaccaaaatcccttaacgtgagttttcgttccactga
gcgtcagaccccgtagaaaagatcaaaggatcttcttgagatcctttttttctgcgcgtaatctgctgcttgcaaacaaaaaaccac
cgctaccagcggtggtttgtttgccggatcaagagctaccaactcttttttccgaaggtaactggcttcagcagagcgcagataccaaa
tactgtccttctagtgtagccgtagttaggccaccacttcaagaactctgtagcaccgcctacatacctcgctctgctaatcctgttacc
agtggctgctgccagtggcgataagtcgtgtcttaccgggttggactcaagacgatagttaccggataaggcgcagcggtcgggctg
aacggggggttcgtgcacacagcccagcttggagcgaacgacctacaccgaactgagatacctacagcgtgagcattgagaaagc
gccacgcttcccgaagggagaaaggcggacaggtatccggtaagcggcagggtcggaacaggagagcgcacgagggagcttcc
agggggaaacgcctggtatctttatagtcctgtcgggtttcgccacctctgacttgagcgtcgatttttgtgatgctcgtcaggggggc
ggagcctatggaaaaacgccagcaacgcggccttttttacggttcctggccttttgctggccttttgctcacatgttctttcctgcgttatc
ccctgattctgtggataaccgtattaccgcctttgagtgagctgataccgctcgccgcagccgaacgaccgagcgcagcgagtcagt
gagcgaggaagcggaagagcgcctgatgcggtattttctccttacgcatctgtgcggtatttcacaccgcagaccagccgcgtaacc
tggcaaaatcggttacggttgagtaataaatggatgccctgcgtaagcgggtgtgggcggacaataaagtcttaaactgaacaaaa
tagatctaaactatgacaataaagtcttaaactagacagaatagttgtaaactgaaatcagtccagttatgctgtgaaaaagcatact
ggactttgttatggctaaagcaaactcttcattttctgaagtgcaaattgcccgtcgtattaaagagggggcgtggccaagggcatggt
aaagactatattcgcggcgttgtgacaatttaccgaacaactccgcggccgggaagccgatctcggcttgaacgaattgttaggtgg
cggtacttgggtcgatatcaaagtgcatcacttcttcccgtatgcccaactttgtatagagagccactgcgggatcgtcaccgtaatct
gcttgcacgtagatcacataagcaccaagcgcgttggcctcatgcttgaggagattgatgagcgcggtggcaatgccctgcctccgg
tgctcgccggagactgcgagatcatagatatagatctcactacgcggctgctcaaacctgggcagaacgtaagccgcgagagcgcc
aacaaccgcttcttggtcgaaggcagcaagcgcgatgaatgtcttactacggagcaagttcccgaggtaatcggagtccggctgatg
ttgggagtaggtggctacgtctccgaactcacgaccgaaaagatcaagagcagcccgcatggatttgacttggtcagggccgagcc
tacatgtgcgaatgatgcccatacttgagccacctaactttgttttagggcgactgccctgctgcgtaacatcgttgctgctgcgtaac
atcgttgctgctccataacatcaaacatcgacccacggcgtaacgcgcttgctgcttggatgcccgaggcatagactgtacaaaaa
acagtcataacaagccatgaaaaccgccactgcgccgttaccaccgctgcgttcggtcaaggttctggaccagttgcgtgagcgcat
acgctacttgcattacagtttacgaaccgaacaggcttatgtcaactgggttcgtgccttcatccgtttccacggtgtgcgtcacccgg
caaccttgggcagcagcgaagtcgaggcatttctgtcctggctggcgaacgagcgcaaggtttcggtctccacgcatcgtcaggcat
tggcggccttgctgttcttctacggcaaggtgctgtgcacggatctgccctggcttcaggagatcggtagacctcggccgtcgcggcg
cttgccggtggtgctgaccccggatgaagtggttcgcatcctcggttttctggaaggcgagcatcgtttgttcgcccaggactctagct
atagttctagtggttggctacgtacccgtagtggctatggcagggcttgcgcttaatgcgccgctacagggcgcgtggggataccccc
tagagccccagctggttcttccgcctcagaagccatagagccaccgcatccccagcatgcctgctattgtcttcccaatcctcccccc
ttgctgtcctgccccacccaccccccagaatagaatgacacctactcagacaatgcgatgcaatttcctcattttattaggaaagga
cagtgggagtggcaccttccagggtcaaggaaggcacggggaggggcaaacaacagatggctggcaactagaaggcacagtc
gaggctgatcagcgggtttaaacgggccctctagactcgagttaaagtcgacgcggggaggcggcccaaagggagatccgactcg
tctgagggcgaaggcgaagacgcggaagagggccgcagagccggcagcaggccgcgggaaggaaggtccgctggattgagggcc
gaagggacgtagcagaaggacgtcccgcgcagaatccaggtggcaacacaggcgagcagcaaggaaaggacgatgatttcccc
gacaacaccacggaattgtcagtgcccaacagccgagcccctgtccagcagcgggcaaggcaggcggcgatgagttccgccgtgg
caatagggaggggggaaagcgaaagtcccggaaaggagctgacaggtggtggcaatgccccaaccagtgggggttgcgtcagcaa
acacagtgcacaccacgccacgttgcctgacaacgggccacaactcctcataaagagacagcaaccaggatttatacaaggagga
gaaaatgaaagcctacgggaagcaatagcatgatacaaaggcattaaagcagcgtatccacatagcgtaaaaggagcaacata
gttaagaataccagtcaatctttcacaaattttgtaatccagaggttgattgtcgacttaacgcgttgaattcTCAATGGTGATG
GTGATGATGACCGGTATGCATATTCAGATCCTCTTCTGAGATGAGTTTTTGTTCGAAGGGCCCCT
TGTACAGCTCGTCCATGCCGAGAGTGATCCCGGCGGCGGTCACGAACTCCAGCAGGACCATGTGA
TCGCGCTTCTCGTTGGGGTCTTTGCTCAGGGCGGACTGGGTGCTCAGGTAGTGGTTGTCGGGCAG
CAGCACGGGGCCGTCGCCGATGGGGGTGTTCTGCTGGTAGTGGTCGGCGAGCTGCACGCTGCCGT
CCTCGATGTTGTGGCGGATCTTGAAGTTCACCTTGATGCCGTTCTTCTGCTTGTCGGCCATGATA

Figure 24B cont.

TAGACGTTGTGGCTGTTGTAGTTGTACTCCAGCTTGTGCCCCAGGATGTTGCCGTCCTCCTTGAA
GTCGATGCCCTTCAGCTCGATGCGGTTCACCAGGGTGTCGCCCTCGAACTTCACCTCGGCGCGGG
TCTTGTAGTTGCCGTCGTCCTTGAAGAAGATGGTGCGCTCCTGGACGTAGCCTTCGGGCATGGCG
GACTTGAAGAAGTCGTGCTGCTTCATGTGGTCGGGGTAGCGGCTGAAGCACTGCACGCCGTAgGT
CAGgGTGGTCACGAGGGTGGGCCAGGGCACGGGCAGCTTGCCGGTGGTGCAGATGAACTTCAGGG
TCAGCTTGCCctaAGTGGCATCGCCCTCGCCCTCGCCGGACACGCTGAACTTGTGGCCGTTTACGT
CGCCGTCCAGCTCGACCAGGATGGGCACCACCCCGGTGAACAGCTCCTCGCCCTTGCTCACCATgg
tggcggcGctagccagcttgggtctccctatagtgagtcgtattaatttcgataagccagtaagccagtaagcagtgggttctctagtt
agccagagagctctgcttatatagacctcccaccgtacacgcctaccgcccatttgcgtcaatggggcggagttgttacgacattttg
gaaagtcccgttgatttggtgccaaaacaaactcccattgacgtcaatggggtggagacttggaaatccccgtgagtcaaaccgct
atccacgcccattgatgtactgccaaaaccgcatcaccatggtaatagcgatgactaatacgtagatgtactgccaagtaggaaagt
cccataaggtcatgtactgggcataatgccaggcgggccatttaccgtcattgacgtcaataggggggcgtacttggcatatgatacac
ttgatgtactgccaagtgggcagtttaccgtaaatagtccacccattgacgtcaatgaaagtccctattggcgttactatgggaacat
acgtcattattgacgtcaatgggcggggggtcgttgggcggtcagccaggcgggccatttaccgtaagttatgtaacgcggaactcca
tatatgggctatgaactaatgaccccgtaattgattactattaataactagtcaataatcaatgtcaacgcgtatatctggcccgtacat
cgcgaagcagcgcaaaacGGATCCtgcaggtatttGCGGCCGCggtccgtatactccggaatattaatagatcatggagata
attaaaatgataaccatctcgcaaataaataagtattttactgttttcgtaacagttttgtaataaaaaaacctataaatattccggatt
attcataccgtcccaccatcgggcgcgAACTCCTAAAAAACCGCCACCatgaagtgccttttgtacttagccttttttattcat
tggggtgaattgcaagttcaccatagttttccacacaaccaaaaaggaaactggaaaaatgttccttctaattaccattattgcccgt
caagctcagatttaaattggcataatgacttaataggcacagccttacaagtcaaaatgcccaagagtcacaaggctattcaagcag
acggttggatgtgtcatgcttccaaatgggtcactacttgtgatttccgctggtatggaccgaagtatataacacattccatccgatcct
tcactccatctgtagaacaatgcaaggaaagcattgaacaaacgaaacaaggaacttggctgaatccaggcttccctcctcaaagtt
gtggatatgcaactgtgacggatgccgaagcagtgattgtccaggtgactcctccaccatgtgctggttgatgaatacacaggagaat
gggttgattcacagttcatcaacggaaaatgcagcaattacatatgccccactgtccataactctacaacctggcattctgactataa
ggtcaaagggctatgtgattctaacctcatttccatggacatcaccttcttctcagaggacggagagctatcatccctgggaaaggag
ggcacagggtcagaagtaactactttgcttatgaaactggaggcaaggcctgcaaaatgcaatactgcaagcattggggagtcag
actcccatcaggtgtctggttcgagatggctgataaggatctctttgctgcagccagattccctgaatgccagaagggtcaagtatct
ctgctccatctcagacctcagtggatgtaagtctaattcaggacgttgagaggatcttggattattccctctgccaagaaacctggagc
aaaatcagagcgggtcttccaatctctccagtggatctcagctatcttgctcctaaaaacccaggaaccggtcctgctttcaccataat
caatggtaccctaaaatactttgagaccagatacatcagagtcgatattgctgctccaatcctctcaagaatggtcggaatgatcagt
ggaactaccacagaaagggaactgtgggatgactgggcaccatatgaagacgtggaaattggacccaatggagttctgaggacca
gttcaggatataagtttccttatacatgattggacatggtatgttggactccgatcttcatcttagctcaaaggctcaggtgttcgaac
atcctcacattcaagacgctgcttcgcaacttcctgatgatgagagtttattttttggtgatactgggctatccaaaaatccaatcgagc
ttgtagaaggttggttcagtagttggaaaagctctattgcctctttttttctttatcatagggttaatcattggactattcttggttctccga
gttggtatccatctttgcattaaattaaagcacaccaagaaaagacagatttatacagacatagagatgaaccgacttggaaagtga
taaggccaggccggccaagcttgtcgagaagtactagaggatcataatcagccataccacatttgtagaggttttacttgctttaaaa
aacctcccacacctcccctgaacctgaaacataaaatgaatgcaattgttgttgttaacttgtttattgcagcttataatggttacaaa
taaagcaatagcatcacaaatttcacaaataaagcatttttttcactgcattctagttgtggttttgtccaaactcatcaatgtatcttatc
atgtctggatctgatcactgcttgagcCTAGGTCGGGCAGGAAGAGGGCCTATTTCCCATGATTCCTTCATA
TTTGCATATACGATACAAGGCTGTTAGAGAGATAATTAGAATTAATTTGACTGTAAACACAAAG
ATATTAGTACAAAATACGTGACGTAGAAAGTAATAATTTCTTGGGTAGTTTGCAGTTTTAAAAT
TATGTTTTAAAATGGACTATCATATGCTTACCGTAACTTGAAAGTATTTCGATTTCTTGGCTTTA
TATATCTTGTGGAAAGGACGAAACACCAGGGCGTAGTTCAATTGGTAGAGCACCGGTCTCtAAA
ACCGGGTGtTGGGAGTTCGAGTCTCTCCGCCCCTGCCATTTTTTgctaggctCAAgcagtgatctccgaacc
agataagtgaaatctagttccaaactattttgtcattttaattttcgtattagcttacgacgctacacccagttccatctatttttgtcact
cttccctaaataatccttaaaaactccatttccaccccctcccagttcccaactattttgtccgcccacagcggggcattttttcttcctgtta
tgttttaatcaaacatcctgccaactccatgtgacaaaccgtcatcttcggctactttt ttctctgtcacagaatgaaaattttctgtcatctcttcgttattaatgtttgtaattgactgaatatcaacgcttatttgcagcctgaatg
gcgaatgggacgcgccctgtagcggcgcattaagcgcggcgggtgtggtggttacgcgcagcgtgaccgctacacttgccagcgcc
ctagcgccgctcctttcgctttcttccctccttctcgccacgttcgccggctttccccgtcaagctctaaatcgggggctcccttagg
gttccgatttagtgctttacggcacctcgaccccaaaaaacttgattagggtgatggttcacgtagtgggccatcgccctgatagacg
gttttcgccctttgacgttggagtccacgttctttaatagtggactcttgttccaaactggaacaacactcaaccctatctcggtctatt
cttttgatttataagggattttgccgatttcggcctattggttaaaaaatgagctgatttaacaaaaatttaacgcgaattttaacaaaa
tattaacgtttacaatttcaggtggcacttttcggggaaatgtgcgcggaacccctatttgtttatttttctaaatacattcaaatatgtat
ccgctcatgagacaataaccctgataaatgcttcaataatattgaaaaaggaagagtatgagtattcaacatttccgtgtcgcccttat
tccctttttttgcggcattttgccttcctgtttttgctcacccagaaacgctggtgaaagtaaaagatgctgaagatcagttgggtgcacg
agtgggttacatcgaactggatctcaacagcggtaagatccttgagagttttcgccccgaagaacgttttccaatgatgagcacttta
aagttctgctatgtggcgcggtattatcccgtattgacgccgggcaagagcaactcggtcgccgcatacactattctcagaatgactt
ggttgagtactcaccagtcacagaaaagcatcttacggatggcatgacagtaagagaattatgcagtgctgccataaccatgagtga
taacactgcggccaacttacttctgacaacgatcggaggaccgaaggagctaaccgcttttttgcacaacatgggggatcatgtaac
tcgccttgatcgttgggaaccggagctgaatgaagccataccaaacgacgagcgtgacaccacgatgcctgtagcaatggcaacaa
cgttgcgcaaactattaactggcgaactacttactctagcttcccggcaacaattaatagactggatggaggcggataaagttgcag
gaccacttctgcgctcggcccttccggctggctggtttattgctgataaatctggagccggtgagcgtgggtctcgcggtatcattgca
gcactggggccagatggtaagccctcccgtatcgtagttatctacacgacggggagtcaggcaactatggatgaacgaaatagaca
gatcgctgagataggtgcctcactgattaagcattggtaactgtcagaccaagtttactcatatatactttagattgatttaaaacttca
tttttaatttaaaaggatctaggtgaagatcctttttgataatctcatgaccaaaatcccttaacgtgagttttcgttccactgagcgtca
gaccccgtagaaaagatcaaaggatcttcttgagatcctttttttctgcgcgtaatctgctgcttgcaaacaaaaaaaccaccgctacc
agcggtggtttgtttgccggatcaagagctaccaactctttttccgaaggtaactggcttcagcagagcgcagataccaaatactgtc
cttctagtgtagccgtagttaggccaccacttcaagaactctgtagcaccgcctacatacctcgctctgctaatcctgttaccagtggct
gctgccagtggcgataagtcgtgtcttaccgggttggactcaagacgatagttaccggataaggcgcagcggtcgggctgaacggg
gggttcgtgcacacagcccagcttggagcgaacgacctacaccgaactgagatacctacagcgtgagcattgagaaagcgccacg
cttcccgaagggagaaaggcggacaggtatccggtaagcggcagggtcggaacaggagagcgcacgagggagcttccaggggg

Figure 25B aaacgcctggtatctttatagtcctgtcgggtttcgccacctctgacttgagcgtcgattttttgtgatgctcgtcagggggggcggagcct
atggaaaaacgccagcaacgcggccttttttacggttcctggccttttttgctggcctttttgctcacatgttctttcctgcgttatcccctgatt
ctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcagaccagccgcgtaacctggcaaa
atcggttacggttgagtaataaatggatgccctgcgtaagcgggtgtggcggacaataaagtcttaaactgaacaaaatagatcta
aactatgacaataaagtcttaaactagacagaatagttgtaaactgaaatcagtccagttatgctgtgaaaaagcatactggacttttt
gttatggctaaagcaaactcttcatttctgaagtgcaaattgcccgtcgtattaaagaggggcgtggccaagggcatggtaaagact
atattcgcggcgttgtgacaatttaccgaacaactccgcggccgggaagccgatctcggcttgaacgaattgttaggtggcggtactt
gggtcgatatcaaagtgcatcacttcttcccgtatgcccaactttgtatagagagccactgcgggatcgtcaccgtaatctgcttgcac
gtagatcacataagcaccaagcgcgttggcctcatgcttgaggagattgatgagcgcggtggcaatgccctgcctccggtgctcgcc
ggagactgcgagatcatagatatagatctcactacgcggctgctcaaacctgggcagaacgtaagccgcgagagcgccaacaacc
gcttcttggtcgaaggcagcaagcgcgatgaatgtcttactacggagcaagttcccgaggtaatcggagtccggctgatgttgggag
taggtggctacgtctccgaactcacgaccgaaaagatcaagagcagcccgcatggatttgacttggtcagggccgagcctacatgtg
cgaatgatgcccatacttgagccacctaactttgttttagggcgactgccctgctgcgtaacatcgttgctgctgcgtaacatcgttgct
gctccataacatcaaacatcgacccacggcgtaacgcgcttgctgcttggatgcccgaggcatagactgtacaaaaaaacagtcat
aacaagccatgaaaaccgccactgcgccgttaccaccgctgcgttcggtcaaggttctggaccagttgcgtgagcgcatacgctact
tgcattacagtttacgaaccgaacaggcttatgtcaactgggttcgtgccttcatccgtttccacggtgtgcgtcaccccggcaaccttg
ggcagcagcgaagtcgaggcatttctgtcctggctggcgaacgagcgcaaggtttcggtctccacgcatcgtcaggcattggcggcc
ttgctgttcttctacggcaaggtgctgtgcacggatctgccctggcttcaggagatcggtagacctcggccgtcgcggcgcttgccggt
ggtgctgaccccggatgaagtggttcgcatcctcggttttctggaaggcgagcatcgtttgttcgcccaggactctagctatagttcta
gtggttggctacgtaccgtagtggctatggcagggcttgcgcttaatgcgccgctacagggcgcgtggggataccccctagagccc
cagctggttctttccgcctcagaagccatagagcccaccgcatcccagcatgcctgctattgtcttccaatcctccccccttgctgtcc
tgccccaccccaccccccagaatagaatgacacctactcagacaatgcgatgcaatttcctcatttattaggaaaggacagtggga
gtggcaccttccagggtcaaggaaggcacggggagggcaaacaacagatggctggcaactagaaggcacagtcgaggctgat
cagcgggtttaaacgggccctctagactcgagttaaagtcgacgcggggaggcggcccaaagggagatccgactcgtctgagggc
gaaggcgaagacgcggaagaggccgcagagccggcagcaggccgcggggaaggaaggtccgctggattgagggccgaagggac
gtagcagaaggacgtcccgcgcagaatccaggtggcaacacaggcgagcagccaaggaaaggacgatgatttccccgacaacac
cacggaattgtcagtgcccaacagccgagcccctgtccagcagcgggcaaggcaggcggcgatgagttccgccgtggcaataggg
aggggggaaagcgaaagtcccggaaaggagctgacaggtggtggcaatgccccaaccagtgggggttgcgtcagcaaacacagtg
cacaccacgccacgttgcctgacaacgggccacaactcctcataaagagacagcaaccaggatttatacaaggaggagaaaatga
aagccatacggggaagcaatagcatgatacaaaggcattaaagcagcgtatccacatagcgtaaaaggagcaacatagttaagaat
accagtcaatctttcacaaattttgtaatccagaggttgattgtcgacttaacgcgttGaattCTTACGGCTTCGCCACAAAA
CCAATCGCTTCGTACACCGCTTTTAGCGTACGGGAAGCGTGCGCGCTGGCTTTTTCCGCGCCATC
TTTCATCACCTGTTGCAGGAAGGCTTCATCGTTGCGGAAACGGTGATAGCGTTCCTGCAATTCAG
TCAGCATACCGGAAACGGCATCAGCCACTTCACCTTTCAGATGACCATACATCTTGCCTTCGAAC
TGTTTTTCCAGTTCTGGGATGCTCTGGCCCGTTACCGCTGAAAGGATATCCAACAGGTTGGAAAC
GCCCGCTTTGTTCTGCACATCGTAGCGAACTACCGGCGGCTCGTCGGAGTCAGTGACCGCACGTT
TGATTTTCTTCACTACCGATTTCGGATCTTCCAGCAGGCCGATAACGTTATTGCGATTATCGTCA
GACTTGGACATCTTCTTGGTCGGCTCCAGCAGCGACATTACGCGCGCCAGATTTCGGAATAAA
CGGCTCCGGCACCTTAAAGATCTCGCCATACAGCGCGTTGAAACGCTGGGCAATATCGCGGCTCA
GTTCGAGGTGCTGTTTCTGGTCTTCACCCACCGGTACCAGATTAGTTTGATACAGCAGGATGTCC
GCTGCCATCAGCACCGGATAGTCAAACAGACCAGCGTTGATGTTCTCGGCATAACGCGCAGATTT
ATCTTTAAACTGCGTCATGCGACTCAGTTCGCCGAAGTAGGTATAGCAGTTCAGTGCCCAGCCTA
ACTGTGCATGTTCCGGCACGTGGGACTGAACAAAAATGGTGCTTTTCTCAGGATCGATACCACAA
GCCAGATACAAGGCCAGCGTATCCAGCGTCGCTTTACGCAGCTTCTGTGCATCCTGGCGCACGGT
GATCGCGTGTTGGTCAACGATACAGTAAATGCAATGGTAGTCATCCTGCATGTTTACCCACTGAC

Figure 25B cont.

```
GCAGCGCACCCATGTAGTTACCAATGGTCAATTCACCTGAGGGCTGTGCGCCACTAAAAACGATG
GGCTTAGTCATgctagccagcttgggtctccctatagtgagtcgtattaatttcgataagccagtaagcagtgggttctctagtta
gccagagagctctgcttatatagacctcccaccgtacacgcctaccgcccatttgcgtcaatggggcggagttgttacgacattttgg
aaagtcccgttgattttggtgccaaaacaaactcccattgacgtcaatggggtggagacttggaaatcccgtgagtcaaaccgctat
ccacgcccattgatgtactgccaaaaccgcatcaccatggtaatagcgatgactaatacgtagatgtactgccaagtaggaaagtcc
cataaggtcatgtactgggcataatgccaggcgggccatttaccgtcattgacgtcaataggggcgtacttggcatatgatacactt
gatgtactgccaagtgggcagtttaccgtaaatagtccacccattgacgtcaatggaaagtcccattggcgttactatgggaacata
cgtcattattgacgtcaatgggcgggggtcgttgggcggtcagccaggcgggccatttaccgtaagttatgtaacgcggaactccat
atatgggctatgaactaatgaccccgtaattgattactattaataactagtcaataatcaatgtcaacgcgtatatctggcccgtacat
cgcgaagcagcgcaaaacGGATCCtgcaggtattTGCGGCCGCggtccgtatactccggaatattaatagatcatggagata
attaaaatgataaccatctcgcaaataaataagtattttactgttttcgtaacagttttgtaataaaaaaacctataaatattccggatt
attcataccgtcccaccatcgggcgcgAACTCCTAAAAACCGCCACCatgaagtgccttttgtacttagccttttattcat
tggggtgaattgcaagttcaccatagtttttccacacaaccaaaaaggaaactggaaaaatgttccttctaattaccattattgcccgt
caagctcagatttaaattggcataatgacttaataggcacagccttacaagtcaaaatgcccaagagtcacaaggctattcaagcag
acggttggatgtgtcatgcttccaaatgggtcactacttgtgatttccgctggtatggaccgaagtatataacacattccatccgatcct
tcactccatctgtagaacaatgcaaggaaagcattgaacaaacgaaacaaggaacttggctgaatccaggcttccctcctcaaagtt
gtggatatgcaactgtgacggatgccgaagcagtgattgtccaggtgactcctcaccatgtgctggttgatgaatacacaggagaat
gggttgattcacagttcatcaacggaaaatgcagcaattacatatgccccactgtccataactctacaacctggcattctgactataa
ggtcaaagggctatgtgattctaacctcatttccatggacatcaccttcttctcagaggacggagagctatcatccctgggaaaggag
ggcacagggttcagaagtaactactttgcttatgaaactggaggcaaggcctgcaaaatgcaatactgcaagcattgggagtcag
actccratcaggtgtctggttcgagatggctgataaggatctctttgctgcagccagattccctgaatgcccagaagggtcaagtatct
ctgctccatctcagacctcagtggatgtaagtctaattcaggacgttgagaggatcttggattattccctctgccaagaaacctggagc
aaaatcagagcgggtcttccaatctctccagtggatctcagctatcttgctcctaaaaacccaggaaccggtcctgctttcaccataat
caatggtaccctaaaatactttgagaccagatacatcagagtcgatattgctgctccaatcctctcaagaatggtcggaatgatcagt
ggaactaccacagaaagggaactgtgggatgactgggcaccatatgaagacgtggaaattggacccaatggagttctgaggacca
gttcaggatataagtttccttttatacatgattggacatggtatgttggactccgatcttcatcttagctcaaaggctcaggtgttcgaac
atcctcacattcaagacgctgcttcgcaacttcctgatgatgagagtttatttttggtgatactgggctatccaaaaatccaatcgagc
ttgtagaaggttggttcagtagttggaaaagctctattgcctcttttttctttatcataggggttaatcattggactattcttggttctccga
gttggtatccatctttgcattaaattaaagcacaccaagaaaagacagatttatacagacatagagatgaaccgacttggaaagtga
taaggccaggccggccaagcttgtcgagaagtactagaggatcataatcagccataccacatttgtagaggttttacttgctttaaaa
aacctcccacacctcccctgaacctgaaacataaaatgaatgcaattgttgttgttaacttgttattgcagcttataatggttacaaa
taaagcaatagcatcacaaatttcacaaataaagcatttttttcactgcattctagttgtggtttgtccaaactcatcaatgtatcttatc
atgtctggatctgatcactgcttgagcCTAGGTCGGGCAGGAAGAGGGCCTATTTCCCATGATTCCTTCATA
TTTGCATATACGATACAAGGCTGTTAGAGAGATAATTAGAATTAATTTGACTGTAAACACAAAG
ATATTAGTACAAAATACGTGACGTAGAAAGTAATAATTTCTTGGGTAGTTTGCAGTTTTAAAAT
TATGTTTTAAAATGGACTATCATATGCTTACCGTAACTTGAAAGTATTTCGATTTCTTGGCTTTA
TATATCTTGTGGAAAGGACGAAACACCAGGGGCGTAGTTCAATTGGTAGAGCACCGGTCTCtAAA
ACCGGGTGtTGGGAGTTCGAGTCTCTCCGCCCCTGCCATTTTTTgctagggctaggagatccgaaccagata
agtgaaatctagttccaaactatttgtcatttttaattttcgtattagcttacgacgctacacccagttcccatctatttgtcactcttcc
ctaaataatccttaaaaactccatttccaccctcccagttcccaactattttgtccgcccacagcggggcatttttcttcctgttatgttt
ttaatcaaacatcctgccaactccatgtgacaaaccgtcatcttcggctacttt
```

Figure 25B cont.

UNIVERSAL PLATFORM FOR GENETIC CODE EXPANSION

RELATED APPLICATIONS

This application is a continuation of U.S. application Ser. No. 15/609,900, filed May 31, 2017, which claims the benefit under 35 USC 119(e) of U.S. Provisional Application No. 62/345,308, filed on Jun. 3, 2016, both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 30, 2017, is named 0342_0005US1_SL.txt and is 116,984 bytes in size.

FIELD OF THE INVENTION

The present invention is directed to a universal platform for genetic code expansion.

BACKGROUND OF THE INVENTION

The ability to site-specifically incorporate unnatural amino acids (UAAs) into a protein in living cells has emerged as a powerful method to probe and manipulate its structure and function. Central to this technology is an engineered tRNA/aminoacyl-tRNA synthetase (aaRS) pair that delivers a desired UAA in response to a nonsense or frameshift codon. Such UAA-specific tRNA/aaRS pair must not cross-react with its host counterparts (i.e., orthogonal) to maintain the fidelity of translation. To ensure the absence of such cross-reactivity, candidates for the development of UAA-specific orthogonal tRNA/aaRS pairs are imported into a host cell from a different domain of life harboring evolutionarily divergent translational components. Thus, genetic code expansion of bacteria relies upon tRNA/aaRS pairs of eukaryotic or archaeal origin, and the same in eukaryotic cell generally utilizes bacterial pairs (homology of archaeal tRNA/aaRS pairs to their eukaryotic counterparts generally precludes their use in eukaryotic cells). The use of two distinct sets of tRNA/aaRS pairs for genetic code expansion in eukaryotes and bacteria has led to a significant disadvantage: each desirable UAA must be separately genetically encoded using two separate platforms.

The archaebacteria derived pyrrolysyl (Pyl) tRNA/PylRS pair is a natural TAG suppressor, and is orthogonal in both bacteria and eukaryotes owing to its unique structural features. As a result, its adaptation for genetic code expansion has created a universal platform that can be used to incorporate UAAs into proteins expressed in both E. coli and eukaryotic cells. The universal pyrrolysyl platform has been particularly beneficial for eukaryotic genetic code expansion for the following reason. Two selection systems have been developed so far to enable the generation of UAA-specific aaRS variants that use E. coli or Saccharomyces cerevisiae (yeast) as selection hosts to enable the directed evolution of eukaryotic-archaeal or bacterial tRNA/aaRS pairs, respectively. Due to its facile nature, the E. coli based selection platform has been significantly more successful for genetically encoding new UAAs relative to its yeast counterpart. The Pyl-tRNA/PylRS pair offers a unique opportunity to genetically encode new UAAs into eukaryotic cells using the facile E. coli based selection system. The advantage of this strategy is evident from the fact that all new UAAs genetically encoded in eukaryotic cells in the last six years have utilized the Pyl-tRNA/PylRS pair.

Development of additional "universal" tRNA/aaRS pairs that share these unique advantages, but provide access to new active site topologies for genetically encoding structurally distinct UAAs inaccessible to the pyrrolysyl system, would significantly augment our ability to expand and diversify the UAA tool box that can be used both in bacterial and eukaryotic cells. Access to multiple mutually orthogonal tRNA/aaRS pairs—each of which enable the incorporation of a rich set of UAAs—will also be crucial to facilitate site-specific incorporation of multiple distinct UAAs into proteins. Prolonged natural evolution has crafted the unique Pyl-tRNA/aaRS pair from a phenylalanyl ancestor—a feat challenging to replicate in the laboratory setting.

SUMMARY OF THE INVENTION

Genetic code expansion of a cell relies on an orthogonal tRNA/aminoacyl-tRNA synthetase pair that is imported into the host from a different domain of life. The current invention demonstrates the feasibility of expanding the genetic code of E. coli using its endogenous tryptophanyl-tRNA/TrpRS pair. This was made possible by first functionally replacing this endogenous pair with an E. coli-optimized counterpart from yeast, and then reintroducing the liberated E. coli-tRNATrp/TrpRS pair into the resulting strain as a nonsense suppressor, followed by its directed evolution to selectively charge several unnatural amino acids. The current invention demonstrates the ability of these engineered E. coli tRNATrp/TrpRS variants to drive efficient unnatural amino acid mutagenesis in mammalian cells. The current invention also provides a general strategy to develop "universal" tRNA/aaRS pairs that can be used for unnatural amino acid mutagenesis of proteins of interest expressed in both E. coli and eukaryotic cells. Methods and compositions are described herein for selecting and identifying orthogonal aminoacyl synthetase-tRNA pairs and their use to incorporate unnatural or atypical amino acids in a site-specific manner in a protein of interest. Specifically described is a novel E. coli tyrptophanyl RNA synthetase-tRNA pair that functions as a highly efficient opal (TGA) suppressor that incorporates tryptophan analogs into proteins.

Compositions are described herein, comprising a genetically-engineered bacterial or archeal tRNA synthetase (RS) that preferentially aminoacylates (e.g., charges), as compared to the endogenous RNA synthetase, tRNA with an unnatural amino acid. For example, described herein, is a composition comprising an E. coli tryptophanyl-tRNA synthetase (EcTrp-RS) wherein the EcTrp-RS preferentially aminoacylates an E. coli tryptophanyl tRNA (Ec-tRNA$^{Trp}$) with a tryptophan analog over the naturally-occurring tryptophan amino acid.

The tryptophanyl analog (also referred to herein as a derivative) is selected from the group consisting of: 5-azidotryptophan, 5-propargyloxytryptophan, 5-aminotryptophan, 5-methoxytryptophan, 5-O-allyltryptophan, or 5-bromotryptophan. These analogs are synthesized as described herein. Other tryptophan analogs suitable for use as described herein can be synthesized by one of skill in the art using known methods.

In particular, the current invention encompasses a composition comprising an E. coli tryptophanyl-tRNA synthetase (EcTrp-RS) wherein the EcTrp-RS comprises the amino acid sequence of E. coli published in the NCBI database for the K-12 E. coli strain (ncbi.nlm.nih.gov/ protein/BAE77907.1) as represented herein by SEQ ID NO: 91 (or a sequence having at least about 80%, about 85%, about 90%, about 95% or greater than about 95% sequence identity). The EcTrp-RS (or a homologous Trp-RS) is mutated at its active-sites to replace the serine at position 8 with alanine; the valine at position 144 is replaced with either serine, glycine or alanine; and the valine at position 146 is replaced with either alanine, isoleucine or cysteine. Polynucleotide sequences encoding this polypeptide are also encompassed herein.

Specifically encompassed by the present inventions are four EcTrp-RNA synthetases wherein the EcTrp-RS comprises the amino acid sequence SEQ ID NO: 91 wherein the EcTrp-RS is mutated (1) to replace the serine at position 8 with alanine; the valine at position 144 with serine; and the valine at position 146 with alanine; (2) wherein the EcTrp-RS comprises the amino acid sequence of SEQ ID NO: 91 wherein the EcTrp-RS is mutated to replace the serine at position 8 with alanine; the valine at position 144 glycine; and the valine at position 146 with isoleucine; (3) wherein the EcTrp-RS comprises the amino acid sequence of SEQ ID NO: 91 wherein the EcTrp-RS is mutated to replace the serine at position 8 with alanine; the valine at position 144 with alanine; and the valine at position 146 with alanine; and (4) wherein the EcTrp-RS comprises the amino acid sequence of SEQ ID NO: 91 wherein the EcTRP-RS is mutated to replace the serine at position 8 alanine; the valine at position 144 with glycine; and the valine at position 146 with cysteine.

The Trp-RNA synthetases encompassed by the present invention further include homologous bacteria-derived Trp-RNA synthetases with active-site residues substituted with mutations as described herein. Such homologous TrpRS genes can be identified by techniques known to those of skill in the art, for example by performing sequence identity/homology searches of TrpRS genetic sequence databases to identify TrpRS gene sequences with, for example, about 80% sequence identity; about 85% sequence identity; about 90% sequence identity; about 95% sequence identity or greater than about 95% sequence identity, which are substantially homologous, or highly homologous to the E. coli TrpRS described herein. A specific example of a homologous bacteria-derived TrpRS is the TrpRS from G. stearothermophilus. Such homologous Trp-RS genes suitable for use as described herein may contain sequence variation from the E. coli Trp-RS wherein such sequence variations do not affect the functionality (aminoacyl activity) of the RNA synthetase. Such nucleotide variations can also be defined as conservative sequence variations or substitutions. Also encompassed by the present invention are complementary polynucleotide sequences and polynucleotide sequences that hybridize under highly stringent conditions over substantially the entire length of the nucleotide sequence, as well as the polypeptides encoded by the polynucleotides.

The homologous bacteria-derived Trp-RS can be mutated at its active-site residues corresponding to Ser 8, Val 144 and Val 146 to, for example, replace the serine at position 8 with alanine; the valine at position 144 is replaced with either serine, glycine or alanine; and the valine at position 146 is replaced with either alanine, isoleucine or cysteine as described herein for the E. coli Trp-RS.

The present invention further encompasses tRNA compositions wherein the tRNA anti-codon loop is modified (e.g., mutated) to specifically bind to (e.g., recognize) an amber (UAG/TAG) or opal (UGA/TGA). In particular, the present invention encompasses compositions wherein the tRNA is the E. coli tyrptophanyl tRNA, or another homologous bacteria-derived tRNA, wherein the polynucleotide sequence comprises SEQ ID NO: 1 or SEQ ID NO: 3 (or with about 80%; about 85%; about 90%, about 95% or greater than about 95% sequence identity) with an anti-codon loop comprising a sequence that specifically binds to a selector sequence of an mRNA selected from the group consisting of an amber codon or an opal codon. Importantly, the tRNA EcTrp UCA described herein is a novel opal suppressor suitable for use in both genetically-engineered bacteria and eukaryotes.

It is important to note that the modified tRNA of E. coli, or a homologous bacteria-derived tRNA, can be combined with an RNA synthetase of another homologous bacteria-derived RNA synthetase to produce novel combinations for unnatural amino acid, e.g., tryptophan analog, incorporation into proteins. Additionally, a combination of two distinct Trp-RS/tRNA pairs can be combined. For example, the EcTrp-RS/tRNA pair described herein, as an opal (TGA) suppressor, can also be combined with other suitable tRNA/RS pairs (e.g., pyrrolysine which is an amber (TAG) suppressor, to site-specifically incorporate two distinct unnatural amino acids into polypeptide/proteins expressed in eukaryotic cells.

Also encompassed by the present invention are cells (either cultured in vitro or in vivo) comprising an orthogonal E. coli tryptophanyl tRNA synthetase (EcTrp-RS), wherein the EcTrp-RS preferentially aminoacylates an E. coli tryptophanyl tRNA with a tryptophan analog, and an orthogonal E. coli tryptophanyl tRNA (Ec-tRNA$^{Trp}$) as a pair. Importantly, the orthogonal TrpRS/tRNA pair) does not cross-react the cell's endogenous TrpRS/tRNA pair. Such cells comprise not only the RS/tRNA pairs described herein, but also all cellular components required for translation of polynucleotides into proteins, including translation system components such as, for example, ribosomes, endogenous tRNAs, translation enzymes, mRNA and amino acids.

The cells of the present invention can be any bacterial cell or eukaryotic cell suitable for use with the RNA synthetase/tRNA pairs described herein. In particular, the cell can be a mammalian cell. In particular, the bacterial cell is a genetically-engineered E. coli cell, or a homologous/analogous bacterial cell. More specifically, the E. coli is the ATMW1 or BL21(DE3) strain of E. coli cell.

Also encompassed by the present invention are methods of producing a polypeptide/protein in a cell with one, or more, unnatural amino acids incorporated into the polypeptide/protein in a site-specific manner by one, or more of the RS/tRNA pairs described herein. Such proteins can be labeled or chemically modified for further post-translational site-specific modifications.

Specifically encompassed by the present invention is a method of incorporating tryptophan analogs at specified positions in a protein of interest expressed in the cell, the method comprising culturing the cell in a culture medium under conditions suitable for growth, wherein the cell comprises a nucleic acid that encodes a protein with one, or more, amber or opal selector codons, wherein the cell further comprises an Ec-tRNA$^{Trp}$ that recognizes the selector codon(s), and wherein the cell further comprises an EcTrp-RS that preferentially aminoacylates the Ec-tRNA$^{Trp}$ with a tryptophan analog. The cell culture medium containing the growing cells is then contacted with one, or more, tryptophan analogs under conditions suitable for incorporation of the one, or more, tryptophan analogs into the protein in response to the selector codon(s), thereby producing the protein with one, or more tryptophan analogs. The method specifically encompasses the use of the EcTrp-RS and the Ec-tRNA$^{Trp}$ pair described herein. Such tryptophan analogs can be selected from the group consisting of: 5-azidotryptophan, 5-propargyloxytryptophan, 5-aminotryptophan, 5-methoxytryptophan, 5-O-allyltryptophan, or 5-bromotryptophan, or other suitable tryptophan analogs.

Also encompassed by the present invention are methods of incorporating two, or more unnatural amino acids at specified positions in a polypeptide/protein expressed in a cell. In these methods the cell further comprises a second tRNA/RS pair that is orthogonal to the cell, wherein the second pair recognizes an amber selector codon in the protein, but does not cross-react with the first RS/tRNA pair (e.g., EcTrp-RS/tRNA$^{Trp}$). The method is performed as above (or in a similar manner) wherein the protein expressed/produced contains one, or more tryptophan analogs and one, or more, distinct unnatural amino acid other than a tryptophan analog incorporated by the first RS/tRNA pair.

Further encompassed by the present invention are kits for producing a protein in a cell, wherein the protein comprises one, or more tryptophan analogs, the kit comprising a container containing a polynucleotide sequence encoding an Ec-tRNA$^{Trp}$ that recognizes an amber or opal selector codon(s) in a nucleic acid of interest in the cell and a container containing an EcTrp-RS that preferentially aminoacylates the Ec-tRNA$^{Trp}$ with a tryptophan analog. Such kits can further comprise one, or more, tryptophan analogs, or other components required for cellular translation such as buffers and/or culture media. The kits can further include instructions for using the components and producing the desired protein.

The present invention encompasses a genetically engineered E. coli bacterial strain having the genotype EcNR1 pUltraG-ScW40CCA trpS::ZeoR trpT::GentR ΔgalK λRED::galK. Procedures for producing such genetically-engineered bacteria are described herein, specifically for the ATMW1 bacterial strain. Also encompassed by the present invention are homologous bacterial strains where analogous genetic modifications are made to the bacteria resulting in a bacterial strain with substantially similar functionality as ATMW1, e.g., as a host for protein expression. Methods described herein for producing ATMW1 are suitable for use in producing homologous genetically-engineered bacteria with essentially the same genotype with substantially similar, or better functionality as ATMW1. In particular, the genetically engineered E. coli strains ATMW1 or BL21 (DE3) are encompassed by the present invention.

The present invention also encompasses methods of producing orthogonal aminoacyl synthetase-tRNA pairs for incorporating unnatural amino acids into specific sites in proteins (e.g., expanding the genetic code) expressed/produced in E. coli and mammalian cells. The methods include the first step of functionally replacing an endogenous aminoacyl synthetase-tRNA pair in an E. coli host cell with a counter-part aminoacyl synthetase-tRNA pair orthogonal to E. coli and mammalian cells, resulting in an altered translational machinery (ATM) E. coli and liberating the endogenous E. coli aminoacyl synthetase-tRNA pair, wherein the liberated E. coli aminoacyl synthetase-tRNA pair is orthogonal to the ATM E. coli and mammalian cells.

The next step is reintroducing the liberated E. coli aminoacyl synthetase-tRNA pair into the ATM E. coli cell as a nonsense suppressor under conditions suitable for genetically selecting and identifying a variant E. coli aminoacyl synthetase that preferentially aminoacylates a tRNA with an unnatural amino acid over a natural amino acid. These steps result in producing an orthogonal aminoacyl synthetase-tRNA pair for incorporating unnatural amino acids into specific sites in proteins produced in E. coli and mammalian cells. The genetically-engineered ATM E. coli can be either ATMW1 or BL21(DE3).

The current invention is the first tryptophanyl tRNA/tryptophanyl-tRNA synthetase platform that enables genetic incorporation of tryptophan analogs in eukaryotic cells (i.e., mammalian cells). The same engineered tryptophanyl tRNA/tryptophanyl-tRNA synthetase pair enables incorporation of the aforementioned Trp analogs into proteins expressed in E. coli (engineered) and eukaryotic cells.

As described herein, an E. coli cell has been developed where the endogenous tryptophanyl tRNA/tryptophanyl-tRNA synthetase was functionally replaced with a counterpart from yeast. This enables the use of the liberated E. coli tryptophanyl tRNA/tryptophanyl-tRNA synthetase pair to drive the incorporation of unnatural amino acids in response to the TGA (opal) nonsense codon.

Also as described herein is the first reported incorporation of 5-azidotryptophan, 5-propargyltryptophan, 5-aminotryptophan, 5-methoxytryptophan, 5-allyltryptophan, and 5-bromotryptophan using engineered tryptophanyl tRNA/tryptophanyl-tRNA synthetase pairs derived from E. coli.

The current invention demonstrates features and advantages that will become apparent to one of ordinary skill in the art upon reading the attached Detailed Description.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. The patent or application file contains at least one drawing executed in color. Copies of this patent or patent application publication with color drawings(s) will be provided by the Office upon request and payment of the necessary fee. Of the drawings:

FIG. 2A-B shows (A) depiction of ATMW1 recombination containing Ec-TrpRS replaced with ZeoR, Ec-Trp tRNA replaced with GentR, and complementation plasmid pUltraG ScW40 CCA. (B) Growth rate comparison of ATMW1 to progenitor EcNR1 strain containing pUltraG.

FIG. 11A-D shows (A) EGFP39*-fluorescence images of EcWRS-h14 and (B) -h9 transfected HEK293T, as previously described. (C) SDS-PAGE of purified EGFP39* containing an UAA incorporated through the pacbac system expressing h14, h9, or the Pyl system. (D) Yields of aforementioned purified EGFP39*.

FIG. 12A-C show the sequences (SEQ ID NOS:75, 76 and 77 respectively) that are the ds DNA PCR products that were electroporated for recombination. Primers are listed in MM and primer list. Important features are mentioned prior to the sequence with color code in parenthesis.

FIG. 13A-B. FIG. 13A shows the plasmid map and FIG. 13B shows the plasmid sequence (SEQ ID NO: 78) for pUltra_ScW40$_{CCA}$. GFP is highlighted in green, CAT/Barnase is orange, T7 RNA polymerase in purple, tRNA in red and aaRS in blue unless otherwise specified.

FIG. 14A-B. FIG. 14A shows the plasmid map and FIG. 14B shows the plasmid sequence (SEQ ID NO: 79) for pRepAC-EcWtR-TAG.

FIG. 15A-B. FIG. 15A shows the plasmid map and FIG. 15B shows the plasmid sequence (SEQ ID NO:80) of pRep-Cm3J-98TGA-EcWtR.

FIG. 16A-B. FIG. 16A shows the plasmid map and FIG. 16B shows the plasmid sequence (SEQ ID NO:81) of pRepJI-EcW.

FIG. 17A-B. FIG. 17A shows the plasmid map and FIG. 17B shows the plasmid sequence (SEQ ID NO: 82) of pEvolT5-EcW-sfGFP151TAG.

FIG. 18A-B. FIG. 18A shows the plasmid map and FIG. 18B shows the sequence (SEQ ID NO:83) of pEvolT5-EcW-sfGFP151TAG.

FIG. 19 shows the plasmid sequence (SEQ ID NO: 84) of pEvoltac-EcW-TGA-h14.

FIG. 20 shows the plasmid sequence (SEQ ID NO: 85) of the plasmid pEvoltac-EcW-TGA-h9. The sequence is identical to pEvoltac-EcW-TGA-h14 except for the V144-146 region. The h9 aaRS is listed with mutations in blue.

FIG. 21A-B. FIG. 21A shows the plasmid map and FIG. 21B shows the plasmid sequence (SEQ ID NO: 86) of pBK-EcWRS.

FIG. 22 shows the sequence (SEQ ID NO:87) of pBK-EcWRS-h14. The pBK sequence is the same as with EcWRS-h14 with mutations shown in blue.

FIG. 23 shows the sequence of pBK-EcWRS h-9 (SEQ ID NO:88). The pBK sequence is the same as with EcWRS-h9 with mutations shown in blue.

FIG. 24A-B. FIG. 24A shows the plasmid map and FIG. 24B shows the plasmid sequence (SEQ ID NO:89) of pAcBac1-EGFP39*-U6-EcWtR-TAG.

FIG. 25A-B. FIG. 25A shows the plasmid map and FIG. 25B shows the sequence (SEQ ID NO:90) of pAcBac1-TrpRS-U6EcWtR-TAG.

DETAILED DESCRIPTION OF THE PREFERRED EMBODIMENTS

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof.

Figure 1:
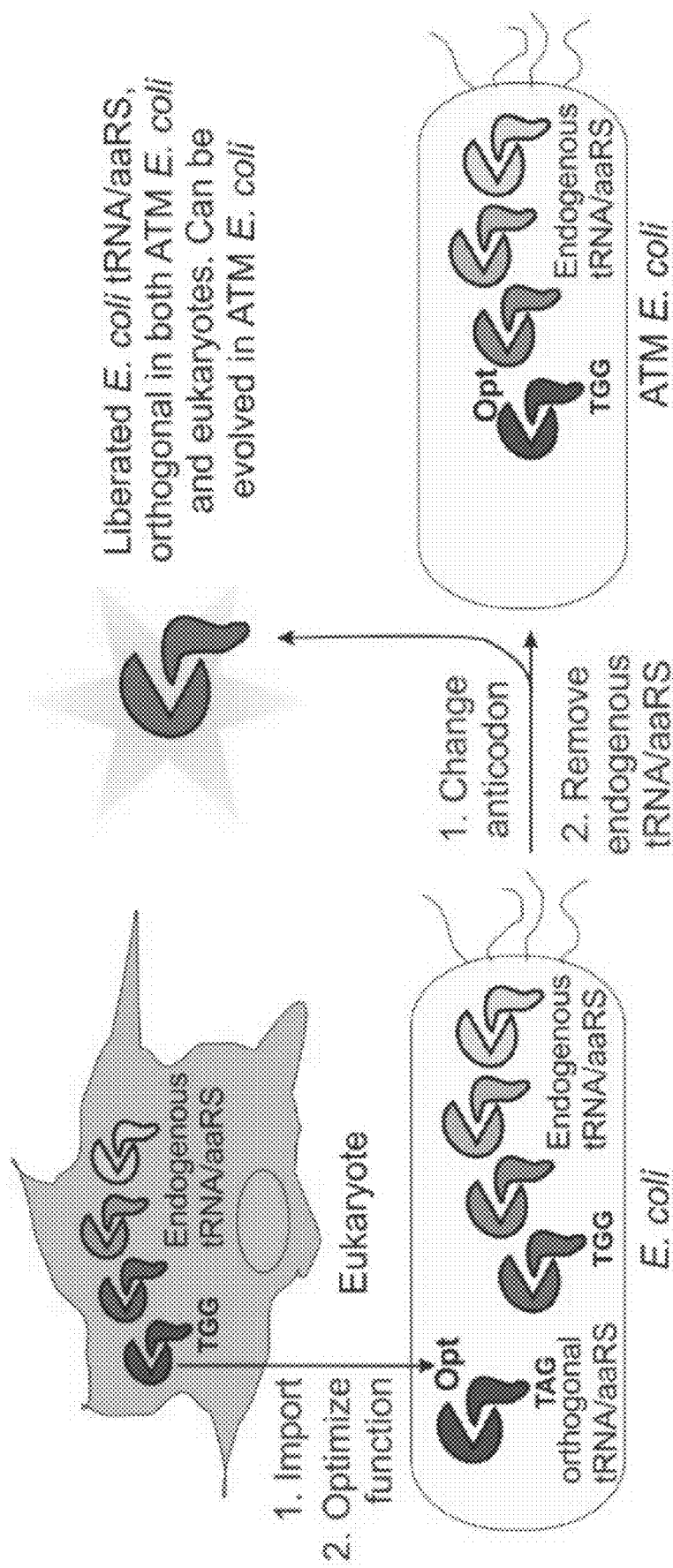
FIG. 1 shows an overview of the general strategy to create ATM E. coli strains.

The present disclosure provides a universal platform for genetic code expansion and involves a bacterial tryptophanyl-tRNA/tryptophanyl-tRNA synthetase pair for site-specific incorporation of tryptophan analogs into proteins expressed in E. coli and eukaryotic cells. The current invention discloses an alternative strategy which takes advantage of an E. coli strain, where one of its native tRNA/aaRS pairs is functionally replaced with a eukaryotic/archaeal counterpart (FIG. 1). The "liberated" tRNA/aaRS pair can then be reintroduced in the resulting "altered translational machinery (ATM)" *E. coli* as a nonsense suppressor, and can be evolved to charge desirable UAAs. Owing to its bacterial origin, the same pair can also be directly used for eukaryotic genetic code expansion.

The feasibility of substituting a tRNA/aaRS pair in *E. coli* with an evolutionarily distant counterpart has previously been demonstrated. However, the resulting strains often exhibit growth defect, presumably due to the suboptimal interaction of the heterologous tRNA/aaRS with the translational apparatus of *E. coli*. Moreover, whether variants of the liberated tRNA/aaRS pair with altered substrate specificity can be developed using the corresponding ATM strain as the selection host remains unknown. Optimizing the performance of the substituting tRNA/aaRS pair in *E. coli* using directed evolution may allow it to functionally replace its endogenous counterpart more efficiently, circumventing the growth defect associated with such substitution. A number of heterologous tRNA/aaRS pairs have already been engineered for efficient suppression of nonsense codons in *E. coli*, providing a pool of potential candidates.

Figure 6:
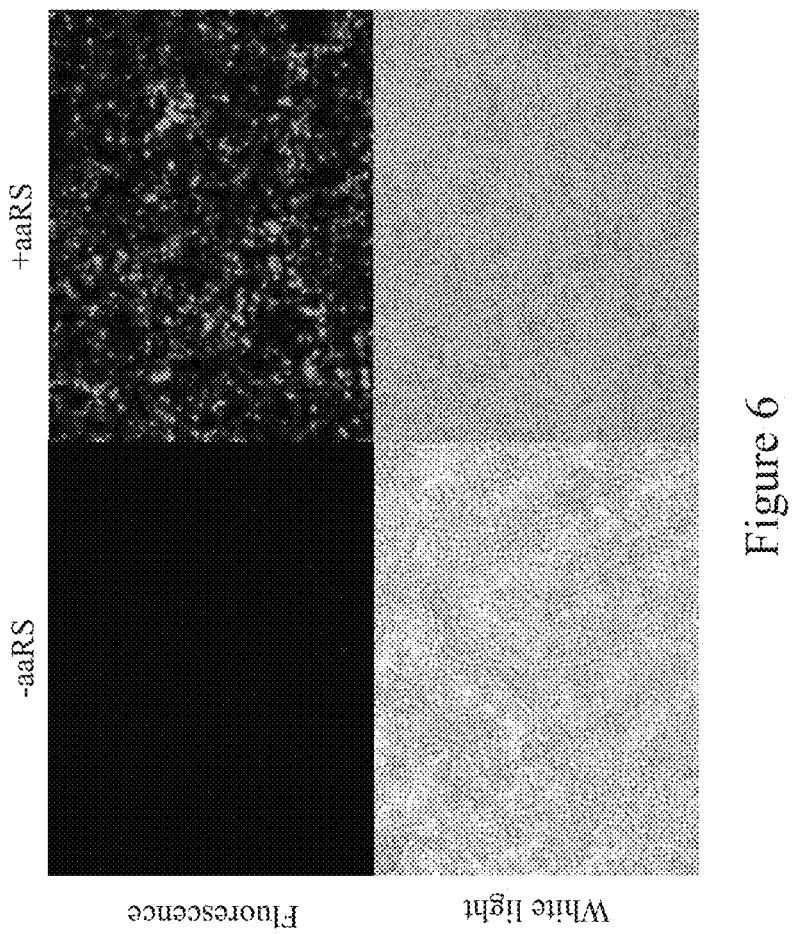
FIG. 6 shows EGFP39*-fluorescence and white light images demonstrating E. coli tRNATrpCUA orthogonality and Trp-aaRS activity in HEK293T, imaged 24 hrs post-transfection with PEI-Max. pAcBac1 system previously described was used, with or without cognate aaRS.

The endogenous tryptophanyl (Trp)-tRNA/aaRS pair in *E. coli* was targeted for functional replacement with a eukaryotic/archaeal counterpart. A *S. cerevisiae* derived tryptophanyl-tRNA/TrpRS pair has already been optimized in *E. coli* for highly efficient nonsense suppression, providing a great candidate for substituting its endogenous counterpart. Additionally, the unique active site of TrpRS should enable the introduction of structurally novel UAAs in the eukaryotic, as well as the bacterial genetic code. To verify if the *E. coli* Trp-tRNA/aaRS pair is indeed suitable for eukaryotic genetic code expansion, HEK293T cells were co-expressed with the TAG-suppressing *E. coli* Trp-tRNA (tRNAEcTrpCUA) and an enhanced green fluorescent protein (EGFP) reporter harboring a stop codon at a permissive site (EGFP-39-TAG), with or without the cognate synthetase. Robust EGFP expression was only observed in the presence of the EcTrpRS (FIG. 6), suggesting that: 1) EcTrpRS/tRNAEcTrpCUA is capable of efficient TAG-suppression in eukaryotic cells, and 2) the pair is non-cross-reactive with its eukaryotic counterparts.

Figures 7A, 7B:
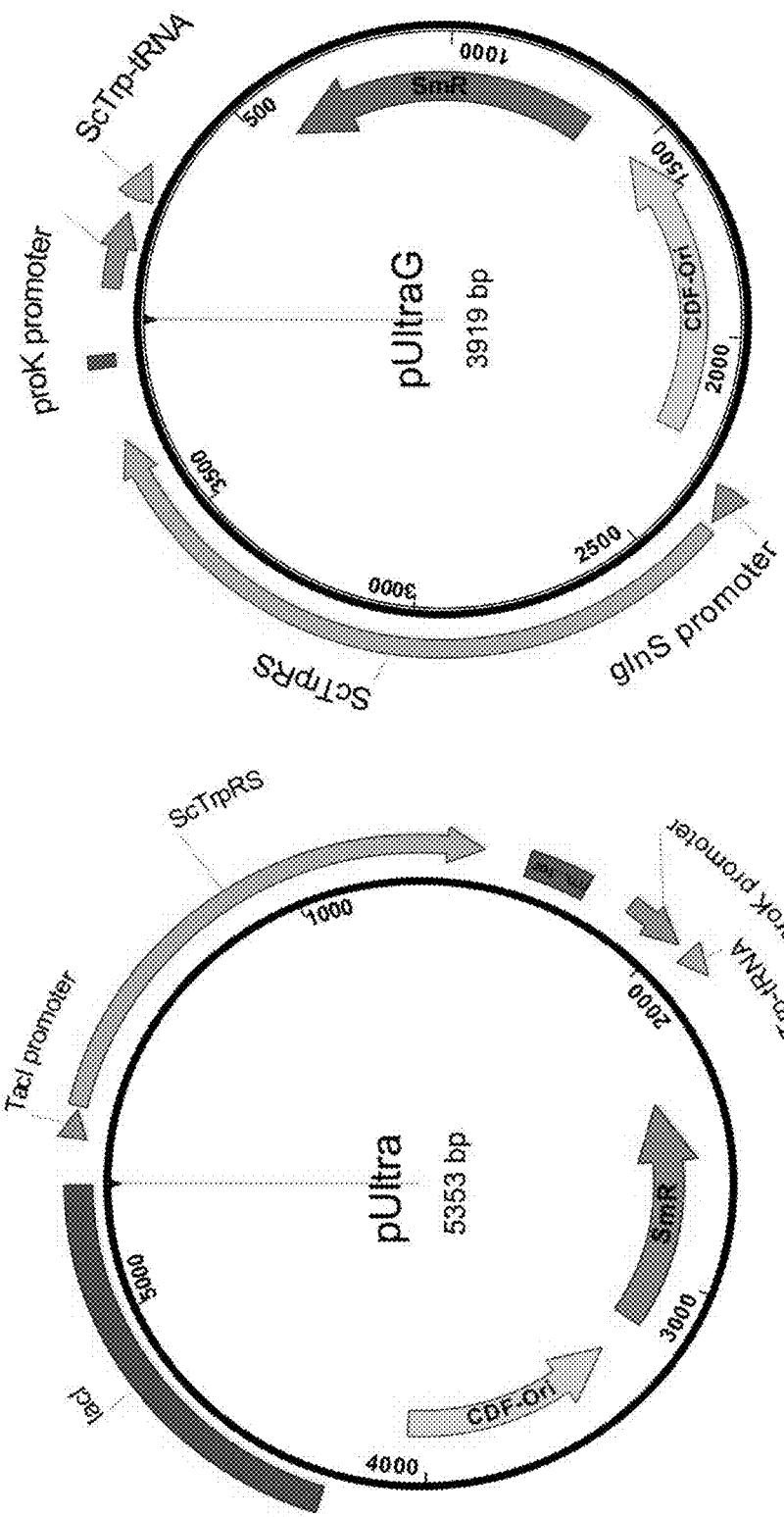
FIG. 7A-B shows the plasmid maps used to complement endogenous E. coli Trp-tRNA/aaRS removal. pUltraG ScW40 CCA contains a glnS' promoted wild-type E. coli TrpRS, prok promoted E. coli Trp-tRNA, CloDF13 origin of replication, and Spectinomycin resistance. pUltra is as previously reported.
Figure 8A:
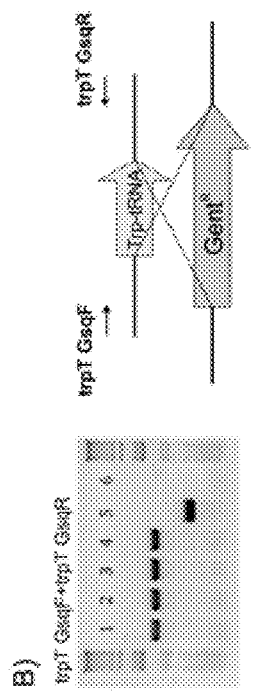
FIG. 8A-D shows Colony PCR assay for genomic recombination. (A) Ec-TrpRS replaced with zeoR screen. Left: Primers anneal 150 bp upstream and downstream from trpS location (Zeocin ~200 bp smaller than Ec-TrpRS). Middle: Forward primer anneals 150 bp upstream and an internal reverse primer anneals only to trpS. Right: Primers anneal directly to the N and C terminus of trpS. Lanes 1-6 are potential hits, lane 7 is EcNR1, and lane 8 is PBS. (B) Ec-Trp tRNA replaced with gentR screen. Primers anneal 150 bp upstream and downstream from the trpT genomic location. Successful hits will have a larger PCR product due to the increased gentamycin cassette. Lanes 1-4 are potential hits, lane 5 is EcNR1 pUG ScW40 trpS::zeoR prior to recombination, and lane 6 is PBS. (C) galK deletion screen: Primers anneal 150 bp upstream and downstream from the galK endogenous location. Successful hits will have a larger PCR product due to the increased gentamycin cassette. Lanes 1-8 are potential hits, lane 9 is EcNR1, lane 10 is C321, and lane 11 is PBS. (D) Genomic λ-Red replaced with galK screen—ATMW1. A: Forward primer anneals 150 bp upstream from the prophage and the reverse primer anneals only to galK. B: Primers anneal 150 bp upstream and downstream from the galK endogenous location. 1-4 are final ATMW1 hits, 5 is EcNR1, 6 is Top 10, and 7 is PBS. Associated primer maps are depicted with each screen.
Figure 8B:
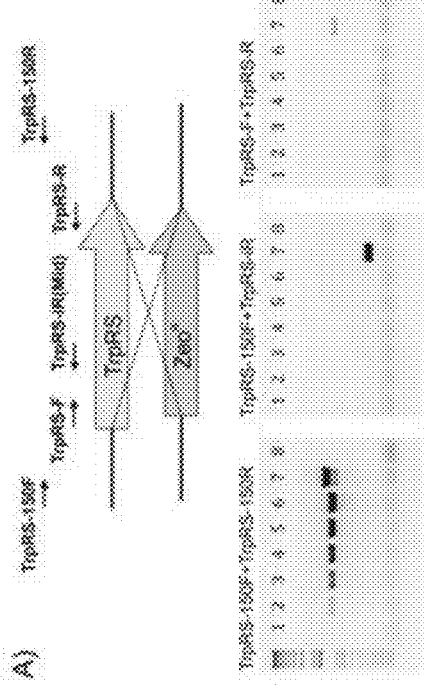
Figure 8C:
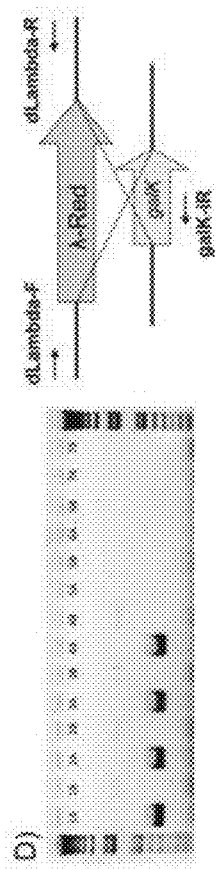
Figure 8D:
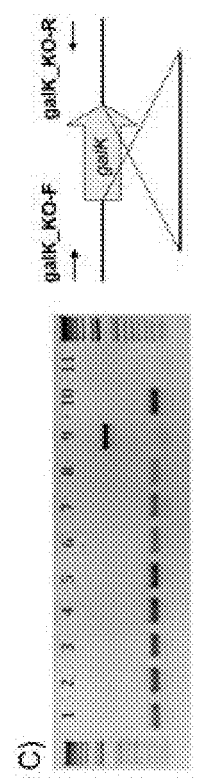

To allow the deletion of the endogenous tryptophanyl pair from the *E. coli* genome, a plasmid (pUltra-ScW40CCA) was first generated expressing the aforementioned engineered ScTrpRS/tRNAScTrpCCA pair derived from yeast (FIG. 7). It harbors a unique CloDF13 origin of replication to maintain compatibility with most commonly used plasmids. The K12-derived EcNR1 strain of *E. coli*, encoding a heat-inducible λ-Red recombination system, was used as the host. Attempts at replacing the trpS (encoding EcTrpRS) and trpT (encoding Trp-tRNA) genes from the EcNR1 genome using a zeocin and gentamycin selectable markers (FIG. 2A), respectively, were successful in the presence of the pUltra-ScW40CCA complementation plasmid (FIG. 8). Finally, the λ-prophage encoding the Red-recombination system was removed from the genome using a galactose-selectable galK marker, to provide a strain named ATMW1, with the following genotype: EcNR1 pUltraG-ScW40CCA trpS::ZeoR trpT::GentR ΔgalK λRED::galK. The *E.coli* ATMW1strain was deposited with the American Type Culture Collection (ATCC®), 10801 University Boulevard, Manassas, Virginia 20110-2209, USA, on May 23, 2022 and designated with Patent Deposit Number PTA-127317 in accordance with the requirements of the Budapest Treaty on the Internationals Recognition of the Deposit of Microorganisms for the Purposes of Patent Procedure. The ATMW1 strain exhibited no observable growth defect when compared to its progenitor EcNR1, confirming efficient functional complementation by the engineered ScTrpRS/tRNA-ScTrpCCA pair (FIG. 2B).

Figure 9A:
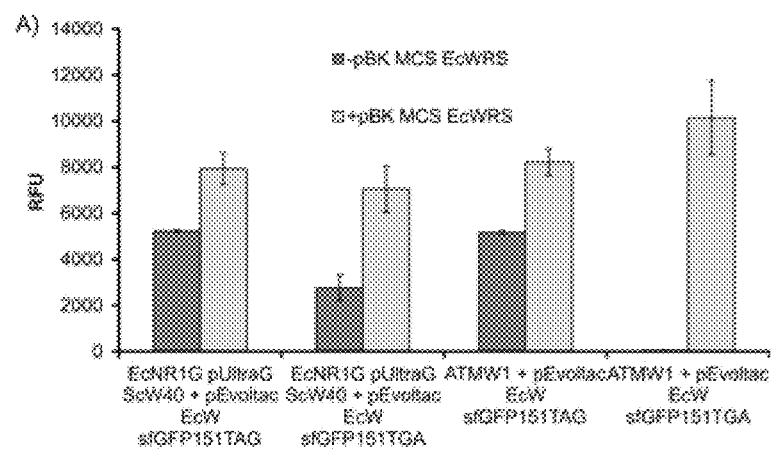
FIG. 9A-C shows (A) cross reactivity comparison with tRNAEcTrp CUA vs UCA via sfGFP151 assay. Strains were transformed with pEvolT5 EcW sfGFP151TAG or TGA, grown to 0.5 OD600 and induced with 1 mM IPTG. Fluorescence/OD600 was measured in a plate reader (488 ex, 534 em, 515CO). (B) LCMS of ATMW1 purified sfGFP151TAG+pBK MCS EcWRS (C) LCMS of ATMW1 purified sfGFP151TAG+pBK MCS EcWRS.
Figures 9B, 9C:
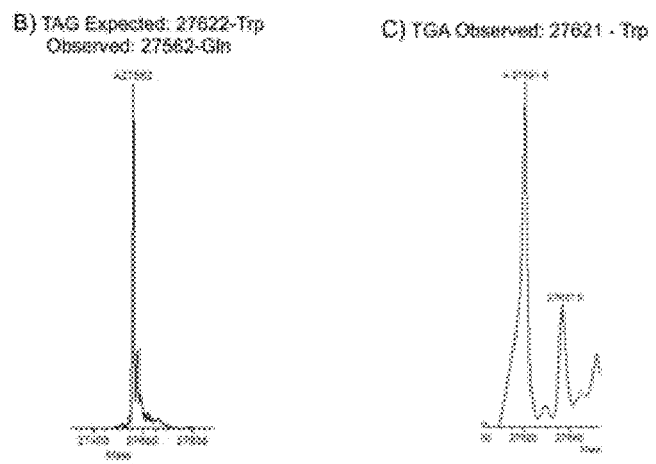
Figures 10A, 10B:
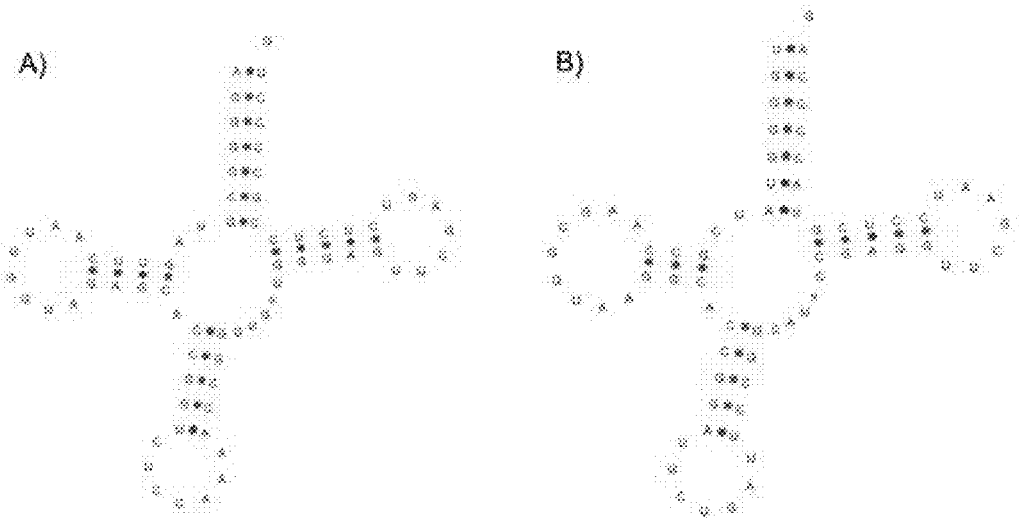
FIG. 10A-C show predicted (A) EcTrp-tRNACCA (trpT) SEQ ID NO: 1 and (B) EcGln-tRNACUG (glnV) structures SEQ ID NO:2. (C) shows the respective DNA sequences and homology alignment of tRNA sequences SEQ ID NOS:3-5.
Figure 10C:
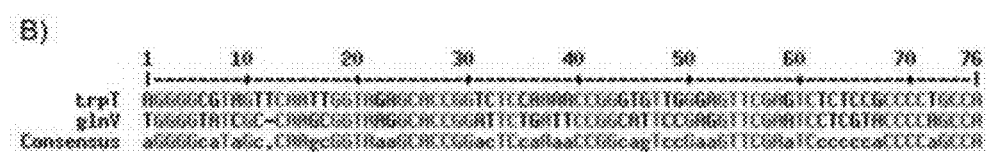
Figure 13A:
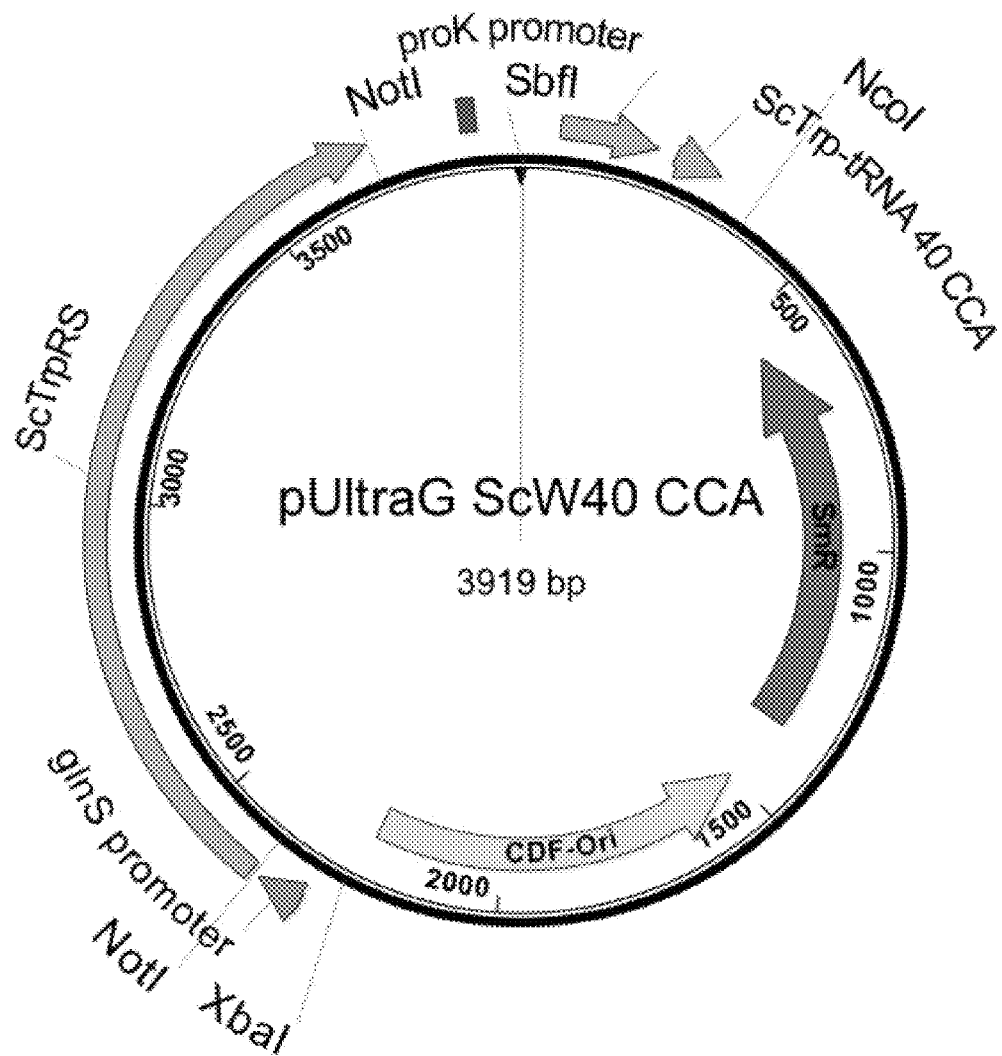
Figure 14A:
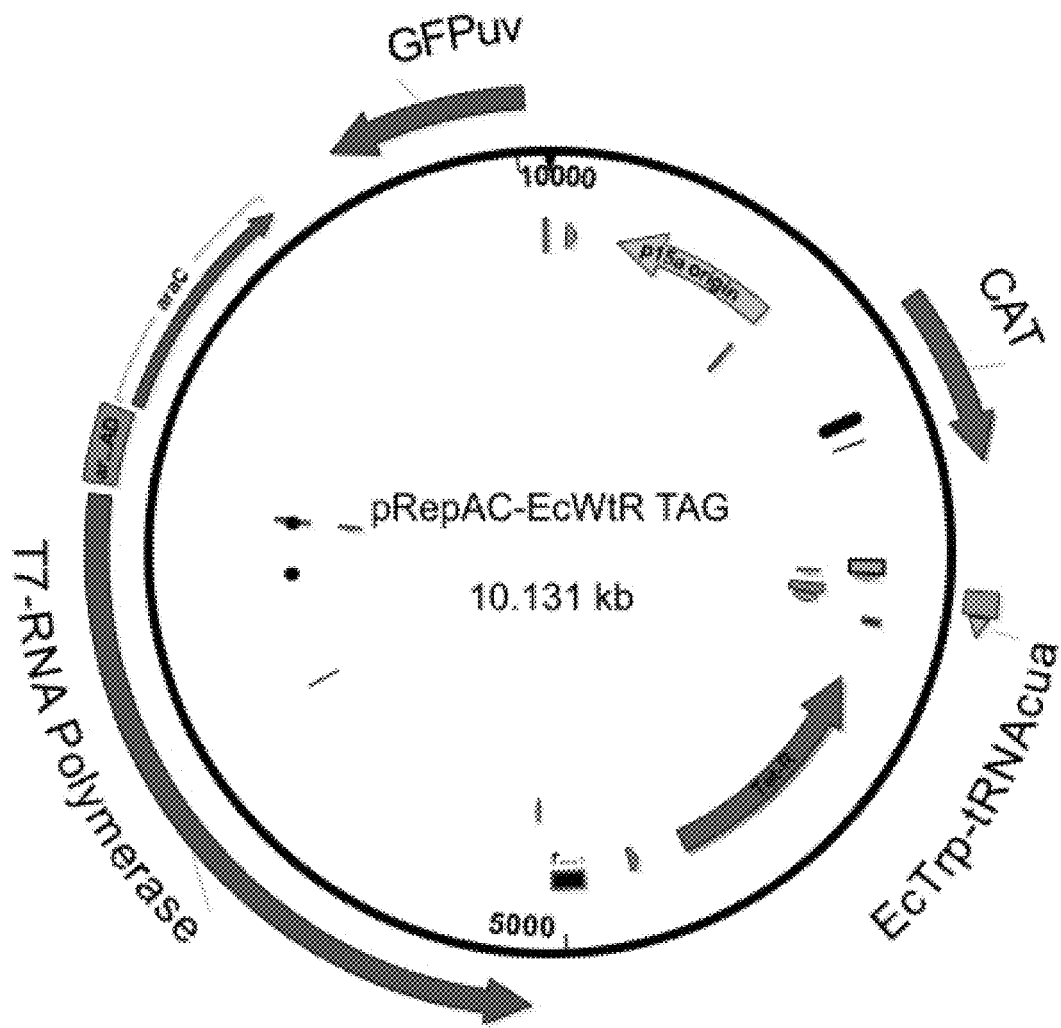
Figure 15A:
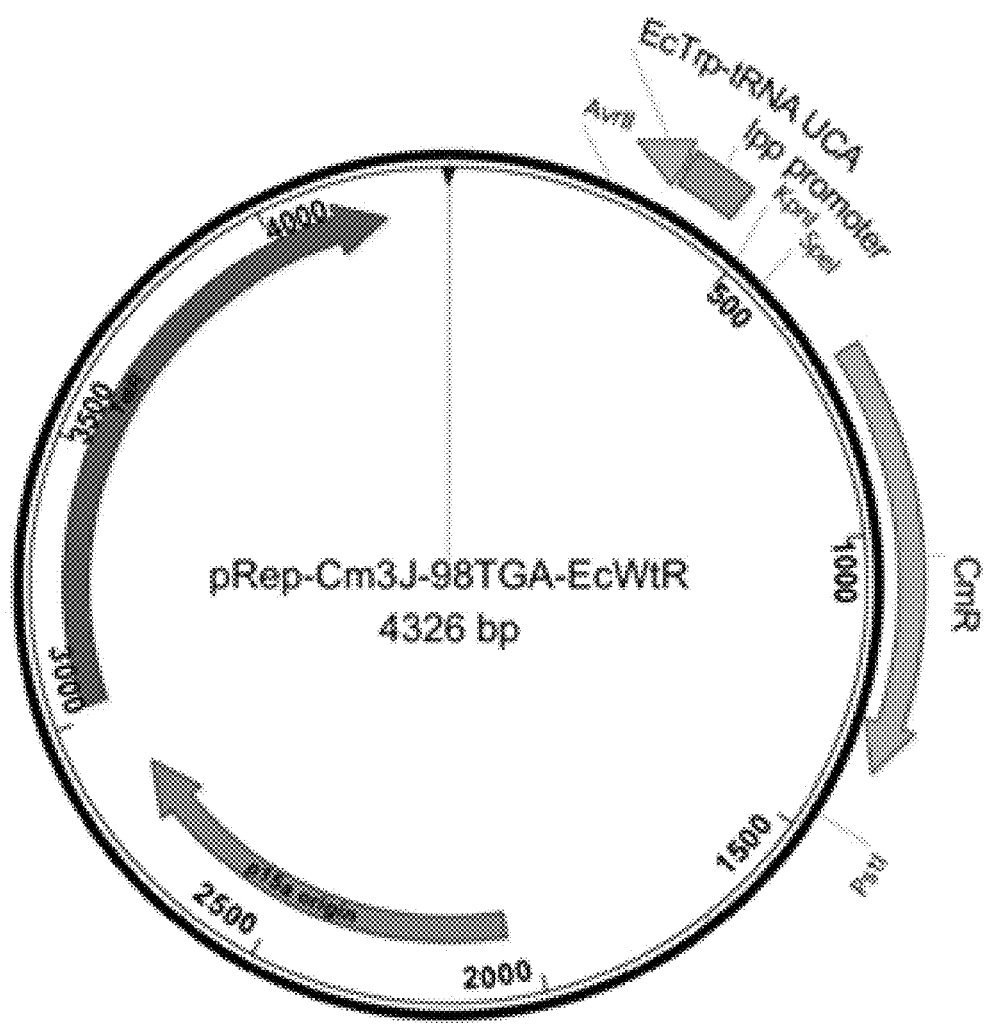
Figure 16A:
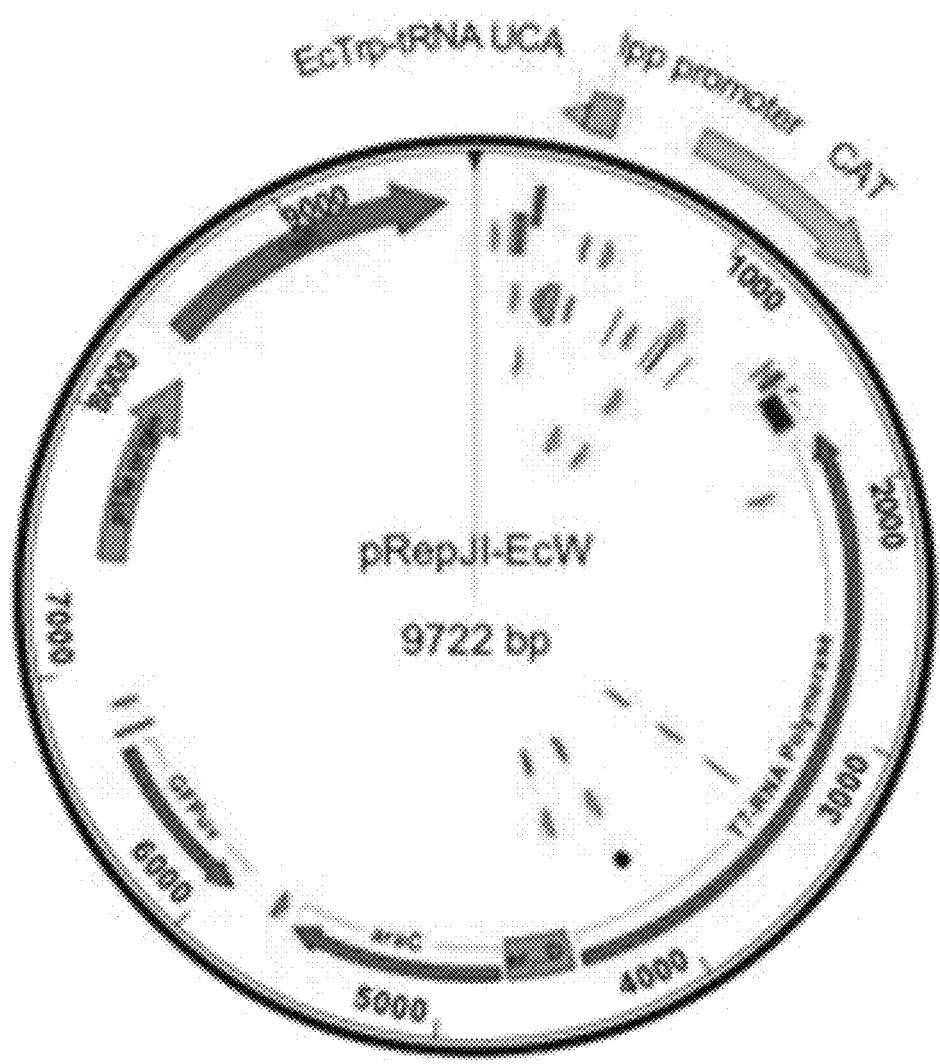
Figure 17A:
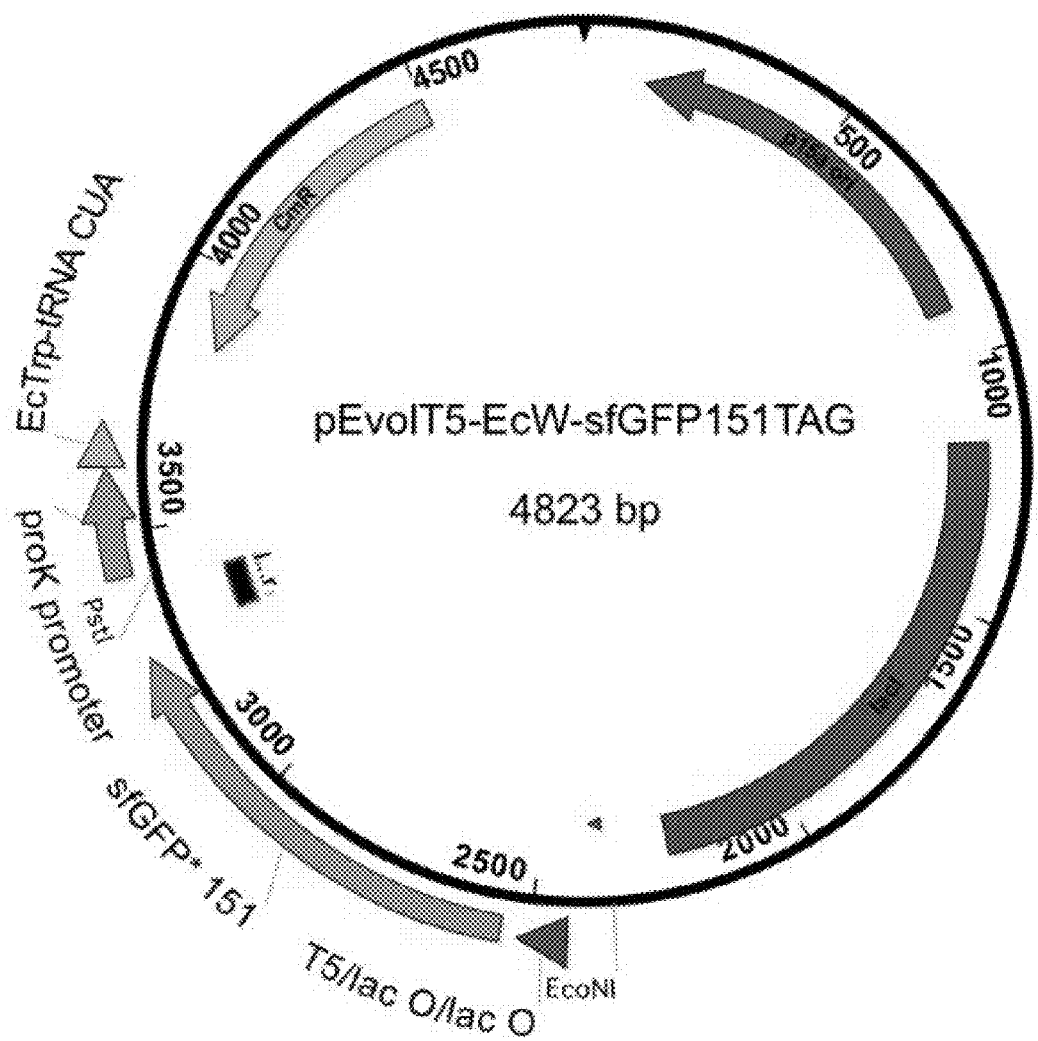
Figure 18A:
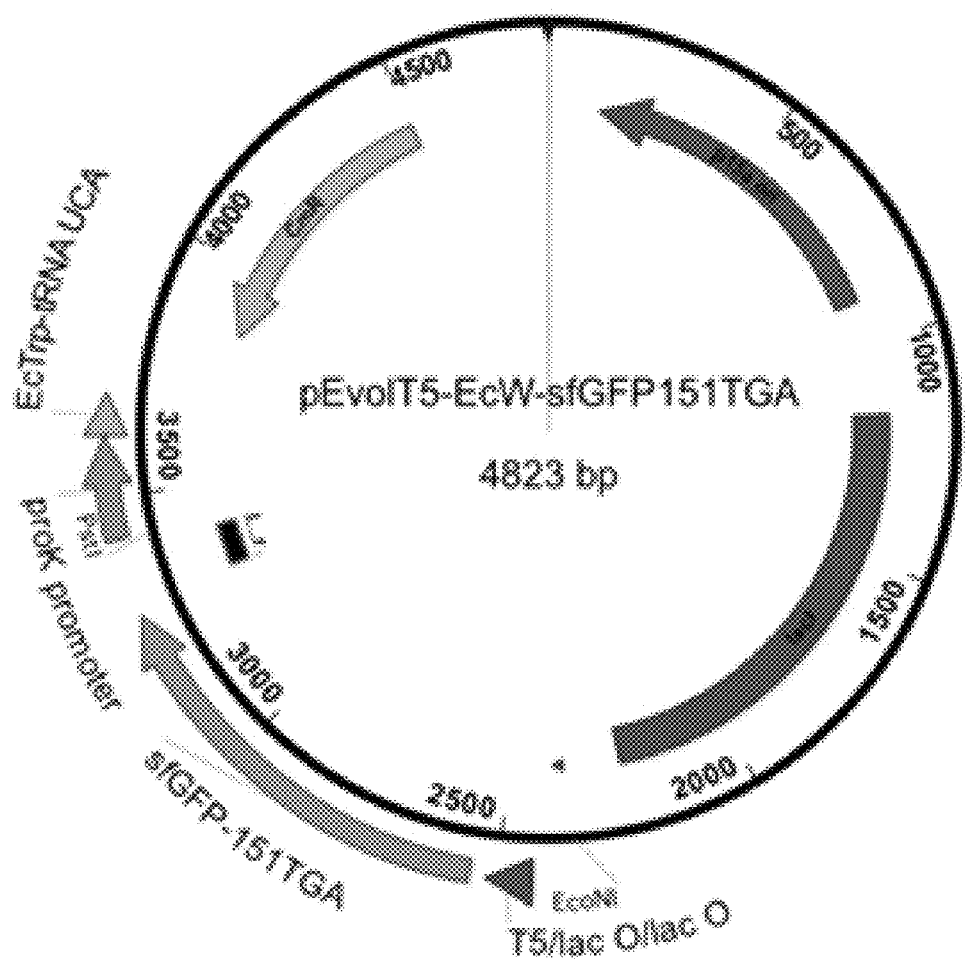
Figure 21A:
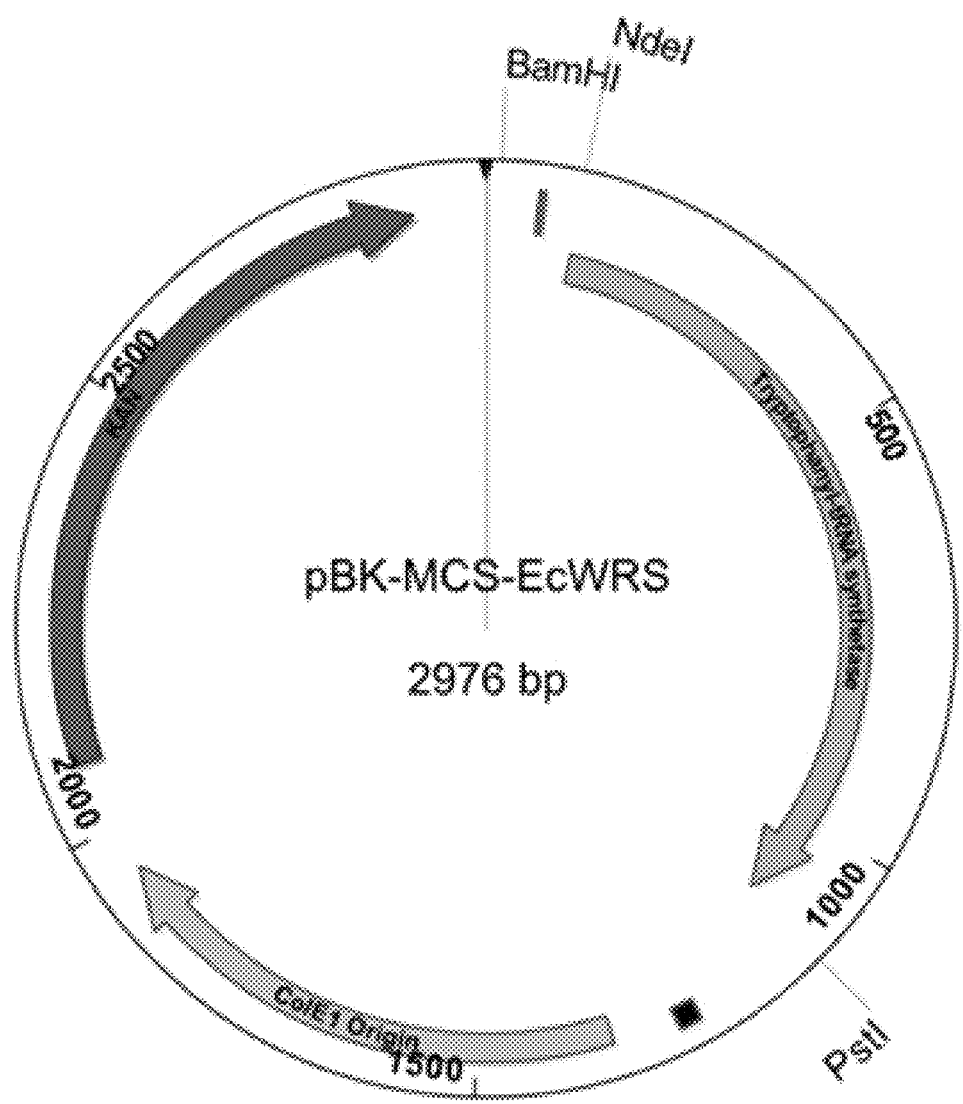
Figure 24A:
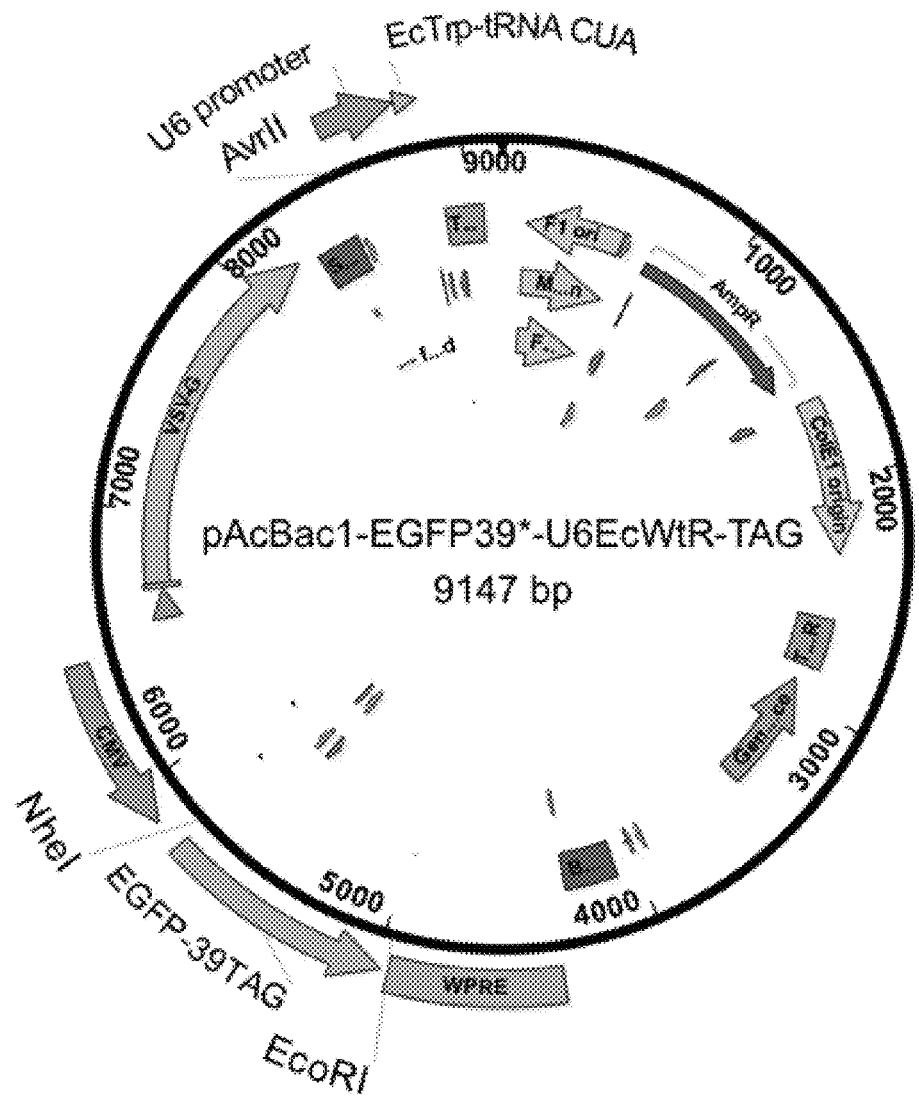
Figure 25A:
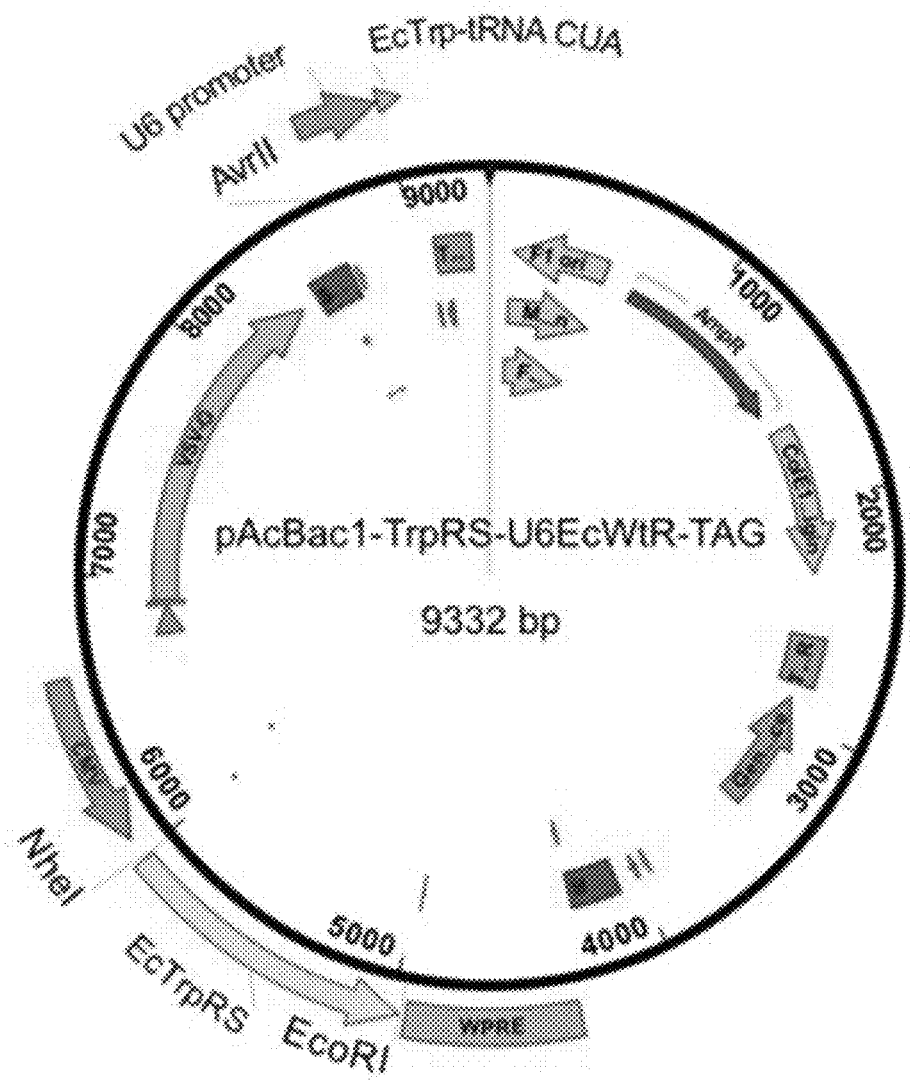

With ATMW1 in hand, the possibility of reintroducing the liberated EcTrpRS/tRNAEcTrp pair for TAG suppression into this strain as a TAG suppressor was investigated. Surprisingly, when the tRNAEcTrpCUA was expressed in ATMW1 along with a superfolder GFP reporter (sfGFP-151-TAG), robust protein expression was observed in the absence of EcTrpRS, indicating cross-reactivity of this tRNA with another *E. coli* aaRS (FIG. 9A). To identify the origin of this cross-reactivity, the reporter protein was isolated by Ni-NTA affinity purification, and subjected to mass-spectrometry analysis (whole protein, as well as tryptic digestion/MS), which identified the amino acid being charged in response to TAG as glutamine (FIG. 9B). Sequence alignment reveals remarkable homology between the tryptophanyl and glutaminyl tRNA of *E. coli* (FIG. 10). The middle U residue in the anticodon of EctRNAGlnCUG is a major identity element in its interaction with EcGlnRS. While the EctRNATrpCCA lacks this residue, enabling its distinction from EctRNAGln, it was inadvertently introduced in the TAG suppressor variant EctRNATrpCUA, leading to cross-reactivity with EcGlnRS.

Circumventing this issue is envisioned by generating a TGA suppressor EctRNATrpUCA that avoids introducing the middle U-residue in the anticodon. Unfortunately, termination at the TGA stop codon in *E. coli* is often "leaky"—a result of non-specific suppression by the endogenous tryptophanyl tRNA—making it a suboptimal choice for genetic code expansion. However, in the ATMW1 strain—where the endogenous tryptophanyl pair was replaced with the yeast counterpart—TGA did not exhibit such leaky behavior (FIG. 9A), suggesting the feasibility of its use for genetic code expansion with high fidelity. When the sfGFP-151-TGA reporter and EctRNATrpUCA were coexpressed in ATMW1, no reporter expression was observed un less the EcWRS was also present, confirming the non-cross-reactivity of EctRNATrpUCA in ATMW1 as well as the efficient opal suppression activity of the EcTrpRS/tRNAEcTrpUCA pair (FIG. 9A). MS analysis of the isolated protein further confirmed incorporation of tryptophan in response to TGA (FIG. 9C)

Figure 3C:
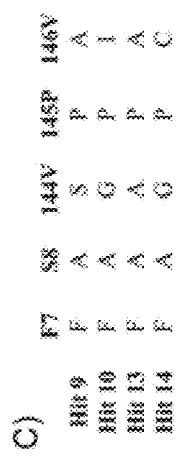
FIG. 3A-E shows (A) *Geobacillus stearothermophilus* TrpRS (PDB 1I6M) active site. (B) Structures of tryptophan and 5-hydroxytryptophan (5HTP). (C) Mutations associated with 5HTP-specific EcTrpRS variants. (D) Expression of sfGFP-151-TGA using EcTrpRS hits 9, 10, 13, and 14 demonstrating 5HTP dependence. (E) SDS-PAGE analysis of sfGFP-151-TGA expression facilitated by various EcTrpRS variants in the presence or absence of added 5HTP.
Figure 3B:
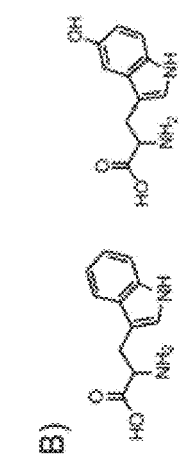
Figure 3A:
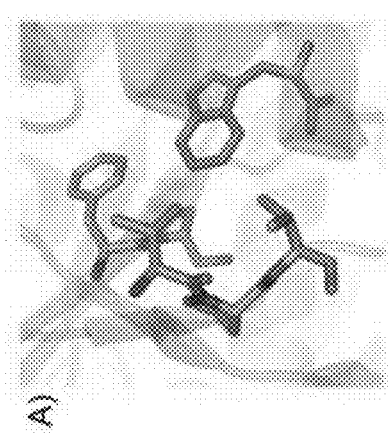
Figure 3E:
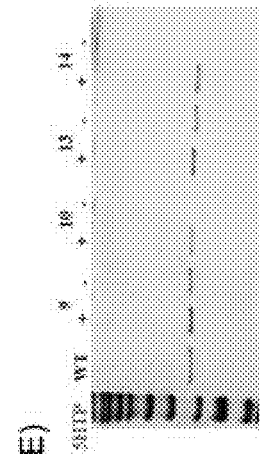

Establishment of an efficient, orthogonal opal suppressing EcTrpRS/tRNAEcTrpUCA pair in the ATMW1 *E. coli* opens up the possibility of altering its substrate specificity using the facile *E. coli*-based selection system. The existing reporter plasmids used for this double-sieved selection scheme, which enables either enrichment (positive selection) or depletion (negative selection) of aaRS variants based on their ability to charge its amber suppressing cognate tRNACUA, were mutated to generate variants that would allow selection based on opal suppression instead. Based on the crystal structure (FIG. 3A) of the highly homologous *Geobacillus stearothermophilus* TrpRS (PDB ID 1I6M), a library of 3.15×10$^6$ EcTrpRS mutants was constructed by simultaneously randomizing Phe 7(NBT), Ser 8(NST), Val 144(NNK), Pro 145(NNK), Val 146(NNK) residues using site-saturation mutagenesis, and covering the library using ~3×10$^7$ unique transformants. These residues point at C4-C5-C6 of the indole ring of the substrate tryptophan. A first attempt at identifying a mutant from this library that selectively charges 5-hydroxytryptophan is shown (5HTP; FIG. 3B). This UAA was previously genetically encoded in bacteria using a yeast-derived tryptophanyl pair. A report claiming its incorporation in mammalian cells using a bacteria-derived tRNA/aaRS pair was recently refuted.

Figure 3D:
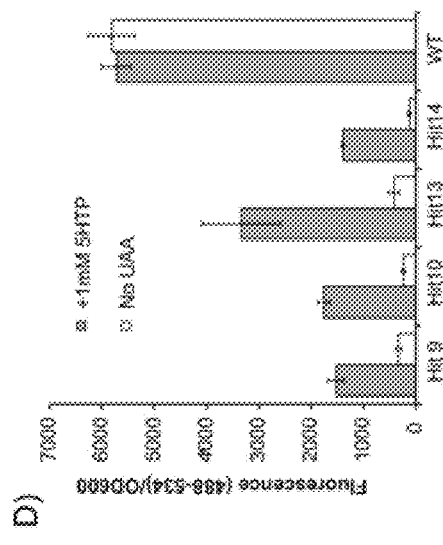

The aforementioned library of EcTrpRS variants was subjected to three rounds of selections (positive selection in the presence of 1 mM 5HTP, negative selection in the absence of the UAA, then another round of positive selection) in the ATMW1 strain, and 96 colonies from the surviving pool were individually screened for conditional survival under the positive selection conditions (40 μg/mL chloramphenicol) in the presence of 5HTP. Sequence analysis of four of the most successful mutants show significant sequence-convergence, where Phe 7 and Pro 145 are conserved, Ser 8 is mutated to Ala, Val 144 changes to a small amino acid (Gly/Ser/Ala), and Val 146 is mutated to different small/hydrophobic amino acids (FIG. 3C). Next the ability of these mutant EcTrpRS variants to drive the expression of a sfGFP-151-TGA reporter along with its cognate tRNAEcTrpUCA were evaluated. All mutants were able to facilitate efficient reporter expression in the presence of 1 mM 5HTP, but EcTrpRS-h14 exhibited the least background in the absence of the UAA (FIG. 3D, E). The reporter protein was isolated using a C-terminal (His)6 tag and MS analysis confirmed 5HTP incorporation (Table 1).

Table 1 below shows whole protein LCMS measurements.

| Reporter | UAA | aaRS | Expected mass | Observed mass | Note |
| --- | --- | --- | --- | --- | --- |
| sfGFP-151-TAG | None | None | No expr. | 27562 | pBK system in ATMW1 |
| sfGFP-151TAG | W | EcWRSwt | 27620 | 27562* | pBK/tac system in ATMW1 (Gln x-rxtive) |
| sfGFP-151-TGA | W | EcWRSwt | 27620 | 27621 | pBK/tac system in ATMW1 |
| sfGFP-151-TGA | 5HTP | Hit 14 | 27636 | 27637 | pBK/tac system in ATMW1 |
| sfGFP-151-TGA | 5MTP | Hit 14 | 27652 | 27652 | pBK/tac system in ATMW1 |
| sfGFP-151-TGA | 5BrW | Hit 14 | 27700 | 27699 | pBK/tac system in ATMW1 |
| sfGFP-151-TGA | 5AzW | Hit 14 | 27663 | 27660 | pBK/tac system in ATMW1 |
| sfGFP-151-TGA | 5PropW | Hit 14 | 27676 | 27674 | pBK/tac system in ATMW1 |
| sfGFP-151-TGA | 5HTP | Hit 9 | 27636 | 27637 | pBK/tac system in ATMW1 |
| sfGFP-151-TGA | 5AmW | Hit 9 | 27636 | 27635 | pBK/tac system in ATMW1 |
| EGFPwt | Y | None | 29683 | 29683 | Pacbac1 system in HEK293T |
| EGFP-39-TAG | BocK | MbPyl | 29748 | 29748 | Pacbac1 system in HEK293T |
| EGFP-39-TAG | AzK | MbPyl | 29761 | 29761 | Pacbac1 system in HEK293T |
| EGFP-39-TAG | W | EcWRSwt | 29707 | 29708 | Pacbac1 system in HEK293T |
| EGFP-39-TAG | 5HTP | Hit 14 | 29723 | 29724 | Pacbac1 system in HEK293T |
| EGFP-39-TAG | 5MTP | Hit 14 | 29736 | 29736 | Pacbac1 system in HEK293T |
| EGFP-39-TAG | 5BrW | Hit 14 | 29786 | 29785 | Pacbac1 system in HEK293T |
| EGFP-39-TAG | 5AzW | Hit 14 | 29748 | 29747 | Pacbac1 system in HEK293T |
| EGFP-39-TAG | 5PropW | Hit 14 | 29761 | 29760 | Pacbac1 system in HEK293T |
| EGFP-39-TAG | 5HTP | Hit 9 | 29723 | 29724 | Pacbac1 system in HEK293T |
| EGFP-39-TAG | 5AmW | Hit 9 | 29722 | 29721 | Pacbac1 system in HEK293T |
| sfGFP-151-TAG | 5AzW | Hit 14 | 28368 | 28366 | Labeled with DBCO-biotin |
| EGFP-39-TAG | 5AzW | Hit 14 | 30453 | 30453 | Labeled with DBCO-biotin |

Figure 4A:
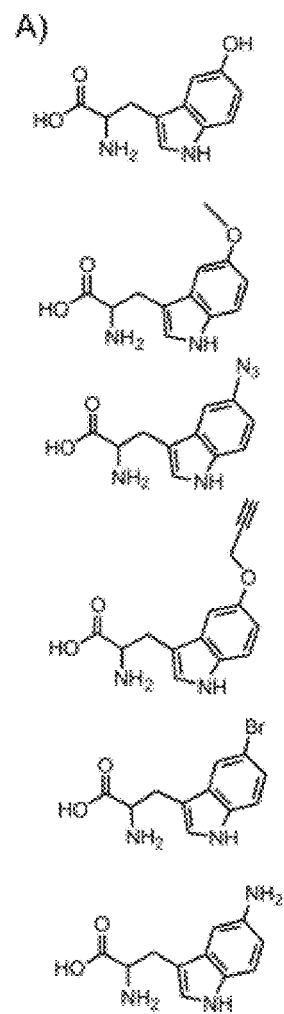
FIG. 4A-D shows (A) Structures of additional tryptophan analogs used here. (B) Demonstration of polyspecificity associated with EcTrpRS-h9 and h14 using sfGFP-151-TGA expression assay. (C) SDS-PAGE of sfGFP-151-TGA containing various 5-position Trp residues. (D) Expression of EGFP-39-TAG reporter incorporating various UAAs in HEK293T cells using EcTrpRS(variant)/tRNAEcTrpCUA pair.
Figure 4C:
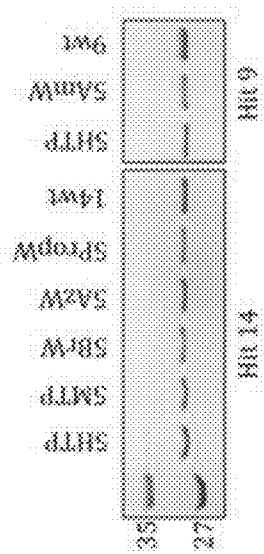
Figure 4B:
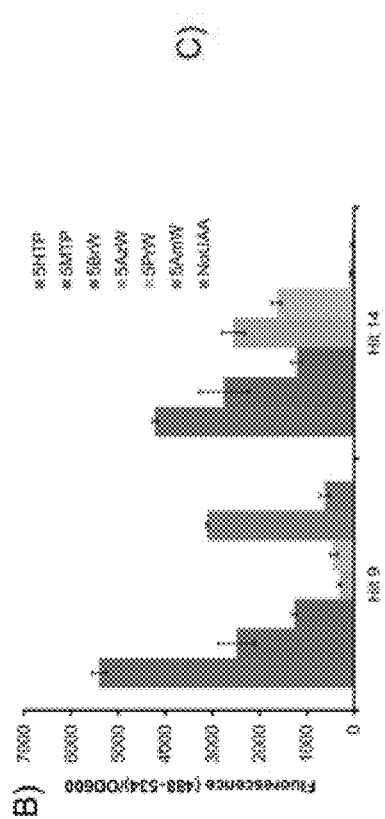
Figure 4D:
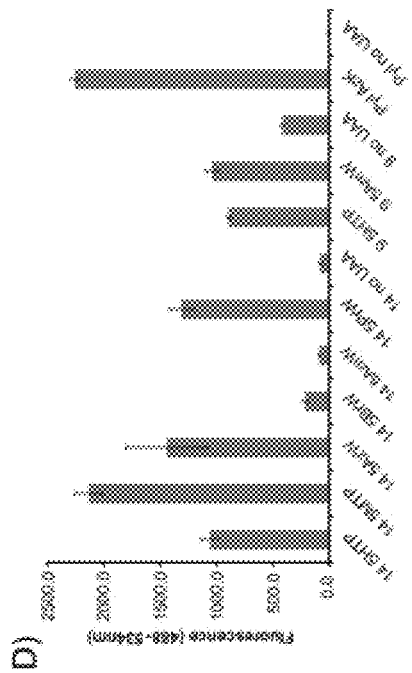
Figure 5B:
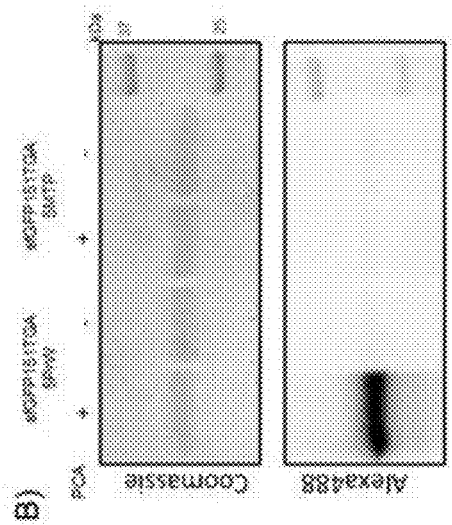
FIG. 5A-D shows (A) EGFP-39-TAG and sfGFP-151-TGA containing 5AzW or 5HTP were labeled with DBCO-Cy5 and imaged. (B) sfGFP151TGA containing 5PrW or 5MTP was labeled with Alexa 488-PCA and imaged. (C) Structure of DBCO-Cy5. (D) Structure of Alexa 488-PCA.
Figure 5D:
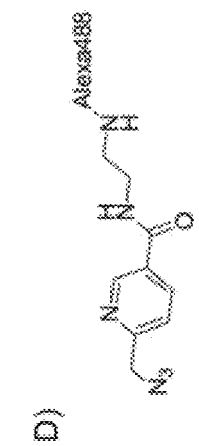
Figure 5A:
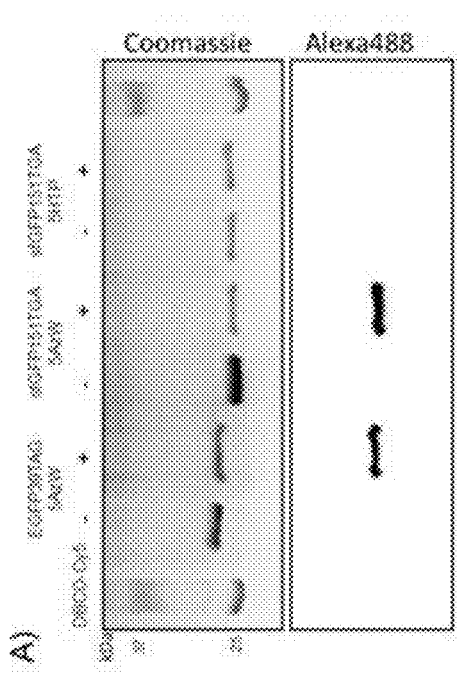
Figure 5C:
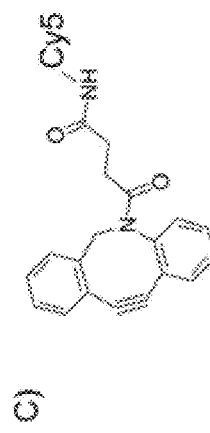

Since the negative selection step in the aforementioned scheme only discriminates against natural amino acids, but not other UAAs, the isolated mutants are sometimes capable of polyspecificity: The ability to charge a number of structurally similar UAAs, while discriminating against the 20 canonical amino acids. The isolated EcTrpRS mutants were screened for polyspecificity towards other 5-substituted tryptophan derivatives (FIG. 4A), using an assay that measures the enhancement of sfGFP-151-TGA expression in the presence of a particular UAA, relative to a no-UAA control. EcTrpRS-h14 exhibited high polyspecificity towards four additional amino acids, whereas EcTrpRS-h9 also enabled the incorporation 5-aminotryptophan (FIG. 4B). In all cases, the reporter protein was isolated and characterized by MS analysis to confirm the incorporation of these UAAs (FIG. 4C, Table 1). To demonstrate the feasibility of the evolved EcTrpRS variants for UAA-incorporation into proteins in mammalian cells, EcTrpRS-h14 and -h9 were cloned into the previously described pAcBac1 plasmid system together with its cognate tRNAEcTrpCUA, driven by CMV and U6 promoters, respectively, and this plasmid was co-transfected into HEK293T cells along with an EGFP-39-TAG reporter. Apart from 5-bromotryptophan, addition of all other UAAs led to robust reporter-expression relative to a no-UAA control (FIG. 4D). Expression levels were comparable with those obtained with the well-established pyrrolysyl system for the same reporter. Incorporation of 5-azidotryptophan (5AzW) and 5-propargyloxytryptophan (5PrW) into proteins introduces unique azido- and alkyne-functionalities, respectively, that can be utilized for bioorthogonal conjugation reactions using Cu-mediated or Cu-free "click" chemistry. This was demonstrated by conjugating DBCO-Cy5 or Alexa Fluor 488 picolyl azide to the 5AzW or 5PrW residue in reporter proteins, using strain-promoted or Cu-dependent click conjugation, respectively (FIG. 5).

In conclusion, the present invention demonstrates here the feasibility of functionally replacing an endogenous tRNA/aaRS in E. coli with an E. coli-optimized counterpart from a different domain of life with no growth-penalty, and that the resulting strain can be used as a selection host for evolving variants of the liberated tRNA/aaRS pair for charging UAAs. In addition to E. coli, these variants also enable genetic code expansion in eukaryotes. Since bacterial tRNA/aaRS pairs are generally orthogonal in eukaryotic cells, this approach holds the potential to provide additional "universal" tRNA/aaRS platforms. The present invention also introduces a new tryptophanyl-tRNA synthetase/tRNA platform, the utility of which was illustrated by introducing several new UAA additions to the genetic code of E. coli as well as eukaryotes, including 5AzW and 5PrW which enable selective bioconjugation reactions. Access to new universal tRNA/aaRS pairs will augment the structural diversity of genetically encoded UAA toolbox, and facilitate the development of powerful new technology involving simultaneous incorporation of multiple UAAs into a polypeptide in both E. coli and eukaryotes.

A number of tRNA/aminoacyl-tRNA synthetase (aaRS) pair has been developed to date to site specifically incorporate novel unnatural amino acids into proteins. The *E. coli* tryptophanyl-tRNA synthetase/tRNA pair developed in the present invention is unique and is a novel system because it can be used to incorporate new unnatural amino acids into proteins both in an engineered *E. coli* (the strain created where the endogenous tryptophanyl tRNA/aaRS pair was replaced with a counterpart from yeast) as well as in eukaryotic cells. This tRNA/aaRS pair has been engineered to enable site specific incorporation of six new unnatural tryptophan analogs into proteins expressed in both *E. coli* as well as eukaryotic cells.

The novel system described in the present invention has a number of potential applications. This includes site-specific bioconjugation using 5-azidotryptophan and 5-propargyltryptophan: These two unnatural amino acids can be incorporated into proteins expressed in both *E. coli* and eukaryotic cells (e.g., mammalian cells), and will allow site-specific bioconjugation using bioorthogonal azide-alkyne click reactions. This reaction can be used to site-specifically attach onto proteins a variety of entities such as drugs (for antibody-drug conjugation), attachment of biophysical probes (such as fluorophores, PET probe, etc.), polyethylene glycol (to improve pharmacokinetic properties of therapeutic proteins), onto recombinantly expressed proteins.

The same strategy can also be used to label the capsid proteins of human viruses, which can be subsequently labeled with either probes to study its infection process, or attach synthetic receptor binding agents that target specific cell-surface receptors to generate cell-specific viral vectors. The site-specific conjugation strategy can also be used to attach relevant proteins on surfaces (e.g., sensor chips, electrodes, etc.) with precise control over its orientation and site of attachment.

Another application involves 5-azidotryptophan, which is an aryl-azide, which upon irradiation forms a highly reactive nitrene intermediate. Its incorporation into proteins will allow light-induced capture of weak protein-protein interactions by the formation of a stable covalent linkage between the reactive nitrene intermediate and various residues from the interacting protein. This can be a powerful tool to interrogate weak or transient protein-protein interactions. Additionally tryptophan residues are frequently found at the interface of protein-protein interactions, making 5-azidotryptophan an ideal candidate to capture such interactions.

The tryptophanyl-tRNA synthetase/tRNA pair of the present invention can be further engineered to incorporate new tryptophan analogs such as fluorinated-tryptophan (NMR as well as fluorescence probe), nitrated tryptophans (these residues form naturally as post-translational modifications, but their physiological relevance remain poorly characterized, since such modified proteins cannot be homogeneously produced; however, the ability to specifically charge these nitrated amino acid into specific sites of proteins using the technology of the present invention will circumvent this problem). The large active site of the tryptophanyl-tRNA synthetase can also be engineered to charge other unnatural amino acids with large side chains, such as fluorophores.

A variety of tryptophan analogs can be incorporated site-specifically into proteins expressed in *E. coli* or eukaryotic cells, enabling the study of the roles of functionally important tryptophan residues. 5-azidotryptophan, 5-propargytryptophan, which can be incorporated site-specifically into any protein expressed in bacteria or eukaryotic cells using our platform, will allow selective conjugation of various molecules to these proteins for applications such as PEGylation, generation of site-specific antibody-drug conjugates. 5-azidotryptophan which can be incorporated site-specifically into any protein expressed in bacteria or eukaryotic cells using the platform of the current invention, can be used as a photo-affinity probe to capture weak or transient protein-protein interactions within a living cell.

The present invention has many commercial applications and could be useful to manufacturers of research kits, and to companies pursuing antibody-drug conjugate or other protein modification (such as PEGylation). Without further elaboration, it is believed that one skilled in the art can, based on the above description, utilize the present invention to its fullest extent. The following specific embodiments and examples are, therefore, to be construed as merely illustrative, and not limitative of the remainder of the disclosure in any way whatsoever.

Without further elaboration, it is believed that one skilled in the art can, based on the above description, utilize the present invention to its fullest extent. The following specific embodiments and examples are, therefore, to be construed as merely illustrative, and not limitative of the remainder of the disclosure in any way whatsoever.

Materials and Methods

For cloning and plasmid propagation, the DH10b (Life Technologies) strain of *E. coli* was used. Polymerase chain reaction (PCR) was performed using the Phusion Hot Start II DNA polymerase (Fisher Scientific) using manufacturer's protocol. For purification of DNA (plasmid as well as PCR products, etc.) spin columns from Epoch Life Science were used. Restriction enzymes and T4 DNA ligase were obtained from New England BioLabs (NEB). DNA oligomers for PCR were purchased from Integrated DNA Technologies (IDT). Verification of cloned DNA by Sanger sequencing was performed by Eton Biosciences. Antibiotics, isopropyl β-D-1- thiogalactopyranoside (IPTG), and L-arabinose were purchased from Sigma-Aldrich or Fisher Scientific. Components of media were obtained from Fisher Scientific. Bacteria were grown on LB or M63 agar plates[17] and LB liquid medium with the following antibiotic concentrations unless otherwise mentioned: 95 µg/mL spectinomycin, 20 µg/mL chloramphenicol, and 100 µg/mL ampicillin, 30 µg/mL kanamycin, 15 µg/mL zeocin, 12 µg/mL tetracycline, 10 µg/mL gentamycin.

Sequences of the oligonucleotides used herein are shown in Table 2, below SEQ ID NOS: 6-74, respectively.

| SEQ ID NO: | | |
|---|---|---|
| 6 | TrpRS.Z.ab-F | ATCAGTCTATAAATGACCTTCTGCCCGCATTAGGGCTTC CGCATAGCGAAAATCAGGAATCGAAAAAGGTGTTGACA ATTAATCATCGGC |
| 7 | TrpRS.Z.ab-R | TGTAGGCCGGATAAGGCGTTCACGCCGCATCCGGCATGA ACAAAGCGCAATTTGCCAGCAATAGTGAAAGCTTGCAA ATTAAAGCCTTCG |

-continued

| SEQ ID NO: | | |
|---|---|---|
| 8 | TrpRS150F | GTCGGCCGACTCACGCAATGATATTCAGGCGGC |
| 9 | TrpRS150R | AGCGAGATGTGGAAACGGCGAGGCACTTCAC |
| 10 | Zeo-iR | CTGGTCCTGGACCGCGCTGATGAAC |
| 11 | TrpRS_sqiR | ATCCTGGCGCACGGTGATCGCGTGTTG |
| 12 | trpTKO.Gent-F | CAGTCGGTTAGAATACCTGCCTGTCACGCAGGGGGTCGC GGGTTCGAGTCCCGTCCGTTCCGCCACCCTAATTACGCA CACCGTGGAAAC |
| 13 | trpTKO.Gent-R | CGGTAGAAGGATTTACTTCGGAGAGGGTTATTTCAGATA AAAAAAATCCTTAGCTTTCGCTAAGGATGATTTCCCGGG AAGCCGATCTCG |
| 14 | trpT_GsqF | GGGGTCTCCCCATGCGAGAGTAGGGAAC |
| 15 | trpT_GsqR | CCGTTGTCGATAGCACAACACTTTCACGGCC |
| 16 | galK.90_del | CGCGCAGTCAGCGATATCCATTTTCGCGAATCCGGAGTG TAAGAACGCGCAGTCAGCGATATCCATTTTCGCGAATCC GGAGTGTAAGAA |
| 17 | galK_KO_verf_F | TGGCAGAGACCCAGCG |
| 18 | galK_KO_verf_R | ACCCCAGTCCATCAGCG |
| 19 | dlambda.gal.K-F | GCTATGAAATAGAAAAATGAATCCGTTGAAGCCTGCTTT TTTATACTAACTTGAGCGAAACGGGAAGCCTGTTGACAA TTAATCATCGGC |
| 20 | dlambda.galK_dterm-R | GCCGCGTTGATTTTCTCCTGCCAGCTCATAATGCTGCCGC GTTGTAATATTCAGCACTGTCCTGCTCCTT |
| 21 | diambda.sqF | GGTTTGATCAGAAGGACGTTGATCGGGCGG |
| 22 | diambda.sqR | TTCAGATACTGGCGATCATCCGCCACCAG |
| 23 | dlambda.sqiR | AGCCCATTGATAGTTTTCATGTGCGACAATGGGCG |
| 24 | EcWRS_mut7_8-F | GAATCCCATATGATGACTAAGCCCATCGTTNBTNSTGGC GCACAGCCCTCAGGTGAATTG |
| 25 | libEcWRS-NdeI-F | TACGCTTTGAGGAATCCCATATGATGACTAAGCCCATCG |
| 26 | EcWRS1_mut-VPViR | CAGATTAGTTTGATACAGCAGGATGTCCGCTGCCATC |
| 27 | EcWRS1_mut144-6-F | GATGGCAGCGGACATCCTGCTGTATCAAACTAATCTGnnk nnknnkGGTGAAGACCAGAAACAGCACCTCGAACTGAGC |
| 28 | EcWRS_NCoI_PstI_termR | agcgtttgaaactgcagccatggtaccTTACGGCTTCGCCA CAAAACCAATCGC |
| 29 | proK-F | GTTAGCCTGCAGGTAATTCCGCTTCGCAACATGTGAG |
| 30 | TrpH_NcoI-R | GGCCGCCATGGCAAATTCGACCCTG |
| 31 | Trp40CCA-iR | GCAACCAGGCGCTTTGGAGGCGCCAGCTCTACCCTTGAG |
| 32 | Trp40CCA-iF | AGCTGGCGCCTCCAAAGCGCCTGGTTGCAGGTTC |
| 33 | SmR-R | CGCGCGCAGATCAGTTGGAAGAATTTGTCCACTACGTG |

| SEQ ID NO: | | |
|---|---|---|
| 34 | PNP-Spet-F | ATAATGGACTAGTGCGCTTGTTTCGGC |
| 35 | pNP-BAB-R | CTCCTTAGATCTTCCTAGGTGGATCCACCATTCC |
| 36 | pEvol CmR SpeI-F | AATAATACTAGTGTTGATACCGGGAAGCCCTGG |
| 37 | pEvol_CmR PstI-R | AATAATCTGCAGCGAATTTCTGCCATTCATCCGCTTATTATCAC |
| 38 | CmR-TGA-7 | GCTAAGGAAGCTAAAATGGAGAAAAAAATCACTTGATATACCACCGTTGATATATCCCAATGGC |
| 39 | CmR-TGA-84 | GCAATGAAAGACGGTGAGCTGGTGTGATGGGATAGTGTTCACCCTTGTTACACC |
| 40 | CmR-TGAT-98 | CCCTTGTTACACCGTTTTCCATGAGTGATCTGAAACGTTTTCATCGCTCTGGAG |
| 41 | pRep-KpnI-tR-F | AATAATaggtaccGTTCTGTTGCCCGTCTCACTGGTG |
| 42 | pRep-EcWtR-NdeI/AvrII-R. | AATAATcatatgCCTAGGTGGCAGGGGCGGAGAGACTC |
| 43 | EcW-TGA-MSDM | GTTCAATTGGTAGAGCACCGGTCTTCAAAACCGGGTGTTGGGAGTTCGAG |
| 44 | T7F1 | CAGGTTCGCAGCGTCAGCCGGAATGGTACCG |
| 45 | T7R3 | GCGCCCGACAGCCTTCCAGTTCCTGTGAGAAATCAAGCCGGAAGCCGTAGCGTAC |
| 46 | T7F3 | GTACGCTACGGCTTCCGGCTTGATTTCTCACAGGAACTGGAAGGCTGTCGGGCGC |
| 47 | T7R4b | CCATGACCATGATTACCGTGCACTGAAATACCATTAACATTGCTAAGAACG |
| 48 | T7F4 | CGTTCTTAGCAATGTTAATGGTATTTCAGTGCACGGTAATCATGGTCATGG |
| 49 | T7R5 | CGAAGGCGAAGCGGCATGCATAATGTGCCTGTCAAATGG |
| 50 | T7 mut-SbfI-F | AATAATcctgcaggCTACTCAGGAGAGCGTTCACCGAC |
| 51 | T7mut-NotI/SbtI-R | AATAATCCTGCAGGGCGGCCGCTACGGGAGGGCTTACCATCTGG |
| 52 | Barnase MSDM 3 TGA | TTTAACTTTAAGAAGGAGATATACATATGGCATGaGTTATCAACACGTTTGACGGGGTTG |
| 53 | Barnase MSDM 45 TGA | GTGGCATCAAAAGGGAACCTTGCATGAGTCGCTCCGGGGAAAAGCATC |
| 54 | EcWIR-PstI-F | TTAGCCTGCAGTGTGCTTCTCAAATGCCTGAGGCCAGTTTGCTC |
| 55 | EcWIR-prok-oF | GCGCCCCGCATTTAGGGGCGTAGTTCAATTGGTAGAGCACCGGTC |
| 56 | EcWtR-proK-oR | ACTACGCCCCTAAATGCGGGGCGCATCTTACTGCGC |
| 57 | EcWtR-KpnI-R | ATATATGGTACCAAAAAATGGCAGGGGCGGAGAGACTCG |
| 58 | GFPflip-NotI-F+ | TCGATCCCGCGAAATTAATACGACTCACTATAG |

-continued

| SEQ ID NO: | | |
|---|---|---|
| 59 | sfGFP-T7 + lam PstI-R. | ATATACTGCAGCGCCAAGCTAGCTTGGATTCTCACCAAT AAAAAACGC |
| 60 | MjYtR del F | TGGCAGGGGCGGAGAGACTCGAACTCC |
| 61 | MjYtR del oR | CGAGTCTCTCCGCCCCTGCCA AATTCGAAAAGCCTGCTCAACGAGCAGG |
| 62 | EcWtR TGA MSDM | GTTCAATTGGTAGAGCACCGGTCTTCAAAACCGGGTGTT GGGAGTTCGAG |
| 63 | sfGFP (pEvol) TGA151 | CTCGAGTACAACTTTAACTCACACAATGTATGAATCACG GCAGACAAACAAAAGAATGG |
| 64 | EcWRS1.F A.NotI-F | AATAATAgcggccgcATGACTAAGCCCATCGTTTTTGCTGGC GCAC |
| 65 | EcWRS-NotI-R | AATAATAgcggccgcTTACGGCTTCGCCACAAAACCAATCG C |
| 66 | pUltraII-tRsqR | GGTGCCCTTAAACGCCTGGTTGC |
| 67 | EcTrpRS-NdeI-F | AAtAAAcatatgATGACTAAGCCCATCGTTTTTAGTGGCGCA C |
| 68 | EcTrpRS-PstI-R | TTATTCTGCAGTTACGGCTTCGCCACAAAACCAATCGC |
| 69 | TrpRS-R EcoRI | ATTATTGAATTCTTACGGCTTCGCCACAA |
| 70 | TrpRS-F-NheI | AATAAATGCTAGCATGACTAAGCCCATC |
| 71 | U6-R tRNAtrp* AvrII | AATTATTGCTAGCAAAAAATGGCAGGGGCG |
| 72 | tRNAtrp* Nhe-R | AATTATTGCTAGCAAAAAATGGCAGGGGCG |
| 73 | EeWRS_mamNheI-F | aataataGCTAGCgccaccATGACTAAGCCCATCGTT |
| 74 | EcWRS_mamEcoRI-R | AATAATAgaattcTTACGGCTTCGCCACAAAACCAATCGC |

Statistical methods. For all expression analysis (sfGFP in bacteria or EGFP in HEK293T cells), mean of three independent experiments were reported, and error bars represent standard deviation. For the growth rate analysis, each data point represent the mean O.D.600 of three independent cultures of the same strain (error bars represent S.D.). In our experience, a mean of three experiments provides adequate levels of accuracy for these experiments.

Strains, cell lines. The EcNR1 strain was a gift from Prof. George M. Church. The HEK293T cell-line was obtained from ATCC, and propagated without further confirmation. Cell lines are regularly monitored for Mycoplasma contamination. Even though HEK293T is listed under misidentified cell lines in ICLAC database, we used it for our expression analyses as a representative mammalian cell-line. Given the wide-spread use of this cell-line as a model mammalian expression host, and since our conclusions does not rely on its specific identity (beyond a representative mammalian cell-line), we believe that the use of this strain is justified.

Lambda-Red recombination. All strains were derived from EcNR1[16]. This strain contains temperature inducible lambda-recombinase genes (Exo, Beta, Gam) and a constitutive ampicillin resistance gene disrupting the bioA/bioB genomic locus. Strains were grown in 10 mL LB at 30° C. to 0.5 $OD_{600}$ and then induced for 15 minutes in a 42° C. water bath (250 rpm). The cell pellet was then washed twice with 10 mL $ddH_2O$ by centrifuging at 4500× g. Cells were resuspended in residual $ddH_2O$ (~250 μL) and 50 μL aliquots were electroporated with 50 ng dsDNA or 2 μM 90 bp oligo containing 45-77 bp genomic homology, depending on the desired recombination. Electroporated cells were recovered for 1-6 hours and plated on either LB or minimal media. Single colonies from selection plates were re-streaked and subjected to colony PCR using KAPA-2G polymerase (Kapa Biosystems), following manufacturer's instructions, to verify desired recombination.

Building ATMW1. EcNR1 was transformed with pUltraG_ScW40$_{CCA}$. To remove the E. coli tryptophanyltRNA synthetase (trpS) from this strain, the gene encoding zeocin resistance (ShBle) driven by the EM-7 promoter and the CYC1 transcription terminator was PCR amplified using primers TrpRS.Z.ab-F and TrpRS.Z.ab-R to generate the PCR product trpS::Zeo$^R$. 50 ng of the trpS::ZeoR PCR cassette was transformed in the recombination following the aforementioned protocol, and the resulting strains were plated on LB-Agar plates supplemented with Zeocin. The resulting colonies were screened via colony PCR using TrpRS150F+TrpRS150R, TrpRS150F+Zeo-iR, and TrpRS150F+TrpRS_sqiR, as well as sequencing these colony PCR products. This strain was named EZ4.

To replace the *E. coli* trp-tRNA$_{CCA}$ (trpT), the trpT::Gent$^R$ PCR cassette was amplified using trpTKO.Gent-F and trpTKO.Gent-R (965 bp). 50 ng of trpT::Gent$^R$ PCR cassette was transformed into EZ4, induced as previously described. Resulting gentamycin resistant colonies were screened for the desired recombination using colony PCR primers trpT GsqF and trpT GsqR, as well as sequencing of the PCR product. The resulting strain was named EZG4.

2 µM 90 bp oligo, galK. 90 del, was used to delete galK from the endogenous genomic location. Following transformation, cells were recovered for 6 hours, washed twice with M9 minimal media at 5000×g for 5 min and 100 µL of a 10$^4$ dilution was plated on M63 minimal media supplemented with glycerol and 2-deoxygalactose to select for successful galK deletion. Colony PCR was used to verify the deletion of galK using galK_KO_verf-F/R. The resulting strain was named G4.

galK.PCR cassette was amplified containing the endogenous promoter dlambda.GalK-F and dlambda.galK dterm-R (1348 bp) and was used to remove the λ-RED genes from the G strain. Following transformation of 50 ng of this PCR product into strain G, successful insertion of the galK.PCR cassette into the λ-RED site was selected by plating the cells on M63 plates containing galactose as the sole carbon source for three days.[17] Surviving colonies were screened by colony PCR using dlambda.sqF with dlambda.sqR or dLambda.sqiR for the desired deletion. This final strain was named ATMW1 (EcNR1 trpS::Zeo$^R$ trpT::Gent$^R$ ΔgalK λ-RED::galK.

Essentially the same procedure as described above for producing ATMW1 was used to produce BL21(DE3).

Growth Comparison. 5 mL starter cultures of EcNR1G, EcNR1G+pUltraG_ScW40$_{CCA}$, and ATMW1 strains were grown for 16 hrs in LB with all strain-dependent antibiotics. For each strain, the starter culture was diluted to an initial OD$_{600}$ of 0.01 in three identical cultures of 80 mL LB with no antibiotics and allowed to grow in 250 mL sterile Erlenmeyer flasks at 30° C., with shaking (250 rpm). Growth was monitored every 30 min by measuring OD$_{600}$ in a 10 mm cuvette.

Assessment of tRNA/aaRS activity using a chloramphenicol reporter. Overnight cultures of ATMW1 harboring pRepAC-EcW-TAG or pRepJI-EcW-TGA, with or without pBK-EcWRSwt, were diluted to an OD$_{600}$ of 0.1 and 3 µL was spot plated on LB agar plates supplemented with kanamycin (+pBK plates), spectinomycin, tetracycline, and varying chloramphenicol concentrations. Growth was analyzed after 48 hrs of incubation at 37° C.

Assessment of tRNA/aaRS activity using a sfGFP151 reporter. EcNR1 or ATMW1 harboring pEvolT5-EcW sfGFP151 (TAG or TGA) with or without pBK-EcWRSwt, pBK-EcWRS-h14, or pBK-EcWRS-h9 were grown overnight in LB. The starter cultures were diluted in LB supplemented with required antibiotics to 0.05 OD$_{600}$. Cultures were grown at 30° C. or 37° C. (30° C. when comparing to progenitor strain EcNR1) until 0.55 OD$_{600}$, at which point the sfGFP expression was induced with a final concentration of 1 mM IPTG. Unnatural amino acids (UAA) were added during induction to a final concentration of 1 mM. Cultures were grown for an additional 17-20 hours at 37° C. with shaking. To evaluate sfGFP expression, cells from 150 µL of the cultures were pelleted at 5000×g, resuspended in 150 µL PBS, and transferred to a 96-well clear-bottom assay plate. Fluorescence was measured by using a SpectraMAX M5 (Molecular Devices) (Ex. 488 nm; Em. 534 nm). Fluorescence for each sample was normalized using its OD$_{600}$.

Protein purification. To maximize the yield of UAA-modified protein expression, a different plasmid combination was used: EcTrpRS-h14 and -h9 was cloned into a pEvoltac plasmid that expresses them from a strong tacI promoter, while the tRNA$^{EcTrp}_{UCA}$ is expressed from the proK promoter. The sfGFP reporter gene (sfGFP-151-TGA or wild type sfGFP) was expressed from pET22b-T5lac plasmid driven by the strong t5.lac promoter. Overnight expression cultures were centrifuged and resuspended in lysis buffer: B-PER Bacterial Protein Extraction Reagent (Thermo Scientific)+1X Halt Protease Inhibitor Cocktail (Thermo Scientific)+0.01% Pierce Universal Nuclease (Thermo Scientific). After 30 min incubation at room temperature, the lysate was clarified by centrifuging at 22,000×g for 5 min. The C-terminally polyhistidine tagged soluble sfGFP in the supernatant was purified using a HisPur Ni-NTA resin (Thermo Scientific) following manufacturer's protocol. Protein purity was confirmed by SDS-PAGE and purified protein molecular weight was confirmed by ESI-MS (Agilent Technologies 1260 Inifinity ESI-TOF).

Construction of the EcWRS-5HTP pBK library. Overlap extension was used to introduce degenerate codons, creating the five-residue tryptophanyl tRNA-synthetase library pBK-EcWRS1.5 (786,432 diversity): F7-NBT, S8-NST, V144-NNK, P145-NST, V146-NNK. Using Phusion HSII (Fisher Scientific) and manufacturer's protocol, EcWRS1_mut7-8-F+EcWRS1_mut-VPViR and EcWRS1_mut144-6_F+EcWRS_NcoI_PstI_termR were used to PCR amplify the N-term and C-term of the EcWRS PCR product, respectively. The N-term and C-term PCR products were joined together by overlap extension PCR using the following terminal primers: libEcWRS-NdeI-F and EcWRS_NcoI_PstI_termR. These inserts were digested with NdeI/NcoI (NEB) and ligated by T4 DNA Ligase (NEB) into pBK vector cut with the same restriction enzymes. The ligation mixture was ethanol precipitated with Yeast-tRNA (Ambion) and transformed into electrocompetent DH10b cells. The library was covered using ~10$^7$ distinct colony forming units.

Selection for Synthetase Charging 5HTP. ATMW1 was co-transformed with the pBK-EcWRS1.5b library and the positive selection reporter plasmid pRepJI EcW TGA. The reporter plasmid harbors a lpp-promoted *E. coli* tRNA$^{Trp}_{UCA}$, a CAT reporter modified to contain TGA codons (Q98TGA), an arabinose-inducible T7 RNA polymerase harboring two TGA nonsense codons (at positions 8 and 114), and a wild-type GFPuv reporter expressed from a t7 promoter. Suppression of CAT leads to chloramphenicol resistance, and suppression of T7 RNA polymerase drives expression of a t7-promoted GFPuv. 9.2×10$^7$ cfu (colony forming units) were plated on LB+0.5× Spec/0.5× Tet/Kan/ 0.02% arabinose+chloramphenicol (25, 35, 45 µg/mL) in the presence of 1 mM 5HTP for 36 hrs at 37° C.

Colonies from the 35 and 45 µg/mL chloramphenicol positive selection plates were harvested, and the pBK plasmids harboring mutant EcTrpRS were purified by miniprep and gel purification. These were co-transformed into ATMW1 harboring the negative selection plasmid pNegJ2-EcW (araBad-Barnase harboring two TGA codons at 3 and 45). 3×10⁷ cfu were plated on LB+Amp/0.5×Kan/0.02% arabinose and incubated for 12 hrs at 37° C. Cells were harvested and library pBK plasmid was purified by miniprep/gel purification.

Isolated pBK plasmids from the negative selection were transformed again into ATMW1 pRepJI-EcW TGA, and 10⁶ cfu were plated on LB+0.5×Spec/Tet/Kan/0.02% arabinose+ chloramphenicol (30, 40, 50 µg/mL) in the presence or absence of 1 mM 5HTP for 18 hrs, 37° C., which revealed significantly higher number of colonies in the presence of the UAA. 96 colonies were picked into a 1 mL LB supplemented with Spec/Tet/Kan in deep 96 well polypropylene plates and grown overnight. The resulting cultures were diluted to ~0.01 OD$_{600}$ and 3 µL of each was spot plated on LB/Agar plates supplemented with Spec/Tet/Kan, and chloramphenicol (50, 60 µg/mL) in the presence or absence of 5HTP. Four clones exhibiting the most prominent UAA dependent growth were picked and sequenced.

Assessing activity of tRNA$^{EcTrp}_{CUA}$ and synthetase hits in HEK293T. Dulbecco's modified Eagle's medium (high glucose DMEM) supplemented with 10% fetal bovine serum (FBS) and Penicillin/Streptomycin (0.5×) was used to culture HEK293T cells. Cells were incubated in a humidified incubator at 37° C. in the presence of 5% CO$_2$. HEK293T were seeded at a density of 600,000 per well for a 12-well plate one day prior to transfection and transfected at ~70% confluence. Polyethylenimine (PEI, Sigma) and DNA were mixed at a ratio of 4 µL PEI (1 mg/mL) to 1 µg DNA in DMEM. After 20 min incubation, 100 µL of this mixture was used to transfect one single well in a 12-well plate. For these transfections, 500 ng of pAcBac EGFP39* U6-EcWtR TAG was transfected in the presence or absence of pAcBac-TrpRS (wt, h14, or h9) U6-EcWtR TAG. UAAs were added to the culture medium to a final concentration of 1 mM at the time of transfection. Fluorescence images were taken at 48 hrs post-transfection using a Zeiss Axio Observer fluorescence microscope.

To obtain EGFP39*-expression data, cells were harvested, washed once with PBS buffer (5000×g), and lysed with CelLytic-M lysis buffer (Sigma) supplemented with 1X Halt protease inhibitor and 0.01% Pierce universal nuclease. 50 µL lysis buffer was used for each well of a 12-well plate, and was allowed to incubate for 20 min. After incubation, the lysate was clarified by centrifuging at 22000×g for 5 minutes and was transferred to a clear bottom 96-well assay plate. Fluorescence was measured using a SpectraMAX M5 (Molecular Devices) (Ex. 488 nm; Em. 534 nm).

Isolation of EGFP-39-TAG reporters from HEK293T. HEK293T cells were cultured as previously described. One day prior to transfection, cells were seeded at a density of 8-million cells/10 cm dish. 50 µL PEI MAX (Polysciences) was mixed with 10 µg total DNA (5 µg reporter, 5 µg tRNA/aaRS plasmid) with 180 µL DMEM (no FBS), incubated for 20 min, and added evenly to the dish at 90% confluence. Desired UAAs were supplemented at a final concentration of 1 mM and cells were allowed to express the desired protein for 48 hours.

Cells from a 10 cm dish were harvested and lysed with 600 µL CelLytic M lysis buffer (Sigma, 1X Halt protease inhibitor, 0.01% Pierce universal nuclease). Lysate was clarified as described and purified via Ni²⁺-NTA, following manufacturer's protocol. Purified protein was analyzed by SDS-PAGE and molecular weight was confirmed by ESI-MS (Agilent Technologies 1260 Infinity ESI-TOF).

Click-labeling of 5AzW and 5PrW residues. Purified proteins containing 5AzW were incubated with or without 20 µM DBCO-Cy5 (Sigma) for 1 hr in the dark at room temp. Proteins samples were resolved by SDS-PAGE gel and imaged using Cy5 specific settings on a Chemidoc MP Imaging System (Bio-Rad). The SDS-PAGE gels were then coomassie stained and imaged.

5PrW containing proteins were labeled using the Click-iT Plus Alexa Fluor Picolyl Azide kit (Life Technologies) with a modified protocol. The following were mixed in order: 1 µg protein (4 µL), 3 µL 10× buffer additive, 0.3 µL 100 mM CuSO$_4$, 0.3 µL copper protectant, 1.2 µL Alexa 488 PCA (50 µM, 2 µM final), 21.2 µL 1× Click-iT reaction buffer, to a final volume of 30 µL. Samples were incubated for 40 min in dark and subsequently resolved by SDS-PAGE and imaged using the Chemidoc MP Imaging System (Bio-Rad) with Alexa 488 specific settings.

Tryptic Digestion and LC-MS/MS Analysis of reporter proteins. 12 µg purified reporter protein was treated with DMSO (0.2 µM) and precipitated with 5 µL 100% solution of trichloracetic acid. Sample was frozen at −80 C overnight. Thawed sample was centrifuged at 15000 rpm for 10 min, room temp. Supernatant was removed and pellets were vortexed to resuspend in 500 µL cold acetone. Samples were then centrifuged at 5000 rpm for 10 min. Acetone was then removed and pellet was allowed to air dry. Pellet was resuspended in 30 µL 8M urea in PBS, followed by 70 µL 100 mM ammonium bicarbonate and then 1.5 µL 1 M DTT was added. Samples were incubated at 65° C. for 15 minutes. After incubation, 2.5 µL of 500 mM iodoacetamide in PBS was added and the sample was left at room temperature for 30 minutes. Following incubation, 120 µL PBS was added to each sample and vortexed rapidly. 4 µL of trypsin was added to samples, followed by 2.5 µL 100 mM CaCl$_2$. Samples were then agitated for 37° C. overnight. Trypsin was then quenched with 10 µL formic acid and pelleted at 15,000 rpm for 20 min. Supernatants were stored at −20° C.

Samples were subsequently analyzed by LC MS/MS using a LTQ Orbitrap XL mass spectrometer (ThermoFisher) coupled to an EASY-nLC 1000 nanoLC (ThermoFisher). 10 µL samples were loaded onto 100 µm fused silica column with a 5 µm tip packed with 10 cm of Aqua C18 reverse phase resin (Phenomenex) using the EASY-nLC 1000 autosampler. The digests were eluted using a gradient 0-100% Buffer B in Buffer A (Buffer A: 95% water, 5% acetonitrile, 0.1% formic acid; Buffer B; 20% water, 80% acetonitrile, 0.1% formic acid). The flow rate through the column was set to 400 nL/min and the spray voltage was set to 3.5 kV. One fuL1 MS scan (FTMS) (400-1800 MW) was followed by 7 data dependent scans (ITMS) of the nth most intense ion from the imported mass list with dynamic exclusion. The tandem MS data were searched using the SEQUEST algorithm using a concatenated target/decoy variant of the human IPI databases. A static modification of +57.02146 on cysteine was specified to account for iodoacetamide alkylation. SEQUEST output files were filtered using DTASelect 2.0.

Construction of Various Plasmids

Complementation plasm id pUltraG_ScW40$_{CCA}$. Previously reported pUltra Hit14, containing a tacI promoted wild type yeast tryptophanyl-tRNA synthetase and proK promoted evolved yeast tRNA amber suppressor,[14] was used to generate additional pUltra derivatives. To generate pUltra_ScW40$_{CUA}$, a previously evolved tRNA 40A was amplified from 40A gblock (IDT) using primers proK-F and TrpH NcoI-R.[15] The full-length proK-tRNA PCR product was cloned into pUltra Hit14 via SbfI/NcoI (NEB), producing pUltra ScW40$_{CUA}$.

To build pUltraG_ScW40$_{CCA}$, a complementation plasmid with a constitutively active synthetase, the tacI promoter region was removed by digesting the pUltra_ScW40$_{CUA}$ vector with XbaI/SbfI, and a glnS'-ScWRS cassette was amplified from an pEVOL[8] derived plasmid, pEvol ScW, using glnS-XbaI-F+glnS-SbfI-R and subsequently cloned using the same set of restriction sites. The 40A tRNA anticodon was then mutated to CCA using overlap extension PCR. The two PCR products were amplified with proK-F+Trp40CCA-iR and Trp40CCA-iF+SmR-R, overlap extended, and cloned into pUltraG_ScW40$_{CUA}$ using SbfI/NcoI, producing the final complementation plasmid pUltraG_ScW40$_{CCA}$.

Construction of selection plasmids. To generate the TAG positive selection plasmid, pRep-ScW14[14] was digested with SpeI/BglII. The lpp-promoted *E. coli* tRNA$^{Trp}_{CUA}$ was amplified from gblock I-EcWtR TAG with pNP-SpeI-F+pNP-BAB-R. The PCR product was digested with SpeI/BamHI, and cloned into the SpeI/BglII sites of the prep vector creating pRepAC-EcWtR-TAG.

In order to create a selection plasmid based on TGA suppression, a smaller pRep-Cm3b[32] was used as a starting template. In order to delete the chloramphenicol-UPP fusion protein, chloramphenicol acetyl transferase was amplified from pEvol[33] with pEvol CmR SpeI-F+pEvol CmR PstI-R, digested with SpeI/PstI, and ligated into the same sites of pRep-Cm3b, creating pRep-Cm3J-wt. TGA sites were introduced into the CAT gene by replacing G7, 184, or Q98 via site-directed mutagenesis using primers CmR-TGA-7, CmR-TGA-84, or CmR-TGAT-98, building three different reporters. The lpp-promoted *E. coli* tRNA$^{Trp}_{CUA}$ was amplified from pRepAC-EcWtR-TAG with pRep-KpnI-tR-F and pRep-EcWtR-NdeI/AvrII-R and cloned via KpnI/AvrII into these pRep-Cm3J plasmids, creating three different pRep-Cm3J-#TGA-EcWtR TAG. The anti-codon of the tRNA was mutated to TGA using site-directed mutagenesis with primer EcWtR-TGA-MSDM. While all three reporter plasmids exhibited desired phenotypes upon TGA suppression, pRep-Cm3J-98TGA-EcWtR was used for the subsequent cloning steps.

To add the T7 RNA polymerase-GFPuv reporter system into pRep-Cm3J-98TGA-EcWtR, these elements were amplified from pRepAC-EcWtR-TAG using multiple overlap extension PCR reactions to change the two TAG nonsense codons in the T7RP gene to TGA: Three PCR products were first amplified using T7F1+T7R3, T7F3+T7R4b, T7F4+T7R5, which were overlapped to produce T7-araC PCR cassette. This cassette was first cloned back into pRepAC-EcWtR-TAG via KpnI/NsiI, and then the entire GFP-T7araC cassette was amplified from the resulting plasmid with T7_mut-SbfI-F+T7_mut-NotI/SbfI-R, digested with SbfI, and ligated into the PstI site of pRep-Cm3J-98TGA-EcWtR vector producing pRepJI-EcW.

The negative selection plasmid was built by modifying an existing pNeg plasmid.[3,4] The two barnase suppression sites (3TAG, 45TAG) were mutated to TGA with site-directed mutagenesis using primers Barnase MSDM 3 TGA and Barnase MSDM 45 TGA, creating plasmid pNegJ2. The *E. coli* tRNA$^{Trp}_{CUA}$ was amplified from pRep-Cm3J-98TGA-EcWtR with pRep_NegtR-EcoRI-R and pRep_KpnI-tR-F and then cloned into pNegJ2, replacing the preexisting tRNA, creating pNegJ2-EcW.

Construction of bacterial suppression plasmids. Since ATMW1 uses the pUltraG plasmid to express the yeast tryptophanyl pair, the suppression plasmids cannot use the CloDF13 origin of replication, or the spectinomycin marker. The previously described pEvoltac MjY plasmid,[8] which harbors a compatible p15a origin of replication and a chloramphenicol resistance marker, was used as the template to generate these plasmids. The plasmids pEvolT5 EcW sfGFP151 (TAG or TGA) were built to allow the rapid evaluation of various EcTrpRS mutants isolated from the selection scheme (encoded in pBK vector). Initially, a t5.lac-promoted sfGFP-151-TAG was amplified from pET22b-T5-sfGFP151TAG using GFPflip-NotI-F+sfGFP-T7+1am-PstI-R and subsequently cloned into pEvoltac MjY using EcoNI/PstI, to generate pEvolT5 MjY sfGFP151TAG.

A proK-promoted *E. coli* tRNA$^{Trp}_{CUA}$ was assembled by overlap extension as follows. The proK promoter was amplified from pUltraG ScW40 using EcWtR-PstI-F+EcWtR proK-oR, which was overlapped with tRNA$^{EcTrp}_{CUA}$ amplified with EcWtR-proK-oF and EcWtR-KpnI-R. This PCR product was cloned into pEvoltac MjY sfGFP151TAG using PstI/KpnI, producing pEvoltac MjY EcWtR sfGFP151TAG. The MjY tRNA was removed by using Polymerase Incomplete Primer Extension (PIPE) cloning with primers MjYtR-del-oF and MjYtR-del-oR, producing the final plasmid pEvolT5-EcW-sfGFP151TAG. Additionally, site-directed mutagenesis was used to build the TGA reporter pEvolT5-EcW-sfGFP151TGA with primers sfGFP(pEvol)TGA151 and EcWtR TGA MSDM.

For more efficient protein expression using evolved tRNA/aaRS pairs, plasmids containing the proK promoted tRNA$^{EcTrp}_{UCA}$ and tacI promoted EcWRS-h14 or -h9 were assembled. The tRNA in pEvoltac MjY was first replaced by amplifying the EcTrp-tRNA$_{UCA}$ from pEvoltac-EcW-sfGFP151TGA with EcWtR PstI-F and pUltraII-tRsqR, and subsequently cloning into PstI/SphI to generate pEvoltac-EcW-MjYRS. EcWRS-h14 and -h9 were then amplified from their respective pBK plasmids using EcWRS1.FA.NotI-F and EcWRS-NotI-R, digested with NotI, and cloned into NotI-digested pEvoltac-EcW-MjYRS-pAcF, producing pEvoltac-EcW-TGA-h14 or h9.

pBK MjYRS[4] was used as a template to introduce tryptophanyl-tRNA synthetase variants. Top 10 genomic DNA was purified using previously described protocols,[34] and used as the template to amplify the EcTrpRS using EcTrpRS-NdeI-F and EcTrpRS-PstI-R. The PCR product was digested with NdeI/PstI, producing pBK EcWRS.

Construction of mammalian suppression plasmids. Previously reported pAcBac1 was used to generate mammalian reporter and suppression plasmids.[30] To build pAcBac1 TrpRS, EcTrpRS was amplified from Top 10 genomic DNA with TrpRS-F-NheI+TrpRS-R-EcoRI and subsequently cloned into pAcBac1 via NheI/EcoRI. U6-EcWtR Gblock was used as a template and amplified with tRNAtrp*-NheI-R+tRNAtrp* Nhe-R to produce the human U6 promoted. *E. coli* tRNA$^{EcTrp}_{CUA}$ PCR product. This PCR product was then digested with AvrII/NheI and cloned into the AvrII site in the pAcBac variants, resulting in pAcBac1-TrpRS-U6EcWtR-TAG and pAcBac1-EGFP39*-U6EcWtR-TAG. EcWRS-h14 and -h9 synthetase variants were cloned into the pAcBac1-TrpRS-U6EcWtR-TAG plasmid via NheI/EcoRI digestion after amplification with EcWRS_mamNheI-F+EcWRS_mamEcoRI-R to make pAcBac1-EcWRS-h14-U6EcWtR-TAG and pAcBac1-EcWRS-h9-U6EcWtR-TAG.

Unnatural amino acids. 5HTP and 5MTP were purchased from Fisher Scientific, 5BrW and 5AmW were purchased from Chem-Impex International (Wood Dale, Ill.). AzK was purchased from Sirius Fine Chemicals. 5AzW was synthesized as previously described.[35]

Yield of sfGFP reporters incorporating various UAAs expressed in ATMW1 are shown in Table 3, below.

TABLE 3

| UAA | aaRS | Yield (mg/L) |
|---|---|---|
| 5HTP | h14 | 92 |
| 5MTP | h14 | 89 |
| 5BrW | h14 | 25 |
| 5AzW | h14 | 80 |
| 5PrW | h14 | 61 |
| 5AmW | h9 | 68 |
| sfGFPwt | N/A | 140 |

REFERENCES

1. Chin, J. W. Expanding and reprogramming the genetic code of cells and animals. *Annu. Rev. Biochem.* 83, 379-408 (2014).
2. Dumas, A., Lercher, L., Spicer, C. D. & Davis, B. G. Designing logical codon reassignment-Expanding the chemistry in biology. *Chem. Sci.* 6, 50-69 (2015).
3. Liu, C. C. & Schultz, P. G. Adding new chemistries to the genetic code. *Annu. Rev. Biochem.* 79, 413-444 (2010).
4. Wang, L., Brock, A., Herberich, B. & Schultz, P. G. Expanding the genetic code of *Escherichia coli, Science* 292, 498-500 (2001).
5. Chin, J. W. et al. An expanded eukaryotic genetic code. *Science* 301, 964-967 (2003).
6. Wan, W., Tharp, J. M. & Liu, W. R. Pyrrolysyl-tRNA synthetase: an ordinary enzyme but an outstanding genetic code expansion tool. *Biochim. Biophys. Acta* 1844, 1059-1070 (2014).
7. Anderson, J. C. et al. An expanded genetic code with a functional quadruplet codon. *Proc. Natl. Acad. Sci. USA* 101, 7566-7571 (2004).
8. Chatterjee, A., Sun, S. B., Furman, J. L., Xiao, H. & Schultz, P. G. A versatile platform for single- and multiple-unnatural amino acid mutagenesis in *Escherichia coli. Biochemistry* 52, 1828-1837 (2013).
9. Neumann, H., Wang, K., Davis, L., Garcia-Alai, M. & Chin, J. W. Encoding multiple unnatural amino acids via evolution of a quadruplet-decoding ribosome. *Nature* 464, 441-444 (2010).
10. Wan, W. et al. A facile system for genetic incorporation of two different noncanonical amino acids into one protein in *Escherichia coli. Angew. Chem. Int. Ed.* 49, 3211-3214 (2010).
11. Xiao, H. et al. Genetic incorporation of multiple unnatural amino acids into proteins in mammalian cells. *Angew. Chem. Int. Ed.* 52, 14080-14083 (2013).
12. Iraha, F. et al. Functional replacement of the endogenous tyrosyl-tRNA synthetase-tRNATyr pair by the archaeal tyrosine pair in *Escherichia coli* for genetic code expansion. *Nucleic Acids Res.* 38, 3682-3691 (2010).
13. Chatterjee, A., Xiao, H. & Schultz, P. G. Evolution of multiple, mutually orthogonal prolyl-tRNA synthetase/tRNA pairs for unnatural amino acid mutagenesis in *Escherichia coli. Proc. Natl. Acad. Sci. USA* 109, 14841-14846 (2012).
14. Chatterjee, A., Xiao, H., Yang, P. Y., Soundararajan, G. & Schultz, P. G. A tryptophanyl-tRNA synthetase/tRNA pair for unnatural amino acid mutagenesis in *E. coli. Angew. Chem. Int. Ed.* 52, 5106-5109 (2013).
15. Ellefson, J. W. et al. Directed evolution of genetic parts and circuits by compartmentalized partnered replication. *Nat. Biotechnol.* 32, 97-101 (2014).
16. Wang, H. H. et al. Programming cells by multiplex genome engineering and accelerated evolution. *Nature* 460, 894-898 (2009).
17. Warming, S., Costantino, N., Court, D. L., Jenkins, N. A. & Copeland, N. G. Simple and highly efficient BAC recombineering using galK selection. *Nucleic Acids Res.* 33, e36 (2005).
18. Soll, L. & Berg, P. Recessive lethal nonsense suppressor in *Escherichia coli* which inserts glutamine. *Nature* 223, 1340-1342 (1969).
19. Jahn, M., Rogers, M. J. & Soll, D. Anticodon and acceptor stem nucleotides in tRNA(Gln) are major recognition elements for *E. coli* glutaminyl-tRNA synthetase. *Nature* 352, 258-260 (1991).
20. Rogers, M. J., Adachi, T., Inokuchi, H. & Soll, D. Switching tRNA(Gln) identity from glutamine to tryptophan. *Proc. Natl. Acad. Sci. USA* 89, 3463-3467 (1992).
21. Kopelowitz, J., Hampe, C., Goldman, R., Reches, M. & Engelberg-Kulka, H. Influence of codon context on UGA suppression and readthrough. *J. Mol. Biol.* 225, 261-269 (1992).
22. O'Donoghue, P. et al. Near-cognate suppression of amber, opal and quadruplet codons competes with aminoacyl-tRNAPyl for genetic code expansion. *FEBS Lett.* 586, 3931-3937 (2012).
23. Santoro, S. W., Wang, L., Herberich, B., King, D. S. & Schultz, P. G. An efficient system for the evolution of aminoacyl-tRNA synthetase specificity. *Nat. Biotechnol.* 20, 1044-1048 (2002).
24. Zhang, Z. et al. Selective incorporation of 5-hydroxytryptophan into proteins in mammalian cells. *Proc. Natl. Acad. Sci. USA* 101, 8882-8887 (2004).
25. Antonczak, A. K. et al. Importance of single molecular determinants in the fidelity of expanded genetic codes. *Proc. Natl. Acad. Sci. USA* 108, 1320-1325 (2011).
26. Cooley, R. B., Karplus, P. A. & Mehl, R. A. Gleaning unexpected fruits from hard-won synthetases: probing principles of permissivity in non-canonical amino acid-tRNA synthetases. *ChemBioChem* 15, 1810-1819 (2014).
27. Young, D. D. et al. An evolved aminoacyl-tRNA synthetase with atypical polysubstrate specificity. *Biochemistry* 50, 1894-1900 (2011).
28. Prather, N. E., Murgola, E. J. & Mims, B. H. Primary structure of an unusual glycine tRNA UGA, suppressor. *Nucleic Acids Res.* 9, 6421-6428 (1981).
29. Raftery, L. A., Egan, J. B., Cline, S. W. & Yarus, M. Defined set of cloned termination suppressors: in vivo activity of isogenetic UAG, UAA, and UGA suppressor tRNAs. *J. Bacteriol.* 158, 849-859 (1984).
30. Chatterjee, A., Xiao, H., Bollong, M., Ai, H. W. & Schultz, P. G. Efficient viral delivery system for unnatural amino acid mutagenesis in mammalian cells. *Proc. Natl. Acad. Sci. USA* 110, 11803-11808 (2013).
31. Guo, J., Melancon, C. E., 3rd, Lee, H. S., Groff, D. & Schultz, P. G. Evolution of amber suppressor tRNAs for efficient bacterial production of proteins containing nonnatural amino acids. *Angew. Chem. Int. Ed.* 48, 9148-9151 (2009).
32. Melancon, C. E., 3rd & Schultz, P. G. One plasmid selection system for the rapid evolution of aminoacyl-tRNA synthetases. *Bioorg. Med. Chem. Lett.* 19, 3845-3847 (2009).
33. Young, T. S., Ahmad, I., Yin, J. A. & Schultz, P. G. An enhanced system for unnatural amino acid mutagenesis in *E. coli. J. Mol. Biol.* 395, 361-374 (2010).
34. Syn, C. K. & Swarup, S. A scalable protocol for the isolation of large-sized genomic DNA within an hour from several bacteria. *Anal. Biochem.* 278, 86-90 (2000).
35. Li, M. & Johnson, M. E. An efficient synthesis of 5-azidotryptophan. *Tetrahedron Lett.* 35, 6255-6258 (1994).

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of producing orthogonal aminoacyl synthetase-tRNA pairs that aminoacylate unnatural amino acids for incorporation of unnatural amino acids into specific sites in proteins produced in *E. coli* or eukaryotic cells, the method comprising the steps of:
   a. introducing into an *E. coli* host cell an orthogonal eukaryotic or archaeal aminoacyl synthetase-tRNA pair for a target amino acid resulting in an *E.coli* host cell comprising an endogenous *E.coli* aminoacyl synthetase-tRNA pair for an amino acid and a counter-part orthogonal eukaryotic or archaeal aminoacyl synthetase-tRNA pair for the same amino acid, wherein:
      i) the introduced orthogonal eukaryotic or archaeal aminoacyl synthetase-tRNA pair does not cross-react with the *E. coli* host cell's counter-part endogenous *E.coli* aminoacyl synthetase-tRNA pair; and
      ii) the introduced orthogonal eukaryotic or archaeal aminoacyl synthetase-tRNA pair does not result in a growth rate defect in the *E. coli* host cell;
   b. deleting the endogenous *E. coli* aminoacyl synthetase-tRNA pair from the *E. coli* host cell, wherein the orthogonal eukaryotic or archaeal aminoacyl synthetase-tRNA pair of step a. replaces the endogenous *E.coli* aminoacyl synthetase-tRNA pair and its aminoacylation function, resulting in an altered translational machinery (ATM) *E. coli* cell;
   c. culturing the ATM *E. coli* cells of step b. under suitable culture conditions and monitoring the growth rate of the ATM *E. coli* cells and the growth rate of the *E. coli* host cells and selecting the ATM *E. coli* cells with no observable growth rate defect when compared to the growth rate of the *E. coli* host cells;
   d. constructing a library of *E. coli* aminoacyl synthetase variants corresponding to the aminoacyl synthetase of the deleted endogenous *E. coli* aminoacyl synthetase-tRNA pair of step b., wherein the variants selectively aminoacylate an unnatural amino acid;
   e. mutating the anti-codon of an *E. coli* tRNA corresponding to the tRNA of the deleted endogenous *E. coli* aminoacyl synthetase-tRNA pair of step b., resulting in a mutated *E.coli* tRNA comprising an anti-codon that recognizes a nonsense or stop codon;
   f. introducing the library of *E. coli* aminoacyl synthetase variants of step d. with the mutated *E.coli* tRNA of step e. and the unnatural amino acid that is selectively aminoacylated in step d. into the selected ATM *E. coli* cells of step c.; and
   g. subjecting the *E.coli* aminoacyl synthetase variants in the ATM *E.coli* cells to directed evolution to select one or more *E. coli* aminoacyl synthetase variants that aminoacylate the mutated *E.coli* tRNA with the unnatural amino acid, thereby producing an orthogonal aminoacyl synthetase-tRNA pair comprising an *E. coli* aminoacyl synthetase variant and a mutated *E. coli* tRNA that aminoacylates unnatural amino acids for incorporation of the unnatural amino acids into specific sites in proteins produced in *E. coli* and eukaryotic cells.

2. The method of claim 1, wherein in step b. the deleted endogenous *E.coli* aminoacyl synthetase-tRNA pair is-a TrpRS-tRNA$^{Trp}$ pair.

3. The method of claim 1, wherein in step e. the mutated *E.coli* tRNA recognizes an amber or opal selector codon.

4. The method of claim 1, wherein in step a., the orthogonal eukaryotic or archaeal aminoacyl synthetase t-RNA pair introduced into the *E. coli* host cell is an aminoacyl-tRNA$^{typ}$ pair; in step d., the unnatural amino acid is a tryptophan analog; in step f., the unnatural amino acid is a tryptophan analog; and in step g., the unnatural amino acid is a tryptophan analog, thereby producing an orthogonal aminoacyl synthetase-tRNA pair that aminoacylates and incorporates a tryptophan analog in specific sites of the *E.coli* or eukaryotic protein.

5. The method of claim 4, wherein the produced orthogonal aminoacyl synthetase-tRNA pair aminoacylates a tryptophan analog selected from the group consisting of: 5-azidotryptophan, 5-propargyloxytryptophan, 5-aminotryptophan, 5-methoxytryptophan, 5-O-allyltryptophan, or 5-bromotryptophan.

6. The method of claim 1, wherein the orthogonal eukaryotic or archaeal aminoacyl synthetase-tRNA pair of step a. is derived from yeast.

7. The method of claim 1, wherein the produced orthogonal aminoacyl synthetase-tRNA pair is an aminoacyl synthetase-tRNAUP pair.

* * * * *

UNITED STATES PATENT AND TRADEMARK OFFICE
CERTIFICATE OF CORRECTION

PATENT NO. : 12,203,115 B2
APPLICATION NO. : 16/934484
DATED : January 21, 2025
INVENTOR(S) : Abhishek Chatterjee et al.

Page 1 of 1

It is certified that error appears in the above-identified patent and that said Letters Patent is hereby corrected as shown below:

In the Claims

In Claim 7, Column 122, Line 43, delete "synthetase-tRNAUP," and insert -- synthetase-tRNA$^{trp}$, --.

Signed and Sealed this
Fourth Day of March, 2025

Coke Morgan Stewart
*Acting Director of the United States Patent and Trademark Office*

SEQUENCE LISTING

<160> NUMBER OF SEQ ID NOS: 91

<210> SEQ ID NO 1
<211> LENGTH: 73
<212> TYPE: RNA
<213> ORGANISM: Escherichia coli
<220> FEATURE:
<223> OTHER INFORMATION: strain K-12

<400> SEQUENCE: 1
aggggcguag uucaauuggu agagcaccgg ucuccaaaac cggguguugg gaguucgagu    60
cucuccgccc cug                                                      73

<210> SEQ ID NO 2
<211> LENGTH: 72
<212> TYPE: RNA
<213> ORGANISM: Escherichia coli
<220> FEATURE:
<223> OTHER INFORMATION: strain K-12

<400> SEQUENCE: 2 uggggu aucg ccaagcggua aggcaccgga uucugauucc ggcauuccga gguucgaauc    60
cucguacccc ag                                                       72

<210> SEQ ID NO 3
<211> LENGTH: 76
<212> TYPE: DNA
<213> ORGANISM: Escherichia coli
<220> FEATURE:
<223> OTHER INFORMATION: strain K-12

<400> SEQUENCE: 3
aggggcgtag ttcaattggt agagcaccgg tctccaaaac cgggtgttgg gagttcgagt    60
ctctccgccc ctgcca                                                   76

<210> SEQ ID NO 4
<211> LENGTH: 75
<212> TYPE: DNA
<213> ORGANISM: Escherichia coli
<220> FEATURE:
<223> OTHER INFORMATION: strain K-12

<400> SEQUENCE: 4
tggggtatcg ccaagcggta aggcaccgga ttctgattcc ggcattccga ggttcgaatc    60
ctcgtacccc agcca                                                    75

<210> SEQ ID NO 5
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MISC_FEATURE
<222> LOCATION: (12)..(12)
<223> OTHER INFORMATION: May or may not be present

<400> SEQUENCE: 5
aggggcatag ctcaagcggt aaagcaccgg actccaaaac cggcagtccg aagttcgaat    60 cccccccaccc cagcca                                                  76

<210> SEQ ID NO 6

```
<211> LENGTH: 90
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 6
atcagtctat aaatgacctt ctgcccgcat tagggcttcc gcatagcgaa aatcaggaat      60
cgaaaaaggt gttgacaatt aatcatcggc                                      90

<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgtaggccgg ataaggcgtt cacgccgcat ccggcatgaa caaagcgcaa tttgccagca      60
atagtgaaag cttgcaaatt aaagccttcg                                      90

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtcggcgact cacgcaatga tattcaggcg gc                                   32

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agcgagatgt ggaaacggcg aggcacttca c                                    31

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctggtcctgg accgcgctga tgaac                                           25

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atcctggcgc acggtgatcg cgtgttg                                         27
```

<210> SEQ ID NO 12
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cagtcggtta gaatacctgc ctgtcacgca gggggtcgcg ggttcgagtc ccgtccgttc    60
cgccacccta attacgcaca ccgtggaaac                                     90

<210> SEQ ID NO 13
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cggtagaagg atttacttcg gagagggtta tttcagataa aaaaaatcct tagctttcgc    60
taaggatgat ttcccgggaa gccgatctcg                                     90

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggggtctccc catgcgagag tagggaac                                       28

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccgttgtcga tagcacaaca ctttcacggc c                                   31

<210> SEQ ID NO 16
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cgcgcagtca gcgatatcca ttttcgcgaa tccggagtgt aagaacgcgc agtcagcgat    60
atccattttc gcgaatccgg agtgtaagaa                                     90

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic

```
                           oligonucleotide

<400> SEQUENCE: 17
tggcagagac ccagcg                                                     16

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
accccagtcc atcagcg                                                    17

<210> SEQ ID NO 19
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gctatgaaat agaaaaatga atccgttgaa gcctgctttt ttatactaac ttgagcgaaa    60
cgggaagcct gttgacaatt aatcatcggc                                      90

<210> SEQ ID NO 20
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gccgcgttga ttttctcctg ccagctcata atgctgccgc gttgtaatat tcagcactgt    60
cctgctcctt                                                            70

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggtttgatca gaaggacgtt gatcgggcgg                                      30

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttcagatact ggcgatcatc cgccaccag                                       29

<210> SEQ ID NO 23
<211> LENGTH: 35
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 23
agcccattga tagttttcat gtgcgacaat gggcg                                35

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other

<400> SEQUENCE: 24
gaatcccata tgatgactaa gcccatcgtt nbtnstggcg cacagccctc aggtgaattg      60

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
tacgctttga ggaatcccat atgatgacta agcccatcg                             39

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
cagattagtt tgatacagca ggatgtccgc tgccatc                               37

<210> SEQ ID NO 27
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 27

```
gatggcagcg acatcctgc tgtatcaaac taatctgnnk nnknnkggtg aagaccagaa      60
acagcacctc gaactgagc                                                  79

<210> SEQ ID NO 28
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agcgtttgaa actgcagcca tggtacctta cggcttcgcc acaaaccaa tcgc            54

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gttagcctgc aggtaattcc gcttcgcaac atgtgag                              37

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggccgccatg gcaaattcga ccctg                                           25

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcaaccaggc gctttggagg cgccagctct acccttgag                            39

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agctggcgcc tccaaagcgc ctggttgcag gttc                                 34

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
```
cgcgcgcaga tcagttggaa gaatttgtcc actacgtg        38

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ataatggact agtgcgcttg tttcggc        27

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ctccttagat cttcctaggt ggatccacca ttcc        34

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aataatacta gtgttgatac cgggaagccc tgg        33

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aataatctgc agcgaatttc tgccattcat ccgcttatta tcac        44

<210> SEQ ID NO 38
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gctaaggaag ctaaaatgga gaaaaaaatc acttgatata ccaccgttga tatatcccaa        60
tggc        64

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcaatgaaag acggtgagct ggtgtgatgg gatagtgttc acccttgtta cacc    54

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cccttgttac accgttttcc atgagtgatc tgaaacgttt tcatcgctct ggag    54

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aataataggt accgttctgt tgcccgtctc actggtg    37

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aataatacat atgcctaggt ggcaggggcg gagagactc    39

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gttcaattgg tagagcaccg gtcttcaaaa ccgggtgttg ggagttcgag    50

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
caggttcgca gcgtcagccg gaatggtacc g    31

<210> SEQ ID NO 45
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
gcgcccgaca gccttccagt tcctgtgaga aatcaagccg gaagccgtag cgtac        55
```

<210> SEQ ID NO 46
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
gtacgctacg gcttccggct tgatttctca caggaactgg aaggctgtcg ggcgc        55
```

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
ccatgaccat gattaccgtg cactgaaata ccattaacat tgctaagaac g            51
```

<210> SEQ ID NO 48
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48

```
cgttcttagc aatgttaatg gtattucagt gcacggtaat catggtcatg g            51
```

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

```
cgaaggcgaa gcggcatgca taatgtgcct gtcaaatgg                          39
```

<210> SEQ ID NO 50
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
aataatcctg caggctactc aggagagcgt tcaccgac                           38
```

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aataatcctg cagggcggcc gctacgggag ggcttaccat ctgg                    44

<210> SEQ ID NO 52
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttaacttta agaaggagat atacatatgg catgagttat caacacgttt gacggggttg   60

<210> SEQ ID NO 53
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtggcatcaa aagggaacct tgcatgagtc gctccgggga aaagcatc                48

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttagcctgca gtgtgcttct caaatgcctg aggccagttt gctc                    44

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcgccccgca tttaggggcg tagttcaatt ggtagagcac cggtc                   45

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
actacgcccc taaatgcggg gcgcatctta ctgcgc                             36

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atatatggta ccaaaaaatg gcaggggcgg agagactcg            39

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tcgatcccgc gaaattaata cgactcacta tag                  33

<210> SEQ ID NO 59
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
atatactgca gcgccaagct agcttggatt ctcaccaata aaaaacgc   48

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tggcaggggc ggagagactc gaactcc                         27

<210> SEQ ID NO 61
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cgagtctctc cgcccctgcc aaattcgaaa agcctgctca acgagcagg  49

<210> SEQ ID NO 62
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gttcaattgg tagagcaccg gtcttcaaaa ccgggtgttg ggagttcgag 50

<210> SEQ ID NO 63
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
ctcgagtaca actttaactc acacaatgta tgaatcacgg cagacaaaca aaagaatgg      59
```

<210> SEQ ID NO 64
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
aataatagcg ccgcatgac taagcccatc gttttgctg gcgcac                     46
```

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

```
aataatagcg ccgcttacg gcttcgccac aaaaccaatc gc                        42
```

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66

```
ggtgcccta aacgcctggt tgc                                             23
```

<210> SEQ ID NO 67
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67

```
aataaacata tgatgactaa gcccatcgtt tttagtggcg cac                      43
```

<210> SEQ ID NO 68
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68

```
ttattctgca gttacggctt cgccacaaaa ccaatcgc                            38
```

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
attattgaat tcttacggct tcgccacaa                                      29

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aataaatgct agcatgacta agcccatc                                       28

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aattattgct agcaaaaaat ggcaggggcg                                     30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aattattgct agcaaaaaat ggcaggggcg                                     30

<210> SEQ ID NO 73
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aataatagct agcgccacca tgactaagcc catcgtt                             37

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aataatagaa ttcttacggc ttcgccacaa aaccaatcgc                          40

<210> SEQ ID NO 75
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
atcagtctat aaatgacctt ctgcccgcat tagggcttcc gcatagcgaa aatcaggaat    60

```
cgaaaaaggt gttgacaatt aatcatcggc atagtatatt ggcatagtat aatacgacaa    120
ggtgaggaac taaccatgg ccaagctgac cagtgccgtt ccggtgctca ccgcgcgcga     180
cgtcgccgga gcggtcgagt tctggaccga ccggctcggg ttctcccggg acttcgtgga   240
ggacgacttc gccggtgtgg tccgggacga cgtgaccctg ttcatcagcg cggtccagga   300
ccaggtggtg ccggacaaca ccctggcctg ggtgtgggtg cgcggcctgg acgagctgta   360
cgccgagtgg tcgaggtcg tgtccacgaa cttccgggac gcctccgggc cggccatgac    420
cgagatcggc gagcagccgt ggggcggga ttcgccctg cgcgacccgg ccggcaactg     480
cgtgcacttc gtggccgagg agcaggactg acacgtccga cggcggccca cgggtcccag   540
gcctcggaga tccgtccccc ttttcctttg tcgatatcat gtaattagtt atgtcacgct   600
tacattcacg ccctccccccc acatccgctc taaccgaaaa ggaaggagtt agacaacctg   660
aagtctaggt ccctatttat tttttatag ttatgttagt attaagaacg ttatttatat    720
ttcaaatttt tctttttttt ctgtacagac gcgtgtacgc atgtaacatt atactgaaaa   780
ccttgcttga gaaggttttg ggacgctcga aggctttaat ttgcaagctt tcactattgc   840
tggcaaattg cgctttgttc atgccggatg cggcgtgaac gccttatccg gcctaca      897
```

<210> SEQ ID NO 76
<211> LENGTH: 965
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
cagtcggtta gaatacctgc ctgtcacgca gggggtcgcg ggttcgagtc ccgtccgttc     60
cgccacccta attacgcaca ccgtggaaac ggatgaaggc acgaacccag ttgacataag   120
cctgttcggt tcgtaaactg taatgcaagt agcgtatgcg ctcacgcaac tggtccagaa   180
ccttgaccga acgcagcggt ggtaacggcg cagtggcggt tttcatggct tgttatgact   240 gttttttgt acagtctatg cctcgggcat ccaagcagca agcgcgttac gccgtgggtc   300
gatgtttgat gttatggagc agcaacgatg ttacgcagca gcaacgatgt tacgcagcag   360
ggcagtcgcc ctaaaacaaa gttaggtggc tcaagtatgg gcatcattcg cacatgtagg   420
ctcggccctg accaagtcaa atccatgcgg gctgctcttg atcttttcgg tcgtgagttc   480
ggagacgtag ccacctactc ccaacatcag ccggactccg attacctcgg gaacttgctc   540
cgtagtaaga cattcatcgc gcttgctgcc ttcgaccaag aagcggttgt tggcgctctc   600
gcggcttacg ttctgcccag gtttgagcag ccgcgtagtg agatctatat ctatgatctc   660
gcagtctccg gcgagcaccg gaggcagggc attgccaccg cgctcatcaa tctcctcaag   720
catgaggcca acgcgcttgg tgcttatgtg atctacgtgc aagcagatta cggtgacgat   780
cccgcagtgg ctctctatac aaagttgggc atacgggaag aagtgatgca ctttgatatc   840
gacccaagta ccgccaccta acaattcgtt caagccgaga tcggcttccc gggaaatcat   900
ccttagcgaa agctaaggat ttttttatc tgaaataacc ctctccgaag taaatccttc    960
taccg                                                              965
```

<210> SEQ ID NO 77
<211> LENGTH: 1348
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 77
gctatgaaat agaaaaatga atccgttgaa gcctgctttt ttatactaac ttgagcgaaa      60
cgggaagcct gttgacaatt aatcatcggc atagtatatc ggcatagtat aatacgacaa     120
ggtgaggaac taaacccagg aggcagatca tgagtctgaa agaaaaaaca caatctctgt     180
ttgccaacgc atttggctac cctgccactc acaccattca ggcgcctggc cgcgtgaatt     240
tgattggtga acacaccgac tacaacgacg gtttcgttct gccctgcgcg attgattatc     300
aaaccgtgat cagttgtgca ccacgcgatg accgtaaagt tcgcgtgatg cagccgatt     360
atgaaaatca gctcgacgag ttttccctcg atgcgcccat tgtcgcacat gaaaactatc     420
aatgggctaa ctacgttcgt ggcgtggtga acatctgca actgcgtaac aacagcttcg     480
gcggcgtgga catggtgatc agcggcaatg tgccgcaggg tgccgggtta agttcttccg     540
cttcactgga agtcgcggtc ggaaccgtat tgcagcagct ttatcatctg ccgctggacg     600
gcgcacaaat cgcgcttaac ggtcaggaag cagaaaacca gtttgtaggc tgtaactgcg     660
ggatcatgga tcagctaatt ccgcgctcg gcaagaaaga tcatgccttg ctgatcgatt     720
gccgctcact ggggaccaaa gcagtttcca tgcccaaagg tgtggctgtc gtcatcatca     780
acagtaactt caaacgtacc ctggttggca gcgaatacaa cacccgtcgt gaacagtgcg     840
aaaccggtgc gcgtttcttc cagcagccag ccctgcgtga tgtcaccatt gaagagttca     900
acgctgttgc gcatgaactg gacccgatcg tggcaaaacg cgtgcgtcat atactgactg     960
aaaacgcccg caccgttgaa gctgccagcg cgctggagca aggcgacctg aaacgtatgg    1020
gcgagttgat ggcggagtct catgcctcta tgcgcgatga tttcgaaatc accgtgccgc    1080
aaattgacac tctggtagaa atcgtcaaag ctgtgattgg cgacaaaggt ggcgtacgca    1140
tgaccggcgg cggatttggc ggctgtatcg tcgcgctgat cccggaagag ctggtgcctg    1200
ccgtacagca agctgtcgct gaacaatatg aagcaaaaac aggtattaaa gagactttt    1260
acgtttgtaa accatcacaa ggagcaggac agtgctgaat attacaacgc ggcagcatta    1320
tgagctggca ggagaaaatc aacgcggc                                       1348

<210> SEQ ID NO 78
<211> LENGTH: 3919
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
ggtaattccg cttcgcaaca tgtgagcacc ggtttattga ctacaggaag cagtgtgacc      60
gtgtgcttct caaatgcctg aggccagttt gctcaggctc tccccgtgga ggtaataatt     120
gacgatatga tcagtgcacg gctaactaag cggcctgctg actttctcgc cgatcaaaag     180
gcattttgct attaagggat tgacgagggc gtatctgcgc agtaagatgc gccccgcatt     240
gaagcggtgg ctcaagggta gagctggcgc ctccaaagcg cctggttgca ggttcaagtc     300
ctgcccgttt caccaaattc gaaaagcctg ctcaacgagc aggctttttt gcatgctcga     360
gcagctcagg gtcgaatttg ccatggcggc caccaggtac caccggcgcc tcaggcattt     420
gagaagcaca cggtcacact gcttccggta gtcaataaac cggtaaacca gcaatagaca     480
```

```
taagcggcta tttaacgacc ctgccctgaa ccgacgaccg ggtcatcgtg gccggatctt      540
gcggcccctc ggcttgaacg aattgttaga cattatttgc cgactacctt ggtgatctcg      600
cctttcacgt agtggacaaa ttcttccaac tgatctgcgc gcgaggccaa gcgatcttct      660
tcttgtccaa gataagcctg tctagcttca agtatgacgg gctgatactg ggccggcagg      720
cgctccattg cccagtcggc agcgacatcc ttcggcgcga ttttgccggt tactgcgctg      780
taccaaatgc gggacaacgt aagcactaca tttcgctcat cgccagccca gtcgggcggc      840
gagttccata gcgttaaggt ttcatttagc gcctcaaata gatcctgttc aggaaccgga      900
tcaaagagtt cctccgccgc tggacctacc aaggcaacgc tatgttctct tgcttttgtc      960
agcaagatag ccagatcaat gtcgatcgtg gctggctcga agatacctgc aagaatgtca     1020
ttgcgctgcc attctccaaa ttgcagttcg cgcttagctg gataacgcca cggaatgatg     1080
tcgtcgtgca caacaatggt gacttctaca gcgcggagaa tctcgctctc tccaggggaa     1140
gccgaagttt ccaaaaggtc gttgatcaaa gctcgccgcg ttgtttcatc aagccttacg     1200
gtcaccgtaa ccagcaaatc aatatcactg tgtggcttca ggccgccatc cactgcggag     1260
ccgtacaaat gtacggccag caacgtcggt tcgagatggc gctcgatgac gccaactacc     1320
tctgatagtt gagtcgatac ttcggcgatc accgcttccc tcatactctt ccttttcaa      1380 tattattgaa gcatttatca gggttattgt ctcatgagcg gatacatatt tgaatgtatt     1440
tagaaaaata aacaaatagc tagctcactc ggtcgctacg ctccgggcgt gagactgcgg     1500
cgggcgctgc ggacacatac aaagttaccc acagattccg tggataagca ggggactaac     1560
atgtgaggca aaacagcagg gccgcgccgg tggcgttttt ccataggctc cgccctcctg     1620
ccagagttca cataaacaga cgcttttccg gtgcatctgt gggagccgtg aggctcaacc     1680
atgaatctga cagtacgggc gaaacccgac aggacttaaa gatccccacc gtttccggcg     1740
ggtcgctccc tcttgcgctc tcctgttccg accctgccgt ttaccggata cctgttccgc     1800
ctttctccct tacgggaagt gtggcgcttt ctcatagctc acacactggt atctcggctc     1860
ggtgtaggtc gttcgctcca agctgggctg taagcaagaa ctccccgttc agcccgactg     1920
ctgcgcctta tccggtaact gttcacttga gtccaacccg gaaaagcacg gtaaaacgcc     1980
actggcagca gccattggta actgggagtt cgcagaggat tgtttagct aaacacgcgg      2040 ttgctcttga agtgtgcgcc aaagtccggc tacactggaa ggacagattt ggttgctgtg     2100
ctctgcgaaa gccagttacc acggttaagc agttccccaa ctgacttaac cttcgatcaa     2160
accacctccc caggtggttt tttcgtttac agggcaaaag attacgcgca gaaaaaaagg     2220
atctcaagaa gatcctttga tcttttctac tgaaccgctc tagagtcatc aatcatcccc     2280
ataatccttg ttagattatc aattttaaaa aactaacagt tgtcagcctg tcccgcttta     2340
atatcatacg ccgttatacg ttgtttacgc tttaaggagg cggccgcatg agcaacgacg     2400
aaactgtaga gaaagtcacc caacaagtgt cggaactaaa aagcacagat gttaagagc      2460 aagtagttac accttgggat gtggaaggtg gggttgatga acaaggtaga gcccaaaata     2520
ttgattacga caaattgatc aaacaattcg gtactaagcc ggtcaacgaa gaaaccctga     2580
agagattcaa gcaagtgacg ggtcgtgaac cacatcattt tttgcgtaag ggattgtttt     2640
tcagtgagcg tgacttcact aaaatattag acctttacga caaggcaaa ccatttttcc      2700 tatacactgg tagaggtcct tcgagcgatt ctatgcactt gggtcatatg atcccttttg     2760
tcttcaccaa atggttacag gaagtgtttg acgtaccatt agtcatagag ttgacagatg     2820
acgaaaaatt tttattcaaa cacaagttga ccatcaatga cgttaagaat tttgcccgtg     2880
```

```
aaaatgccaa ggatatcatt gctgttggct ttgacccaaa gaacacctTt atcttttctg    2940
atttgcaata catgggtggt gcattttacg aaactgtagt aagagtttcc agacaaatta    3000
caggatccac tgcaaaggct gttttcgggt ttaatgactc cgactgtatt ggtaagttcc    3060
attttgcctc cattcaaatt gctaccgcat tcccaagctc atttcctaat gtgttaggct    3120
tgcctgataa gacaccatgt ttgattccat gtgcaattga ccaagatcca tatttcagag    3180
tttgtaggga tgtcgcggat aaattgaagt actccaaacc tgctttgctt cattccagat    3240
tctttccagc tttgcaaggt tccacgacca aaatgtcagc ctctgatgat accactgcca    3300
ttttcatgac cgatacacca aagcaaattc aaaagaaaat taacaagtac gcattcagcg    3360
gtggtcaagt gtccgccgac ctacatagag aattaggtgg taatcccgat gtcgatgttg    3420
cataccaata cttgtcattt ttcaaggatg acgatgtttt cttgaaggaa tgctatgaca    3480
aatataagtc cggtgaatta ctatcaggtg aaatgaagaa actgtgtatc gagactctgc    3540
aagaattcgt taaggcgttc caggaacgca gagctcaggt ggacgaagag accttggaca    3600
aattcatggt cccacataag ttggtttggg gcgaaaagga aagacttgtc gcacctaagc    3660
caaaaactaa gcaagaaaag aagtaagcgg ccgctttcaa acgctaaatt gcctgatgcg    3720
ctacgcttat caggcctaca tgatctctgc aatatattga gtttgcgtgc ttttgtaggc    3780
cggataaggc gttcacgccg catccggcaa gaaacagcaa acaatccaaa cgccgcgtt    3840 cagcggcgtt ttttctgctt ttcttcgcga attaattccg cttcgcaaca tgtgagcacc    3900
ggtttattga ctacctgca                                                3919

<210> SEQ ID NO 79
<211> LENGTH: 10131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
gcccttccgg ctggctggtt tattgctgat aaatctggag ccggtgagcg tgggtctcgc      60
ggtatcattg cagcactggg gccagatggt aagccctccc gtatcgtagt tatctacacg     120
acggggagtc aggcaactat ggatgaacga aatagacaga tcgctgagat aggtgcctca     180
ctgattaagc attggtaact gtcagaccaa gtttactcat atatacttta gattgattta     240
aaacttcatt tttaatttaa aaggatctag gtgaagatcc ttttTgataa tctcatgacc     300
aaaatccctt aacgtgagtt ttcgttccac tgagcgtcag accccttaat aagatgatct     360
tcttgagatc gttttggtct gcgcgtaatc tcttgctctg aaaacgaaaa accgccttg      420 cagggcggtt tttcgaaggt tctctgagct accaactctt tgaaccgagg taactggctt     480
ggaggagcgc agtcaccaaa acttgtcctt tcagtttagc cttaaccggc gcatgacttc     540
aagactaact cctctaaatc aattaccagt ggctgctgcc agtggtgctt ttgcatgtct     600
ttccggggtg gactcaagac gatagttacc ggataaggcg cagcggtcgg actgaacggg     660
gggttcgtgc atacagtcca gcttggagcg aactgcctac ccggaactga gtgtcaggcg     720
tggaatgaga caaacgcggc cataacagcg gaatgacacc ggtaaaccga aggcaggaa     780 caggagagcg cacgagggag ccgccagggg gaaacgcctg gtatctttat agtcctgtcg     840
ggtttcgcca ccactgattt gagcgtcaga tttcgtgatg cttgtcaggg gggcggagcc     900
tatggaaaaa cggctttgcc gcggccctct cacttccctg ttaagtatct tcctggcatc     960
```

```
ttccaggaaa tctccgcccc gttcgtaagc catttccgct cgccgcagtc gaacgaccga    1020
gcgtagcgag tcagtgagcg aggaagcgga atatatcctg tatcacatat tctgctgacg    1080
caccggtgca gccttttttc tcctgccaca tgaagcactt cactgacacc ctcatcagtg    1140
ccaacatagt aagccagtat acactccgct agcgctgatg tccggcggtg cttttgccgt    1200
tacgcaccac cccgtcagta gctgaacagg agggacagct gatagaaaca gaagccactg    1260
gagcacctca aaacaccat catacactaa atcagtaagt tggcagcatc acccgacgca    1320
ctttgcgccg aataaatacc tgtgacggaa gatcacttcg cagaataaat aaatcctggt    1380
gtccctgttg ataccgggaa gccctgggcc aacttttggc gaaaatgaga cgttgatcgg    1440
cacgtaagag gttccaactt tcaccataat gaaataagat cactaccggg cgtatttttt    1500
gagttatcga gattttcagg agctaaggaa gctaaaatgg agaaaaaaat cactggatat    1560
accaccgttg atatatccca atggcatcgt aaagaacatt ttgaggcatt tcagtcagtt    1620
gctcaatgta cctataacca gaccgttcag ctggatatta cggcctttt aaagaccgta    1680 aagaaaaata agcacaagtt ttatccggcc tttattcaca ttcttgcccg cctgatgaat    1740
gctcatccgg aattccgtat ggcaatgaaa gacggtgagc tggtgatatg ggatagtgtt    1800
cacccttgtt acaccgtttt ccatgagcaa actgaaacgt tttcatcgct ctggagtgaa    1860
taccactagg atttccggca gtttctacac atatattcgc aagatgtggc gtgttacggt    1920
gaaaacctgg cctatttccc taaagggttt attgagaata tgttttcgt ctcagccaat    1980 ccctgggtga gtttcaccag ttttgattta aacgtggcca atatggacaa cttcttcgcc    2040
cccgttttca ccatgggcaa atattatacg caaggcgaca aggtgctgat gccgctggcg    2100
attcaggttc atcatgccgt ttgtgatggc ttccatgtcg cagaatgct taatgaatta    2160 caacagtact gcgatgagtg cagggcggg gcgtaatttt tttaaggcag ttattggtgc    2220
ccttaaacgc ctggttgcta cgcctgaata agtgataata gcggatgaa tggcagaaat    2280 tcgaaagcaa attcgacccg tcgtcggtt cagggcaggg tcgttaaata gccgcttatg    2340
tctattgctg gtttaccggt ttattgacta ccggaagcag tgtgaccgtg tgcttctcaa    2400
atgcctgagg ccagtttgct caggctctcc ccgtggaggt aataattgac gatatgatca    2460
tttattctgc ctcccagagc atgataaaaa cggttagcgc ttcgttaata cagatgtagg    2520
tgttccacag ggtagccagc agcatcctgc gatgcagatc cggaacataa tggactagtg    2580
cgcttgtttc ggcgggactg ttgtaactca gaataagaaa tgaggccgct catggcgttc    2640
tgttgcccgt ctcactggtg aaaagaaaaa caaccctggc gccgcttctt tgagcgaacg    2700
atcaaaaata gtggcgccc catcaaaaaa atattctcaa cataaaaaac tttgtgtaat    2760
acttgtaacg ctgaattcag gggcgtagtt caattggtag agcaccggtc tctaaaaccg    2820
ggtgttggga gttcgagtct ctccgcccct gccactgcag atccttagcg aaagctaagg    2880 attttttta agcttggcac tggccgtcgt tttacaacgt cgtgactggg aaaaccctgg    2940
cgttacccaa cttaatcgcc ttgcagcaca tccccctttc gccagttgag caccgccgcc    3000
gcaaggaatg gtgaattcag gatctaagga gcccgagatg cgccgcgtgc ggctgctgga    3060
gatggcggac gcgatggata tgttctgcca agggttggtt tgcgcattca cagttctccg    3120
caagaattga ttggctccaa ttcttggagt ggtgaatccg ttagcgaggt gccgccggct    3180
tccattcagg tcgaggtggc ccggctccat gcaccgcgac gcaacgcggg gaggcagaca    3240
aggtataggg cggcgcctac aatccatgcc aacccgttcc atgtgctcgc cgaggcggca    3300
```

```
taaatcgccg tgacgatcag cggtccaatg atcgaagtta ggctggtaag agccgcgagc    3360
gatccttgaa gctgtccctg atggtcgtca tctacctgcc tggacagcat ggcctgcaac    3420
gcgggcatcc cgatgccgcc ggaagcgaga agaatcataa tggggaaggc catccagcct    3480
cgcgtcgcga acgccagcaa gacgtagccc agcgcgtcgg ccgccatgcc ggcgataatg    3540
gcctgcttct cgccgaaacg tttggtggcg ggaccagtga cgaaggcttg agcgagggcg    3600
tgcaagattc cgaataccgc aagcgacagg ccgatcatcg tcgcgctcca gcgaaagcgg    3660
tcctcgccga aaatgaccca gagcgctgcc ggcacctgtc ctacgagttg catgataaag    3720
aagacagtca taagtgcggc gacgatagtc atgccccgcg cccaccggaa ggagctgact    3780
gggttgaagg ctctcaaggg catcggtcga cgctctccct tatgcgactc ctgcattagg    3840
aagcagccca gtagtaggtt gaggccgttg agcaccgccg ccgcaaggaa tggtgcatgc    3900
aaggagatgg cgcccaacag tccccggcc acggggcctg ccaccatacc cacgccgaaa    3960
caagcgctca tgagcccgaa gtggcgagcc cgatcttccc catcggtgat gtcggcgata    4020
taggcgccag caaccgcacc tgtggcgccg gtgatgccgg ccacgatgcg tccggcgtag    4080
aggatccaca ggacgggtgt ggtcgccatg atcgcgtagt cgatagtggc tccaagtagc    4140
gaagcgagca ggactgggcg gcggccaaag cggtcggaca gtgctccgag aacgggtgcg    4200
catagaaatt gcatcaacgc atatagcgct agcagcacgc catagtgact ggcgatgctg    4260
tcggaatgga cgatatcccg caagaggccc ggcagtaccg gcataaccaa gcctatgcct    4320
acagcatcca gggtgacggt gccgaggatg acgatgagcg cattgttaga tttcatacac    4380
ggtgcctgac tgcgttagca atttaactgt gataaactac cgcattaaag cttatcgatg    4440
ataagctgtc aaacatgaga attacaactt atatcgtatg gggctgactt caggtgctac    4500
attgctcaaa gatgcagggg taaaagctaa ccgcatcttt accgacaagg catccggcag    4560
ttcaacagat cgggaagggc tggatttgct gaggatgaag gtggaggaag gtgatgtcat    4620
tctggtgaag aagctcgacc gtcttggccg cgacaccgcc gacatgatcc aactgataaa    4680
agagtttgat gctcagggtg tagcggttcg gtttattgac gacgggatca gtaccgacgg    4740
tgatatgggg caaatggtgg tcaccatcct gtcggctgtg gcacaggctg aacgccggag    4800
gatcctccgg gccgttgctt cgcaacgttc aaatccgctc ccggcggatt tgtcctactc    4860
aggagagcgt tcaccgacaa acaacagata aaacgaaagg cccagtcttt cgactgagcc    4920
tttcgtttta tttgatgcct ggcagttccc tactctcgca tggggagacc ccacactacc    4980
atcggcgcta cggcgtttca cttctgagtt cggcatgggg tcaggtggga ccaccgcgct    5040
actgccgcca ggcaaattct gttttatcag accgcttctg cgttctgatt taatctgtat    5100
caggctgaaa atcttctctc atccgacgtc ttaggcgaag gcgaagtccg actctaagat    5160
gtcacggagg ttcaagttac ctttagccgg aagtgctggc attttgtcca attgagactc    5220
gtgcaactgg tcagcgaact ggtcgtagaa atcagccagt acatcacaag actcatatgt    5280
gtcaaccata gtttcgcgca ctgctttgaa caggttcgca gcgtcagccg gaatggtacc    5340
gaaggagtcg tgaatcagtg caaaagattc gattccgtac ttctcgtgtg cccacactac    5400
agtcttacga aggtggctac cgtcttggct gtgtacaaag ttaggagcga taccagactc    5460
ctgtttgtgt gcatcaatct cgctatcttt gttggtgtta atggtaggct gtaagcggaa    5520
ctgaccgagg aacatcaggt tcaagcgcgt ctgaataggc ttcttgtatt cctgccacac    5580
agggaaacca tcaggagtta cccaatgcac agcgcaacgc ttgcgaagaa tctctccagt    5640
cttcttatct ttgacctcag cagccagcag cttagcagca gacttaagcc agttcattgc    5700
```

```
ttcaaccgca gctaccaccg tcacgctcac agattcccaa atcagcttag ccatgtatcc    5760
agcagcctga ttcggctgag tgaacatcag acccttgccg gaatcaatag ctggctgaat    5820
ggtatcttcc agcacttgtt gacggaagcc gaactctttg gacccgtaag ccagcgtcat    5880
gactgaacgc ttagtcacac tgcgagtaac accgtaagcc agccattgac cagccagtgc    5940
cttagtgccc agcttgactt tctcagagat ttcaccagtg ttctcatcgg tcacggtaac    6000
tacttcgtta tcggtcccat tgattgcgtc tgcttgtaga atctcgttga ctttcttagc    6060
aacaatcccg tagatgtcct gaacggtttc actaggaagc aagttaaccg cgcgaccacc    6120
tacctcatct cggagcatcg cggagaagtg ctggatgcca gagcaagacc cgtcaaacgc    6180
cagcggaagg gagcagttat agctcaggcc gtggtgctgt accccagcgt actcaaagca    6240
gaacgcaagg aagcagaacg gagaatcttg ctcagcccac caagtgttct ccagtggaga    6300
cttagcgcaa gccatgatgt tctcgtggtt ttcctcaatg aacttgatgc gctcagggaa    6360
cggaacctta tcgacacccg cacagtttgc accgtggatt ttcagccagt agtaaccttc    6420
cttaccgatt ggtttacctt tcgccagcgt aagcagtcct ttggtcatat cgttaccttg    6480
cgggttgaac attgacacag cgtaaacacg accgcgccag tccatgttgt aagggaacca    6540
gatggcctta tggttagcaa acttattggc ttgctcaagc atgaactcaa ggctgatacg    6600
gcgagacttg cgagccttgt ccttgcggta cacagcagcg gcagcacgtt tccacgcggt    6660
gagagcctca ggattcatgt cgatgtcttc cggtttcatc gggagttctt cacgctcaat    6720
cgcagggatg tcctcgaccg gacaatgctt ccacttggtg attacgttgg cgaccgctag    6780
gactttcttg ttgattttcc atgcggtgtt ttgcgcaatg ttaatcgctt tgtacacctc    6840
aggcatgtaa acgtcttcgt agcgcatcag tgctttctta ctgtgagtac gcaccagcgc    6900
cagaggacga cgaccgttag cccaatagcc accaccagta atgccagtcc acggcttagg    6960
aggaactacg caaggttgga acatcggaga gatgccagcc agcgcacctg cacgggttgc    7020
gatagcctca gcgtattcag gtgcgagttc gatagtctca gagtcttgac ctactacgcc    7080
agcattttgg cggtgtaagc taaccattcc ggttgactca atgagcatct cgatgcagcg    7140
tactcctaca tgaatagagt cttccttatg ccacgaagac cacgcctcgc caccgagtag    7200
acccttagag agcatgtcag cctcgacaac ttgcataaat gctttcttgt agacgtgccc    7260
tacgcgcttg ttgagttgtt cctcaacgtt tttcttgaag tgcttagctt caaggtcacg    7320
gatacgaccg aagcgagcct cgtcctcaat ggcccgaccg attgcgcttg ctacagcctg    7380
aacggttgta ttgtcagcac tggttaggca agccagagtg gtcttaatgg tgatgtacgc    7440
tacggcttcc ggcttgattt cctacaggaa ctggaaggct gtcgggcgct tgccgcgctt    7500
agctttcact tcctcaaacc agtcgttgat gcgtgcaatc atcttaggga gtagggtagt    7560
gatgagaggc ttggcggcag cgttatccgc aacctcacca gctttaagtt gacgctcaaa    7620
catcttgcgg aagcgtgctt cacccatctc gtaagactca tgctcaaggg ccaactgttc    7680
gcgagctaaa cgctcaccgt aatggtcagc cagagtgttg aacgggatag cagccagttc    7740
gatgtcagag aagtcgttct tagcaatgtt aatggtattc tagtgcacgg taatcatggt    7800
catggttaat tcctcctgtt agcccaaaaa acgggtatga agaaacagta gagagttgcg    7860
ataaaaagcg tcaggtagga tccgctaatc ttatggataa aaatgctatg gcatagcaaa    7920
gtgtgacgcc gtgcaaataa tcaatgtgga cttttctgcc gtgattatag acactttttgt    7980 tacgcgtttt tgtcatggct ttggtcccgc tttgttacag aatgctttta ataagcgggg    8040
```

```
ttaccggttt ggttagcgag aagagccagt aaaagacgca gtgacggcaa tgtctgatgc    8100
aatatggaca attggtttct tctctgaatg gcgggagtat gaaaagtatg gctgaagcgc    8160
aaaatgatcc cctgctgccg ggatactcgt ttaatgccca tctggtggcg ggtttaacgc    8220
cgattgaggc caacggttat ctcgattttt ttatcgaccg accgctggga atgaaaggtt    8280
atattctcaa tctcaccatt cgcggtcagg gggtggtgaa aaatcaggga cgagaatttg    8340
tttgccgacc gggtgatatt tgctgttcc cgccaggaga gattcatcac tacggtcgtc    8400
atccggaggc tcgcgaatgg tatcaccagt gggtttactt tcgtccgcgc gcctactggc    8460
atgaatggct taactggccg tcaatatttg ccaatacggg gttctttcgc ccggatgaag    8520
cgcaccagcc gcatttcagc gacctgtttg ggcaaatcat taacgccggg caaggggaag    8580
ggcgctattc ggagctgctg gcgataaatc tgcttgagca attgttactg cggcgcatgg    8640
aagcgattaa cgagtcgctc catccaccga tggataatcg ggtacgcgag gcttgtcagt    8700
acatcagcga tcacctggca gacagcaatt ttgatatcgc cagcgtcgca cagcatgttt    8760
gcttgtcgcc gtcgcgtctg tcacatcttt tccgccagca gttagggatt agcgtcttaa    8820
gctggcgcga ggaccaacgt atcagccagg cgaagctgct tttgagcacc acccggatgc    8880
ctatcgccac cgtcggtcgc aatgttggtt ttgacgatca actctatttc tcgcgggtat    8940
ttaaaaaatg caccggggcc agcccgagcg agttccgtgc cggttgtgaa gaaaaagtga    9000
atgatgtagc cgtcaagttg tcataattgg taacgaatca gacaattgac ggcttgacgg    9060
agtagcatag ggtttgcaga atccctgctt cgtccatttg acaggcacat tatgcatgcc    9120
gcttcgcctt cgcgcgcgaa ttgatctgct gcctcgcgcg tttcggtgat gacggtgaaa    9180
acctctgaca catgcagctc ccggagacgg tcacagcctg cagcaaaaaa cccctcaaga    9240
cccgtttaga ggccccaagg ggttatgcta gttattgctc agcggtggca gcagccaact    9300
cagcttcctt tcgggctttg ttatttgtag agctcatcca tgccatgtgt aatcccagca    9360
gcagttacaa actcaagaag gaccatgtgg tcacgctttt cgttgggatc tttcgaaagg    9420
gcagattgtg tcgacaggta atggttgtct ggtaaaagga cagggccatc gccaattgga    9480
gtattttgtt gataatggtc tgctagttga acggatccat cttcaatgtt gtggcgaatt    9540
ttgaagttag ctttgattcc attcttttgt ttgtctgccg tgatgtatac attgtgtgag    9600
ttatagttgt actcgagttt gtgtccgaga atgtttccat cttctttaaa atcaatacct    9660
tttaactcga tacgattaac aagggtatca ccttcaaact tgacttcagc acgcgtcttg    9720
tagttcccgt catctttgaa agatatagtg cgttcctgta cataaccttc gggcatggca    9780
ctcttgaaaa agtcatgccg tttcatatga tccggataac gggaaaagca ttgaacacca    9840
taagagaaag tagtgacaag tgttggccat ggaacaggta gttttccagt agtgcaaata    9900
aatttaaggg taagttttcc gtatgttgca tcaccttcac cctctccact gacagaaaat    9960
ttgtgcccat taacatcacc atctaattca acaagaattg ggacaactcc agtgaaaagt    10020
tcttctcctt tactcatatg tatatctcct tcttaaagtt aaacaaaatt atttctagag    10080
ggaaaccgtt gtggtctccc tatagtgagt cgtattaatt tcgcgggatc g            10131
```

<210> SEQ ID NO 80  
<211> LENGTH: 4326  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 80

```
cgcgtccgcc atctccagca gccgcacgcg gcgcatcttg ggctccttgc atgcaccatt      60
ccttgcggcg gcggtgctca acggcctcaa cctactactg ggctgcttcc taatgcagga     120
gtcgcataag ggagagcgtc tggcgaaagg gggatgtgct gcaaggcgat taagttgggt     180
aacgccaggg ttttcccagt cacgacgttg taaaacgacg gccagtgcca agcttaaaaa     240
aaatccttag ctttcgctaa ggatcatatg cctaggtggc aggggcggag agactcgaac     300
tcccaacacc cggttttgaa gaccggtgct ctaccaattg aactacgccc ctgaattcag     360
cgttacaagt attacacaaa gttttttatg ttgagaatat ttttttgatg gggcgccact     420
tattttgat cgttcgctca agaagcggc gccagggttg tttttctttt caccagtgag      480
acgggcaaca gaacggtacc tctagacaat tggtgcactt caaaaatcga tgagctgttg     540
acaattaatc atcgaactag tgttgatacc gggaagccct gggccaactt ttggcgaaaa     600
tgagacgttg atcggcacgt aagaggttcc aactttcacc ataatgaaat aagatcacta     660
ccgggcgtat ttttgagtt atcgagattt tcaggagcta aggaagctaa aatggagaaa      720
aaaatcactg gatataccac cgttgatata tcccaatggc atcgtaaaga acattttgag     780
gcatttcagt cagttgctca atgtacctat aaccagaccg ttcagctgga tattacggcc     840
ttttaaaga ccgtaaagaa aaataagcac aagttttatc cggcctttat tcacattctt      900
gcccgcctga tgaatgctca tccggaattc cgtatgcaa tgaaagacgg tgagctggtg      960
atatgggata gtgttcaccc ttgttacacc gttttccatg agtgatctga acgttttca    1020
tcgctctgga gtgaatacca cgacgatttc cggcagtttc tacacatata ttcgcaagat   1080
gtggcgtgtt acgtgaaaa cctggcctat ttccctaaag ggtttattga gaatatgttt   1140
ttcgtctcag ccaatccctg ggtgagtttc accagttttg atttaaacgt ggccaatatg   1200
gacaacttct tcgcccccgt tttcaccatg ggcaaatatt atacgcaagg cgacaaggtg   1260
ctgatgccgc tggcgattca ggttcatcat gccgtttgtg atggcttcca tgtcggcaga   1320
atgcttaatg aattacaaca gtactgcgat gagtggcagg gcggggcgta attttttaa    1380
ggcagttatt ggtgcccta aacgcctggt tgctacgcct gaataagtga taataagcgg    1440
atgaatggca gaaattcgct gcagcagcat caaagttctg gtgctggtag ctgcgccaga   1500
aggtatcgct gcgctggaaa aagcgcaccc ggacgtcgaa ctgtataccg catcgattga   1560
tcagggactg aacgagcacg gatacattat tccgggcctc ggcgatgccg gtgacaaaat   1620
ctttggtacg aaataaagaa ttcgaagctt gggcccgaac aaaaactcat ctcagaagag   1680
gatctgaata gcgccgtcga ccatcaccat catcatcatt gagtttaaac gacgtccagc   1740
ttggctgttt tggcggatga gaagagattt tcagcctgat acagattaaa tcagaacgca   1800
gaagcggtct gataaaacag aatttgcctg gcggcagtag cgcggtggtc ccacctgacc   1860
ccatgccgaa ctcagaagtg aaacgccgta gcgccgatgg tagtgtgagg cctcccatgc   1920
gagagtaggg aactgccagg catcaaataa aacgaaaggc tcagtcgaaa gactgggcct   1980
ttcgttttat ctgttgtttg tcggtgaacg atatctgctt ttcttcggat ccctcgagag   2040
atctccatgg gctagcggag tgtatactgg cttactatgt tggcactgat gagggtgtca   2100
gtgaagtgct tcatgtggca ggagaaaaaa ggctgcaccg gtgcgtcagc agaatatgtg   2160
atacaggata tattccgctt cctcgctcac tgactcgcta cgctcggtcg ttcgactgcg   2220
gcgagcggaa atggcttacg aacggggcgg agatttcctg gaagatgcca ggaagatact   2280
taacagggaa gtgagagggc cgcggcaaag ccgtttttcc ataggctccg ccccctgac    2340
```

```
aagcatcacg aaatctgacg ctcaaatcag tggtggcgaa acccgacagg actataaaga    2400
taccaggcgt ttccccctgg cggctccctc gtgcgctctc ctgttcctgc ctttcggttt    2460
accggtgtca ttccgctgtt atggccgcgt ttgtctcatt ccacgcctga cactcagttc    2520
cgggtaggca gttcgctcca agctggactg tatgcacgaa ccccccgttc agtccgaccg    2580
ctgcgcctta tccggtaact atcgtcttga gtccaacccg aaagacatg caaaagcacc     2640 actggcagca gccactggta attgatttag aggagttagt cttgaagtca tgcgccggtt    2700
aaggctaaac tgaaaggaca agttttggtg actgcgctcc tccaagccag ttacctcggt    2760
tcaaagagtt ggtagctcag agaaccttcg aaaaaccgcc ctgcaaggcg ttttttcgt     2820 tttcagagca agagattacg cgcagaccaa aacgatctca agaagatcat cttattaagg    2880
ggtctgacgc acatgtaatg tagcacctga agtcagcccc atacgatata agttgtaatt    2940
ctcatgtttg acagcttatc atcgataagc tttaatgcgg tagtttatca cagttaaatt    3000
gctaacgcag tcaggcaccg tgtatgaaat ctaacaatgc gctcatcgtc atcctcggca    3060
ccgtcaccct ggatgctgta ggcataggct tggttatgcc ggtactgccg ggcctcttgc    3120
gggatatcgt ccattccgac agcatcgcca gtcactatgg cgtgctgcta gcgctatatg    3180
cgttgatgca atttctatgc gcacccgttc tcggagcact gtccgaccgc tttggccgcc    3240
gcccagtcct gctcgcttcg ctacttggag ccactatcga ctacgcgatc atggcgacca    3300
cacccgtcct gtggattctc tacgccggac gcatcgtggc cggcatcacc ggcgccacag    3360
gtgcggttgc tggcgcctat atcgccgaca tcaccgatgg ggaagatcgg gctcgccact    3420
tcgggctcat gagcgcttgt ttcggcgtgg gtatggtggc aggccccgtg gccggggggac   3480 tgttgggcgc catctccttg catgcaccat tccttgcggc ggcggtgctc aacggcctca    3540
acctactact gggctgcttc ctaatgcagg agtcgcataa gggagagcgt cgaccgatgc    3600
ccttgagagc cttcaaccca gtcagctcct ccggtgggc gcggggcatg actatcgtcg     3660
ccgcacttat gactgtcttc tttatcatgc aactcgtagg acaggtgccg gcagcgctct    3720
gggtcatttt cggcgaggac cgctttcgct ggagcgcgac gatgatcggc ctgtcgcttg    3780
cggtattcgg aatcttgcac gccctcgctc aagccttcgt cactggtccc gccaccaaac    3840
gtttcggcga aagcaggcc attatcgccg gcatggcggc cgacgcgctg ggctacgtct     3900
tgctggcgtt cgcgacgcga ggctggatgg ccttccccat tatgattctt ctcgcttccg    3960
gcggcatcgg gatgcccgcg ttgcaggcca tgctgtccag gcaggtagat gacgaccatc    4020
agggacagct tcaaggatcg ctcgcggctc ttaccagcct aacttcgatc attgaccgc     4080 tgatcgtcac ggcgatttat gccgcctcgg cgagcacatg gaacgggttg gcatggattg    4140
taggcgccgc cctataccttt gtctgcctcc ccgcgttgcg tcgcggtgca tggagccggg    4200
ccacctcgac ctgaatggaa gccggcggca cctcgctaac ggattcacca ctccaagaat    4260
tggagccaat caattcttgc ggagaactgt gaatgcgcaa accaacccttt ggcagaacat   4320 atccat                                                              4326
```

<210> SEQ ID NO 81
<211> LENGTH: 9722
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
cgcgtccgcc atctccagca gccgcacgcg gcgcatcttg ggctccttgc atgcaccatt      60
ccttgcggcg gcggtgctca acggcctcaa cctactactg ggctgcttcc taatgcagga     120
gtcgcataag ggagagcgtc tggcgaaagg gggatgtgct gcaaggcgat taagttgggt     180
aacgccaggg ttttcccagt cacgacgttg taaaacgacg ccagtgcca  agcttaaaaa     240
aaatccttag ctttcgctaa ggatcatatg cctaggtggc aggggcggag agactcgaac     300
tcccaacacc cggttttgaa gaccggtgct ctaccaattg aactacgccc ctgaattcag     360
cgttacaagt attacacaaa gttttttatg ttgagaatat ttttttgatg gggcgccact     420
tattttgat cgttcgctca aagaagcggc gccaggttg  tttttctttt caccagtgag     480
acgggcaaca gaacggtacc tctagacaat tggtgcactt caaaaatcga tgagctgttg     540
acaattaatc atcgaactag tgttgatacc gggaagccct gggccaactt ttggcgaaaa     600
tgagacgttg atcggcacgt aagaggttcc aactttcacc ataatgaaat aagatcacta     660
ccgggcgtat ttttgagtt  atcgagattt tcaggagcta aggaagctaa aatggagaaa     720
aaaatcactg gatataccac cgttgatata tcccaatggc atcgtaaaga acattttgag     780
gcatttcagt cagttgctca atgtacctat aaccagaccg ttcagctgga tattacggcc     840
tttttaaaga ccgtaaagaa aaataagcac aagttttatc cggcctttat tcacattctt     900
gcccgcctga tgaatgctca tccggaattc cgtatggcaa tgaaagacgg tgagctggtg     960
atatgggata gtgttcaccc ttgttacacc gttttccatg agtgatctga aacgttttca    1020
tcgctctgga gtgaatacca cgacgatttc cggcagtttc tacacatata ttcgcaagat    1080
gtggcgtgtt acggtgaaaa cctggcctat ttccctaaag ggtttattga atatgtttt    1140
ttcgtctcag ccaatccctg ggtgagtttc accagttttg atttaaacgt ggccaatatg    1200
gacaacttct tcgcccccgt tttcaccatg ggcaaatatt atacgcaagg cgacaaggtg    1260
ctgatgccgc tggcgattca ggttcatcat gccgtttgtg atggcttcca tgtcggcaga    1320
atgcttaatg aattacaaca gtactgcgat gagtggcagg gcggggcgta atttttttaa    1380
ggcagttatt ggtgccctta aacgcctggt tgctacgcct gaataagtga taataagcgg    1440
atgaatggca gaaattcgct gcaggctact caggagagcg ttcaccgaca aacaacagat    1500
aaaacgaaag gcccagtctt tcgactgagc ctttcgtttt atttgatgcc tggcagttcc    1560
ctactctcgc atggggagac cccacactac catcggcgct acggcgtttc acttctgagt    1620
tcggcatggg gtcaggtggg accaccgcgc tactgccgcc aggcaaattc tgttttatca    1680
gaccgcttct gcgttctgat ttaatctgta tcaggctgaa atcttctct  catccgacgt    1740
cttaggcgaa ggcgaagtcc gactctaaga tgtcacggag gttcaagtta cctttagccg    1800
gaagtgctgc cattttgtcc aattgagact cgtgcaactg tcagcgaac  tggtcgtaga    1860
aatcagccag tacatcacaa gactcatatg tgtcaaccat agtttcgcgc actgctttga    1920
acaggttcgc agcgtcagcc ggaatggtac cgaaggagtc gtgaatcagt gcaaaagatt    1980
cgattccgta cttctcgtgt gcccacacta cagtcttacg aaggtggcta ccgtcttggc    2040
tgtgtacaaa gttaggagcg ataccagact cctgtttgtg tgcatcaatc tcgctatctt    2100
tgttggtgtt aatggtaggc tgtaagcgga actgaccgag gaacatcagg ttcaagcgcg    2160
tctgaatagg cttcttgtat tcctgccaca cagggaaacc atcaggagtt acccaatgca    2220
cagcgcaacg cttgcgaaga atctctccag tcttcttatc tttgacctca gcagccagca    2280
gcttagcagc agacttaagc cagttcattg cttcaaccgc agctaccacc gtcacgctca    2340
```

```
cagattccca aatcagctta gccatgtatc cagcagcctg attcggctga gtgaacatca    2400
gacccttgcc ggaatcaata gctggctgaa tggtatcttc cagcacttgt tgacggaagc    2460
cgaactcttt ggacccgtaa gccagcgtca tgactgaacg cttagtcaca ctgcgagtaa    2520
caccgtaagc cagccattga ccagccagtg ccttagtgcc cagcttgact ttctcagaga    2580
tttcaccagt gttctcatcg gtcacggtaa ctacttcgtt atcggtccca ttgattgcgt    2640
ctgcttgtag aatctcgttg actttcttag caacaatccc gtagatgtcc tgaacggttt    2700
cactaggaag caagttaacc gcgcgaccac ctacctcatc tcggagcatc gcggagaagt    2760
gctggatgcc agagcaagac ccgtcaaacg ccagcggaag ggagcagtta tagctcaggc    2820
cgtggtgctg taccccagcg tactcaaagc agaacgcaag gaagcagaac ggagaatctt    2880
gctcagccca ccaagtgttc tccagtggag acttagcgca agccatgatg ttctcgtggt    2940
tttcctcaat gaacttgatg cgctcaggga acggaacctt atcgacaccc gcacagtttg    3000
caccgtggat tttcagccag tagtaacctt ccttaccgat tggtttacct ttcgccagcg    3060
taagcagtcc tttggtcata tcgttacctt gcggttgaa cattgacaca gcgtaaacac     3120
gaccgcgcca gtccatgttg taagggaacc agatggcctt atggttagca aacttattgg    3180
cttgctcaag catgaactca aggctgatac ggcgagactt gcgagccttg tccttgcggt    3240
acacagcagc ggcagcacgt ttccacgcgg tgagagcctc aggattcatg tcgatgtctt    3300
ccggtttcat cgggagttct tcacgctcaa tcgcagggat gtcctcgacc ggacaatgct    3360
tccacttggt gattacgttg gcgaccgcaa ggactttctt gttgattttc catgcggtgt    3420
tttgcgcaat gttaatcgct ttgtacacct caggcatgta acgtcttcg tagcgcatca     3480 gtgctttctt actgtgagta cgcaccagcg ccagaggacg acgaccgtta gcccaatagc    3540
caccaccagt aatgccagtc cacggcttag gaggaactac gcaaggttgg aacatcggag    3600
agatgccagc cagcgcacct gcacgggttg cgatagcctc agcgtattca ggtgcgagtt    3660
cgatagtctc agagtcttga cctactacgc cagcattttg gcggtgtaag ctaaccattc    3720
cggttgactc aatgagcatc tcgatgcagc gtactcctac atgaatagag tcttccttat    3780
gccacgaaga ccacgcctcg ccaccgagta gaccccttaga gagcatgtca gcctcgacaa   3840
cttgcataaa tgctttcttg tagacgtgcc ctacgcgctt gttgagttgt tcctcaacgt    3900
ttttcttgaa gtgcttagct tcaaggtcac ggatacgacc gaagcgagcc tcgtcctcaa    3960
tggcccgacc gattgcgctt gctacagcct gaacggttgt attgtcagca ctggttaggc    4020
aagccagagt ggtcttaatg gtgatgtacg ctacggcttc cggcttgatt tctcacagga    4080
actggaaggc tgtcgggcgc ttgccgcgct tagctttcac ttcctcaaac cagtcgttga    4140
tgcgtgcaat catcttaggg agtagggtag tgatgagagg cttggcggca gcgttatccg    4200
caacctcacc agctttaagt tgacgctcaa acatcttgcg gaagcgtgct tcacccatct    4260
cgtaagactc atgctcaagg gccaactgtt cgcgagctaa acgctcaccg taatggtcag    4320
ccagagtgtt gaacgggata gcagccagtt cgatgtcaga gaagtcgttc ttagcaatgt    4380
taatggtatt tcagtgcacg gtaatcatgg tcatggttaa ttcctcctgt tagcccaaaa    4440
aacgggtatg gagaaacagt agagagttgc gataaaagc gtcaggtagg atccgctaat     4500
cttatggata aaaatgctat ggcatagcaa agtgtgacgc cgtgcaaata atcaatgtgg    4560
acttttctgc cgtgattata gacacttttg ttacgcgttt ttgtcatggc tttggtcccg    4620
ctttgttaca gaatgctttt aataagcggg gttaccggtt tggttagcga gaagagccag    4680
taaaagacgc agtgacggca atgtctgatg caatatggac aattggtttc ttctctgaat    4740
```

```
ggcgggagta tgaaaagtat ggctgaagcg caaaatgatc ccctgctgcc gggatactcg   4800
tttaatgccc atctggtggc gggtttaacg ccgattgagg ccaacggtta tctcgatttt   4860
tttatcgacc gaccgctggg aatgaaaggt tatattctca atctcaccat tcgcggtcag   4920
ggggtggtga aaaatcaggg acgagaattt gtttgccgac cgggtgatat tttgctgttc   4980
ccgccaggag agattcatca ctacggtcgt catccggagg ctcgcgaatg gtatcaccag   5040
tgggtttact ttcgtccgcg cgcctactgg catgaatggc ttaactggcc gtcaatattt   5100
gccaatacgg ggttctttcg cccggatgaa gcgcaccagc cgcatttcag cgacctgttt   5160
gggcaaatca ttaacgccgg gcaagggaa gggcgctatt cggagctgct ggcgataaat   5220
ctgcttgagc aattgttact gcggcgcatg gaagcgatta acgagtcgct ccatccaccg   5280
atggataatc gggtacgcga ggcttgtcag tacatcagcg atcacctggc agacagcaat   5340
tttgatatcg ccagcgtcgc acagcatgtt tgcttgtcgc cgtcgcgtct gtcacatctt   5400
ttccgccagc agtagggat tagcgtctta agctggcgcg aggaccaacg tatcagccag   5460
gcgaagctgc ttttgagcac cacccggatg cctatcgcca ccgtcggtcg caatgttggt   5520
tttgacgatc aactctattt ctcgcgggta tttaaaaaat gcaccggggc cagcccgagc   5580
gagttccgtg ccggttgtga agaaaaagtg aatgatgtag ccgtcaagtt gtcataattg   5640
gtaacgaatc agacaattga cggcttgacg gagtagcata gggtttgcag aatccctgct   5700
tcgtccattt gacaggcaca ttatgcatgc cgcttcgcct tcgcgcgcga attgatctgc   5760
tgcctcgcgc gtttcggtga tgacggtgaa aacctctgac acatgcagct cccggagacg   5820
gtcacagcct gcagcaaaaa acccctcaag acccgtttag aggccccaag gggttatgct   5880
agttattgct cagcggtggc agcagccaac tcagcttcct ttcgggcttt gttatttgta   5940
gagctcatcc atgccatgtg taatcccagc agcagttaca aactcaagaa ggaccatgtg   6000
gtcacgcttt tcgttgggat ctttcgaaag ggcagattgt gtcgacaggt aatggttgtc   6060
tggtaaaagg acagggccat cgccaattgg agtatttgt tgataatggt ctgctagttg   6120
aacggatcca tcttcaatgt tgtggcgaat tttgaagtta gctttgattc cattcttttg   6180
tttgtctgcc gtgatgtata cattgtgtga gttatagttg tactcgagtt tgtgtccgag   6240
aatgttccca tcttctttaa aatcaatacc ttttaactcg atacgattaa caagggtatc   6300
accttcaaac ttgacttcag cacgcgtctt gtagttcccg tcatctttga aagatatagt   6360
gcgttcctgt acataacctt cgggcatggc actcttgaaa aagtcatgcc gtttcatatg   6420
atccggataa cgggaaaagc attgaacacc ataagagaaa gtagtgacaa gtgttggcca   6480
tggaacaggt agttttccag tagtgcaaat aaatttaagg gtaagttttc cgtatgttgc   6540
atcaccttca ccctctccac tgacagaaaa tttgtgccca ttaacatcac catctaattc   6600
aacaagaatt gggacaactc cagtgaaaag ttcttctcct ttactcatat gtatatctcc   6660
ttcttaaagt taaacaaaat tatttctaga gggaaaccgt tgtggtctcc ctatagtgag   6720
tcgtattaat ttcgcgggat cggcccttcc ggctggctgg tttattgctg ataaatctgg   6780
agccggtgag cgtgggtctc gcggtatcat tgcagcactg gggccagatg gtaagccctc   6840
ccgtagcggc gcccctgcag cagcatcaaa gttctggtgc tggtagctgc gccagaaggt   6900
atcgctgcgc tggaaaaagc gcacccggac gtcgaactgt ataccgcatc gattgatcag   6960
ggactgaacg agcacggata cattattccg ggcctcggcg atgccggtga caaaatcttt   7020
ggtacgaaat aaagaattcg aagcttgggc ccgaacaaaa actcatctca gaagaggatc   7080
```

```
tgaatagcgc cgtcgaccat caccatcatc atcattgagt ttaaacgacg tccagcttgg    7140
ctgtttggc ggatgagaga agattttcag cctgatacag attaaatcag aacgcagaag    7200
cggtctgata aaacagaatt tgcctggcgg cagtagcgcg gtggtcccac ctgaccccat    7260
gccgaactca gaagtgaaac gccgtagcgc cgatggtagt gtgaggcctc ccatgcgaga    7320
gtagggaact gccaggcatc aaataaaacg aaaggctcag tcgaaagact gggcctttcg    7380
ttttatctgt tgtttgtcgg tgaacgatat ctgcttttct tcggatccct cgagagatct    7440
ccatgggcta gcggagtgta tactggctta ctatgttggc actgatgagg gtgtcagtga    7500
agtgcttcat gtggcaggag aaaaaaggct gcaccggtgc gtcagcagaa tatgtgatac    7560
aggatatatt ccgcttcctc gctcactgac tcgctacgct cggtcgttcg actgcggcga    7620
gcggaaatgg cttacgaacg gggcggagat ttcctggaag atgccaggaa gatacttaac    7680
agggaagtga gagggccgcg gcaaagccgt ttttccatag gctccgcccc cctgacaagc    7740
atcacgaaat ctgacgctca atcagtggt ggcgaaaccc gacaggacta taaagatacc    7800
aggcgtttcc ccctggcggc tccctcgtgc gctctcctgt tcctgccttt cggtttaccg    7860
gtgtcattcc gctgttatgg ccgcgtttgt ctcattccac gcctgacact cagttccggg    7920
taggcagttc gctccaagct ggactgtatg cacgaacccc ccgttcagtc cgaccgctgc    7980
gccttatccg gtaactatcg tcttgagtcc aacccggaaa gacatgcaaa agcaccactg    8040
gcagcagcca ctggtaattg atttagagga gttagtcttg aagtcatgcg ccggttaagg    8100
ctaaactgaa aggacaagtt ttggtgactg cgctcctcca agccagttac ctcggttcaa    8160
agagttggta gctcagagaa ccttcgaaaa accgccctgc aaggcggttt tttcgttttc    8220
agagcaagag attacgcgca gaccaaaacg atctcaagaa gatcatctta ttaaggggtc    8280
tgacgcacat gtaatgtagc acctgaagtc agccccatac gatataagtt gtaattctca    8340
tgtttgacag cttatcatcg ataagcttta atgcggtagt ttatcacagt taaattgcta    8400
acgcagtcag gcaccgtgta tgaaatctaa caatgcgctc atcgtcatcc tcggcaccgt    8460
caccctggat gctgtaggca taggcttggt tatgccggta ctgccgggcc tcttgcggga    8520
tatcgtccat tccgacagca tcgccagtca ctatggcgtg ctgctagcgc tatatgcgtt    8580
gatgcaattt ctatgcgcac ccgttctcgg agcactgtcc gaccgctttg ccgccgccc    8640
agtcctgctc gcttcgctac ttggagccac tatcgactac gcgatcatgg cgaccacacc    8700
cgtcctgtgg attctctacg ccggacgcat cgtggccggc atcaccggcg ccacaggtgc    8760
ggttgctggc gcctatatcg ccgacatcac cgatggggaa atcgggctc gccacttcgg    8820
gctcatgagc gcttgtttcg gcgtgggtat ggtggcaggc cccgtggccg gggactgtt    8880
gggcgccatc tccttgcatg caccattcct gcggcggcg gtgctcaacg gcctcaacct    8940
actactgggc tgcttcctaa tgcaggagtc gcataaggga gagcgtcgac cgatgccctt    9000
gagagccttc aacccagtca gctccttccg gtgggcgcgg ggcatgacta tcgtcgccgc    9060
acttatgact gtcttcttta tcatgcaact cgtaggacag gtgccggcag cgctctgggt    9120
cattttcggc gaggaccgct ttcgctggag cgcgacgatg atcggcctgt cgcttgcggt    9180
attcggaatc ttgcacgccc tcgctcaagc cttcgtcact ggtcccgcca ccaaacgttt    9240
cggcgagaag caggccatta tcgccggcat ggcggccgac gcgctgggct acgtcttgct    9300
ggcgttcgcg acgcgaggct ggatggcctt ccccattatg attcttctcg cttccggcgg    9360
catcgggatg cccgcgttgc aggccatgct gtccaggcag gtagatgacg accatcaggg    9420
acagcttcaa ggatcgctcg cggctcttac cagcctaact tcgatcattg gaccgctgat    9480
```

| | |
|---|---|
| cgtcacggcg atttatgccg cctcggcgag cacatggaac gggttggcat ggattgtagg | 9540 |
| cgccgcccta taccttgtct gcctccccgc gttgcgtcgc ggtgcatgga gccgggccac | 9600 |
| ctcgacctga atggaagccg gcggcacctc gctaacggat tcaccactcc aagaattgga | 9660 |
| gccaatcaat tcttgcggag aactgtgaat gcgcaaacca acccttggca gaacatatcc | 9720 |
| at | 9722 |

<210> SEQ ID NO 82
<211> LENGTH: 4823
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

| | |
|---|---|
| gggtggtgcg taacggcaaa agcaccgccg gacatcagcg ctagcggagt gtatactggc | 60 |
| ttactatgtt ggcactgatg agggtgtcag tgaagtgctt catgtggcag gagaaaaaag | 120 |
| gctgcaccgg tgcgtcagca gaatatgtga tacaggatat attccgcttc ctcgctcact | 180 |
| gactcgctac gctcggtcgt tcgactgcgg cgagcggaaa tggcttacga acggggcgga | 240 |
| gatttcctgg aagatgccag gaagatactt aacaggaag tgagagggcc gcggcaaagc | 300 |
| cgttttccca taggctccgc cccctgaca agcatcacga atctgacgc tcaaatcagt | 360 |
| ggtggcgaaa cccgacagga ctataaagat accaggcgtt tccccctggc ggctccctcg | 420 |
| tgcgctctcc tgttcctgcc tttcggttta ccggtgtcat tccgctgtta tggccgcgtt | 480 |
| tgtctcattc cacgcctgac actcagttcc gggtaggcag ttcgctccaa gctggactgt | 540 |
| atgcacgaac ccccgttca gtccgaccgc tgcgccttat ccggtaacta tcgtcttgag | 600 |
| tccaacccgg aaagacatgc aaaagcacca ctggcagcag ccactggtaa ttgatttaga | 660 |
| ggagttagtc ttgaagtcat gcgccggtta aggctaaact gaaaggacaa gttttggtga | 720 |
| ctgcgctcct ccaagccagt tacctcggtt caaagagttg gtagctcaga gaaccttcga | 780 |
| aaaaccgccc tgcaaggcgg ttttttcgtt ttcagagcaa gagattacgc gcagaccaaa | 840 |
| acgatctcaa gaagatcatc ttattaatca gataaaatat ttctagattt cagtgcaatt | 900 |
| tatctcttca aatgtagcac ctgaagtcag ccccatacga tataagttgt aattctcatg | 960 |
| tttgacagct tatcatcgat aagcttgcaa tttatctctt caaatgtagc acctgaagtc | 1020 |
| agccccatac gatataagtt gtaattctca tgttagtcat gccccgcgcc caccggaagg | 1080 |
| agctgactgg gttgaaggct ctcaagggca tcggtcgaga tcccggtgcc taatgagtga | 1140 |
| gctaacttac attaattgcg ttgcgctcac tgcccgcttt ccagtcggga aacctgtcgt | 1200 |
| gccagctgca ttaatgaatc ggccaacgcg cggggagagg cggtttgcgt attgggcgcc | 1260 |
| agggtggttt ttcttttcac cagtgagacg ggcaacagct gattgccctt caccgcctgg | 1320 |
| ccctgagaga gttgcagcaa gcggtccacg ctggtttgcc ccagcaggcg aaaatcctgt | 1380 |
| ttgatggtgg ttaacggcgg gatataacat gagctgtctt cggtatcgtc gtatcccact | 1440 |
| accgagatgt ccgcaccaac gcgcagcccg gactcggtaa tggcgcgcat tgcgcccagc | 1500 |
| gccatctgat cgttggcaac cagcatcgca gtgggaacga tgccctcatt cagcatttgc | 1560 |
| atggtttgtt gaaaaccgga catggcactc cagtcgcctt cccgttccgc tatcggctga | 1620 |
| atttgattgc gagtgagata tttatgccag ccagccagac gcagacgcgc cgagacagaa | 1680 |
| cttaatgggc ccgctaacag cgcgatttgc tggtgaccca atgcgaccag atgctccacg | 1740 |

```
cccagtcgcg taccgtcttc atgggagaaa ataatactgt tgatgggtgt ctggtcagag    1800
acatcaagaa ataacgccgg aacattagtg caggcagctt ccacagcaat ggcatcctgg    1860
tcatccagcg gatagttaat gatcagccca ctgacgcgtt gcgcgagaag attgtgcacc    1920
gccgctttac aggcttcgac gccgcttcgt tctaccatcg acaccaccac gctggcaccc    1980
agttgatcgg cgcgagattt aatcgccgcg acaatttgcg acggcgcgtg cagggccaga    2040
ctggaggtgg caacgccaat cagcaacgac tgtttgcccg ccagttgttg tgccacgcgg    2100
ttgggaatgt aattcagctc cgccatcgcc gcttccactt tttcccgcgt tttcgcagaa    2160
acgtggctgg cctggttcac cacgcgggaa acggtctgat aagagacacc ggcatactct    2220
gcgacatcgt ataacgttac tggtttcaca ttcaccaccc tgaattgact ctcttccggg    2280
cgctatcatg ccataccgcg aaaggttttg cgccattcga tggtgtccgg gatctcgacg    2340
ctctcccta tgcgactcct gcattaggct cactataggg gaattgtgag cggataacaa    2400
ttcccctcta gagtttgaca gcattatcat cgatctcgag aaatcataaa aaatttattt    2460
gctttgtgag cggataacaa ttataataga ttcaattgtg agcggataac aatttcacac    2520
agaattcatt aaagaggaga aattacatat gagcaaagga gaagaacttt tcactggagt    2580
tgtcccaatt cttgttgaat tagatggtga tgttaatggg cacaaatttt ctgtccgtgg    2640
agagggtgaa ggtgatgcta caaacggaaa actcacccct taaatttattt gcactactgg    2700
aaaactacct gttccgtggc caacacttgt cactactctg acctatggtg ttcaatgctt    2760
ttcccgttat ccggatcaca tgaaacggca tgacttttc aagagtgcca tgcccgaagg    2820
ttatgtacag gaacgcacta tatctttcaa agatgacggg acctacaaga cgcgtgctga    2880
agtcaagttt gaaggtgata cccttgttaa tcgtatcgag ttaaagggta ttgattttaa    2940
agaagatgga acacattcttg gacacaaact cgagtacaac tttaactcac acaatgtata    3000
gatcacggca gacaaacaaa gaatggaat caaagctaac ttcaaaattc gccacaacgt    3060
tgaagatggt tccgttcaac tagcagacca ttatcaacaa aatactccaa ttggcgatgg    3120
ccctgtcctt ttaccagaca accattacct gtcgacacaa tctgtccttt cgaaagatcc    3180
caacgaaaag cgtgaccaca tggtccttct tgagtttgta actgctgctg ggattacaca    3240
tggcatggat gagctctaca aaggatccca ccaccaccac caccactaaa agcttaatta    3300
gctgagcttg gactcctgtt gatagatcca gtaatgacct cagaactcca tctggatttg    3360
ttcagaacgc tcggttgccg ccgggcgttt tttattggtg agaatccaag ctagcttggc    3420
gctgcagtgt gcttctcaaa tgcctgaggc cagtttgctc aggctctccc cgtggaggta    3480
ataattgacg atatgatcag tgcacggcta actaagcggc ctgctgactt tctcgccgat    3540
caaaaggcat tttgctatta agggattgac gagggcgtat ctgcgcagta agatgcgccc    3600
cgcatttagg ggcgtagttc aattggtaga gcaccggtct ctaaaaccgg tgttgggag    3660
ttcgagtctc tccgccctg ccaaattcga aagcctgct caacgagcag gcttttttgc    3720
atgctcgagc agctcagggt cgaatttgct ttcgaatttc tgccattcat ccgcttatta    3780
tcacttattc aggcgtagca accaggcgtt taagggcacc aataactgcc ttaaaaaaat    3840
tacgccccgc cctgccactc atcgcagtac tgttgtaatt cattaagcat tctgccgaca    3900
tggaagccat cacaaacggc atgatgaacc tgaatcgcca gcggcatcag caccttgtcg    3960
ccttgcgtat aatatttgcc catggtgaaa acggggcga agaagttgtc catattggcc    4020
acgtttaaat caaaactggt gaaactcacc cagggattgg ctgagacgaa aaacatattc    4080
```

```
tcaataaacc ctttagggaa ataggccagg ttttcaccgt aacacgccac atcttgcgaa     4140
tatatgtgta gaaactgccg gaaatcgtcg tggtattcac tccagagcga tgaaaacgtt     4200
tcagtttgct catggaaaac ggtgtaacaa gggtgaacac tatcccatat caccagctca     4260
ccgtctttca ttgccatacg gaattccgga tgagcattca tcaggcgggc aagaatgtga     4320
ataaaggccg gataaaactt gtgcttattt ttctttacgg tctttaaaaa ggccgtaata     4380
tccagctgaa cggtctggtt ataggtacat tgagcaactg actgaaatgc ctcaaaatgt     4440
tctttacgat gccattggga tatatcaacg gtggtatatc cagtgatttt tttctccatt     4500
ttagcttcct tagctcctga aaatctcgat aactcaaaaa atacgcccgg tagtgatctt     4560
atttcattat ggtgaaagtt ggaacctctt acgtgccgat caacgtctca ttttcgccaa     4620
aagttggccc agggcttccc ggtatcaaca gggacaccag gatttattta ttctgcgaag     4680
tgatcttccg tcacaggtat ttattcggcg caaagtgcgt cgggtgatgc tgccaactta     4740
ctgatttagt gtatgatggt gttttttgagg tgctccagtg gcttctgttt ctatcagctg     4800
tccctcctgt tcagctactg acg                                              4823

<210> SEQ ID NO 83
<211> LENGTH: 4823
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
gggtggtgcg taacggcaaa agcaccgccg gacatcagcg ctagcggagt gtatactggc       60
ttactatgtt ggcactgatg agggtgtcag tgaagtgctt catgtggcag gagaaaaaag      120
gctgcaccgg tgcgtcagca gaatatgtga tacaggatat attccgcttc ctcgctcact      180
gactcgctac gctcggtcgt tcgactgcgg cgagcggaaa tggcttacga acggggcgga      240
gatttcctgg aagatgccag gaagatactt aacaggaagt gagagggcc gcggcaaagc      300 cgttttttcca taggctccgc ccccctgaca gcatcacga atctgacgc tcaaatcagt      360 ggtggcgaaa cccgacagga ctataaagat accaggcgtt tcccccctggc ggctccctcg      420 tgcgctctcc tgttcctgcc tttcggttta ccggtgtcat tccgctgtta tggccgcgtt      480
tgtctcattc cacgcctgac actcagttcc gggtaggcag ttcgctccaa gctggactgt      540
atgcacgaac cccccgttca gtccgaccgc tgcgccttat ccggtaacta tcgtcttgag      600
tccaacccgg aaagacatgc aaaagcacca ctggcagcag ccactggtaa ttgatttaga      660
ggagttagtc ttgaagtcat gcgccggta aggctaaact gaaaggacaa gttttggtga      720
ctgcgctcct ccaagccagt tacctcggtt caaagagttg gtagctcaga gaaccttcga      780
aaaaccgccc tgcaaggcgg ttttttcgtt ttcagagcaa gagattacgc gcagaccaaa      840
acgatctcaa gaagatcatc ttattaatca gataaaatat ttctagattt cagtgcaatt      900
tatctcttca aatgtagcac ctgaagtcag ccccatacga tataagttgt aattctcatg      960
tttgacagct tatcatcgat aagcttgcaa tttatctctt caaatgtagc acctgaagtc     1020
agccccatac gatataagtt gtaattctca tgttagtcat gccccgcgcc caccggaagg     1080
agctgactgg gttgaaggct ctcaagggca tcggtcgaga tcccggtgcc taatgagtga     1140
gctaacttac attaattgcg ttgcgctcac tgcccgcttt ccagtcggga aacctgtcgt     1200
gccagctgca ttaatgaatc ggccaacgcg cggggagagg cggtttgcgt attgggcgcc     1260
```

```
agggtggttt ttcttttcac cagtgagacg ggcaacagct gattgccctt caccgcctgg    1320
ccctgagaga gttgcagcaa gcggtccacg ctggtttgcc ccagcaggcg aaaatcctgt    1380
ttgatggtgg ttaacggcgg gatataacat gagctgtctt cggtatcgtc gtatcccact    1440
accgagatgt ccgcaccaac gcgcagcccg gactcggtaa tggcgcgcat tgcgcccagc    1500
gccatctgat cgttggcaac cagcatcgca gtgggaacga tgccctcatt cagcatttgc    1560 atggttttgtt gaaaaccgga catggcactc cagtcgcctt cccgttccgc tatcggctga    1620
atttgattgc gagtgagata tttatgccag ccagccagac gcagacgcgc cgagacagaa    1680
cttaatgggc ccgctaacag cgcgatttgc tggtgaccca atgcgaccag atgctccacg    1740
cccagtcgcg taccgtcttc atgggagaaa ataatactgt tgatgggtgt ctggtcagag    1800
acatcaagaa ataacgccgg aacattagtg caggcagctt ccacagcaat ggcatcctgg    1860
tcatccagcg gatagttaat gatcagccca ctgacgcgtt gcgcgagaag attgtgcacc    1920
gccgctttac aggcttcgac gccgcttcgt tctaccatcg acaccaccac gctggcaccc    1980
agttgatcgg cgcgagattt aatcgccgcg acaatttgcg acgcgcgtg cagggccaga    2040 ctggaggtgg caacgccaat cagcaacgac tgtttgcccg ccagttgttg tgccacgcgg    2100
ttgggaatgt aattcagctc cgccatcgcc gcttccactt ttcccgcgt tttcgcagaa    2160 acgtggctgg cctggttcac cacgcgggaa acggtctgat aagagacacc ggcatactct    2220
gcgacatcgt ataacgttac tggtttcaca ttcaccaccc tgaattgact ctcttccggg    2280
cgctatcatg ccataccgcg aaaggttttg cgccattcga tggtgtccgg gatctcgacg    2340
ctctccctta tgcgactcct gcattaggct cactataggg gaattgtgag cggataacaa    2400
ttcccctcta gagtttgaca gcattgtcat cgatctcgag aaatcataaa aaatttattt    2460
gctttgtgag cggataacaa ttataataga ttcaattgtg agcggataac aatttcacac    2520
agaattcatt aaagaggaga attacatat gagcaaagga gaagaacttt tcactggagt    2580
tgtcccaatt cttgttgaat tagatggtga tgttaatggg cacaaatttt ctgtccgtgg    2640
agagggtgaa ggtgatgcta caaacggaaa actcaccctt aaatttattt gcactactgg    2700
aaaactacct gttccgtggc caacacttgt cactactctg acctatggtg ttcaatgctt    2760
ttcccgttat ccggatcaca tgaaacggca tgacttttc aagagtgcca tgcccgaagg    2820
ttatgtacag gaacgcacta tatctttcaa agatgacggg acctacaaga cgcgtgctga    2880
agtcaagttt gaaggtgata cccttgttaa tcgtatcgag ttaaagggta ttgattttaa    2940
agaagatgga aacattcttg gacacaaact cgagtacaac tttaactcac acaatgtatg    3000
aatcacggca gacaaacaaa gaatggaat caaagctaac ttcaaaattc gccacaacgt    3060
tgaagatggt tccgttcaac tagcagacca ttatcaacaa atactccaa ttggcgatgg    3120 ccctgtcctt ttaccagaca accattacct gtcgacacaa tctgtccttt cgaaagatcc    3180
caacgaaaag cgtgaccaca tggtccttct tgagtttgta actgctgctg ggattacaca    3240
tggcatggat gagctctaca aggatccca ccaccaccac cactaaa agcttaatta    3300 gctgagcttg gactcctgtt gatagatcca gtaatgacct cagaactcca tctggatttg    3360
ttcagaacgc tcggttgccg ccgggcgttt tttattggtg agaatccaag ctagcttggc    3420
gctgcagtgt gcttctcaaa tgcctgaggc cagtttgctc aggctctccc cgtggaggta    3480
ataattgacg atatgatcag tgcacggcta actaagcggc ctgctgactt tctcgccgat    3540
caaaaggcat tttgctatta agggattgac gagggcgtat ctgcgcagta agatgcgccc    3600
cgcatttagg ggcgtagttc aattggtaga gcaccggtct tcaaaaccgg gtgttgggag    3660
```

```
ttcgagtctc tccgcccctg ccaaattcga aaagcctgct caacgagcag gcttttttgc    3720
atgctcgagc agctcagggt cgaatttgct ttcgaatttc tgccattcat ccgcttatta    3780
tcacttattc aggcgtagca accaggcgtt taagggcacc ataactgcc ttaaaaaaat     3840 tacgccccgc cctgccactc atcgcagtac tgttgtaatt cattaagcat tctgccgaca    3900
tggaagccat cacaaacggc atgatgaacc tgaatcgcca gcggcatcag caccttgtcg    3960
ccttgcgtat aatatttgcc catggtgaaa acggggcga agaagttgtc catattggcc     4020
acgtttaaat caaaactggt gaaactcacc cagggattgg ctgagacgaa aaacatattc    4080
tcaataaacc ctttagggaa ataggccagg ttttcaccgt aacacgccac atcttgcgaa    4140
tatatgtgta gaaactgccg gaaatcgtcg tggtattcac tccagagcga tgaaaacgtt    4200
tcagtttgct catggaaaac ggtgtaacaa gggtgaacac tatcccatat caccagctca    4260
ccgtctttca ttgccatacg gaattccgga tgagcattca tcaggcgggc aagaatgtga    4320
ataaaggccg gataaaactt gtgcttattt ttctttacgg tctttaaaaa ggccgtaata    4380
tccagctgaa cggtctggtt ataggtacat tgagcaactg actgaaatgc ctcaaaatgt    4440
tctttacgat gccattggga tatatcaacg gtggtatatc cagtgatttt tttctccatt    4500
ttagcttcct tagctcctga aaatctcgat aactcaaaaa atacgcccgg tagtgatctt    4560
atttcattat ggtgaaagtt ggaacctctt acgtgccgat caacgtctca ttttcgccaa    4620
aagttggccc agggcttccc ggtatcaaca gggacaccag gatttattta ttctgcgaag    4680
tgatcttccg tcacaggtat ttattcggcg caaagtgcgt cgggtgatgc tgccaactta    4740
ctgatttagt gtatgatggt gttttgagg tgctccagtg gcttctgttt ctatcagctg      4800
tccctcctgt tcagctactg acg                                             4823
```

<210> SEQ ID NO 84
<211> LENGTH: 5171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
gggtggtgcg taacggcaaa agcaccgccg gacatcagcg ctagcggagt gtatactggc      60
ttactatgtt ggcactgatg agggtgtcag tgaagtgctt catgtggcag gagaaaaaag     120
gctgcaccgg tgcgtcagca gaatatgtga tacaggatat attccgcttc ctcgctcact     180
gactcgctac gctcggtcgt tcgactgcgg cgagcggaaa tggcttacga acggggcgga     240
gatttcctgg aagatgccag gaagatactt aacaggaag tgagagggcc gcggcaaagc      300
cgttttccca taggctccgc cccctgaca agcatcacga atctgacgc tcaaatcagt       360 ggtggcgaaa cccgacagga ctataaagat accaggcgtt tccccctggc ggctccctcg    420
tgcgctctcc tgttcctgcc tttcggttta ccggtgtcat tccgctgtta tggccgcgtt    480
tgtctcattc cacgcctgac actcagttcc gggtaggcag ttcgctccaa gctggactgt    540
atgcacgaac ccccgttca gtccgaccgc tgcgccttat ccgtaactaa tcgtcttgag    600
tccaacccgg aaagacatgc aaaagcacca ctggcagcag ccactggtaa ttgatttaga    660
ggagttagtc ttgaagtcat gcgccggtta aggctaaact gaaaggacaa gttttggtga    720
ctgcgctcct ccaagccagt tacctcggtt caaagagttg gtagctcaga gaaccttcga    780
aaaaccgccc tgcaaggcgg ttttttcgtt ttcagagcaa gagattacgc gcagaccaaa    840
```

```
acgatctcaa gaagatcatc ttattaatca gataaaatat ttctagattt cagtgcaatt      900
tatctcttca aatgtagcac ctgaagtcag ccccatacga tataagttgt aattctcatg      960
tttgacagct tatcatcgat aagcttgcaa tttatctctt caaatgtagc acctgaagtc     1020
agccccatac gatataagtt gtaattctca tgttagtcat gccccgcgcc caccggaagg     1080
agctgactgg gttgaaggct ctcaagggca tcggtcgaga tcccggtgcc taatgagtga     1140
gctaacttac attaattgcg ttgcgctcac tgcccgcttt ccagtcggga aacctgtcgt     1200
gccagctgca ttaatgaatc ggccaacgcg cggggagagg cggtttgcgt attgggcgcc     1260
agggtggttt ttcttttcac cagtgagacg ggcaacagct gattgccctt caccgcctgg     1320
ccctgagaga gttgcagcaa gcggtccacg ctggtttgcc ccagcaggcg aaaatcctgt     1380
ttgatggtgg ttaacggcgg gatataacat gagctgtctt cggtatcgtc gtatcccact     1440
accgagatgt ccgcaccaac gcgcagcccg gactcggtaa tggcgcgcat tgcgcccagc     1500
gccatctgat cgttggcaac cagcatcgca gtgggaacga tgccctcatt cagcatttgc     1560
atggtttgtt gaaaaccgga catggcactc cagtcgcctt cccgttccgc tatcggctga     1620
atttgattgc gagtgagata tttatgccag ccagccagac gcagacgcgc cgagacagaa     1680
cttaatgggc ccgctaacag cgcgatttgc tggtgaccca atgcgaccag atgctccacg     1740
cccagtcgcg taccgtcttc atgggagaaa ataatactgt tgatgggtgt ctggtcagag     1800
acatcaagaa ataacgccgg aacattagtg caggcagctt ccacagcaat ggcatcctgg     1860
tcatccagcg gatagttaat gatcagccca ctgacgcgtt gcgcgagaag attgtgcacc     1920
gccgctttac aggcttcgac gccgcttcgt tctaccatcg acaccaccac gctggcaccc     1980
agttgatcgg cgcgagattt aatcgccgcg acaatttgcg acggcgcgtg cagggccaga     2040
ctggaggtgg caacgccaat cagcaacgac tgtttgcccg ccagttgttg tgccacgcgg     2100
ttgggaatgt aattcagctc cgccatcgcc gcttccactt tttcccgcgt tttcgcagaa     2160
acgtggctgg cctggttcac cacgcgggaa acggtctgat aagagacacc ggcatactct     2220
gcgacatcgt ataacgttac tggtttcaca ttcaccaccc tgaattgact ctcttccggg     2280
cgctatcatg ccataccgcg aaaggttttg cgccattcga tggtgtccgg atctcgacg     2340 ctctccctta tgcgactcct gcattaggga gctgttgaca attaatcatc ggctcgtata     2400
atgtgtggaa ttgtgagcgg ataacaattt cacaaggag gtgcggccgc atgactaagc     2460
ccatcgtttt tgctggcgca cagccctcag gtgaattgac cattggtaac tacatgggtg     2520
cgctgcgtca gtgggtaaac atgcaggatg actaccattg catttactgt atcgttgacc     2580
aacacgcgat caccgtgcgc caggatgcac agaagctgcg taaagcgacg ctggatacgc     2640
tggccttgta tctggcttgt ggtatcgatc ctgagaaaag caccattttt gttcagtccc     2700
acgtgccgga acatgcacag ttaggctggg cactgaactg ctatacctac ttcggcgaac     2760
tgagtcgcat gacgcagttt aaagataaat ctgcgcgtta tgccgagaac atcaacgctg     2820
gtctgtttga ctatccggtg ctgatggcag cggacatcct gctgtatcaa actaatctgg     2880
gtccttgtgg tgaagaccag aaacagcacc tcgaactgag ccgcgatatt gcccagcgtt     2940
tcaacgcgct gtatgcgag atctttaagg tgccggagcc gtttattccg aaatctggcg     3000
cgcgcgtaat gtcgctgctg agccgaccag agaagatgtc caagtctgac gataatcgca     3060
ataacgttat cggcctgctg gaagatccga atcggtagt gaagaaaatc aaacgtgcgg     3120
tcactgactc cgacgagccg ccggtagttc gctacgatgt gcagaacaaa gcgggcgttt     3180
```

```
ccaacctgtt ggatatcctt tcagcggtaa cgggccagag catcccagaa ctggaaaaac    3240
agttcgaagg caagatgtat ggtcatctga aggtgaagt ggctgatgcc gtttccggta     3300
tgctgactga attgcaggaa cgctatcacc gtttccgcaa cgatgaagcc ttcctgcaac    3360
aggtgatgaa agatggcgcg gaaaaagcca gcgcgcacgc ttcccgtacg ctaaaagcgg    3420
tgtacgaagc gattggtttt gtggcgaagc cgtaagcggc cgcgtttaaa cggtctccag    3480
cttggctgtt ttggcggatg agagaagatt ttcagcctga tacagattaa atcagaacgc    3540
agaagcggtc tgataaaaca gaatttgcct ggcggcagta gcgcggtggt cccacctgac    3600
cccatgccga actcagaagt gaaacgccgt agcgccgatg gtagtgtggg gtctccccat    3660
gcgagagtag ggaactgcca ggcatcaaat aaaacgaaag gctcagtcga agactgggc     3720
cttgtttgtg agctcccggt catcaatcat ccccataatc cttgttagcc tgcagtgtgc    3780
ttctcaaatg cctgaggcca gtttgctcag gctctccccg tggaggtaat aattgacgat    3840
atgatcagtg cacggctaac taagcggcct gctgactttc tcgccgatca aaaggcattt    3900
tgctattaag ggattgacga gggcgtatct gcgcagtaag atgcgccccg catttagggg    3960
cgtagttcaa ttggtagagc accggtcttc aaaaccgggt gttgggagtt cgagtctctc    4020
cgcccctgcc aaattcgaaa agcctgctca acgagcaggc ttttttgcat gctcgagcag    4080
ctcagggtcg aatttgcttt cgaatttctg ccattcatcc gcttattatc acttattcag    4140
gcgtagcaac caggcgttta agggcaccaa taactgcctt aaaaaaatta cgccccgccc    4200
tgccactcat cgcagtactg ttgtaattca ttaagcattc tgccgacatg gaagccatca    4260
caaacggcat gatgaacctg aatcgccagc ggcatcagca ccttgtcgcc ttgcgtataa    4320
tatttgccca tggtgaaaac gggggcgaag aagttgtcca tattggccac gtttaaatca    4380
aaactggtga aactcaccca gggattggct gagacgaaaa acatattctc aataaaccct    4440
ttagggaaat aggccaggtt ttcaccgtaa cacgccacat cttgcgaata tatgtgtaga    4500
aactgccgga atcgtcgtg gtattcactc cagagcgatg aaaacgtttc agtttgctca     4560
tggaaaacgg tgtaacaagg gtgaacacta tcccatatca ccagctcacc gtctttcatt    4620
gccatacgga attccggatg agcattcatc aggcgggcaa gaatgtgaat aaaggccgga    4680
taaaacttgt gcttattttt ctttacggtc tttaaaaagg ccgtaatatc cagctgaacg    4740
gtctggttat aggtacattg agcaactgac tgaaatgcct caaaatgttc tttacgatgc    4800
cattgggata tatcaacggt ggtatatcca gtgattttt tctccatttt agcttcctta    4860
gctcctgaaa atctcgataa ctcaaaaaat acgcccggta gtgatcttat ttcattatgg    4920
tgaaagttgg aacctcttac gtgccgatca acgtctcatt ttcgccaaaa gttggcccag    4980
ggcttcccgg tatcaacagg gacaccagga tttatttatt ctgcgaagtg atcttccgtc    5040
acaggtattt attcggcgca aagtgcgtcg ggtgatgctg ccaacttact gatttagtgt    5100
atgatggtgt ttttgaggtg ctccagtggc ttctgtttct atcagctgtc cctcctgttc    5160
agctactgac g                                                         5171
```

<210> SEQ ID NO 85
<211> LENGTH: 1005
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atgactaagc ccatcgtttt tgctggcgca cagccctcag gtgaattgac cattggtaac    60
tacatgggtg cgctgcgtca gtgggtaaac atgcaggatg actaccattg catttactgt   120
atcgttgacc aacacgcgat caccgtgcgc caggatgcac agaagctgcg taaagcgacg   180
ctggatacgt tggccttgta tctggcttgt ggtatcgatc ctgagaaaag caccattttt   240
gttcagtccc acgtgccgga acatgcacag ttaggctggg cactgaactg ctatacctac   300
ttcggcgaac tgagtcgcat gacgcagttt aaagataaat ctgcgcgtta tgccgagaac   360
atcaacgctg gtctgtttga ctatccggtg ctgatggcag cggacatcct gctgtatcaa   420
actaatctga gtcctgctgg tgaagaccag aaacagcacc tcgaactgag ccgcgatatt   480
gcccagcgtt tcaacgcgct gtatggcgag atctttaagg tgccggagcc gtttattccg   540
aaatctggcg cgcgcgtaat gtcgctgctg gagccgacca agaagatgtc caagtctgac   600
gataatcgca ataacgttat cggcctgctg gaagatccga atcggtagt gaagaaaatc    660 aaacgtgcgg tcactgactc cgacgagccg ccggtagttc gctacgatgt gcagaacaaa   720
gcgggcgttt ccaacctgtt ggatatcctt tcagcggtaa cgggccagag catcccagaa   780
ctggaaaaac agttcgaagg caagatgtat ggtcatctga aggtgaagt ggctgatgcc    840 gtttccggta tgctgactga attgcaggaa cgctatcacc gtttccgcaa cgatgaagcc   900
ttcctgcaac aggtgatgaa agatggcgcg gaaaaagcca gcgcgcacgc ttcccgtacg   960
ctaaaagcgg tgtacgaagc gattggtttt gtggcgaagc cgtaa                 1005
```

<210> SEQ ID NO 86
<211> LENGTH: 2976
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
cttttgctga gttgaaggat ccgcggccgc tcgggttgtc agcctgtccc gcttataaga    60
tcatacgccg ttatacgttg tttacgcttt gaggaatccc atatgatgac taagcccatc   120 gttttagtg gcgcacagcc ctcaggtgaa ttgaccattg gtaactacat gggtgcgctg    180
cgtcagtggg taaacatgca ggatgactac cattgcattt actgtatcgt tgaccaacac   240
gcgatcaccg tgcgccagga tgcacagaag ctgcgtaaag cgacgctgga tacgctggcc   300
ttgtatctgg cttgtggtat cgatcctgag aaaagcacca ttttgttca gtcccacgtg    360 ccggaacatg cacagttagg ctgggcactg aactgctata cctacttcgg cgaactgagt   420
cgcatgacgc agtttaaaga taaatctgcg cgttatgccg agaacatcaa cgctggtctg   480
tttgactatc cggtgctgat ggcagcggac atcctgctgt atcaaactaa tctggtaccg   540
gtgggtgaag accagaaaca gcacctcgaa ctgagccgcg atattgccca gcgtttcaac   600
gcgctgtatg cgagatctt taaggtgccg gagccgttta ttccgaaatc tggcgcgcgc    660
gtaatgtcgc tgctggagcc gaccaagaag atgtccaagt ctgacgataa tcgcaataac   720
gttatcggcc tgctggaaga tccgaaatcg gtagtgaaga aaatcaaacg tgcggtcact   780
gactccgacg agccgccggt agttcgctac gatgtgcaga acaaagcggg cgtttccaac   840
ctgttggata tcctttcagc ggtaacgggc cagagcatcc cagaactgga aaaacagttc   900
gaaggcaaga tgtatggtca tctgaaaggt gaagtggctg atgccgtttc cggtatgctg   960
actgaattgc aggaacgcta tcaccgtttc cgcaacgatg aagccttcct gcaacaggtg  1020
```

```
atgaaagatg gcgcggaaaa agccagcgcg cacgcttccc gtacgctaaa agcggtgtac    1080
gaagcgattg gttttgtggc gaagccgtaa ctgcagtttc aaacgctaaa ttgcctgatg    1140
cgctacgctt atcaggccta catgatctct gcaatatatt gagtttgcgt gcttttgtag    1200
gccggataag gcgttcacgc cgcatccggc aagaaacagc aaacaatcca aaacgccgcg    1260
ttcagcggcg ttttttctgc ttttcttcgc gaattaattc cgcttcgcac atgtgagcaa    1320
aaggccagca aaaggccagg aaccgtaaaa aggccgcgtt gctggcgttt tccataggc     1380 tccgccccc tgacgagcat cacaaaaatc gacgctcaag tcagaggtgg cgaaacccga    1440
caggactata agataccag gcgtttcccc ctggaagctc cctcgtgcgc tctcctgttc     1500
cgaccctgcc gcttaccgga tacctgtccg cctttctccc ttcgggaagc gtggcgcttt    1560
ctcatagctc acgctgtagg tatctcagtt cggtgtaggt cgttcgctcc aagctgggct    1620
gtgtgcacga accccccgtt cagcccgacc gctgcgcctt atccggtaac tatcgtcttg    1680
agtccaaccc ggtaagacac gacttatcgc cactggcagc agccactggt aacaggatta    1740
gcagagcgag gtatgtaggc ggtgctacag agttcttgaa gtggtggcct aactacggct    1800
acactagaag gacagtattt ggtatctgcg ctctgctgaa gccagttacc ttcggaaaaa    1860
gagttggtag ctcttgatcc ggcaaacaaa ccaccgctgg tagcggtggt ttttttgttt    1920
gcaagcagca gattacgcgc agaaaaaaag gatctcaaga agatcctttg atcttttcta    1980
cggggtctga cgctcagtgg aacgaaaact cacgttaagg gattttggtc atgaacaata    2040
aaactgtctg cttacataaa cagtaataca aggggtgtta tgagccatat tcaacgggaa    2100
acgtcttgct cgaggccgcg attaaattcc aacatggatg ctgatttata tgggtataaa    2160
tgggctcgcg ataatgtcgg gcaatcaggt gcgacaatct atcgattgta tgggaagccc    2220
gatgcgccag agttgtttct gaaacatggc aaaggtagcg ttgccaatga tgttacagat    2280
gagatggtca gactaaactg gctgacggaa tttatgcctc ttccgaccat caagcatttt    2340
atccgtactc ctgatgatgc atggttactc accactgcga tccccgggaa aacagcattc    2400
caggtattag aagaatatcc tgattcaggt gaaaatattg ttgatgcgct ggcagtgttc    2460
ctgcgccggt tgcattcgat tcctgtttgt aattgtcctt ttaacagcga tcgcgtattt    2520
cgtctcgctc aggcgcaatc acgaatgaat aacggtttgg ttgatgcgag tgattttgat    2580
gacgagcgta atggctggcc tgttgaacaa gtctggaaag aaatgcataa gcttttgcca    2640
ttctcaccgg attcagtcgt cactcatggt gatttctcac ttgataacct tattttttgac   2700 gagggggaaat taataggttg tattgatgtt ggacgagtcg gaatcgcaga ccgataccag    2760
gatcttgcca tcctatggaa ctgcctcggt gagttttctc cttcattaca gaaacggctt    2820
tttcaaaaat atggtattga taatcctgat atgaataaat tgcagtttca tttgatgctc    2880
gatgagtttt tctaatcaga attggttaat tggttgtaac actggcagag cattacgctg    2940
acttgacggg acggcggctt tgttgaataa atcgaa                              2976
```

<210> SEQ ID NO 87
<211> LENGTH: 1005
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
atgactaagc ccatcgtttt tgctggcgca cagccctcag gtgaattgac cattggtaac      60
```

```
tacatgggtg cgctgcgtca gtgggtaaac atgcaggatg actaccattg catttactgt    120
atcgttgacc aacacgcgat caccgtgcgc caggatgcac agaagctgcg taaagcgacg    180
ctggatacgc tggccttgta tctggcttgt ggtatcgatc ctgagaaaag caccattttt    240
gttcagtccc acgtgccgga acatgcacag ttaggctggg cactgaactg ctatacctac    300
ttcggcgaac tgagtcgcat gacgcagttt aaagataaat ctgcgcgtta tgccgagaac    360
atcaacgctg gtctgtttga ctatccggtg ctgatggcag cggacatcct gctgtatcaa    420
actaatctgg gtccttgtgg tgaagaccag aaacagcacc tcgaactgag ccgcgatatt    480
gcccagcgtt tcaacgcgct gtatggcgag atctttaagg tgccggagcc gtttattccg    540
aaatctggcg cgcgcgtaat gtcgctgctg agccgaccaa agaagatgtc caagtctgac    600
gataatcgca ataacgttat cggcctgctg aagatccga  aatcggtagt gaagaaaatc    660
aaacgtgcgg tcactgactc cgacgagccg ccggtagttc gctacgatgt gcagaacaaa    720
gcgggcgttt ccaacctgtt ggatatcctt tcagcggtaa cgggccagag catcccagaa    780
ctggaaaaac agttcgaagg caagatgtat ggtcatctga aggtgaagt ggctgatgcc    840 gtttccggta tgctgactga attgcaggaa cgctatcacc gtttccgcaa cgatgaagcc    900
ttcctgcaac aggtgatgaa agatggcgcg gaaaaagcca gcgcgcacgc ttcccgtacg    960
ctaaaagcgg tgtacgaagc gattggtttt gtggcgaagc cgtaa                  1005
```

<210> SEQ ID NO 88
<211> LENGTH: 1005
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
atgactaagc ccatcgtttt tgctggcgca cagccctcag gtgaattgac cattggtaac     60
tacatgggtg cgctgcgtca gtgggtaaac atgcaggatg actaccattg catttactgt    120
atcgttgacc aacacgcgat caccgtgcgc caggatgcac agaagctgcg taaagcgacg    180
ctggatacgc tggccttgta tctggcttgt ggtatcgatc ctgagaaaag caccattttt    240
gttcagtccc acgtgccgga acatgcacag ttaggctggg cactgaactg ctatacctac    300
ttcggcgaac tgagtcgcat gacgcagttt aaagataaat ctgcgcgtta tgccgagaac    360
atcaacgctg gtctgtttga ctatccggtg ctgatggcag cggacatcct gctgtatcaa    420
actaatctga gtcctgctgg tgaagaccag aaacagcacc tcgaactgag ccgcgatatt    480
gcccagcgtt tcaacgcgct gtatggcgag atctttaagg tgccggagcc gtttattccg    540
aaatctggcg cgcgcgtaat gtcgctgctg agccgaccaa agaagatgtc caagtctgac    600
gataatcgca ataacgttat cggcctgctg aagatccga  aatcggtagt gaagaaaatc    660
aaacgtgcgg tcactgactc cgacgagccg ccggtagttc gctacgatgt gcagaacaaa    720
gcgggcgttt ccaacctgtt ggatatcctt tcagcggtaa cgggccagag catcccagaa    780
ctggaaaaac agttcgaagg caagatgtat ggtcatctga aggtgaagt ggctgatgcc    840 gtttccggta tgctgactga attgcaggaa cgctatcacc gtttccgcaa cgatgaagcc    900
ttcctgcaac aggtgatgaa agatggcgcg gaaaaagcca gcgcgcacgc ttcccgtacg    960
ctaaaagcgg tgtacgaagc gattggtttt gtggcgaagc cgtaa                  1005
```

<210> SEQ ID NO 89

<211> LENGTH: 9147
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

| | |
|---|---|
| ttctctgtca cagaatgaaa attttctgt catctcttcg ttattaatgt tgtaattga | 60 |
| ctgaatatca acgcttattt gcagcctgaa tggcgaatgg gacgcgccct gtagcggcgc | 120 |
| attaagcgcg gcgggtgtgg tggttacgcg cagcgtgacc gctacacttg ccagcgccct | 180 |
| agcgcccgct cctttcgctt tcttcccttc ctttctcgcc acgttcgccg gctttccccg | 240 |
| tcaagctcta atcgggggc tccctttagg gttccgattt agtgctttac ggcacctcga | 300 |
| ccccaaaaaa cttgattagg gtgatggttc acgtagtggg ccatcgccct gatagacggt | 360 |
| ttttcgccct tgacgttgg agtccacgtt ctttaatagt ggactcttgt tccaaactgg | 420 |
| aacaacactc aaccctatct cggtctattc ttttgattta tagggattt tgccgatttc | 480 |
| ggcctattgg ttaaaaaatg agctgattta acaaaaattt aacgcgaatt ttaacaaaat | 540 |
| attaacgttt acaatttcag gtggcacttt tcggggaaat gtgcgcggaa ccccctatttg | 600 |
| tttattttc taaatacatt caaatatgta tccgctcatg agacaataac cctgataaat | 660 |
| gcttcaataa tattgaaaaa ggaagagtat ggcgtagagt attcaacatt tccgtgtcgc | 720 |
| ccttattccc ttttttgcgg cattttgcct tcctgttttt gctcacccag aaacgctggt | 780 |
| gaaagtaaaa gatgctgaag atcagttggg tgcacgagtg ggttacatcg aactggatct | 840 |
| caacagcggt aagatccttg agagttttcg ccccgaagaa cgttttccaa tgatgagcac | 900 |
| ttttaaagtt ctgctatgtg gcgcggtatt atcccgtatt gacgccgggc aagagcaact | 960 |
| cggtcgccgc atacactatt ctcagaatga cttggttgag tactcaccag tcacagaaaa | 1020 |
| gcatcttacg gatggcatga cagtaagaga attatgcagt gctgccataa ccatgagtga | 1080 |
| taacactgcg gccaacttac ttctgacaac gatcggagga ccgaaggagc taaccgcttt | 1140 |
| tttgcacaac atgggggatc atgtaactcg ccttgatcgt tgggaaccgg agctgaatga | 1200 |
| agccatacca aacgacgagc gtgacaccac gatgcctgta gcaatggcaa caacgttgcg | 1260 |
| caaactatta actggcgaac tacttactct agcttcccgg caacaattaa tagactggat | 1320 |
| ggaggcggat aaagttgcag gaccacttct gcgctcggcc cttccggctg gctggtttat | 1380 |
| tgctgataaa tctggagccg gtgagcgtgg gtctcgcggt atcattgcag cactggggcc | 1440 |
| agatggtaag ccctcccgta tcgtagttat ctacacgacg gggagtcagg caactatgga | 1500 |
| tgaacgaaat agacagatcg ctgagatagg tgcctcactg attaagcatt ggtaactgtc | 1560 |
| agaccaagtt tactcatata ctttagat tgatttaaaa cttcattttt aatttaaaag | 1620 |
| gatctaggtg aagatccttt ttgataatct catgaccaaa atcccttaac gtgagttttc | 1680 |
| gttccactga gcgtcagacc ccgtagaaaa gatcaaagga tcttcttgag atccttttt | 1740 |
| tctgcgcgta atctgctgct tgcaaacaaa aaaaccaccg ctaccagcgg tggtttgttt | 1800 |
| gccggatcaa gagctaccaa ctcttttcc gaaggtaact ggcttcagca gagcgcagat | 1860 |
| accaaatact gtccttctag tgtagccgta gttaggccac cacttcaaga actctgtagc | 1920 |
| accgcctaca tacctcgctc tgctaatcct gttaccagtg gctgctgcca gtggcgataa | 1980 |
| gtcgtgtctt accgggttgg actcaagacg atagttaccg gataaggcgc agcggtcggg | 2040 |
| ctgaacgggg ggttcgtgca cacagcccag cttggagcga acgacctaca ccgaactgag | 2100 |

```
atacctacag cgtgagcatt gagaaagcgc cacgcttccc gaagggagaa aggcggacag    2160
gtatccggta agcggcaggg tcggaacagg agagcgcacg agggagcttc caggggggaaa   2220 cgcctggtat ctttatagtc ctgtcgggtt tcgccacctc tgacttgagc gtcgattttt    2280
gtgatgctcg tcaggggggc ggagcctatg gaaaaacgcc agcaacgcgg ccttttttacg   2340 gttcctggcc ttttgctggc cttttgctca catgttcttt cctgcgttat ccctgattc     2400 tgtggataac cgtattaccg cctttgagtg agctgatacc gctcgccgca gccgaacgac    2460
cgagcgcagc gagtcagtga gcgaggaagc ggaagagcgc ctgatgcggt attttctcct    2520
tacgcatctg tgcggtattt cacaccgcag accagccgcg taacctggca aaatcggtta    2580
cggttgagta ataaatggat gccctgcgta agcgggtgtg ggcggacaat aaagtcttaa    2640
actgaacaaa atagatctaa actatgacaa taaagtctta aactagacag aatagttgta    2700
aactgaaatc agtccagtta tgctgtgaaa aagcatactg gacttttgtt atggctaaag    2760
caaactcttc attttctgaa gtgcaaattg cccgtcgtat taaagagggg cgtggccaag    2820
ggcatggtaa agactatatt cgcggcgttg tgacaattta ccgaacaact ccgcggccgg    2880
gaagccgatc tcggcttgaa cgaattgtta ggtggcggta cttgggtcga tatcaaagtg    2940
catcacttct tcccgtatgc ccaactttgt atagagagcc actgcgggat cgtcaccgta    3000
atctgcttgc acgtagatca cataagcacc aagcgcgttg gcctcatgct tgaggagatt    3060
gatgagcgcg gtggcaatgc cctgcctccg gtgctcgccg gagactgcga gatcatagat    3120
atagatctca ctacgcggct gctcaaacct gggcagaacg taagccgcga gagcgccaac    3180
aaccgcttct tggtcgaagg cagcaagcgc gatgaatgtc ttactacgga gcaagttccc    3240
gaggtaatcg gagtccggct gatgttggga gtaggtggct acgtctccga actcacgacc    3300
gaaaagatca agagcagccc gcatggattt gacttggtca gggccgagcc tacatgtgcg    3360
aatgatgccc atacttgagc cacctaactt tgttttaggg cgactgccct gctgcgtaac    3420
atcgttgctc ctgcgtaaca tcgttgctgc tccataacat caaacatcga cccacgcgt    3480 aacgcgcttg ctgcttggat gcccgaggca tagactgtac aaaaaaacag tcataacaag    3540
ccatgaaaac cgccactgcg ccgttaccac cgctgcgttc ggtcaaggtt ctggaccagt    3600
tgcgtgagcg catacgctac ttgcattaca gtttacgaac cgaacaggct tatgtcaact    3660
gggttcgtgc cttcatccgt ttccacggtg tgcgtcaccc ggcaaccttg ggcagcagcg    3720
aagtcgaggc atttctgtcc tggctggcga acagagcgcaa ggtttcggtc tccacgcatc   3780
gtcaggcatt ggcggccttg ctgttcttct acggcaaggt gctgtgcacg gatctgccct    3840
ggcttcagga gatcggtaga cctcggccgt cgcggcgctt gccggtggtg ctgaccccgg    3900
atgaagtggt tcgcatcctc ggttttctgg aaggcgagca tcgtttgttc gcccaggact    3960
ctagctatag ttctagtggt tggctacgta cccgtagtgg ctatggcagg gcttgcgctt    4020
aatgcgccgc tacagggcgc gtggggatac cccctagagc cccagctggt tctttccgcc    4080
tcagaagcca tagagcccac cgcatcccca gcatgcctgc tattgtcttc ccaatcctcc    4140
cccttgctgt cctgccccac cccacccccc agaatagaat gacacctact cagacaatgc    4200
gatgcaattt cctcattta ttaggaaagg acagtgggag tggcaccttc cagggtcaag     4260
gaaggcacgg gggagggggca acaacagat ggctggcaac tagaaggcac agtcgaggct    4320
gatcagcggg tttaaacggg ccctctagac tcgagttaaa gtcgacgcgg ggaggcggcc    4380
caaagggaga tccgactcgt ctgagggcga aggcgaagac gcggaagagg ccgcagagcc    4440
ggcagcaggc cgcgggaagg aaggtccgct ggattgaggg ccgaagggac gtagcagaag    4500
```

```
gacgtcccgc gcagaatcca ggtggcaaca caggcgagca gccaaggaaa ggacgatgat    4560
ttccccgaca acaccacgga attgtcagtg cccaacagcc gagcccctgt ccagcagcgg    4620
gcaaggcagg cggcgatgag ttccgccgtg gcaataggga gggggaaagc gaaagtcccg    4680
gaaaggagct gacaggtggt ggcaatgccc caaccagtgg gggttgcgtc agcaaacaca    4740
gtgcacacca cgccacgttg cctgacaacg ggccacaact cctcataaag agacagcaac    4800
caggatttat acaaggagga gaaatgaaa gccatacggg aagcaatagc atgatacaaa     4860
ggcattaaag cagcgtatcc acatagcgta aaaggagcaa catagttaag aataccagtc    4920
aatctttcac aaattttgta atccagaggt tgattgtcga cttaacgcgt tgaattctca    4980
atggtgatgg tgatgatgac cggtatgcat attcagatcc tcttctgaga tgagttttg     5040 ttcgaagggc cccttgtaca gctcgtccat gccgagagtg atcccggcgg cggtcacgaa    5100
ctccagcagg accatgtgat cgcgcttctc gttgggtct ttgctcaggg cggactgggt      5160
gctcaggtag tggttgtcgg gcagcagcac ggggccgtcg ccgatggggg tgttctgctg    5220
gtagtggtcg gcgagctgca cgctgccgtc ctcgatgttg tggcggatct tgaagttcac    5280
cttgatgccg ttcttctgct tgtcggccat gatatagacg ttgtggctgt tgtagttgta    5340
ctccagcttg tgcccagga tgttgccgtc ctccttgaag tcgatgccct tcagctcgat     5400
gcggttcacc agggtgtcgc cctcgaactt cacctcggcg cgggtcttgt agttgccgtc    5460
gtccttgaag aagatggtgc gctcctggac gtagccttcg ggcatggcgg acttgaagaa    5520
gtcgtgctgc ttcatgtggt cggggtagcg gctgaagcac tgcacgccgt aggtcagggt    5580
ggtcacgagg gtgggccagg gcacgggcag cttgccggtg gtgcagatga acttcagggt    5640
cagcttgccc taagtggcat cgccctcgcc ctcgccggac acgctgaact tgtggccgtt    5700
tacgtcgccg tccagctcga ccaggatggg caccaccccg gtgaacagct cctcgccctt    5760
gctcaccatg gtggcggcgc tagccagctt gggtctccct atagtgagtc gtattaattt    5820
cgataagcca gtaagccagt aagcagtggg ttctctagtt agccagagag ctctgcttat    5880
atagacctcc caccgtacac gcctaccgcc catttgcgtc aatggggcgg agttgttacg    5940
acattttgga aagtcccgtt gattttggtg ccaaaacaaa ctcccattga cgtcaatggg    6000
gtggagactt ggaaatcccc gtgagtcaaa ccgctatcca cgccattga tgtactgcca      6060 aaaccgcatc accatggtaa tagcgatgac taatacgtag atgtactgcc aagtaggaaa    6120
gtcccataag gtcatgtact gggcataatg ccaggcgggc catttaccgt cattgacgtc    6180 aataggggc gtacttggca tatgatacac ttgatgtact gccaagtggg cagtttaccg      6240
taaatagtcc acccattgac gtcaatggaa agtccctatt ggcgttacta tgggaacata    6300
cgtcattatt gacgtcaatg gcgggggtc gttgggcggt cagccaggcg ggccatttac      6360
cgtaagttat gtaacgcgga actccatata tgggctatga actaatgacc ccgtaattga    6420
ttactattaa taactagtca ataatcaatg tcaacgcgta tatctggccc gtacatcgcg    6480
aagcagcgca aaacggatcc tgcaggtatt tgcggccgcg gtccgtatac tccggaatat    6540
taatagatca tggagataat taaaatgata accatctcgc aaataaataa gtatttact     6600 gttttcgtaa cagtttttgta ataaaaaaac ctataaatat tccggattat tcataccgtc    6660
ccaccatcgg gcgcgaactc ctaaaaaacc gccaccatga agtgcctttt gtacttagcc    6720 ttttttattca ttggggtgaa ttgcaagttc accatagttt ttccacacaa ccaaaaagga    6780
aactggaaaa atgttccttc taattaccat tattgcccgt caagctcaga tttaaattgg    6840
```

```
cataatgact taataggcac agccttacaa gtcaaaatgc ccaagagtca caaggctatt    6900
caagcagacg gttggatgtg tcatgcttcc aaatgggtca ctacttgtga tttccgctgg    6960
tatggaccga agtatataac acattccatc cgatccttca ctccatctgt agaacaatgc    7020
aaggaaagca ttgaacaaac gaaacaagga acttggctga atccaggctt ccctcctcaa    7080
agttgtggat atgcaactgt gacggatgcc gaagcagtga ttgtccaggt gactcctcac    7140
catgtgctgg ttgatgaata cacaggagaa tgggttgatt cacagttcat caacggaaaa    7200
tgcagcaatt acatatgccc cactgtccat aactctacaa cctggcattc tgactataag    7260
gtcaaagggc tatgtgattc taacctcatt tccatggaca tcaccttctt ctcagaggac    7320
ggagagctat catccctggg aaaggagggc acagggttca gaagtaacta ctttgcttat    7380
gaaactggag gcaaggcctg caaaatgcaa tactgcaagc attggggagt cagactccca    7440
tcaggtgtct ggttcgagat ggctgataag gatctctttg ctgcagccag attccctgaa    7500
tgcccagaag ggtcaagtat ctctgctcca tctcagacct cagtggatgt aagtctaatt    7560
caggacgttg agaggatctt ggattattcc ctctgccaag aaacctggag caaaatcaga    7620
gcgggtcttc caatctctcc agtggatctc agctatcttg ctcctaaaaa cccaggaacc    7680
ggtcctgctt tcaccataat caatggtacc ctaaaatact ttgagaccag atacatcaga    7740
gtcgatattg ctgctccaat cctctcaaga atggtcggaa tgatcagtgg aactaccaca    7800
gaaagggaac tgtgggatga ctgggcacca tatgaagacg tggaaattgg acccaatgga    7860
gttctgagga ccagttcagg atataagttt cctttataca tgattggaca tggtatgttg    7920
gactccgatc ttcatcttag ctcaaaggct caggtgttcg aacatcctca cattcaagac    7980
gctgcttcgc aacttcctga tgatgagagt ttattttttg gtgatactgg gctatccaaa    8040
aatccaatcg agcttgtaga aggttggttc agtagtggaa aaagctctat tgcctctttt    8100
ttctttatca tagggttaat cattggacta ttcttggttc tccgagttgg tatccatctt    8160
tgcattaaat taaagcacac caagaaaaga cagatttata cagacataga gatgaaccga    8220
cttggaaagt gataaggcca ggccggccaa gcttgtcgag aagtactaga ggatcataat    8280
cagccatacc acatttgtag aggttttact tgctttaaaa aacctcccac acctcccct    8340
gaacctgaaa cataaaatga atgcaattgt tgttgttaac ttgtttattg cagcttataa    8400
tggttacaaa taaagcaata gcatcacaaa tttcacaaat aaagcatttt ttcactgca    8460
ttctagttgt ggtttgtcca aactcatcaa tgtatcttat catgtctgga tctgatcact    8520
gcttgagcct aggtcgggca ggaagagggc ctatttccca tgattccttc atatttgcat    8580
atacgataca aggctgttag agagataatt agaattaatt tgactgtaaa cacaaagata    8640
ttagtacaaa atacgtgacg tagaaagtaa taatttcttg ggtagtttgc agttttaaaa    8700
ttatgtttta aaatggacta tcatatgctt accgtaactt gaaagtattt cgatttcttg    8760
gctttatata tcttgtggaa aggacgaaac accaggggcg tagttcaatt ggtagagcac    8820
cggtctctaa aaccgggtgt tgggagttcg agtctctccg cccctgccat ttttgctag    8880
gctcaagcag tgatctccga accagataag tgaaatctag ttccaaacta ttttgtcatt    8940
tttaattttc gtattagctt acgacgctac acccagttcc catctatttt gtcactcttc    9000
cctaaataat ccttaaaaac tccatttcca cccctcccag ttcccaacta ttttgtccgc    9060
ccacagcggg gcattttctt tcctgttatg tttttaatca acatcctgc caactccatg    9120
tgacaaaccg tcatcttcgg ctacttt                                        9147
```

<210> SEQ ID NO 90
<211> LENGTH: 9332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
ttctctgtca cagaatgaaa attttctgt catctcttcg ttattaatgt ttgtaattga      60
ctgaatatca acgcttattt gcagcctgaa tggcgaatgg gacgcgccct gtagcggcgc     120
attaagcgcg gcgggtgtgg tggttacgcg cagcgtgacc gctacacttg ccagcgccct     180
agcgcccgct cctttcgctt tcttcccttc ctttctcgcc acgttcgccg gctttccccg     240
tcaagctcta atcgggggc tcccttagg gttccgattt agtgctttac ggcacctcga     300
ccccaaaaaa cttgattagg gtgatggttc acgtagtggg ccatcgccct gatagacggt     360
ttttcgccct tgacgttgg agtccacgtt ctttaatagt ggactcttgt tccaaactgg     420
aacaacactc aaccctatct cggtctattc ttttgattta taaggatttt tgccgatttc     480
ggcctattgg ttaaaaaatg agctgattta acaaaaattt aacgcgaatt ttaacaaaat     540
attaacgttt acaatttcag gtggcacttt tcggggaaat gtgcgcggaa cccctatttg     600
tttatttttc taaatacatt caaatatgta tccgctcatg agacaataac cctgataaat     660
gcttcaataa tattgaaaaa ggaagagtat gagtattcaa catttccgtg tcgcccttat     720
tccctttttt gcggcatttt gccttcctgt ttttgctcac ccagaaacgc tggtgaaagt     780
aaaagatgct gaagatcagt tgggtgcacg agtgggttac atcgaactgg atctcaacag     840
cggtaagatc cttgagagtt ttcgccccga agaacgtttt ccaatgatga gcacttttaa     900
agttctgcta tgtggcgcgg tattatcccg tattgacgcc gggcaagagc aactcggtcg     960
ccgcatacac tattctcaga atgacttggt tgagtactca ccagtcacag aaaagcatct    1020
tacgatggg atgacagtaa gagaattatg cagtgctgcc ataaccatga gtgataacac    1080
tgcggccaac ttacttctga caacgatcgg aggaccgaag gagctaaccg cttttttgca    1140
caacatgggg gatcatgtaa ctcgccttga tcgttgggaa ccggagctga atgaagccat    1200
accaaacgac gagcgtgaca ccacgatgcc tgtagcaatg gcaacaacgt tgcgcaaact    1260
attaactggc gaactactta ctctagcttc ccggcaacaa ttaatagact ggatggaggc    1320
ggataaagtt gcaggaccac ttctgcgctc ggcccttccg gctggctggt ttattgctga    1380
taaatctgga gccggtgagc gtgggtctcg cggtatcatt gcagcactgg ggccagatgg    1440
taagccctcc cgtatcgtag ttatctacac gacggggagt caggcaacta tggatgaacg    1500
aaatagacag atcgctgaga taggtgcctc actgattaag cattggtaac tgtcagacca    1560
agtttactca tatatacttt agattgattt aaaacttcat ttttaattta aaaggatcta    1620
ggtgaagatc ctttttgata atctcatgac caaaatccct taacgtgagt ttcgttcca    1680
ctgagcgtca gaccccgtag aaaagatcaa aggatcttct tgagatcctt ttttctgcg    1740
cgtaatctgc tgcttgcaaa caaaaaaacc accgctacca gcggtggttt gtttgccgga    1800
tcaagagcta ccaactcttt ttccgaaggt aactggcttc agcagagcgc agataccaaa    1860
tactgtcctt ctagtgtagc cgtagttagg ccaccacttc aagaactctg tagcaccgcc    1920
tacatacctc gctctgctaa tcctgttacc agtggctgct gccagtggcg ataagtcgtg    1980
tcttaccggg ttggactcaa gacgatagtt accggataag gcgcagcggt cgggctgaac    2040
ggggggttcg tgcacacagc ccagcttgga gcgaacgacc tacaccgaac tgagatacct    2100
```

```
acagcgtgag cattgagaaa gcgccacgct tcccgaaggg agaaaggcgg acaggtatcc   2160
ggtaagcggc agggtcggaa caggagagcg cacgagggag cttccagggg gaaacgcctg   2220
gtatctttat agtcctgtcg ggtttcgcca cctctgactt gagcgtcgat ttttgtgatg   2280
ctcgtcaggg gggcggagcc tatggaaaaa cgccagcaac gcggccttttt acggttcct   2340 ggccttttgc tggccttttg ctcacatgtt ctttcctgcg ttatcccctg attctgtgga   2400
taaccgtatt accgcctttg agtgagctga taccgctcgc cgcagccgaa cgaccgagcg   2460
cagcgagtca gtgagcgagg aagcggaaga gcgcctgatg cggtattttc tccttacgca   2520
tctgtgcggt atttcacacc gcagaccagc cgcgtaacct ggcaaaatcg gttacggttg   2580
agtaataaat ggatgccctg cgtaagcggg tgtgggcgga caataaagtc ttaaactgaa   2640
caaaatagat ctaaactatg acaataaagt cttaaactag acagaatagt tgtaaactga   2700
aatcagtcca gttatgctgt gaaaaagcat actggacttt tgttatggct aaagcaaact   2760
cttcattttc tgaagtgcaa attgcccgtc gtattaaaga ggggcgtggc caagggcatg   2820
gtaaagacta tattcgcggc gttgtgacaa tttaccgaac aactccgcgg ccgggaagcc   2880
gatctcggct tgaacgaatt gttaggtggc ggtacttggg tcgatatcaa agtgcatcac   2940
ttcttcccgt atgcccaact ttgtatagag agccactgcg gatcgtcac cgtaatctgc    3000 ttgcacgtag atcacataag caccaagcgc gttggcctca tgcttgagga gattgatgag   3060
cgcggtggca atgccctgcc tccggtgctc gccggagact gcgagatcat agatatagat   3120
ctcactacgc ggctgctcaa acctgggcag aacgtaagcc gcgagagcgc caacaaccgc   3180
ttcttggtcg aaggcagcaa gcgcgatgaa tgtcttacta cggagcaagt tcccgaggta   3240
atcggagtcc ggctgatgtt gggagtaggt ggctacgtct ccgaactcac gaccgaaaag   3300
atcaagagca gcccgcatgg atttgacttg gtcagggccg agcctacatg tgcgaatgat   3360
gcccatactt gagccaccta actttgtttt agggcgactg ccctgctgcg taacatcgtt   3420
gctgctgcgt aacatcgttg ctgctccata acatcaaaca tcgacccacg gcgtaacgcg   3480
cttgctgctt ggatgcccga ggcatagact gtacaaaaaa acagtcataa caagccatga   3540
aaaccgccac tgcgccgtta ccaccgctgc gttcggtcaa ggttctggac cagttgcgtg   3600
agcgcatacg ctacttgcat tacagtttac gaaccgaaca ggcttatgtc aactgggttc   3660
gtgccttcat ccgtttccac ggtgtgcgtc acccggcaac cttgggcagc agcgaagtcg   3720
aggcatttct gtcctggctg gcgaacgagc gcaaggtttc ggtctccacg catcgtcagg   3780
cattggcggc cttgctgttc ttctacggca aggtgctgtg cacggatctg ccctggcttc   3840
aggagatcgg tagacctcgg ccgtcgcggc gcttgccggt ggtgctgacc ccggatgaag   3900
tggttcgcat cctcggtttt ctggaaggcg agcatcgttt gttcgcccag gactctagct   3960
atagttctag tggttggcta cgtacccgta gtggctatgg cagggcttgc gcttaatgcg   4020
ccgctacagg gcgcgtgggg ataccccta gagcccagc tggttctttc cgcctcagaa    4080
gccatagagc ccaccgcatc cccagcatgc ctgctattgt cttcccaatc ctcccccttg   4140
ctgtcctgcc ccaccccacc ccccagaata gaatgacacc tactcagaca atgcgatgca   4200
atttcctcat tttattagga aaggacagtg ggagtggcac cttccagggt caaggaaggc   4260 acggggagg ggcaaacaac agatggctgg caactagaag gcacagtcga ggctgatcag    4320
cgggtttaaa cgggccctct agactcgagt taaagtcgac gcggggaggc ggcccaaagg   4380
gagatccgac tcgtctgagg gcgaaggcga agacgcggaa gaggccgcag agccggcagc   4440
```

| | |
|---|---|
| aggccgcggg aaggaaggtc cgctggattg agggccgaag ggacgtagca gaaggacgtc | 4500 |
| ccgcgcagaa tccaggtggc aacacaggcg agcagccaag gaaaggacga tgatttcccc | 4560 |
| gacaacacca cggaattgtc agtgcccaac agccgagccc ctgtccagca gcgggcaagg | 4620 |
| caggcggcga tgagttccgc cgtggcaata gggaggggga aagcgaaagt cccggaaagg | 4680 |
| agctgacagg tggtggcaat gccccaacca gtggggttg cgtcagcaaa cacagtgcac | 4740 |
| accacgccac gttgcctgac aacgggccac aactcctcat aaagagacag caaccaggat | 4800 |
| ttatacaagg aggagaaaat gaaagccata cgggaagcaa tagcatgata caaaggcatt | 4860 |
| aaagcagcgt atccacatag cgtaaaagga gcaacatagt taagaatacc agtcaatctt | 4920 |
| tcacaaattt tgtaatccag aggttgattg tcgacttaac gcgttgaatt cttacggctt | 4980 |
| cgccacaaaa ccaatcgctt cgtacaccgc ttttagcgta cgggaagcgt gcgcgctggc | 5040 |
| tttttccgcg ccatctttca tcacctgttg caggaaggct tcatcgttgc ggaaacggtg | 5100 |
| atagcgttcc tgcaattcag tcagcatacc ggaaacggca tcagccactt cacctttcag | 5160 |
| atgaccatac atcttgcctt cgaactgttt ttccagttct gggatgctct ggcccgttac | 5220 |
| cgctgaaagg atatccaaca ggttggaaac gcccgctttg ttctgcacat cgtagcgaac | 5280 |
| taccggcggc tcgtcggagt cagtgaccgc acgtttgatt ttcttcacta ccgatttcgg | 5340 |
| atcttccagc aggccgataa cgttattgcg attatcgtca gacttggaca tcttcttggt | 5400 |
| cggctccagc agcgacatta cgcgcgcgcc agatttcgga ataaacggct ccggcacctt | 5460 |
| aaagatctcg ccatacagcg cgttgaaacg ctgggcaata tcgcggctca gttcgaggtg | 5520 |
| ctgtttctgg tcttcaccca ccggtaccag attagtttga tacagcagga tgtccgctgc | 5580 |
| catcagcacc ggatagtcaa acagaccagc gttgatgttc tcggcataac gcgcagattt | 5640 |
| atctttaaac tgcgtcatgc gactcagttc gccgaagtag gtatagcagt tcagtgccca | 5700 |
| gcctaactgt gcatgttccg gcacgtggga ctgaacaaaa atggtgcttt tctcaggatc | 5760 |
| gataccacaa gccagataca aggccagcgt atccagcgtc gctttacgca gcttctgtgc | 5820 |
| atcctggcgc acggtgatcg cgtgttggtc aacgatacag taaatgcaat ggtagtcatc | 5880 |
| ctgcatgttt acccactgac gcagcgcacc catgtagtta ccaatggtca attcacctga | 5940 |
| gggctgtgcg ccactaaaaa cgatgggctt agtcatgcta gccagcttgg gtctccctat | 6000 |
| agtgagtcgt attaatttcg ataagccagt aagcagtggg ttctctagtt agccagagag | 6060 |
| ctctgcttat atagacctcc caccgtacac gcctaccgcc catttgcgtc aatggggcgg | 6120 |
| agttgttacg acattttgga aagtcccgtt gattttggtg ccaaaacaaa ctcccattga | 6180 |
| cgtcaatggg gtggagactt ggaaatcccc gtgagtcaaa ccgctatcca cgcccattga | 6240 |
| tgtactgcca aaaccgcatc accatggtaa tagcgatgac taatacgtag atgtactgcc | 6300 |
| aagtaggaaa gtcccataag gtcatgtact gggcataatg ccaggcgggc catttaccgt | 6360 |
| cattgacgtc aataggggc gtacttggca tatgatacac ttgatgtact gccaagtggg | 6420 |
| cagtttaccg taaatagtcc acccattgac gtcaatgaa agtccctatt ggcgttacta | 6480 |
| tgggaacata cgtcattatt gacgtcaatg ggcggggtc gttggcggt cagccaggcg | 6540 |
| ggccatttac cgtaagttat gtaacgcgga actccatata tgggctatga actaatgacc | 6600 |
| ccgtaattga ttactattaa taactagtca ataatcaatg tcaacgcgta tatctggccc | 6660 |
| gtacatcgcg aagcagcgca aaacggatcc tgcaggtatt tgcggccgcg gtccgtatac | 6720 |
| tccggaatat taatagatca tggagataat taaaatgata accatctcgc aaataaataa | 6780 |
| gtattttact gttttcgtaa cagttttgta ataaaaaaac ctataaatat tccggattat | 6840 |

```
tcataccgtc ccaccatcgg gcgcgaactc ctaaaaaacc gccaccatga agtgccttt      6900
gtacttagcc tttttattca ttggggtgaa ttgcaagttc accatagttt ttccacacaa    6960
ccaaaaagga aactggaaaa atgttccttc taattaccat tattgcccgt caagctcaga    7020
tttaaattgg cataatgact taataggcac agccttacaa gtcaaaatgc ccaagagtca    7080
caaggctatt caagcagacg gttggatgtg tcatgcttcc aaatgggtca ctacttgtga    7140
tttccgctgg tatggaccga agtatataac acattccatc cgatccttca ctccatctgt    7200
agaacaatgc aaggaaagca ttgaacaaac gaaacaagga acttggctga atccaggctt    7260
ccctcctcaa agttgtggat atgcaactgt gacggatgcc gaagcagtga ttgtccaggt    7320
gactcctcac catgtgctgg ttgatgaata cacaggagaa tgggttgatt cacagttcat    7380
caacggaaaa tgcagcaatt acatatgccc cactgtccat aactctacaa cctggcattc    7440
tgactataag gtcaaagggc tatgtgattc taacctcatt tccatggaca tcaccttctt    7500
ctcagaggac ggagagctat catccctggg aaaggagggc acagggttca gaagtaacta    7560
ctttgcttat gaaactggag gcaaggcctg caaaatgcaa tactgcaagc attggggagt    7620
cagactccca tcaggtgtct ggttcgagat ggctgataag gatctctttg ctgcagccag    7680
attccctgaa tgcccagaag ggtcaagtat ctctgctcca tctcagacct cagtggatgt    7740
aagtctaatt caggacgttg agaggatctt ggattattcc ctctgccaag aaacctggag    7800
caaaatcaga gcgggtcttc caatctctcc agtggatctc agctatcttg ctcctaaaaa    7860
cccaggaacc ggtcctgctt tcaccataat caatggtacc ctaaaatact ttgagaccag    7920
atacatcaga gtcgatattg ctgctccaat cctctcaaga atggtcggaa tgatcagtgg    7980
aactaccaca gaaagggaac tgtgggatga ctgggcacca tatgaagacg tggaaattgg    8040
acccaatgga gttctgagga ccagttcagg atataagttt cctttataca tgattggaca    8100
tggtatgttg gactccgatc ttcatcttag ctcaaaggct caggtgttcg aacatcctca    8160
cattcaagac gctgcttcgc aacttcctga tgatgagagt ttatttttg gtgatactgg     8220
gctatccaaa aatccaatcg agcttgtaga aggttggttc agtagttgga aaagctctat    8280
tgcctctttt ttctttatca tagggttaat cattggacta ttcttggttc tccgagttgg    8340
tatccatctt tgcattaaat taaagcacac caagaaaaga cagatttata cagacataga    8400
gatgaaccga cttggaaagt gataaggcca ggccggccaa gcttgtcgag aagtactaga    8460
ggatcataat cagccatacc acatttgtag aggttttact tgcttaaaaa aacctcccac    8520
acctccccct gaacctgaaa cataaaatga atgcaattgt tgttgttaac ttgtttattg    8580
cagcttataa tggttacaaa taaagcaata gcatcacaaa tttcacaaat aaagcatttt    8640
tttcactgca ttctagttgt ggtttgtcca aactcatcaa tgtatcttat catgtctgga    8700
tctgatcact gcttgagcct aggtcgggca ggaagagggc ctatttccca tgattccttc    8760
atatttgcat atacgataca aggctgttag agagataatt gaattaatt tgactgtaaa    8820
cacaaagata ttagtacaaa atacgtgacg tagaaagtaa taatttcttg ggtagtttgc    8880
agttttaaaa ttatgtttta aaatggacta tcatatgctt accgtaactt gaaagtattt    8940
cgatttcttg gctttatata tcttgtggaa aggacgaaac accaggggcg tagttcaatt    9000
ggtagagcac cggtctctaa accgggtgt tgggagttcg agtctctccg cccctgccat     9060
tttttgctag ggctaggaga tccgaaccag ataagtgaaa tctagttcca aactattttg    9120
tcattttaa ttttcgtatt agcttacgac gctacaccca gttcccatct attttgtcac     9180
```

-continued

```
tcttccctaa ataatcctta aaaactccat ttccacccct cccagttccc aactatttg    9240 tccgcccaca gcggggcatt tttcttcctg ttatgttttt aatcaaacat cctgccaact    9300
ccatgtgaca aaccgtcatc ttcggctact tt                                  9332
```

<210> SEQ ID NO 91
<211> LENGTH: 334
<212> TYPE: PRT
<213> ORGANISM: Escherichia coli
<220> FEATURE:
<223> OTHER INFORMATION: strain K-12

<400> SEQUENCE: 91

```
Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
            20                  25                  30

Asp Asp Tyr His Cys Ile Tyr Cys Ile Val Asp Gln His Ala Ile Thr
        35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
            100                 105                 110

Lys Ser Ala Arg Tyr Ala Glu Asn Ile Asn Ala Gly Leu Phe Asp Tyr
        115                 120                 125

Pro Val Leu Met Ala Ala Asp Ile Leu Leu Tyr Gln Thr Asn Leu Val
    130                 135                 140

Pro Val Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
            180                 185                 190

Thr Lys Lys Met Ser Lys Ser Asp Asp Asn Arg Asn Asn Val Ile Gly
        195                 200                 205

Leu Leu Glu Asp Pro Lys Ser Val Val Lys Lys Ile Lys Arg Ala Val
    210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
            260                 265                 270

Leu Lys Gly Glu Val Ala Asp Ala Val Ser Gly Met Leu Thr Glu Leu
        275                 280                 285

Gln Glu Arg Tyr His Arg Phe Arg Asn Asp Glu Ala Phe Leu Gln Gln
    290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330
```